(12) United States Patent
Lynn et al.

(10) Patent No.: US 11,821,821 B1
(45) Date of Patent: Nov. 21, 2023

(54) NONINVASIVE POINT OF CARE BIOMARKER DETECTION FROM BREATH SAMPLES

(71) Applicant: Hound Labs, Inc., Oakland, CA (US)

(72) Inventors: Michael Scott Lynn, Piedmont, CA (US); Joseph A. Heanue, Oakland, CA (US); Samartha G. Anekal, San Jose, CA (US); Kevin M. Limtao, Temple City, CA (US); Kevin Bradford Dunk, Castro Valley, CA (US); Jeffrey A. Schuster, Alameda, CA (US); Jeffrey A. Stoll, San Mateo, CA (US)

(73) Assignee: Hound Labs, Inc., Oakland, CA (US)

( * ) Notice: Subject to any disclaimer, the term of this patent is extended or adjusted under 35 U.S.C. 154(b) by 332 days.

(21) Appl. No.: 16/776,501

(22) Filed: Jan. 29, 2020

Related U.S. Application Data

(60) Provisional application No. 62/799,675, filed on Jan. 31, 2019.

(51) Int. Cl.
*G01N 1/22* (2006.01)
*G01N 33/497* (2006.01)
*G01N 33/94* (2006.01)

(52) U.S. Cl.
CPC .......... *G01N 1/22* (2013.01); *G01N 33/497* (2013.01); *G01N 33/948* (2013.01); *G01N 1/2208* (2013.01); *G01N 2001/2223* (2013.01); *G01N 2001/2244* (2013.01)

(58) Field of Classification Search
CPC ............... G01N 1/22; G01N 1/2208; G01N 2001/2223; G01N 2001/2244; G01N 33/948; G01N 33/66; G01N 33/497; Y10T 436/25875

USPC .................. 436/63, 95, 149, 164, 172, 181; 422/82.01, 82.05, 83, 84
See application file for complete search history.

(56) References Cited

U.S. PATENT DOCUMENTS

| | | |
|---|---|---|
| 3,676,072 A | 7/1972 | Krivis |
| 4,133,202 A | 1/1979 | Marple |
| 4,771,005 A | 9/1988 | Spiro |
| 4,796,475 A | 1/1989 | Marpel |
| 4,926,679 A | 5/1990 | Dewhurst |
| 5,140,993 A | 8/1992 | Opekun, Jr. et al. |
| 5,196,306 A | 3/1993 | Bobrow et al. |
| 5,361,771 A | 11/1994 | Craine et al. |

(Continued)

FOREIGN PATENT DOCUMENTS

| | | |
|---|---|---|
| EP | 0132313 B1 | 9/1991 |
| EP | 2498093 A1 | 9/2012 |

(Continued)

OTHER PUBLICATIONS

Pardon et al. Sensors and Actuators B: Chemical, vol. 212, Feb. 9, 2015, pp. 344-352.*

(Continued)

*Primary Examiner* — Maureen Wallenhorst
(74) *Attorney, Agent, or Firm* — Mahamedi IP Law LLP

(57) ABSTRACT

Methods, systems and techniques for the accurate measurement of breath-borne biomarkers are disclosed. Such methods, systems and techniques may be used for the purposes of detection and/or measurement in breath samples of biomarkers, e.g., biomarkers relating to a disease or a physiological condition.

18 Claims, 58 Drawing Sheets

(56) References Cited

U.S. PATENT DOCUMENTS

| | | | |
|---|---|---|---|
| 5,583,001 A | 12/1996 | Bobrow et al. | |
| 5,589,346 A * | 12/1996 | Kanan | G01N 33/68 |
| | | | 435/7.92 |
| 5,922,610 A | 7/1999 | Alving et al. | |
| 6,040,191 A | 3/2000 | Grow | |
| 6,067,983 A | 5/2000 | Stenzler | |
| 6,460,539 B1 | 10/2002 | Japuntich et al. | |
| 6,582,376 B2 | 6/2003 | Baghdassarian | |
| 6,605,444 B1 | 8/2003 | Klein et al. | |
| 6,727,067 B2 | 4/2004 | Russman et al. | |
| 6,780,617 B2 | 8/2004 | Chen | |
| 6,964,862 B2 | 11/2005 | Chen | |
| 7,337,072 B2 | 2/2008 | Chen | |
| 7,364,553 B2 | 4/2008 | Paz et al. | |
| 7,547,285 B2 | 6/2009 | Kline | |
| 7,718,421 B2 | 5/2010 | Chen et al. | |
| 7,833,489 B2 | 11/2010 | Chen | |
| 7,935,504 B2 | 5/2011 | Chen | |
| 8,237,118 B2 | 8/2012 | Prox et al. | |
| 8,707,758 B2 | 4/2014 | Keays | |
| 8,936,933 B2 | 1/2015 | Chen et al. | |
| 8,955,366 B2 | 2/2015 | Abraham-Fuchs et al. | |
| 9,239,323 B2 | 1/2016 | Keays | |
| 9,429,564 B2 | 8/2016 | Beck | |
| 9,617,582 B2 * | 4/2017 | Milton | G01N 33/5308 |
| 9,662,652 B2 | 5/2017 | Chen | |
| 9,708,599 B2 | 7/2017 | Chen et al. | |
| 9,709,581 B1 | 7/2017 | Gordon et al. | |
| 9,709,582 B1 | 7/2017 | Gordon et al. | |
| 9,921,234 B1 | 3/2018 | Lynn et al. | |
| 9,933,445 B1 | 4/2018 | Lynn et al. | |
| 9,945,878 B1 | 4/2018 | Gordon et al. | |
| 9,970,950 B1 | 5/2018 | Lynn et al. | |
| 9,976,944 B2 | 5/2018 | Olin et al. | |
| 10,226,201 B2 | 3/2019 | Ahmad et al. | |
| 10,247,742 B1 | 4/2019 | Lynn et al. | |
| 10,443,050 B2 | 10/2019 | Chen et al. | |
| 11,026,596 B1 | 6/2021 | Lynn et al. | |
| 11,187,711 B1 | 11/2021 | Lynn et al. | |
| 2002/0177232 A1 | 11/2002 | Melker et al. | |
| 2003/0190259 A1 | 10/2003 | Alley | |
| 2004/0043479 A1 | 3/2004 | Briscoe et al. | |
| 2005/0137491 A1 | 6/2005 | Paz et al. | |
| 2005/0279181 A1 | 12/2005 | Trakumas et al. | |
| 2007/0031283 A1 | 2/2007 | Davis et al. | |
| 2007/0077660 A1 | 4/2007 | Glas | |
| 2008/0004542 A1 | 1/2008 | Allen et al. | |
| 2008/0038154 A1 | 2/2008 | Longbottom et al. | |
| 2008/0045825 A1 * | 2/2008 | Melker | A61B 5/1486 |
| | | | 600/365 |
| 2008/0050839 A1 | 2/2008 | Suslick et al. | |
| 2009/0017555 A1 | 1/2009 | Jehanli et al. | |
| 2010/0297635 A1 | 11/2010 | Olin et al. | |
| 2011/0086364 A1 | 4/2011 | Takkinen et al. | |
| 2012/0302907 A1 | 11/2012 | Palmskog et al. | |
| 2013/0006068 A1 | 1/2013 | Gemer et al. | |
| 2013/0011859 A1 | 1/2013 | Putnam et al. | |
| 2013/0021153 A1 | 1/2013 | Keays | |
| 2013/0102018 A1 | 4/2013 | Schentag et al. | |
| 2014/0120633 A1 | 5/2014 | Gandini et al. | |
| 2014/0276100 A1 * | 9/2014 | Satterfield | A61B 5/7271 |
| | | | 600/476 |
| 2014/0288454 A1 | 9/2014 | Paz et al. | |
| 2014/0296089 A1 | 10/2014 | Holmes et al. | |
| 2014/0311215 A1 | 10/2014 | Keays et al. | |
| 2014/0366609 A1 | 12/2014 | Beck et al. | |
| 2015/0033824 A1 * | 2/2015 | Hammarlund | A61B 5/097 |
| | | | 73/23.3 |
| 2015/0065901 A1 | 3/2015 | Bhatnagar et al. | |
| 2015/0265184 A1 | 9/2015 | Wondka et al. | |
| 2015/0305651 A1 | 10/2015 | Attariwala et al. | |
| 2015/0369830 A1 | 12/2015 | Crichlow | |
| 2016/0000358 A1 | 1/2016 | Lundin et al. | |
| 2016/0032798 A1 | 2/2016 | Herman et al. | |
| 2016/0055359 A1 | 2/2016 | Jensen et al. | |
| 2016/0069810 A1 | 3/2016 | Walavalkar et al. | |
| 2016/0069919 A1 | 3/2016 | Holmes et al. | |
| 2016/0299125 A1 | 10/2016 | Cristoni et al. | |
| 2017/0023546 A1 | 1/2017 | Holmes et al. | |
| 2017/0122851 A1 | 5/2017 | Thatcher et al. | |
| 2017/0128692 A1 | 5/2017 | Christopher et al. | |
| 2017/0184609 A1 | 6/2017 | Milton et al. | |
| 2017/0197213 A1 | 7/2017 | Nielsen et al. | |
| 2017/0303822 A1 | 10/2017 | Allsworth et al. | |
| 2017/0303823 A1 | 10/2017 | Allsworth et al. | |
| 2018/0038798 A1 | 2/2018 | Zhang et al. | |
| 2018/0224471 A1 | 8/2018 | Lynn et al. | |
| 2018/0238916 A1 | 8/2018 | Lynn et al. | |
| 2018/0243523 A1 | 8/2018 | Nason et al. | |
| 2018/0306775 A1 | 10/2018 | Beck et al. | |
| 2019/0160460 A1 | 5/2019 | Keatch et al. | |
| 2020/0124625 A1 | 4/2020 | Dunlop et al. | |
| 2020/0245899 A1 | 8/2020 | Heanue et al. | |
| 2020/0278275 A1 | 9/2020 | Turgul et al. | |
| 2020/0300876 A1 * | 9/2020 | Lynn | G01N 33/497 |
| 2020/0397340 A1 | 12/2020 | Dweik | |
| 2021/0330516 A1 | 10/2021 | Letourneau et al. | |

FOREIGN PATENT DOCUMENTS

| | | | |
|---|---|---|---|
| EP | 2762880 A1 | 8/2014 | |
| EP | 2781917 A1 | 9/2014 | |
| WO | 9014043 A1 | 11/1990 | |
| WO | 2006083269 A2 | 8/2006 | |
| WO | 2011029889 A1 | 3/2011 | |
| WO | 2016065300 A1 | 4/2016 | |
| WO | 2018076099 A1 | 5/2018 | |
| WO | 2018185164 A1 | 10/2018 | |
| WO | 2018211280 A1 | 11/2018 | |
| WO | 2019011750 A1 | 1/2019 | |

OTHER PUBLICATIONS

Coucke et al., "Tetrahydrocannabinol concentrations in exhaled breath and physiological effects following cannabis intake—A pilot study using illicit cannabis", Clinical Biochemistry, 2016, pp. 1072-1077.

Alexander, Brentan R., "Design of a microbreather for two-phase microchannel devices", Dissertation submitted to Massachusetts Institute of Technology. Dept. of Mechanical Engineering, (Jun. 2008), 59 pages.

Beaudet L, Rodriguez-Suarez R, Venne MH, Caron M, Bedard J, Brechler V, Parent S, Bielefeld-Sevigny M. "AlphaLISA immunoassays: the No. wash alternative to ELISAs for research and drug discovery", Nature Methods, (Dec. 2008), 5(12):an8-9.

"SensAbues AB—Next generation drug detection and health monitoring", SensAbues AB—Home, downloaded on Mar. 25, 2019 from http://sensabues.com/home.

"Exhaled breath biological sample matrix. EB", SensAbues AB—Product, downloaded on Mar. 25, 2019 from http://sensabues.com/product.

"FAIMS Breathalyzer Device", downloaded on Mar. 25, 2019 from https://algernonpharmaceuticals.com/faims-breathalyzer-device/.

Grob NM, Aytekin M, Dweik RA. "Biomarkers in exhaled breath condensate: a review of collection, processing and analysis", Journal of breath research, (Sep. 8, 2008), 2(3):037004.

Le Ru EC, Blackie E, Meyer M, Etchegoin PG. Surface enhanced Raman scattering enhancement factors: A Comprehensive Study. The Journal of Physical Chemistry C. Sep. 20, 2007;111(37):13794-13803.

"Low cost, non-invasive and non-intrusive", SensAbues AB—Benefits, downloaded on Mar. 25, 2019 from http://sensabues.com/benefits.

Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.

"Owlstone—FAIMS technology", downloaded on Mar. 25, 2019 from https://www.owlstonemedical.com/science-technology/faims-technology/.

(56) References Cited

OTHER PUBLICATIONS

"Owlstone Medical—Products", downloaded on Mar. 21, 2019 from https://www.owlstonemedical.com/products/.
"Owlstone Medical—The Home of Breath Biopsy: Breath Biopsy—VOC Biomarkers", downloaded on Mar. 25, 2019 from https://www.owlstonemedical.com/#.
Pardon, G, et al., "Aerosol sampling using an electrostatic precipitator integrated with a microfluidic interface", Sensors and Actuators B: Chemical. Feb. 2015, vol. 212, pp. 344-352.
"Pexa—How PExA works", downloaded on Mar. 25, 2019 from http://pexa.se/en/product-services/how-pexa-works/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product & Services", downloaded on Mar. 25, 2019 from http://pexa.se/en/product-services/.
"Pexa—Product-Sheet", Sep. 2016.
"Pexa—Research & Development", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Exhaled breath sampling company", SensAbues AB—About, downloaded on Mar. 25, 2019 from http://sensabues.com/about.
Stevenson H, Bacon A, Joseph KM, Gwandaru WR, Bhide A, Sankhala D, Dhamu VN, Prasad S. "A rapid response electrochemical biosensor for detecting THC in saliva" Scientific reports. Sep. 3, 2019; 9(1):1-11. (11 pages) // 9:12701 | https://doi.org/10.1038/s41598-019-49185-y.
Tan et al., "Direct detection of delta9-tetrahydrocannabinol in aqueous samples using a homogeneous increasing fluorescence immunoassay (HiFi)," Anal Bioaanal Chem, 2010. 8 pgs.
Teshima et al, "Determination of acetone in breath", Analytica Chimica Acta, 2005, 535, pp. 189-199.
"Volatile Organic Compounds (VOC) as non-invasive biomarkers for a range of diseases", downloaded on Mar. 25, 2019 from https://www.owlstonemedical.com/science-technology/voc-biomarkers/.

* cited by examiner

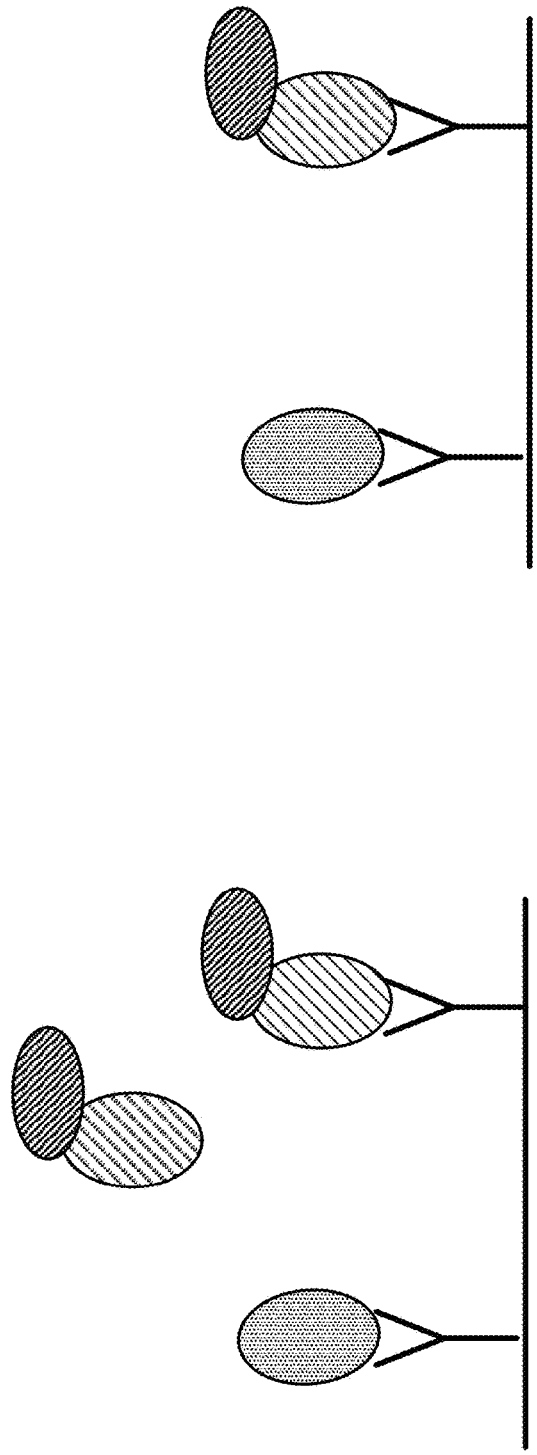
FIG. 4A
FIG. 4B
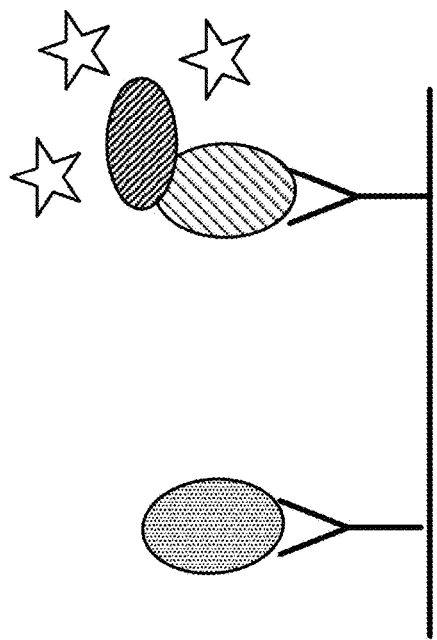
FIG. 4C

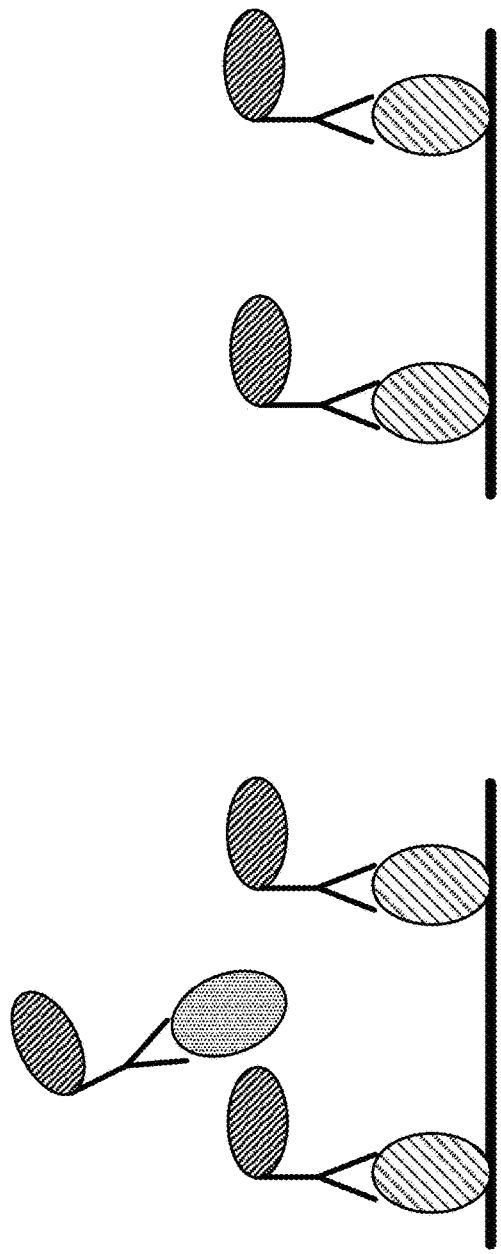
FIG. 5A
FIG. 5B
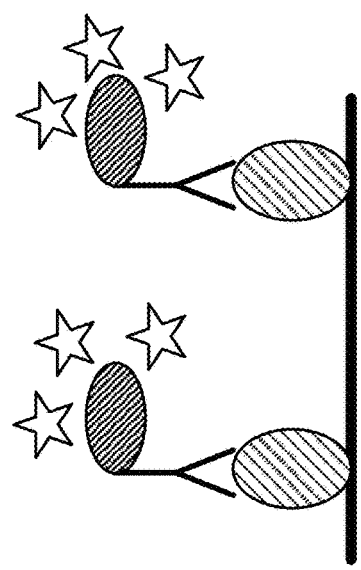
FIG. 5C

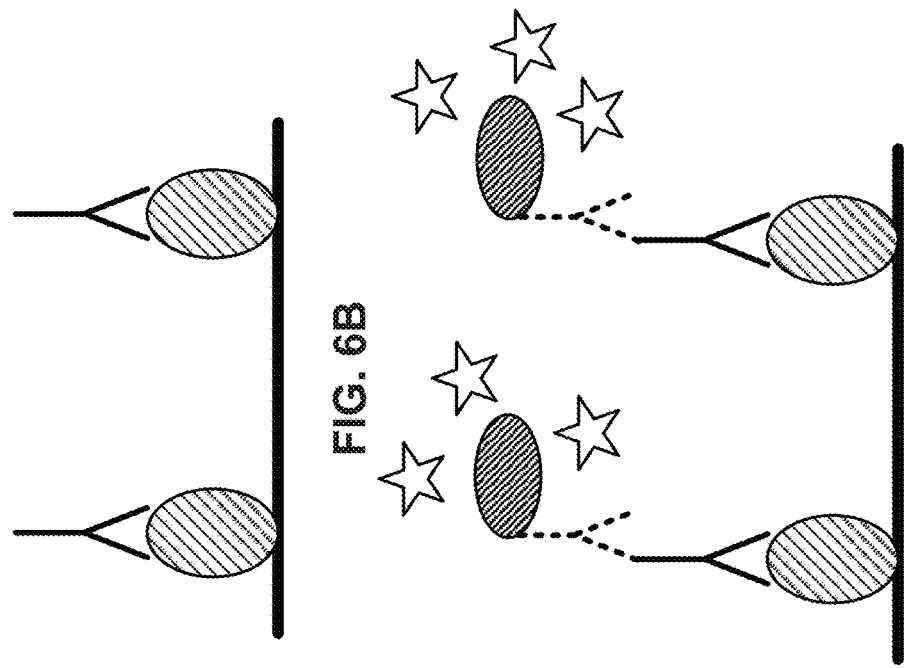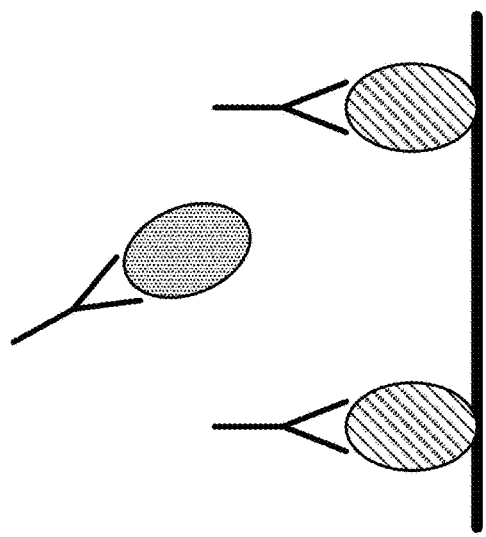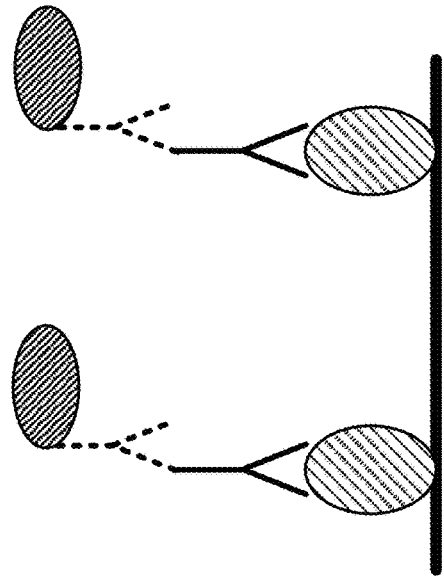

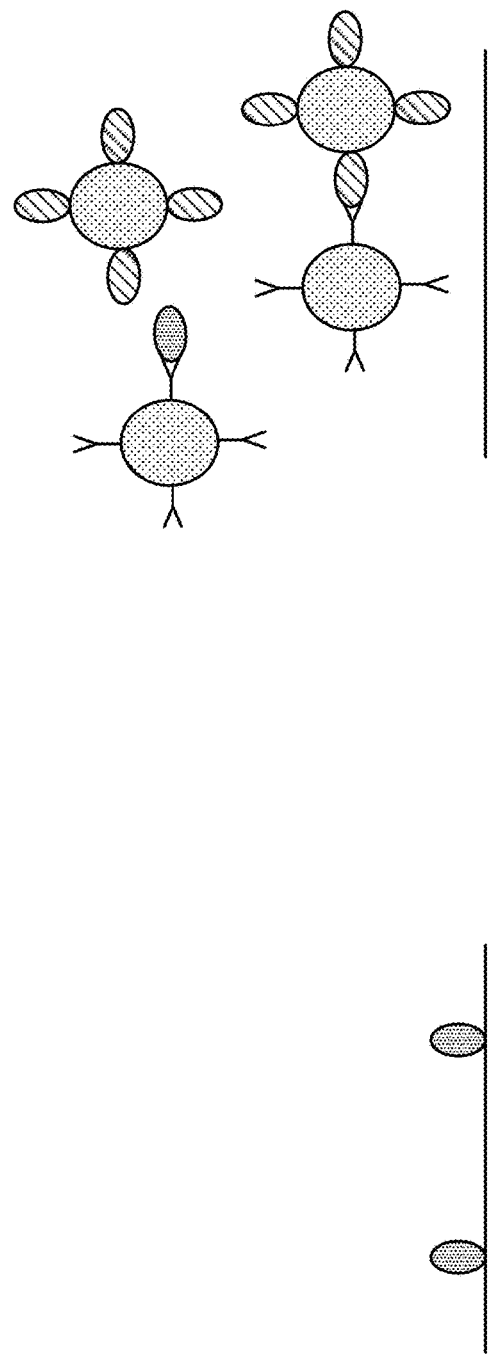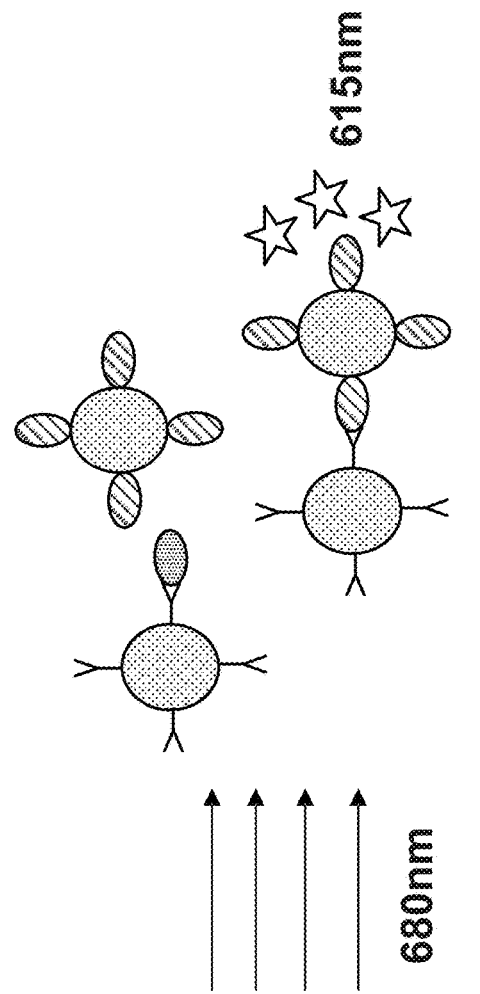

| Biomarker | Target Indications of use | Category | | | Assay Methods - Chemistry Based | | Detection | | Assay Methods - Electrical | |
|---|---|---|---|---|---|---|---|---|---|---|
| | | Reportable Type | Species Type | Assay Method(s) | Signal Generation Method(s) | Signal Readout Method(s) | Signal Generation Method(s) | Signal Readout Method(s) | | |
| d9-THC | DUI, controlled substance use, workplace testing | Drugs of Abuse | Small Molecule | Immunoassay | Absorbance, Chemiluminescence, Fluorescence | | Antibody-assisted mass change | Impedance spectroscopy | | |
| Na+ | Overall health/normalizing biomarker | Electrolytes | Ions | Co-factor dependent Enzyme Activity | Absorbance | | Ion-selective electrode | Voltammetry, Amperometry, Impedance | | |
| K+ | Overall health/normalizing biomarker | Electrolytes | Ions | Co-factor dependent Enzyme Activity | Absorbance | | Ion-selective electrode | Voltammetry, Amperometry, Impedance | | |
| Cl- | Overall health/normalizing biomarker | Electrolytes | Ions | Chemistry | Absorbance | | Ion-selective electrode | Voltammetry, Amperometry, Impedance | | |
| Ca++ | Overall health/normalizing biomarker | Electrolytes | Ions | Chemistry | Absorbance | | Ion-selective electrode | Voltammetry, Amperometry, Impedance | | |
| Glucose | Diabetes | Metabolites | Small Molecule | Enzyme-aided redox chemistry | Absorbance, Chemiluminescence | | Enzyme-assisted redox electrode | Voltammetry, Amperometry, Impedance | | |
| Ammonia/Ammonium | Overall health/normalizing biomarker | Metabolites | Small Molecule, Ions | Chemistry | Absorbance | | Electrode | Voltammetry, Amperometry, Impedance | | |
| Lactate | Sepsis, acidosis | Metabolites | Ions | Chemistry | Absorbance | | Enzyme-assisted redox electrode | Voltammetry, Amperometry, Impedance | | |
| Acetone | Diabetes | Metabolites | Small Molecule | Chemistry | Absorbance | | Enzyme-assisted redox electrode | Voltammetry, Amperometry, Impedance | | |
| 8-isoprostane | Sleep apnea, asthma, lung disease | Inflammatory | Small Molecule | Immunoassay | Absorbance, Chemiluminescence, Fluorescence | | | | | |
| TNF-alpha | Inflammatory conditions, including rheumatoid arthritis, and as a marker for drug effectiveness, etc. | Inflammatory | Protein | Immunoassay | Absorbance, Chemiluminescence, Fluorescence | | | | | |
| IL-6 | Inflammatory conditions, including rheumatoid arthritis, and as a marker for drug effectiveness, etc. | Inflammatory | Protein | Immunoassay | Absorbance, Chemiluminescence, Fluorescence | | | | | |
| GFAP/UCH-L1 | TBI, Concussion | Inflammatory | Protein | Immunoassay | Absorbance, Chemiluminescence, Fluorescence | | | | | |
| Nitrites | Chronic Obstructive Pulmonary Disease (COPD) | Inflammatory | Small Molecule | Chemistry | Absorbance | | Enzyme-assisted redox electrode | Voltammetry, Amperometry, Impedance | | |
| Lipopolysaccharide-binding protein | Rheumatoid arthritis | Inflammatory | protein | Immunoassay | Absorbance, Chemiluminescence, Fluorescence | | | | | |
| Leukotriene B4 | Inflammation | Inflammatory | Small Molecule | Immunoassay | Absorbance, Chemiluminescence, Fluorescence | | | | | |
| endothelin 1 | Inflammation, pulmonary arterial hypertension | Inflammatory | Peptide | Immunoassay | Absorbance, Chemiluminescence, Fluorescence | | | | | |
| BNP, and NT-pro-BNP | Monitoring of heart failure and other cardiac and pulmonary conditions such as pulmonary | Cardiac | Peptide | Immunoassay, Enzymatic | Absorbance, Chemiluminescence, Fluorescence | | Enzyme-assisted redox electrode | Voltammetry, Amperometry, Impedance | | |
| Troponin - C, I, T | Myocardial damage, including infarction | Cardiac | Protein | Immunoassay | Absorbance, Chemiluminescence, Fluorescence | | | | | |
| D-dimer | Deep vein thromboses, pulmonary embolism, disseminated intravascular coagulation | Vascular | Protein | Immunoassay | Absorbance, Chemiluminescence, Fluorescence | | | | | |
| ALT | Liver Function | Liver Function Tests | Enzyme | Chemistry | Absorbance | | | | | |
| AST | Liver Function | Liver Function Tests | Enzyme | Chemistry | Absorbance | | | | | |
| ALP | Liver Function | Liver Function Tests | Enzyme | Chemistry | Absorbance, Chemiluminescence | | | | | |
| Influenza sp. | Flu monitoring/diagnosis | Pathogens | Virus | Immunoassay | Absorbance, Chemiluminescence, Fluorescence | | | | | |
| Ebola | Monitoring populations for disease or biological weapon release | Pathogens | Virus | Immunoassay | Absorbance, Chemiluminescence, Fluorescence | | | | | |
| Tuluremia | Monitoring populations for disease or biological weapon release | Pathogens | Virus | Immunoassay | Absorbance, Chemiluminescence, Fluorescence | | | | | |

Fig. 10

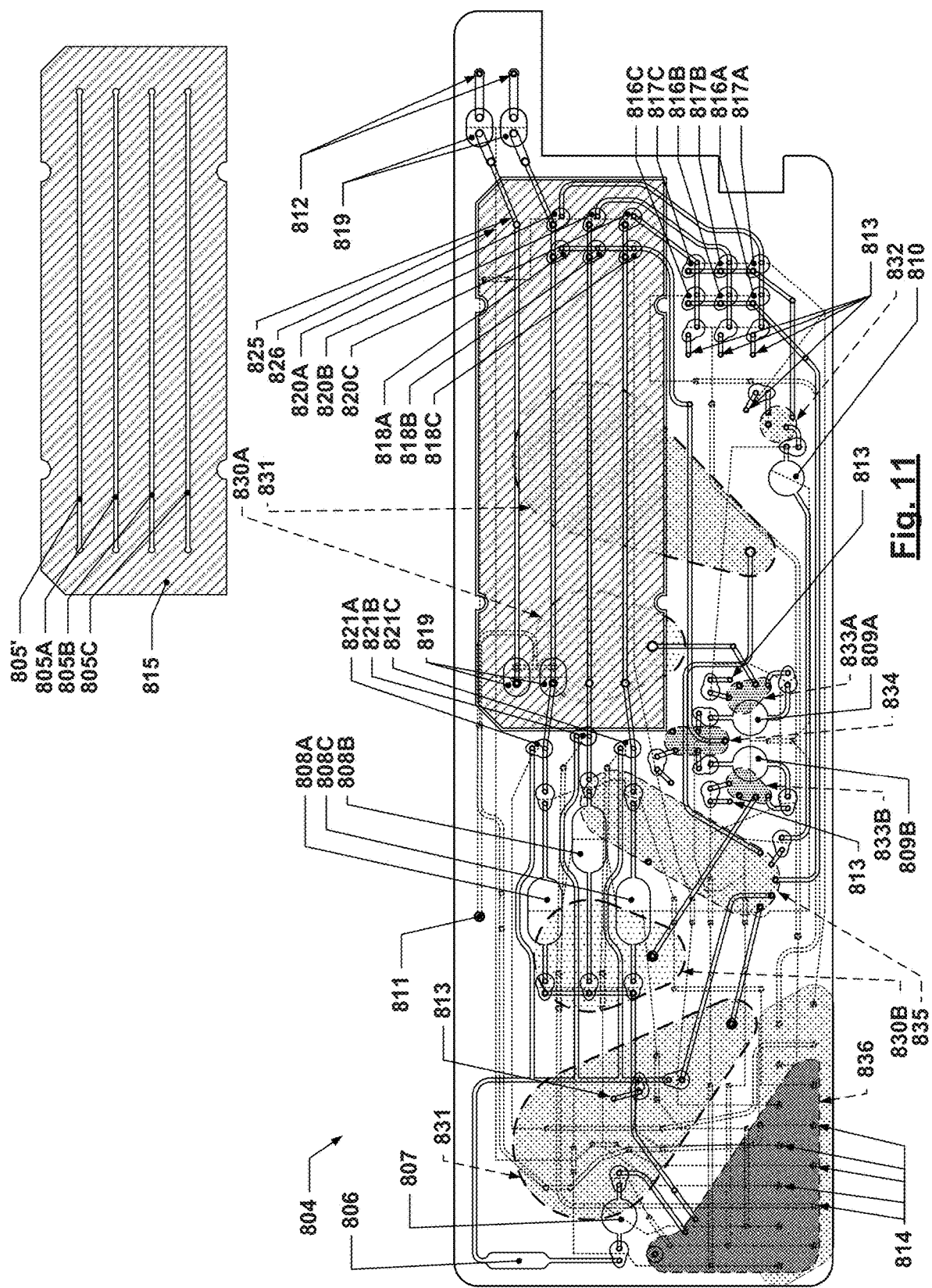

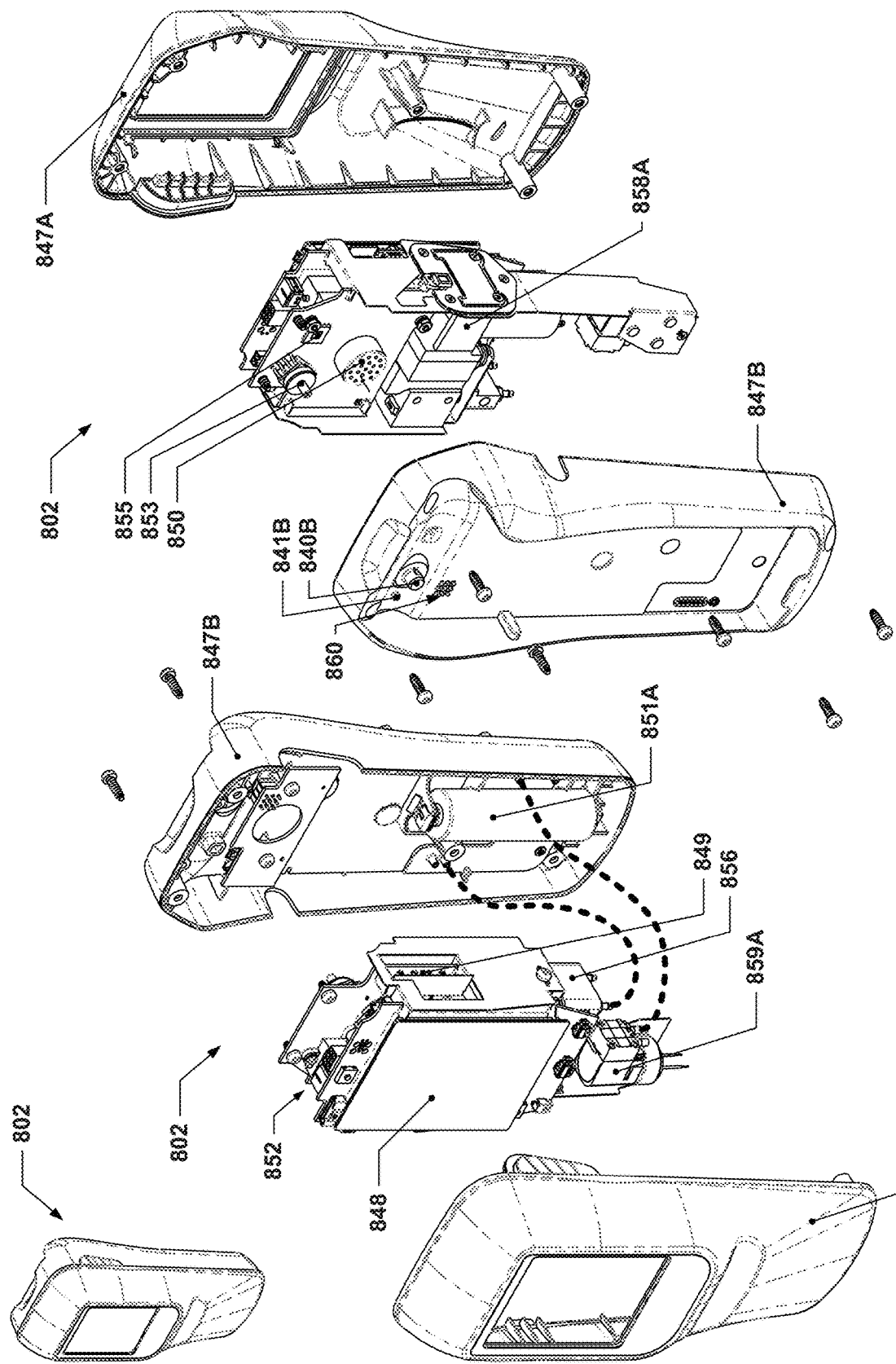

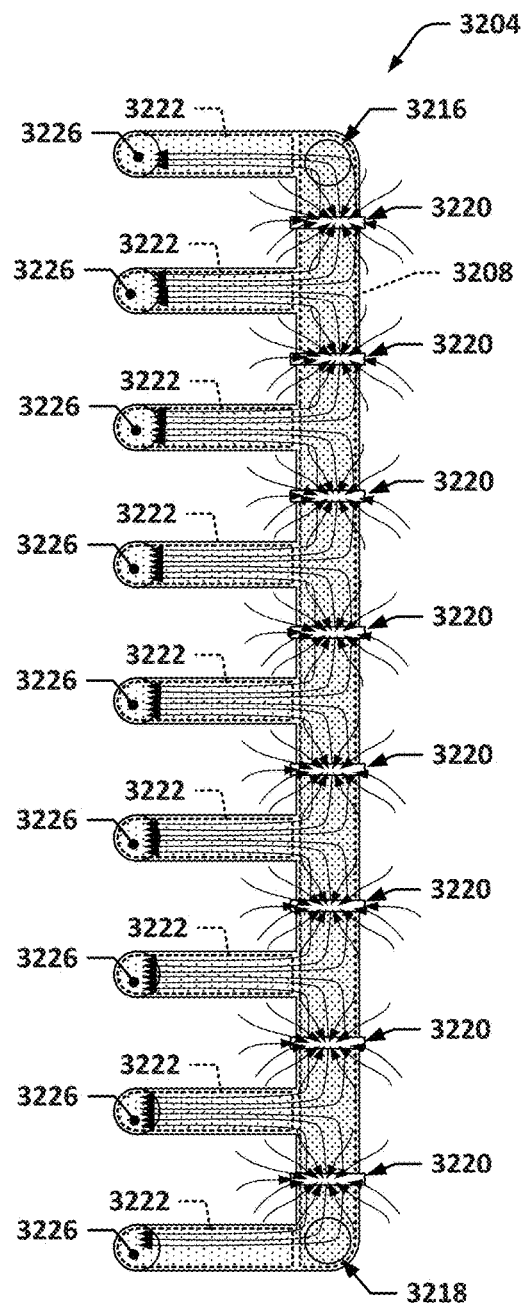
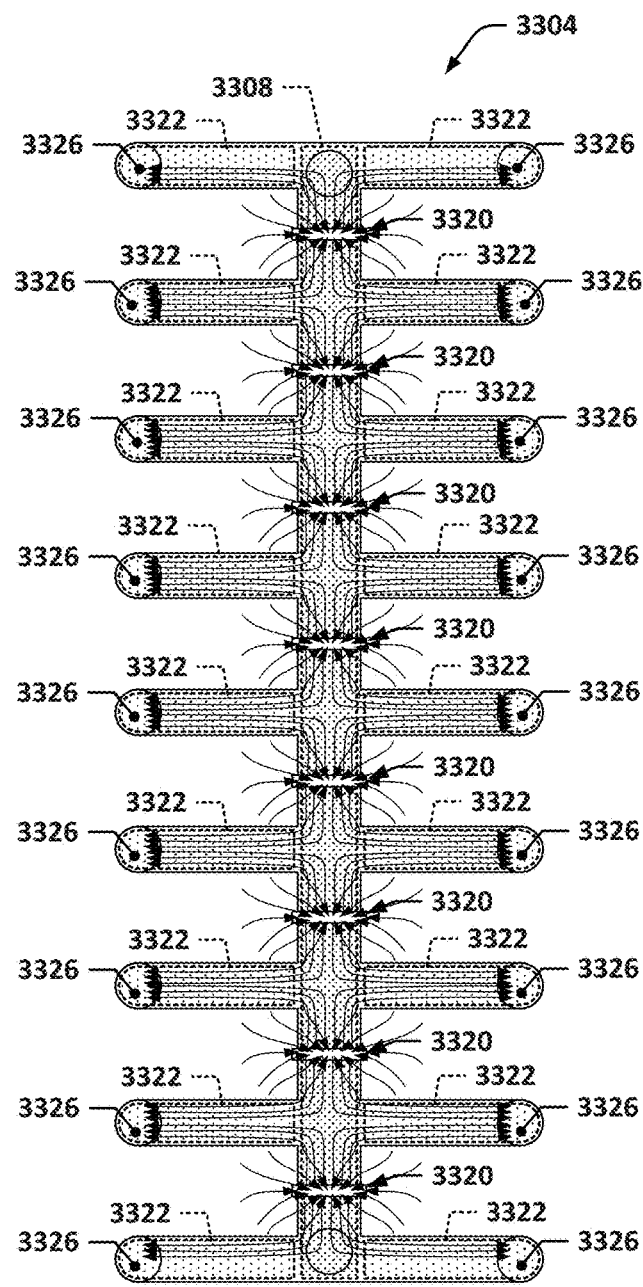
Figure 32                    Figure 33

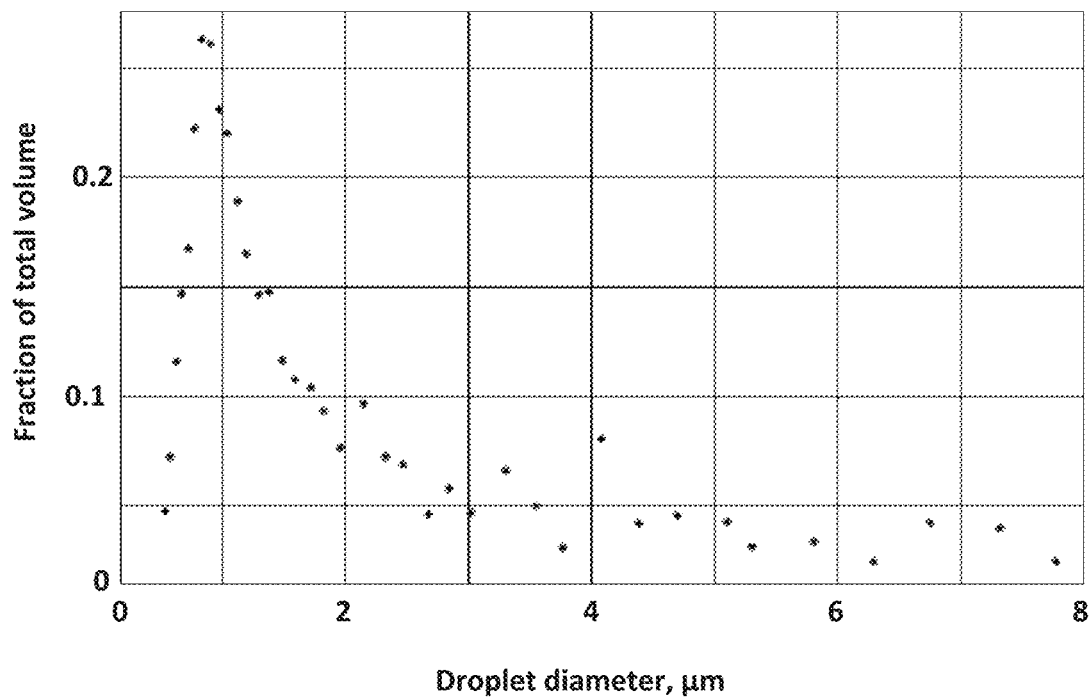
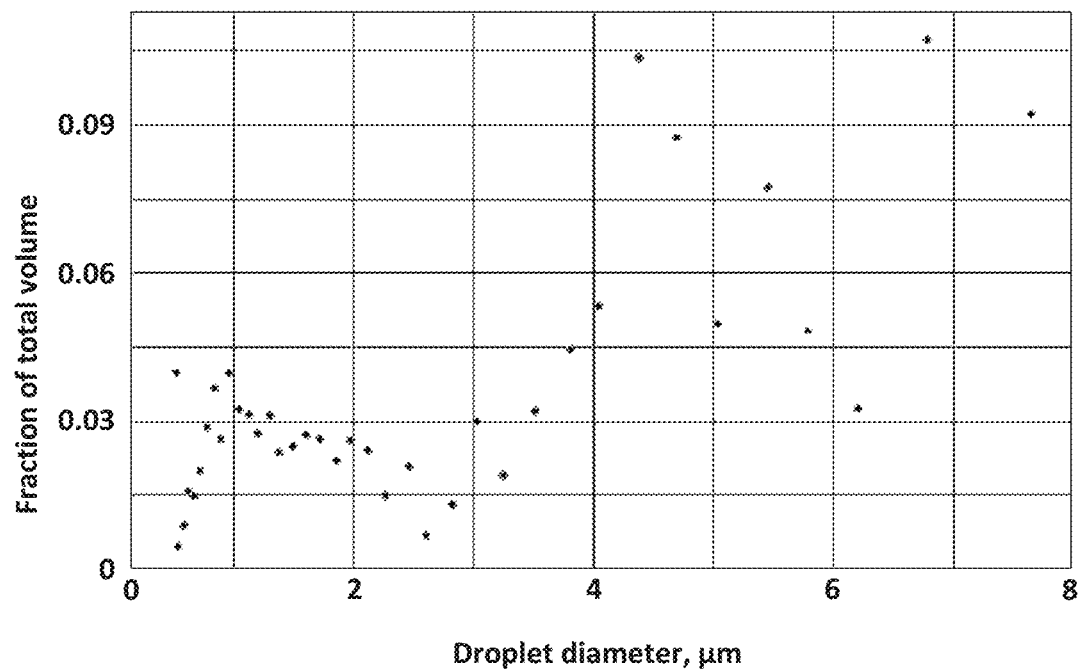
Figure 44

NONINVASIVE POINT OF CARE BIOMARKER DETECTION FROM BREATH SAMPLES

CROSS-REFERENCE TO RELATED APPLICATIONS

This application claims the priority benefit of U.S. Provisional Patent Application No. 62/799,675 filed on Jan. 31, 2019 and entitled "Noninvasive Point of Care Biomarker Detection from Breath Samples". The disclosure of the above-referenced application is hereby incorporated by reference herein in its entirety for all purposes.

BACKGROUND

With legalization of marijuana expanding and the risk of marijuana-associated impaired driving increasing, it is anticipated by the present inventors that there will be an increased need for portable and accurate measurement systems, methods and devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute—much more so than is the case with alcohol.

Furthermore, THC detection in human breath is generally the only reliable way to determine if a suspected marijuana user is under the influence. Unlike with alcohol, which the body can purge in relatively short order, e.g., less than a day, THC compounds may be present in a person's body long after they are no longer under the influence of the THC. Thus, detection of THC via blood or urine sample may result in false positives in terms of being under the influence of marijuana. Breath-testing for THC in breath at the roadside, alone or in combination with alcohol, would be convenient, non-invasive, and leverages the wide acceptance of administering a breath test at the roadside, as is commonly employed for alcohol.

SUMMARY

Details of one or more implementations of the subject matter described in this specification are set forth in the accompanying drawings and the description below. Other features, aspects, and advantages will become apparent from the description, the drawings, and the claims.

Methods, systems and apparatus for evaluating tetrahydrocannabinol (THC) level from a breath sample are disclosed. In various embodiments, the disclosed methods include immunoassay-based detection systems and methods. Among the potential benefits of such methods and systems are enhanced sensitivity and device scalability. The disclosed methods and systems may be implemented in variety of ways as contemplated by this disclosure. Among the features of the disclosure are systems and methods that may be implemented in devices that provide for convenient and reliable roadside detection and determination of THC recent use that may be correlated with impairment. The systems, methods and contemplated devices may also be adaptable to combining testing for THC and alcohol (ethanol) impairment, and/or to the detection and evaluation of other airborne substances, including controlled substances, and breath-borne indicators of various disease states.

According to various embodiments, a method in accordance with this disclosure involves determining an amount of THC captured from a breath sample obtained from a subject, comparing the determined amount of THC captured from the breath sample to a threshold level for THC in breath, and indicating whether or not the determined amount of THC captured from the breath sample exceeds the threshold. A reliably detectable picogram-level threshold may be correlated with a maximum baseline level of THC in breath associated with consumption of THC outside a window of THC-associated impairment and/or an average amount of THC in breath between 2 and 3 hours after inhalation for a range of users. The threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is independent of the frequency of the test subject's THC use. Such a method, then, may be adapted for breath-testing for THC, alone or in combination with alcohol, at the roadside.

THC, however, is much less prevalent in breath compared to alcohol, and is measured in the parts per trillion (picograms, pg) range in breath. According to various embodiments, the threshold referenced in the comparison may be less than 10 picogram/liter (pg/L) of breath, or from 2 to 5 pg/L of breath, or from 2 to 3 pg/L of breath, for example, about 2.4 pg/L of breath. The threshold may vary depending upon the capture efficiency of the device or system with which the method is conducted.

In various embodiments, the method may include obtaining the breath sample from the subject in manner suitable to conduct measurements in the picogram range in a roadside sobriety testing context, in particular using a device having a handheld form factor for obtaining the breath sample and conducting an analysis on site in a prescribed period of time. Such a method may involve drawing a portion of the breath sample exhaled by the subject into a reaction channel in a test cartridge with negative pressure. So that sufficient THC can be captured from a breath sample for use in a roadside sobriety testing context, the reaction channel may be configured to have a particular hydraulic diameter and length and/or shape.

In various embodiments, in order achieve picogram sensitivity the determining aspect of the method may involve an immunoassay. Suitable immunoassays may include surface-based antibody-down immunoassays, surface-based antigen-down immunoassays, noncompetitive immunoassays, heterogeneous competitive immunoassays, and homogeneous competitive immunoassays.

In various embodiments, in order to meet the evidentiary standards associated with roadside sobriety tests, an equal portion of the breath sample as drawn into the reaction channel may be drawn into an evidence channel on the test cartridge.

In various embodiments, the test cartridge comprises a microfluidic device.

In various embodiments, data corresponding to one or more of the determining the amount of THC captured from the breath sample obtained from the subject, the comparing the determined amount of THC from the breath sample to a threshold level for THC in breath, and the indicating whether or not the determined amount of THC captured from the breath sample exceeds the threshold, may be wirelessly transmitted to a remote location.

In various embodiments, both THC and ethanol are measured from the same breath sample.

The methods, systems and apparatus described herein may also be adaptable as a platform for detection and evaluation of other airborne/breath-borne substances, including controlled substances, and breath-borne indicators of various disease states. In this regard, this disclosure also relates to a method for evaluating a substance, more generally, in air, such as a human breath, the method involving determining an amount of a substance captured from a breath sample obtained from a subject, comparing the determined amount of the substance from the breath sample to a threshold level for the substance in breath, and indicating whether or not the determined amount of the substance captured from the breath sample exceeds the threshold. The substance may be associated with a human disease condition, such as stomach cancer, lung cancer, heart failure, kidney failure or diabetes, for example, and the threshold may, for example, be correlated with a baseline maximum level of the substance in human breath for a subject not suffering from the disease condition, and the substance is associated with a human disease condition, such as stomach cancer, lung cancer, heart failure, kidney failure or diabetes.

This disclosure also relates to systems and apparatus for measuring tetrahydrocannabinol (THC) level from a breath sample in accordance with the methods herein described.

According to various additional disclosed embodiments, a method and system for evaluating a biomarker in a breath sample may be provided that includes: measuring an amount of a biomarker associated with a physiological condition captured from aerosol drops in a breath sample obtained from a subject and determining, based on the measurement, existence of the physiological condition in the subject. Also disclosed is an apparatus suitable for conducting such evaluations.

The determination operation can further include comparing the measured amount of the biomarker captured from the breath sample to a threshold level for the biomarker in breath, the threshold level correlated with a manifestation of the physiological condition.

The threshold level for the biomarker in breath may be correlated with a baseline minimum level of the biomarker in breath correlated with the manifestation of the physiological condition as a disease state.

In particular embodiments, the biomarker may be aerosolized in forcefully exhaled aerosol drops.

In particular embodiments, the aerosol drops may be of a size range of about 3-5 µL, for example about 4.5 µL.

In some embodiments, the threshold level may be less than 10 pg/L of breath.

In some embodiments, the aerosol drops may be captured by a device configured for impact and collection of aerosol drops forcefully exhaled into the device, as further described below.

Details of one or more implementations of the subject matter described in this specification are set forth in the accompanying drawings and the description below. Other features, aspects, and advantages will become apparent from the description, the drawings, and the claims.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 4A-C depict a surface-based competitive antibody-down, chemiluminescence immunoassay.

FIGS. 5A-C depict a surface-based antigen-down, heterogeneous, competitive single-antibody immunoassay.

FIGS. 6A-D depict a surface-based antigen-down, heterogeneous, competitive two-antibody immunoassay.

FIGS. 7A-C depict a homogeneous competitive immunoassay.

FIG. 10 is a table summarizing various biomarkers, their potential applicability, and options for detection methods.

FIG. 11 depicts an example microfluidic plate that may be used with the example breath sampling and analysis system of FIG. 8.

FIGS. 12A-12F depict schematic views of an example microfluidic pump similar to microfluidic pumps that are depicted in the example microfluidic plate of FIGS. 11, 20, 21, and 22.

FIGS. 13A and 13B depict exploded views of an example handheld unit of the example breath sampling and analysis system of FIG. 8.

FIGS. 32 and 33 depict alternate arrangements of droplet traps.

FIG. 44 shows plots of droplet size distributions for exhaled breath measured from a subject breathing regularly (top) and forced exhalation (bottom).

FIGS. 8 through 43*i*, aside from the schematic Figures, are drawn to-scale within each Figure, although not necessarily to the same scale from Figure to Figure.

DETAILED DESCRIPTION

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

Methods, systems and apparatus for measuring tetrahydrocannabinol (THC) level from a breath sample are disclosed. In various embodiments, the disclosed methods include immunoassay-based detection systems and methods. Among the potential benefits of such methods and systems are enhanced sensitivity and device scalability. The disclosed methods and systems may be implemented in variety of ways as contemplated by this disclosure. Among the features of the disclosure are systems and methods that may be implemented in devices that provide for convenient and reliable roadside detection and determination of THC recent use that may be correlated with impairment. The systems, methods and contemplated devices may also be adaptable to combining testing for THC and alcohol (ethanol) impairment, and/or to the detection of other airborne substances, including controlled substances, and breath-borne indicators of various disease states.

In *Marijuana-Impaired Driving: A Report to Congress* dated July 2017, the National Highway Traffic Safety Administration (NHTSA) found that impairment is observed for two to three hours after smoking marijuana. Data collected and processed by the inventors has shown that a reliably detectable picogram-level threshold may be correlated with a maximum baseline level of THC in breath for chronic or frequent THC smokers and/or an average amount of THC in breath between 2 and 3 hours after inhalation for a range of users. More generally, it appears that the threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is therefore independent of the frequency of the test subject's THC use. Such a method, then, may be adapted for breath-testing for THC at the roadside.

Figure 1:
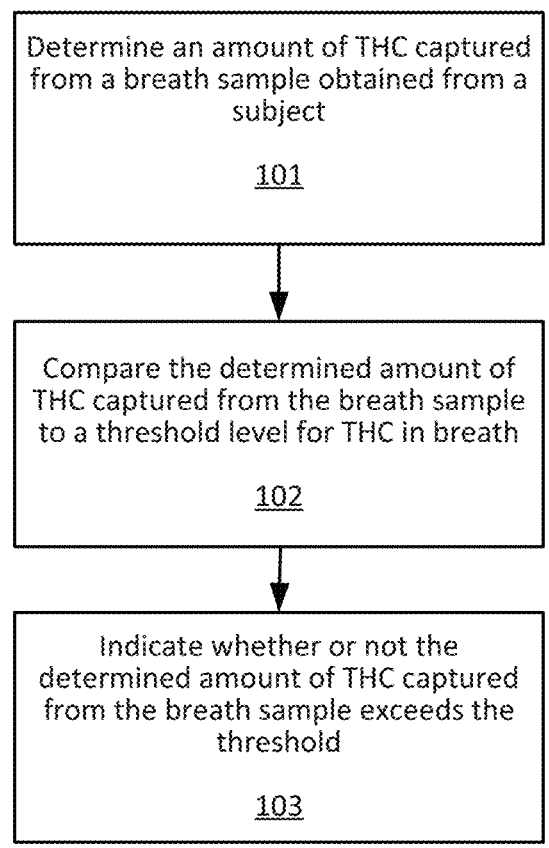
FIG. 1 depicts a process flow chart for method in accordance with the present disclosure.

Referring to FIG. 1, a general flow chart for a method in accordance with the present disclosure is depicted. According to various embodiments, the method involves determining an amount of THC captured from a breath sample obtained from a subject (101), comparing the determined amount of captured THC from the breath sample to a threshold level of THC in breath (102), and indicating whether or not the determined amount of captured THC from the breath sample exceeds the threshold (103).

Figure 2:
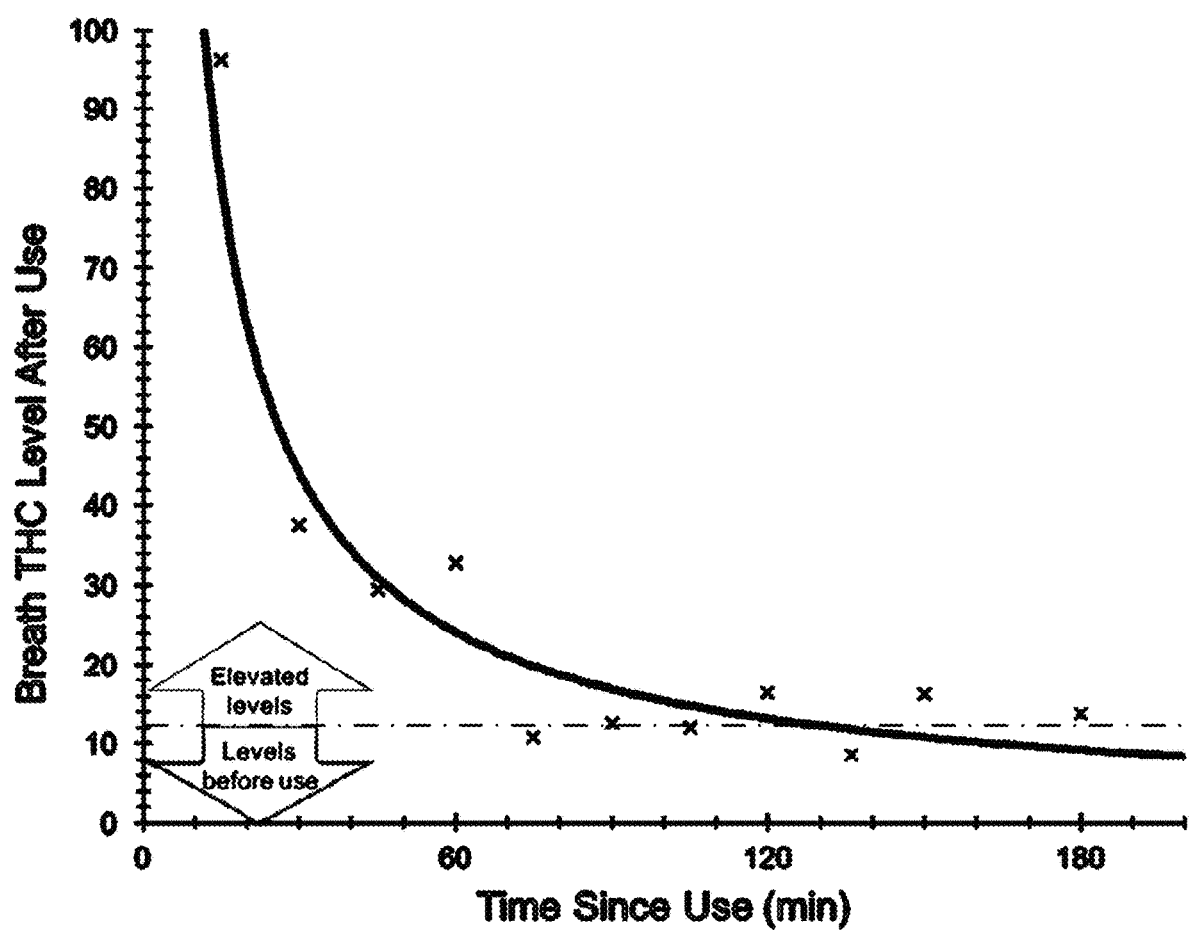
FIG. 2 depicts a plot showing breath THC level vs. time since use.

FIG. 2 depicts a plot showing breath THC level in picograms (pg) per breath (5 L) vs. time in minutes (min) since use in chronic or frequent THC smokers. From the plot it can be seen that THC level in breath drops substantially in the first hour, and after 2 hours it drops below the maximum baseline threshold for chronic users. Testing has determined a maximum baseline THC level in breath for chronic users to be in the picogram per liter of breath range. Based on data obtained through testing, it appears that the threshold may represent a baseline mean level of residual THC in breath associated with consumption of THC across a broad demographic, regardless of use frequency, outside a window from inhalation to between 2 and 3 hours after inhalation, which has been associated with THC impairment. The threshold referenced in the comparison of the disclosed method may be less than 10 picogram/liter (pg/L) of breath, or from 2 to 5 pg/L of breath, or from 2 to 3 pg/L of breath, for example, about 2.4 pg/L of breath. The maximum baseline 12 pg/5 L (2.4 pg/L) breath is superimposed on the plot. The threshold may vary depending upon the capture efficiency of the device or system with which the method is conducted, and can be tuned in practice.

It should also be understood that breath-testing for THC at the roadside may be combined with breath-testing for alcohol where another portion of the breath sample is tested for blood alcohol content (BAC) according to any suitable BAC analysis, such as are well-known in the art, as further discussed below.

In various embodiments, the method may include obtaining and processing the breath sample from the subject in manner suitable to conduct measurements in the picogram range in a roadside sobriety testing context, in particular using a device having a handheld form factor for obtaining the breath sample in a prescribed period of time and conducting an analysis on-site. Such a method may involve drawing a portion of the breath sample exhaled by the subject into a reaction channel in a test cartridge with negative pressure. So that sufficient THC can be captured from a breath sample for use in a roadside sobriety testing context, the reaction channel may be configured to have a particular hydraulic diameter and length and/or shape for to enhance capture efficiency.

One way to configure the reaction channel is according to the following parameters: For a minimum channel volume of 15 μL, the hydraulic diameter (d) may range from 0.1-1 mm, and the channel length may range from 15 μL/(d$^2$) to 45 μL/(d$^2$) (assuming d in mm). In specific implementations, the reaction channel may have a hydraulic diameter of less than 1 mm and a length of at least 15 mm, and at least 0.5 L of the breath sample may be flowed through the reaction channel in no more than 90 s. In some embodiments, the reaction channel may have a hydraulic diameter of less than 0.8 mm and a length of at least 40 mm, for example a hydraulic diameter of about 0.7 mm and a length of about 57 mm, and at least 0.7 L of the breath sample may be flowed through the reaction channel in about 60 s.

The preceding discussion of channel configuration relates to straight channels. But it should also be understood that the shape of a channel may also be manipulated to enhance capture efficiency. Other channel geometries, including hydraulic diameters, lengths and shapes may be desired depending on a particular capture target(s). The size, shape and form of the molecule or particle, etc. to be captured is generally a significant factor in configuring the channel to enhance capture efficiency. In general, larger targets would be better captured in channels that are not straight, such as zigzag, curved, spiral, etc.-shaped channels. It should be understood that the channel geometry can be designed to improve capture efficiency, and can change depending upon the capture target(s).

Also, a device can have multiple channels with same or different geometry configured to enhance the capture of different analytes or different forms of the same analyte, (e.g., molecular vs. aerosol THC), or one or more other analytes. In one example, a test for a plurality of different disease conditions from a single breath sample is contemplated. A device for implementing such a test might have a plurality of channels configured and/or designed for capture of a plurality of different breath-borne substances, which could then be processed in a manner as described herein.

The principles of operation of the methods, systems and apparatus described herein, while primarily developed and described with reference to inhalation of THC via marijuana smoking, are also expected to be applicable to ingestion of THC. While timeframes and biochemistry are different for edibles, the same thresholds correlated with THC breath concentration in breath are contemplated to be applicable in such contexts as well. Edibles generally contain a form of THC that is not psychoactive when ingested, but is subsequently metabolized to a psychoactive form. Antibodies for THC, or other THC binders as described herein, also bind to the THC metabolite rendering the methods described herein effective for measuring THC breath associated with edibles and comparing to a breath THC concentration threshold that has been associated with impairment.

In various embodiments, in order achieve picogram sensitivity the determining aspect of the method may involve an immunoassay. Suitable immunoassays may include surface-based antibody-down immunoassays, surface-based antigen-down immunoassays, noncompetitive immunoassays, heterogeneous competitive immunoassays, and homogeneous competitive immunoassays. Several suitable immunoassays will now be described with reference to FIGS. 3-7. The operation of these immunoassays and their generalization to other recognition elements will be well understood and implementation details for these immunoassays will be readily ascertained by those of ordinary skill in the art.

Figure 3A:
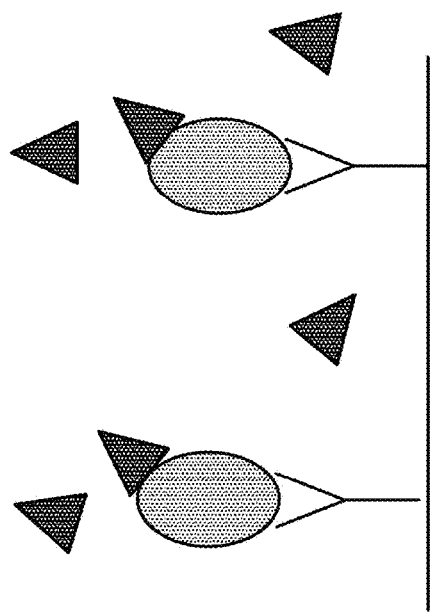
FIGS. 3A-D depict a surface-based antibody-down, direct diazonium reporter immunoassay.

FIGS. 3A-D depict a surface-based antibody-down, direct diazonium reporter immunoassay. According to this immunoassay, a THC binder, such as a monoclonal or polyclonal antibody, peptides, or aptamers, is/are surface-bound to the reaction channel walls according to well-known techniques. Surface binding to the reaction channel walls may be accomplished by passive adsorption, covalent binding, or a combination, for example. THC from the breath sample portion drawn into the reaction channel is captured by binding to the THC antibody, as depicted in FIG. 3A. Suitable reagents and reaction conditions are well or readily ascertained by those of ordinary skill in the art given the description provided herein. For example, in one implementation, mouse monoclonal anti-THC antibody is immobilized on the surface via passive adsorption. In solution, THC from breath sample binds to the antibody immobilized on the capture surface.

Figure 3C:
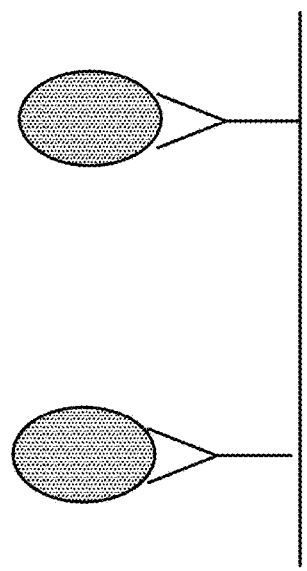
Figure 3B:
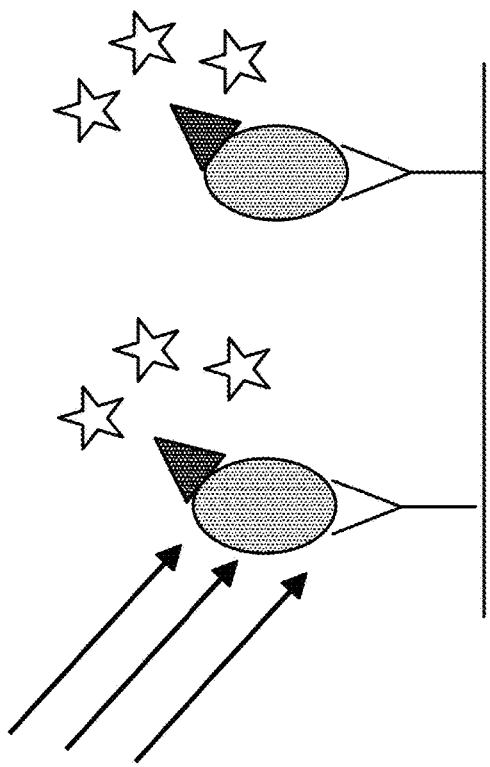

Determining an amount of THC captured from a breath sample obtained from a subject via this immunoassay involves flowing a diazotized fluorophore into the reaction channel and forming a solution such that the diazotized fluorophore binds to any THC from the breath sample portion captured by binding to the THC antibody to form a diazotized fluorophore-THC adduct, as depicted in FIG. 3B.

In various embodiments, the diazotized fluorophore has the formula:

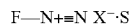

wherein:

F is a functionalized fluorophore;

N+≡N is a diazo functional group;

X$^-$ is a negatively charged ion balancing the charge on the diazo functional group; and S is a diazo functional group stabilizer.

F can be an amine-functionalized fluorophore, such as a primary amine-functionalized fluorophore. The fluorophore can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group.

The F—N+≡N group of a suitable diazotized fluorophore is selected to bind to a cannabinoid. In various embodiments, the F—N+≡N binds to the para or ortho position of a phenol ring of tetrahydrocannabinol forming an N=N azo bond such that an adduct is formed having the formula:

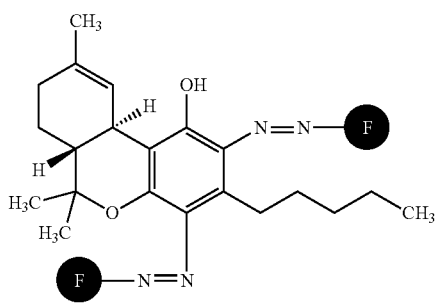

wherein F is the functionalized fluorophore, and only one or the other —N=N—F group is present.

The acidic diazotized fluorophore solution is formed from constituent materials in an acidic solution. For example, the acidic solution may contain dilute HCl, such as 100 μM HCl. Indicators/labels containing stabilized $N^+{\equiv}N$ diazo functional groups can be been synthesized to rapidly (e.g., <2 min) and selectively bind to THC and/or derivatives thereof at the para or ortho position of the phenol ring forming an N=N azo bond. The binding produces a chemically bonded fluorescent-labeled THC adduct. The diazotized fluorophore indicator/label is generally of the form:

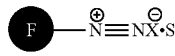

where:
- F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;
- $N^+{\equiv}N$ is a diazo-functional group that is chemically bonded/grafted/functionalized/conjugated to F;
- $N^-$ is a negatively charged ion that charge balances the positively charged diazo functional group $N^+{\equiv}N$, examples of which may include fluoride, sulfide, chloride, nitride, bromide, iodide, arsenate, phosphate, arsenite, hydrogen phosphate, dihydrogen phosphate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof;
- S is a $N^+{\equiv}N$ stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfirtic acid, sulfonic acid, camphosulphonic acid, thiocyanate, thione, thial, sulfonyl chloride, carbonyl chloride, phosphine, phosphonic acid, phosphate, phosphodiester, boronic acid, boronic ester, boronic acid, borinic ester, or any combination thereof.

Indicators including stabilized $N^+{\equiv}N$ diazo functional groups can be synthesized, for example, by a process including the combination of a primary amine (—NH$_2$) functionalized fluorophore, F (listed above), in an acidic solution ($H^+X^-$) with sodium nitrite (NaNO$_2$) and stabilizers, S (listed above):

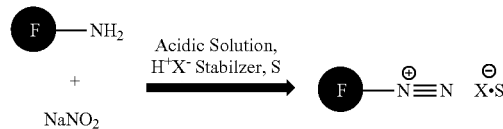

Figure 3D:
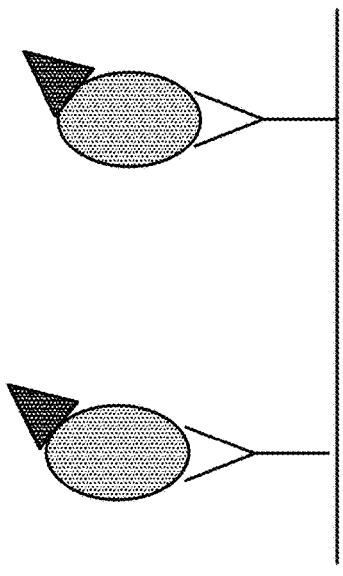

The diazotized fluorophore-THC adduct is then exposed to a light source in situ in the reaction channel to produce a fluorescence, as depicted in FIG. 3D. For example, the diazotized fluorophore may be rhodamine 123 diazotized at a primary amine group, the excitation wavelength may be 511 nm and the emission wavelength may be 534 nm. The fluorescence may be measured, the amount of THC captured from the breath sample determined based on the measured fluorescence.

In this direct immunoassay, the measured fluorescence is directly proportional to the amount of THC captured from the breath sample.

In various embodiments, prior to exposing the diazotized fluorophore-THC adduct to the light source to produce the fluorescence, any unbound breath constituents and unbound diazotized fluorophore is washed away from the reaction channel, as depicted in FIG. 3C. For example, the washing operation may involve flowing a buffer such as Phosphate Buffered Saline with surfactant such as 0.01% tween-20. Other suitable buffers include tris-buffered saline and similar buffers. Particularly suitable wash buffer is generally derived empirically by the person of ordinary skill in the art. While the fluorescent signal of the adduct has a spectral difference from unbound diazotized fluorophore and so can be likely detected in a homogeneous assay (without a wash step), a wash step is generally used to remove any other breath constituents that could also bind the diazotized fluorophore and therefore contaminate the assay.

FIGS. 4A-C depict a surface-based competitive antibody-down, chemiluminescence immunoassay. According to this immunoassay, a THC binder, such as a monoclonal or polyclonal antibody, peptides, or aptamers, is/are surface-bound to the reaction channel walls according to well-known techniques. Surface binding to the reaction channel walls may be accomplished by passive adsorption, covalent binding, or a combination, for example. THC from the breath sample portion drawn into the reaction channel is captured by binding to the THC antibody, as depicted in FIG. 4A. Suitable reagents and reaction conditions are well or readily ascertained by those of ordinary skill in the art given the description provided herein, for example, as described above.

Determining an amount of THC captured from a breath sample obtained from a subject via this immunoassay involves flowing a known amount of an enzyme-conjugated synthetic THC antigen into the reaction channel and forming a solution such that any THC from the breath sample portion captured by binding to the THC antibody competes with the enzyme-conjugated synthetic THC antigen to bind to the surface-bound THC antibody, as further depicted in FIG. 4A.

Then, as depicted in FIG. 4B, any unbound THC from the breath sample portion and any unbound enzyme-conjugated synthetic THC antigen is washed away from the reaction channel.

After the wash operation, a chemiluminescent substrate for the enzyme is flowed into the reaction channel and the enzyme is allowed to activate the chemiluminescent substrate, as depicted in FIG. 4C, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidically-connected channel or chamber.

In this competitive immunoassay, the measured fluorescence is inversely proportional to the amount of THC captured from the breath sample.

FIGS. 5A-C depicts a surface-based antigen-down, heterogeneous, competitive single-antibody immunoassay. According to this immunoassay, a synthetic THC antigen, such as THC-BSA hapten, is surface-bound to the reaction channel walls. Surface binding to the reaction channel walls may be accomplished by passive adsorption, covalent binding, or a combination. Suitable reagents and reaction conditions are well or readily ascertained by those of ordinary skill in the art given the description provided herein.

THC from the breath sample portion drawn into the reaction channel is captured by adsorption on the reaction channel walls. Determining an amount of THC captured from a breath sample obtained from a subject via this immunoassay involves flowing a known amount of an enzyme-conjugated THC antibody into the reaction channel and forming a solution with any THC from the breath sample portion, such that any THC from the breath sample portion competes with the surface bound THC antigen for the enzyme-conjugated THC antibody in the solution, as depicted in FIG. 5A.

Then, as depicted in FIG. 5B, any unbound THC from the breath sample portion and any unbound enzyme-conjugated THC antibody is washed away from the reaction channel.

After the wash operation, a chemiluminescent substrate for the enzyme is flowed into the reaction channel and the enzyme is allowed to activate the chemiluminescent substrate, as depicted in FIG. 5C, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidically-connected channel or chamber.

In this competitive immunoassay, the measured fluorescence is inversely proportional to the amount of THC captured from the breath sample.

FIGS. 6A-D depicts a surface-based antigen-down, heterogeneous, competitive two-antibody immunoassay. According to this immunoassay, a synthetic THC antigen is surface-bound to the reaction channel walls according to well-known procedures, such as described above. Suitable reagents and reaction conditions are well or readily ascertained by those of ordinary skill in the art given the description provided herein.

THC from the breath sample portion drawn into the reaction channel is captured by adsorption on the reaction channel walls. Determining an amount of THC captured from a breath sample obtained from a subject via this immunoassay involves flowing a known amount of a THC antibody into the reaction channel and forming a solution with any THC from the breath sample portion, such that any THC from the breath sample portion competes with the surface bound THC antigen for the THC antibody in the solution, as depicted in FIG. 6A.

Then, as depicted in FIG. 6B, any unbound THC from the breath sample portion and any unbound THC antibody is washed away from the reaction channel.

After this wash operation an enzyme-conjugated second antibody is flowed into the reaction channel forming a solution, such that the enzyme-conjugated second antibody binds to the THC antibody on the surface bound THC antigen, as depicted in FIG. 6C.

Then, any unbound THC from the breath sample portion and any unbound THC antibody is washed away from the reaction channel.

After this second wash operation, a chemiluminescent substrate for the enzyme is flowed into the reaction channel and the enzyme is allowed to activate the chemiluminescent substrate, as depicted in FIG. 6D, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidly-connected channel or chamber.

In this competitive immunoassay, the measured fluorescence is inversely proportional to the amount of THC captured from the breath sample.

In various implementations of the chemiluminescent embodiments described above with reference to FIGS. 4, 5 and 6, the enzyme may horseradish peroxidase (HRP) and the substrate may be, for example, TMB (3,3',5,5'-tetramethylbenzidine), which gives blue reaction products upon reaction with HRP that have major absorbance peaks at 370 nm and 652 nm; OPD (o-phenylenediamine) which gives a yellow-orange, water-soluble reaction product with an absorbance maximum of 492 nm upon reaction with HRP; or ABTS (2,2'-Azinobis [3-ethylbenzothiazoline-6-sulfonic acid]) which gives a green, water-soluble end reaction product upon reaction with HRP that gives two major absorbance peaks at 410 nm and 650 nm. These reagents are available from Sigma-Aldrich.

FIGS. 7A-C depicts a homogeneous competitive immunoassay. According to this immunoassay, THC from the breath sample portion drawn into the reaction channel is captured by adsorption on the reaction channel walls, as depicted in FIG. 7A. Determining an amount of THC captured from a breath sample obtained from a subject via this immunoassay involves a luminescent oxygen channeling immunoassay (LOCI™) or AlphaLISA™ immunoassay, such as are described in *Luminescent oxygen channeling assay (LOCI™): sensitive, broadly applicable homogeneous immunoassay method*, E. F. Ullman et al., Clinical Chemistry, 42:9, 1518 (1996); and *AlphaLISA immunoassays: the no-wash alternative to ELISAs for research and drug dis-*

*covery*, L. Beaudet et al., Perkin Elmer Application Notes, December 2008; incorporated by reference herein for background and details of the two assays. Antibody specific to THC is immobilized on donor beads, either by direct adsorption or via Streptavidin-Biotin linkage. Acceptor beads are prepared by adsorbing a synthetic THC antigen.

In this context, these immunoassays involve flowing donor beads and acceptor beads into the reaction channel and forming a solution with any THC from the breath sample portion, such that any THC from the breath sample portion competes with synthetic THC bound to the acceptor beads to bind to antibody immobilized on the donor beads, as depicted in FIG. 7B. Donor beads bind either to free THC from the breath sample portion or to the acceptor beads' immobilized THC. The higher the concentration of free THC from breath sample, the lower the concentration of donor bead—acceptor bead pairs.

The donor bead-acceptor bead pairs in the solution are then exposed to a light source in situ in the reaction channel to produce a fluorescence, as depicted in FIG. 7C. For example, the, the excitation wavelength may be 680 nm and the emission wavelength may be 615 nm. This fluorescence signal is only emitted when the donor and acceptor beads are in close proximity to each other. This results in only bound pairs emitting light, while free beads do not emit any light. This reaction, which only occurs between beads which are in close proximity is what allows the homogenous phase immunoassay, without the requirement for washing, which is integral to traditional surface-based immunoassays.

The fluorescence may be measured, and the amount of THC captured from the breath sample determined based on the measured fluorescence.

In this competitive, homogeneous immunoassay, the measured fluorescence is inversely proportional to the amount of THC captured from the breath sample.

Following completion of one of the immunoassay formats described above, the determined amount of THC captured the breath sample may be compared to a threshold level for THC in breath, such as described above with reference to FIG. 2, for example, less than 10 picogram/liter (pg/L) of breath, or from 2 to 5 pg/L of breath, or from 2 to 3 pg/L of breath, for example, about 2.4 pg/L of breath. However, as noted above, the threshold may vary depending upon the capture efficiency of the device or system with which the method is conducted.

Then, it may be indicated whether or not the amount of THC captured from the breath sample exceeds the threshold. A result wherein the amount of THC in the breath sample exceeds the threshold may be a positive test result for recent inhalation of THC, which may be correlated to THC impairment. In various embodiments, the indicating may include a visible and/or audible signal and/or readout on a display associated with a device on which the determination and comparison is conducted.

In various embodiments, the test cartridge on which methods described herein, particularly immunoassays, are conducted may be a microfluidic device.

In various embodiments, data corresponding to one or more of the determining the amount of THC captured from the breath sample obtained from the subject, the comparing the determined amount of THC from the breath sample to a threshold level for THC in breath, and the indicating whether or not the determined amount of THC captured from the breath sample exceeds the threshold, may be wirelessly transmitted to a remote location. In some instances, one or more processors and memory may include at least one processor and memory that are part of a device associated with the test cartridge. In such cases, there may be processors and memory distributed between two or more components, and the components may communicate with one another, either through a wireless communications interface or a wired connection. In some implementations, one or more of the components may also have a wireless communications interface, e.g., a cellular interface, that allows the one or more processors to wirelessly communicate information to a remote device, e.g., a server. For example, the device associated with the test cartridge may include a wireless interface that may transmit data corresponding to one or more of the determining the amount of THC in the breath sample obtained from the subject, the comparing the amount of THC determined to be in the breath sample to the threshold level of THC in breath, and the indicating whether or not the amount of THC in the breath sample exceeds the threshold, (as either entered manually by a user or as obtained automatically, e.g., through use of a GPS receiver located in the device or in another nearby piece of equipment, such as a paired smartphone or police car), and possibly other data such as one or more fingerprints of a subject, and/or a picture of the subject providing the sample, e.g., as taken by a paired smartphone or by a camera that may be built in to the device. The same wireless communications interface, or a different wireless communications interface, may also communicate test results to the same remote device in association with such information or in association with a record identifier linking such further information to previously transmitted information, allowing test results to be associated with a particular subject and sampling time/location. In some implementations, the wireless interface that may allow for such long-range communications, e.g., a cellular interface, may be integrated into only one of the components of the device, and the other components may communicate wirelessly with the base station using shorter-range communications systems, e.g., Bluetooth, and the base station may then act as a relay and send data collected by the other components on to the remote device.

In various embodiments, the breath sample obtained from the subject is also tested for a second substance, in particular ethanol, such that both THC and ethanol are measured from the same breath sample. According to such embodiments, another portion of the breath sample may be routed through a blood alcohol concentration (BAC) sensor for ethanol measurement. BAC sensors and their operation are well known in the art. Briefly, in a typical example of a fuel call-based BAC sensor, when a subject exhales into a breath analyzer, any ethanol present in their breath is oxidized to acetic acid at the anode. At the cathode, atmospheric oxygen is reduced. The overall reaction is the oxidation of ethanol to acetic acid and water. The electric current produced by this reaction is measured by a microcontroller, and displayed as an approximation of overall blood alcohol content (BAC). Blood alcohol content or concentration is not measured directly, which would require the analysis of a blood sample. Instead, a BAC sensor determines BAC indirectly by measuring breath alcohol level. Any suitable BAC sensors may be integrated with a device associated with the test cartridge, for example fuel cell based sensors from PAS Systems, Inc.

In various embodiments, the breath sample may be obtained from the subject after exposing the subject to a well-ventilated area (for example, outdoors) for at least 15 minutes. Subjects exposed to secondhand smoke will only have THC in their breath for a very brief time, and it disappears after a person is no longer exposed to this smoke. Accordingly, subjects exposed to secondhand smoke can be placed outdoors or in a well-ventilated area for 15 minutes before a breath test is performed to avoid a false positive associated with secondhand smoke exposure.

In various embodiments, in order to meet the evidentiary standards associated with roadside sobriety tests, an equal portion of the breath sample as drawn into the reaction channel may be drawn into an evidence channel on the test cartridge. This "B" sample can be retained for future testing to validate the test result. The "B" sample may be eluted from the evidence channel into a solution in a separate receptacle, or left in the evidence channel on the test cartridge channel, for storage or off-site analysis.

The methods, systems and apparatus described herein may also be adaptable as a platform for detection and evaluation of other airborne/breath-borne substances, including controlled substances, and breath-borne indicators of various disease states. In this regard, this disclosure also relates to a method for evaluating a substance (or analyte), more generally, in human breath, the method involving determining an amount of a substance captured from a breath sample obtained from a subject, comparing the determined amount of the substance captured from the breath sample to a threshold level for the substance in breath, and indicating whether or not the determined amount of the substance captured from the breath sample exceeds the threshold. The substance may be associated with a human disease condition, and the threshold may be correlated with a baseline maximum level of the substance in human breath for a subject not suffering from the disease condition. The substance may be associated with a human disease condition such as stomach cancer, lung cancer, heart failure, kidney failure or diabetes, for example. Substances associated with various human disease conditions are described, for example, in *Biomarkers in exhaled breath condensate: a review of collection, processing and analysis*, N M Grob, M Aytekin, and R A Dweik, J Breath Res. 2008 September; 2(3): 037004, which is incorporated by reference herein for its disclosure relating to breath-borne substances associated with various human disease conditions. As noted above, in one example, a test for a plurality of different disease conditions from a single breath sample is contemplated. A device for implementing such a test might have a plurality of channels configured and/or designed for capture of a plurality of different breath-borne substances, which could then be processed in a manner as described herein.

In view of the above, it will be understood that methods, systems, and apparatuses for measuring or detecting breath-borne biomarkers from an exhaled breath sample are disclosed herein. In various implementations, the disclosed methods may include sample capture systems designed to collect aerosol droplets originating from the deep lung, and may then use immunoassay-based detection systems and methods to analyze such samples. Among the potential benefits of such methods and systems are enhanced sensitivity and device scalability. The disclosed methods and systems may be implemented in variety of ways as contemplated by this disclosure.

This disclosure also relates to systems and apparatus for measuring tetrahydrocannabinol (THC) level from a breath sample in accordance with the methods herein described. Such a system, and variants thereof, is discussed in more detail below.

Figure 8:
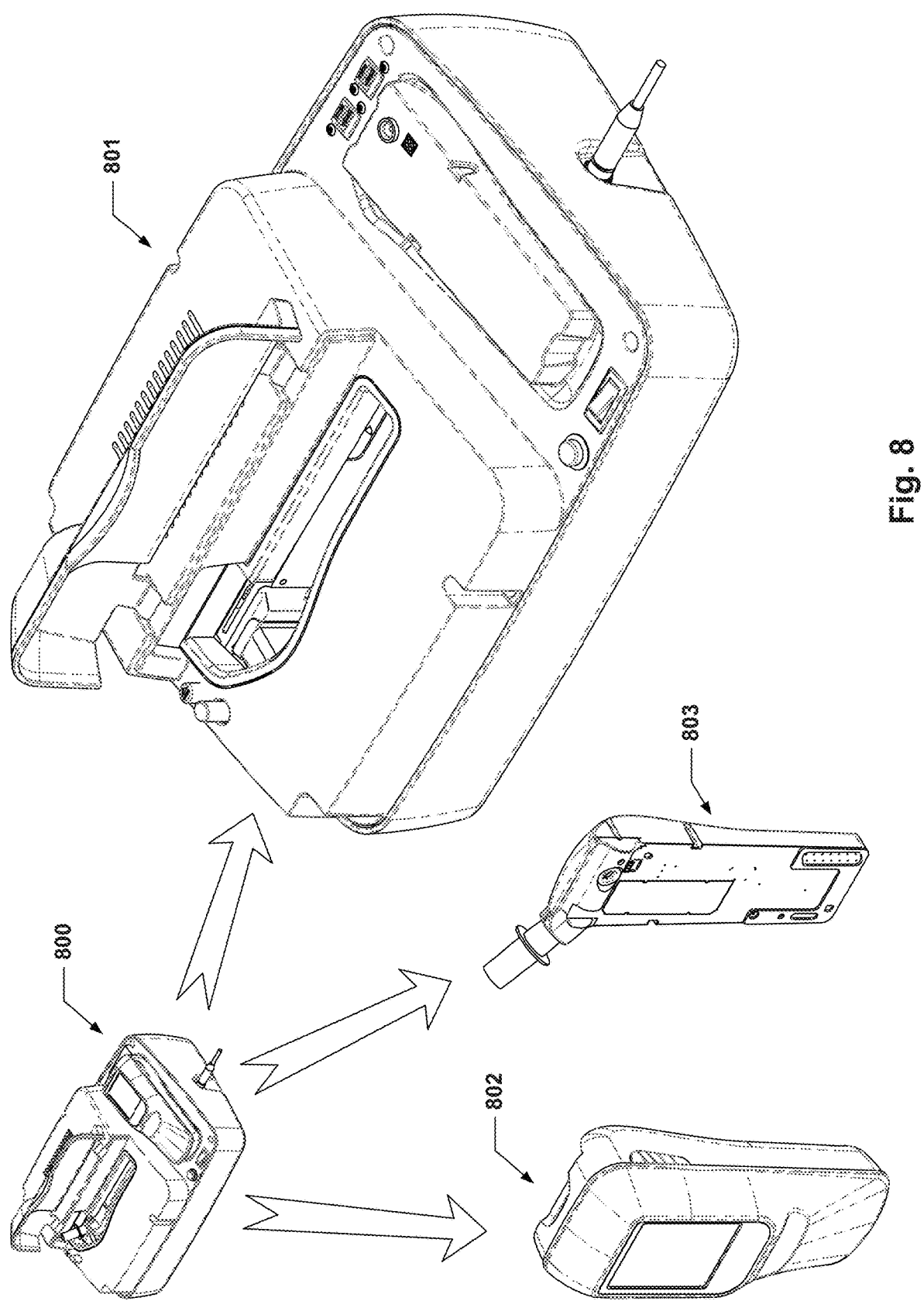
FIG. 8 depicts an example breath sampling and analysis system.

FIG. 8 depicts an example breath sampling and analysis system. In the depicted example system 800, the system includes three main components—a base station 801, a handheld unit 802, and a cartridge, or disposable, 803. This example breath sampling and analysis system will be used herein to discuss various aspects of breath sampling and analysis systems according to the present disclosure in general, but it will be understood that other implementations of breath sampling and analysis systems according to the concepts disclosed herein may take other forms. For example, while the example system features the base station 801, the handheld unit 802, and the cartridge 803, other systems may combine or otherwise distribute the functionality of one or more of these elements into other components. For example, the handheld unit 802 may be connected with the cartridge 803 in order to collect a breath sample, as the handheld unit 802 is small, relatively lightweight, and easily wielded by whomever is obtaining the breath sample. The cartridge 803 may then be removed from the handheld unit 802 and both elements separately docked in the base station 801 in order to perform the analysis and report out the results. However, it will be understood that, for example, the base station 801 and the handheld unit 802 could be combined into one device, although the resulting apparatus would not be as portable as the handheld unit 802 and obtaining a breath sample using such an apparatus would likely require extra effort on behalf of the subject. Similarly, the functionality of the cartridge 803 could be combined with the handheld unit 802, although doing so may complicate cleaning and re-use of the handheld unit 802.

While the breath sampling and analysis system 800 discussed herein as an example is designed for use as a THC and alcohol detection system, it will be understood that similar systems, with appropriate modification, may be used to detect one or more additional or alternative analytes, as noted earlier. For example, the breath sampling and analysis system architecture discussed herein may also be used generally to capture breath samples that may then be analyzed to determine amounts of other controlled substances (or byproducts of using such controlled substances), symptomatic byproducts or biomarkers of particular medical conditions such as diabetes (in which high levels of acetone or other ketones may be present in a person's breath), or indicators of particular physiological states such as ketosis (in which acetone levels may be elevated as well). In general, the systems and architecture provided herein allow for breath samples containing potentially very small volumetric densities or concentrations of analytes, e.g., with magnitudes on the picogram-per-liter scale, to be captured and concentrated in reaction volumes on the order of microliters or tens of microliters within microfluidic circuits/plates. Once captured, such volumes may be analyzed to determine the presence and quantity of a particular analyte of interest, e.g., according to any of the assay techniques discussed earlier. As discussed, while most of the discussion herein is with reference to an example such system for detecting THC, the principles set forth herein, and the overall architecture, may be applicable to systems for detecting a variety of different analytes, and the concepts laid out herein should not be viewed as being solely directed to THC detection systems and methods.

Figure 9:
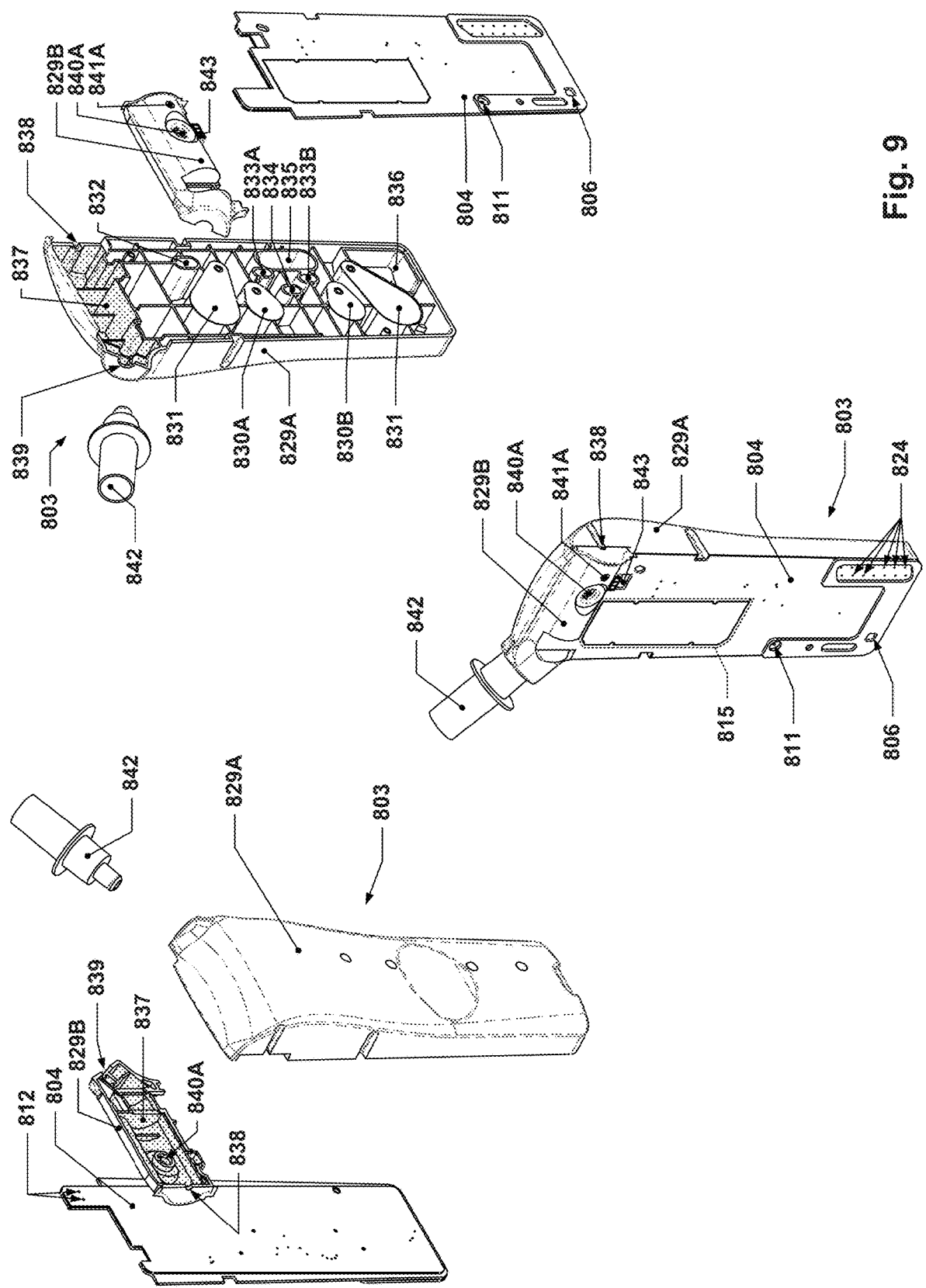
FIG. 9 depicts an example disposable element, or cartridge, of the example breath sampling and analysis system of FIG. 8.

FIG. 9 depicts an example disposable element, or cartridge, of the example breath sampling and analysis system of FIG. 8. Three views of the cartridge are shown; isometric exploded views of the cartridge from the front (right) and back (left) and an isometric assembled view of the front (middle). The cartridge 803 may include a housing 829, here shown as housing 829A and housing 829B, the walls of which may define a plenum 837 (the shaded volume). The plenum 837 may be a sealed volume that has an inlet 839, a flow restrictor 838, a pressure port 840A, and, in some implementations, a BAC (blood alcohol content) port 841A.

The cartridge 803 may also include a microfluidic plate 804 (which may also be referred to herein as a μfluidic plate) that houses a network of microfluidic passages, pneumatic passages, pumps, valves, vents, and so forth that may provide one or more sample collection, preparation, and/or analysis functions. The microfluidic plate 804 may, for example, include one or more sample ports 812 in fluidic communication with the plenum 837. In some implementations, the microfluidic plate 804 may include a separate sub-module 815 that may be tailored to particular different types of analyses—thus, a variety of different sub-modules 815 may be provided and a suitable sub-module 815 selected for assembly with the underlying microfluidic plate 804, thus customizing the microfluidic plate 804 to a particular type of analysis. Such functionality will be explained further with reference to FIG. 11. It will be understood that some implementations of the microfluidic plate 804 may not have any such sub-module; in such implementations, the entire microfluidic plate 804 may be designed to detect and measure the amount of a specific analyte; entirely different microfluidic plates 804 would be used for detecting and/or measuring other analytes. Different sub-modules 815 may, for example, have reaction channels with reagents specific to different types of analytes immobilized on them. Such reagents may, for example, include antibodies or reagents specific to different types of analytes, but may also, for example, include non-immuno reagents. For example, e.g., an immune-based THC sub-module may have THC-specific antibodies or THC antigens immobilized on the reaction channel surfaces, whereas a sub-module for detecting acetone in breath, such as may be used in diagnosing some types of diabetes, may have acetone-specific reagents immobilized on the reaction channel surfaces. Thus, the microfluidic plate may be easily customized to allow it to be tailored to facilitate detecting any one of a variety of different types of analytes by installing an appropriate sub-module 815.

The sub-module may, for example, include a flat plate containing multiple, generally equal-length reaction channels. In various implementations, there may be 3 or 4 such reaction channels, although alternate implementations may have more or fewer reaction channels. In implementations with 3 reaction channels, one reaction channel may be reserved for collecting breath sample, and the other two may be reserved for containing control amounts of the analyte for which the sub-module is tailored to be used. In implementations with 4 reaction channels, the extra channel may also be reserved for collecting breath sample, but with the intention of simply preserving the breath sample for later analysis or for evidentiary purposes. In systems in which control amounts are not used, the sub-module may only have a single reaction channel or multiple reaction channels that are only reserved for sample collection. In other implementations, a sub-module may have additional reaction channels beyond four, e.g., additional reaction channels for additional control amounts of analyte, or additional reaction channels for sample collection.

The sub-module may generally be a flat plate having a surface that is intended to be bonded with the larger microfluidic plate, e.g., with a pressure-sensitive adhesive. In some implementations, the pressure-sensitive adhesive may be a layer that is adhered to the sub-module, thus providing the surface with an adhesive character that allows the sub-module to be adhered to the larger microfluidic plate. In some implementations, the reaction channels may be sealed entirely within the sub-module, e.g., such that no part of the reaction channel is exposed except for the very ends of the reaction channels. In such implementations, the ends of the reaction channels may terminate at inlet and outlet ports that penetrate through to the surface that is intended to be bonded to the microfluidic cartridge. Such inlet and outlet ports may be positioned in the sub-module such that they align with corresponding ports in the microfluidic plate when the sub-module is installed in the microfluidic plate. In other implementations, the reaction channels may simply be open trenches or troughs etched or cut into the surface of the sub-module that is intended to be bonded to the microfluidic plate. In such implementations, the reaction channels may each span between two locations that align with inlet and outlet ports of the microfluidic plate. When such a sub-module is installed, the surface of the microfluidic plate to which the sub-module is adhered may cover/seal the reaction channel trench or trough such that only the ends of the reaction channel may be collocated with the reaction channel inlet and outlet ports of the microfluidic plate.

It will be understood that the above-described structure of the sub-modules may be similar between sub-modules tailored for a plurality of different analyte analyses, but may differ with respect to what antibodies, antigens, and or other binding agents are immobilized on the surfaces of the reaction channels. Furthermore, sub-modules may optionally be loaded with different types and quantities of control analytes; such loading may occur prior to installation of the sub-module on the microfluidic plate, or may occur after such installation. Such loading may include, for example, flowing a known quantity of vapor-phase analyte into the control reaction channels and allowing the analyte to then adsorb onto the reaction channel walls.

For example, a non-limiting list of example sub-module customized analysis chemistries for detecting analytes that may be indicative of a variety of potential physiological conditions or infectious diseases may include:

| Target analyte | Physiological condition to be detected/ diagnosed | Immobilized antigen or antibody on surfaces of reaction channels in sub-module |
|---|---|---|
| THC | Recent THC usage | THC-specific antibody or THC antigen |
| Acetone | Diabetes | Acetone-specific antibody, acetone antigen, or acetone reagent |
| Nitrites | Chronic Obstructive Pulmonary Disease (COPD) | Nitrite-specific antibody or nitrite antigen |
| 8-Isoprotane | Cystic Fibrosis | 8-isoprotane-specific antibody or 8-isoprotane antigen |
| Chromium | Lung cancer | Chromium-specific antibody or chromium antigen |
| Ammonia | Kidney failure | Ammonia-specific antibody or ammonia antigen |
| Glucose | Diabetes and related complications | May utilize enzymatic assay approach instead of immunoassay approach. For example, a fluorescence-based or chemiluminescence-based enzymatic assay to detect glucose |

A further non-limiting list of example biomarkers that may be detected and measured in accordance with this disclosure, as further described below, and their associated physiological conditions and detection techniques is provided in the table of FIG. 10, which summarizes various biomarkers, their potential applicability, and options for detection methods. The first column lists various biomarkers. The second column providing a non-exclusive indication of potential physiological conditions and/or contexts in which the presence, absence, concentration, or quantity of such biomarkers in a breath sample may provide diagnostic value. The third and fourth columns indicate categorizations of such biomarkers, e.g., for what they may help detect and how such biomarkers may manifest, e.g., as small molecules, ions, proteins, etc. The fifth and sixth columns, under "Assay Method(s)—Chemistry Based," indicate non-limiting lists of different suitable chemistry-based assay types (fifth column) that may be used to generate a signal, e.g., fluorescence, luminescence, etc., that may then be quantified using one of the readout methods listed in the sixth column, for example. Columns 7 and 8 provide similar information for electrical-based assays.

The cartridge 803 may also include various liquids for use during a breath sample analysis. For example, the cartridge 803 includes two buffer blisters 831, a substrate blister 830A, and a substrate blister 830B. The blisters, in this example, are blister packs, e.g., compressible bladders that house liquid, although other types of liquid storage may be used in other implementations. In addition to the buffer blisters 831 and the substrate blisters 830A/B, the cartridge 803 also provides structures that, in conjunction with the microfluidic plate 804, define a number of different reservoirs. For example, the housing 829A may include a buffer reservoir 835, substrate reservoirs 833A and 833B, a substrate mixing reservoir 834, an antibody reservoir 832, and a waste reservoir 836.

During use, the cartridge 803 may have a mouthpiece 842 inserted into the inlet 839; the subject may then breath through the mouthpiece. The exhaled breath may then travel through the plenum 837 and out through the restrictor 838. Since the restrictor 838 is of a smaller cross-sectional area than the inlet 839, a positive pressure of 1-2 psi may develop within the plenum 837 when the subject breathes into the mouthpiece 842; this positive pressure may be measured by a pressure sensor, e.g., one internal to the cartridge 803 or one that measures the pressure via the pressure port 840A, to characterize the breathing behavior of the subject. The positive pressure may cause portions of the breath sample collected to flow through the BAC port 841A, if present, and through the sample ports 812 on the microfluidic plate 804. The cartridge 803 may also include a memory device 843 that may, for example, be used to store data pertaining to a sample collected using the cartridge 803. The memory device 843 may, for example, be an encrypted data storage device or non-volatile memory that may be used to store, for example, one or more types of information collected at various times through use of the system, such as subject vital statistics (name, age, driver's license number, social security number, date of birth, photograph, fingerprint, signature, voiceprint, etc.), environmental information relating to sample collection (ambient temperature, ambient humidity, ambient barometric pressure, etc.), sample collection information (identity of person taking sample, time and date of sample collection, location of sample collection, etc.), and/or sample metrics (amount of breath sample passing through microfluidic plate, duration of breath sample collection, pressure-time history of plenum 837 during breath sample collection, and measured levels of one or more analytes).

In some implementations, the microfluidic plate 804 may have a vacuum assist port 811 that may be fluidically connected with the sample ports 812 via one or more sample collection passages within the microfluidic plate 804. During sample collection, negative pressure may be applied to the vacuum assist port 811 in order to decrease the pressure in the sample collection passages and the sample ports 812, thereby increasing the pressure differential between the plenum 837 and the sample collection passages of the microfluidic plate 804 and causing an increased proportion of the breath sample to pass through the sample collection passages. This can increase the concentration of analyte that may be collected within the sample collection passages.

Fluidic communication, as the phrase is used herein, refers to a state in which two or more volumes are connected by one or more passages, orifices, or other features such that fluid may flow between them. Generally speaking, the phrase should be understood to imply that there is some form of structure providing the fluidic communication, rather than just exposure to the ambient environment. For example, two open-topped buckets positioned side-by-side in upright positions would not be considered to be in "fluidic communication" (even though fluid, e.g., gas, could conceivably waft of diffuse from one bucket to the other), whereas placing an end of a hose into each of those same two open-topped buckets would cause the buckets to be viewed as being in "fluidic communication" with each other since there is structure that serves to provide a fluid flow passage between them.

Fluidically interposed, as the phrase is used herein, refers to a condition where fluid flowing from a first component to a second component generally flows through a third component before reaching the second component; the third component would be described as being fluidically interposed between the first and second components. For example, a furnace may be connected with a heating register by a duct; the duct would be described as being fluidically interposed between the furnace and the heating register since the heated air from the furnace would generally flow through the duct before reaching the heating register. In systems using gas as the fluid, there may be some leak paths or other flow paths that allow for the fluid to flow from one component to another without flowing through a component that is fluidically interposed between those two components, but it should be understood that if the majority of the fluid that flows between those two components passes through a third component before reaching the latter of the two components, then that third component may still be deemed to be "fluidically interposed" between the two components. It will be further understood that a component that is fluidically interposed between two other components does not necessarily mean that the component is physically located in between the other two components. For example, components A, B, and C may be physically arranged in a line in that order, with B physically located between A and C. However, hoses may connect A to C and then C to B such that C is fluidically interposed between A and B.

The microfluidic plate 804 may also include an optical measurement site 806 that is optically transparent (at least, transparent in the portion of the microfluidic plate interposed between the optical measurement site and the device used to take the optical measurements) to allow optical measurements to be taken of samples that are contained within the optical measurement site 806. The microfluidic plate 804 may also include a plurality of pneumatic control ports 814 that may be interfaced with corresponding pneumatic sources in order to actuate valves within the microfluidic plate 804.

FIG. 11 depicts an example microfluidic plate that may be used with the example breath sampling and analysis system of FIG. 8. As shown in FIG. 11, the microfluidic plate 804 is a bonded stack of multiple layers of material—some material which is rigid, e.g., acrylic, and some material which is flexible, e.g., an elastomer. For reference, the microfluidic plate 804 of FIG. 11 also includes indications of the locations of reservoirs and blisters that are housed within the housing 829A, e.g., the buffer blisters 831, the substrate blisters 830A/B, the substrate reservoirs 833A/B, the substrate mixing reservoir 834, the waste reservoir 836, the buffer reservoir 835, and the antibody reservoir 832. Such reservoir and blister locations are indicated using broken/dashed lines and the regions occupied by such structures are shaded for enhanced clarity.

The microfluidic plate 804 includes several reaction channels 805; such reaction channels 805 may include, for example, two reaction channels 805' and 805A that may be used to collect a breath sample from a subject, e.g., breath sample may be flowed into sample ports 812 and through such reaction channels 805' and 805A and any analyte therein may thus be provided an opportunity to adhere or adsorb on the walls of such reaction channels, thereby capturing the analyte for later analysis. In this particular example, the reaction channel 805' is intended to capture a sample for later laboratory analysis, e.g., for analysis in a criminal forensics laboratory (or for preservation of evidence in a criminal proceeding), and the reaction channel 805A is intended to capture a sample for immediate or near-immediate analysis. There are also, in this example, two additional reaction channels 805B and 805C, that may be used to house, for example, control amounts of the analyte being detected and measured. Since the reaction channels 805B and 805C in this example are used to house control amounts of the analyte in question, the reaction channels 805B and 805C are not configured to have breath sample flowed through them during sample collection.

As noted earlier, the microfluidic plate 804 may include a sub-module 815 that may include the reaction channels 805. The sub-module 815 is also shown removed, and the reaction channels 805' and 805A/B/C may be clearly seen. Also visible in the microfluidic plate 804 are the vacuum assist port 811, the optical measurement site 806, and a plurality of vents 813 (each of which may be sealable by way of a corresponding valve).

The microfluidic plate 804 may have a number of valves and pumps located at different points within the microfluidic plate 804; such valves and pumps may be controlled, for example, by pneumatic passages 825 (only one is indicated, but, generally speaking, the pneumatic passages extend from the pneumatic control ports 814; fourteen such ports are shown in this example, but it will be recognized that different numbers of pneumatic control ports 814 may be used in other implementations—in this Figure, the pneumatic control passages are represented by dotted lines or dotted channels/double lines). The microfluidic plate 804, in addition to containing the reaction channels 805, may also include various fluidic flow passages 826 (only one is specifically indicated) that may be used to route or control the flow of liquids (and, in some instances, also air, e.g., during purge/cleaning/washing operations); such fluidic flow passages are represented in FIG. 11 by channels with solid lines. The operation of such valves and pumps is discussed more fully later in this disclosure with reference to FIG. 12.

For example, the microfluidic plate 804 may include isolation valves 819, which may be actuated to seal or unseal the reaction channels 805' and 805A, e.g., during breath sample collection, the isolation valves 819 may be actuated to an open state, thereby allowing fluid to flow from the sample ports 812, through the reaction channels 805' and 805A, and into a pneumatic passage fluidically connected with the vacuum assist port 811. Once breath collection is complete, the isolation valves 819 may be allowed to close (or actuated so as to cause them to close), thereby sealing the collected breath samples within the reaction channels 805' and 805A. It will be understood that such "sealing" of the reaction samples may, after positive pressure is removed from the isolation valves 819 (such as when the handheld unit is deactivated or the cartridge 803 removed from the handheld unit 802), no longer be present due to the construction of some microfluidic diaphragm valves. While isolation valves 819 are depicted as diaphragm valves in this example, other suitable mechanisms for sealing off the reaction channels 805' and 805A may be used in place of the depicted valves.

The microfluidic plate 804 may, in addition to the isolation valves 819, also include a number of other valves, e.g., buffer valves 816A/B/C, antibody valves 817A/B/C, substrate valves 818A/B/C, reaction channel valves 820A/B/C, and optical site valves 821A/B/C.

As noted above, the microfluidic plate 804 may also include a number of pumps that may be actuated to move liquids between various locations within the microfluidic plate 804. For example, the microfluidic plate 804 may include one or more optical measurement site pumps 807, one or more reaction channel pumps 808A/B/C, one or more substrate pumps 809A/B, and one or more antibody pumps 810. In the depicted microfluidic plate 804, each included pump may generally include three elements—two valves and a chamber fluidically interposed between them. The operation of such a pump is discussed more fully later in this disclosure with reference to FIG. 12.

The implementation of FIG. 11 depicts only one example of a microfluidic plate that may be used to perform the microfluidic analysis protocols discussed elsewhere herein. Other examples are discussed later herein, although microfluidic plates falling within the scope of this disclosure are not limited to only the depicted examples.

Figure 12:
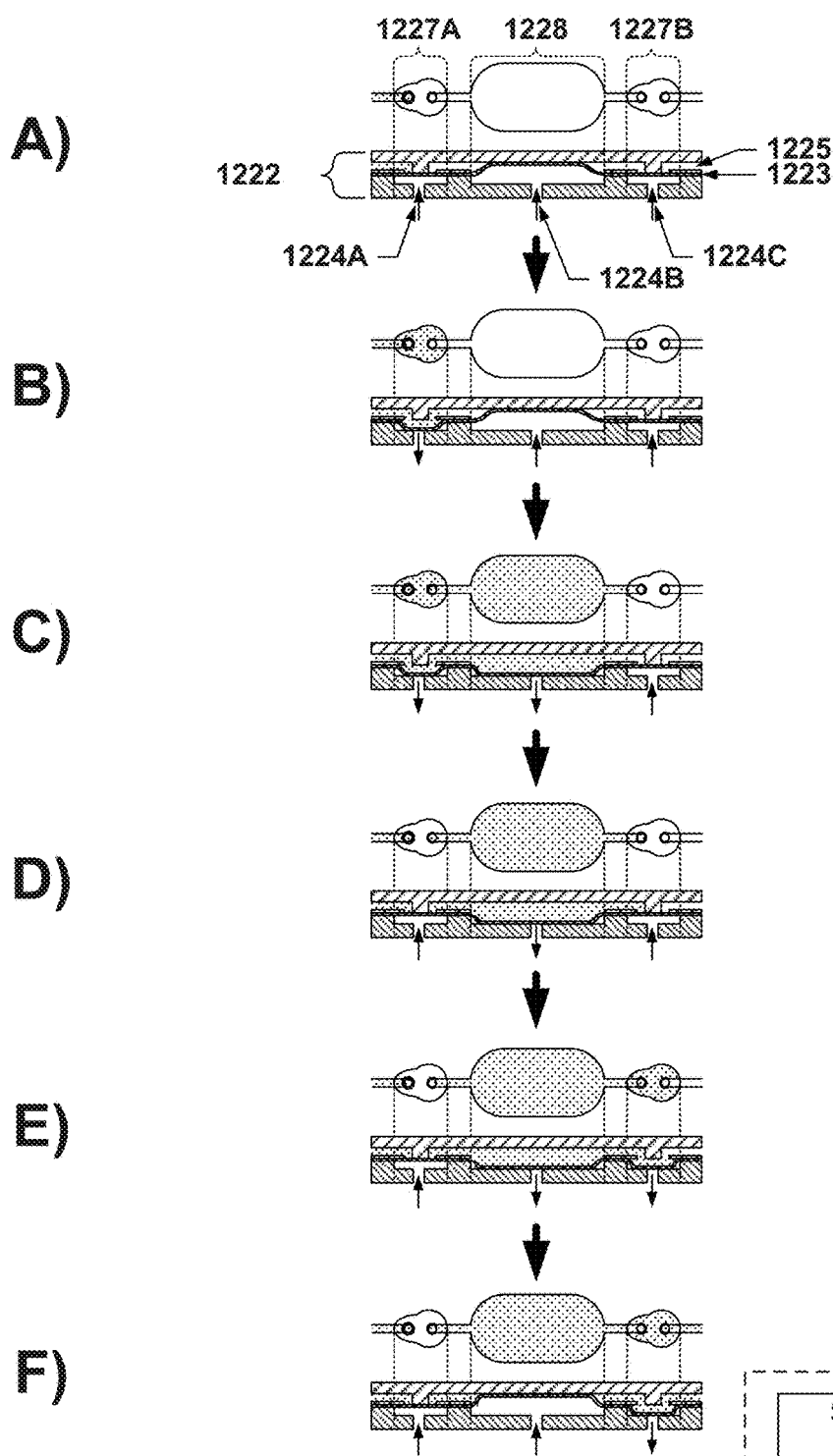

FIG. 12 depicts schematic views of an example microfluidic pump similar to microfluidic pumps that are depicted in the example microfluidic plates of FIGS. 11, 20, 21, and 22. In FIG. 12, a microfluidic pump is shown in various stages of operation (stages A-F); a plan view (above) and a side cross-section view (below) of the pump is provided for each stage. The microfluidic pump includes a chamber 1228 that is fluidically interposed between two valves 1227 and 1227B; these structures are provided in a microfluidic layer stack 1222. The microfluidic layer stack 1222 may include a number of discrete layers, although in this example, these layers are not individually shown except for membrane 1223, which may be made of an elastomeric material. In the depicted microfluidic layer stack 1222, a fluid channel 1225 passes through the portion of the microfluidic layer stack 1222 located above the membrane 1223, and pneumatic ports or features 1224A/B/C are located in the portion of the microfluidic layer stack 1222 located below the membrane 1223. For illustration purposes, a fluid being pumped through the pump in FIG. 12 is indicated through use of shading.

In state (A), the pump has not yet initiated a stroke cycle; all three pneumatic ports 1224A/B/C are pressurized. This causes the valves 1227A and 1227B to seal shut since the positive pressure received via pneumatic ports 1224A and 1224C pushes the membrane 1223 in the valve regions flat against the upper portion of the microfluidic layer stack 1222, thereby sealing off the fluid channel 1225 in those regions. The positive pressure received via the pneumatic port 1224B, in the interim, causes the membrane to distend into the chamber 1228, reducing the free volume within the chamber 1228. In state (B), the valve 1227A has been opened by providing a negative pressure to the membrane 1223 via the pneumatic port 1224A; this causes the membrane 1223 in the region of the valve 1227A to distend downwards (with regard to the figure orientation), thereby opening a fluid flow path into the chamber 1228. In state (C), the valve 1227A is kept open, and a negative pressure is applied to pneumatic port 1224B, thereby causing the membrane in the chamber 1228 to distend downwards, which, in turn, causes fluid to be sucked into the chamber 1228 via the valve 1227A. In state (D), positive pressure is again applied to pneumatic port 1224A, thereby causing the membrane 1223 in the region of the valve 1227A to flatten against the upper portion of the microfluidic layer stack 1222, thereby sealing the chamber 1228 with a volume of fluid trapped inside. In state (E), negative pressure is applied to pneumatic port 1224C, thereby causing the membrane 1223 to distend downwards and open a fluid flow path from the chamber 1228 through the valve 1227B. In state (F), the valve 1227B is kept open and positive pressure is then applied to the pneumatic port 1224B to cause the membrane 1223 in the region of the chamber to distend upwards, thereby forcing the fluid within the chamber to flow out through the valve 1227B. These operations may then be repeated as desired to deliver a desired amount of fluid volume to a location downstream of the pump. It will be understood that such pumps may be operated in reverse to cause fluid to flow in the opposite direction, and that such pumps may be referred to herein as "diaphragm pumps" or the like. In FIG. 11 and other microfluidic plate Figures herein, it is to be understood that the callouts indicating pumps generally only point to the "chamber" portion of the pumps; the valves that are included in such pumps may be determined by locating the valves immediately upstream and downstream of such chambers (these valves are not separately called out in FIG. 11).

Figure 13B:
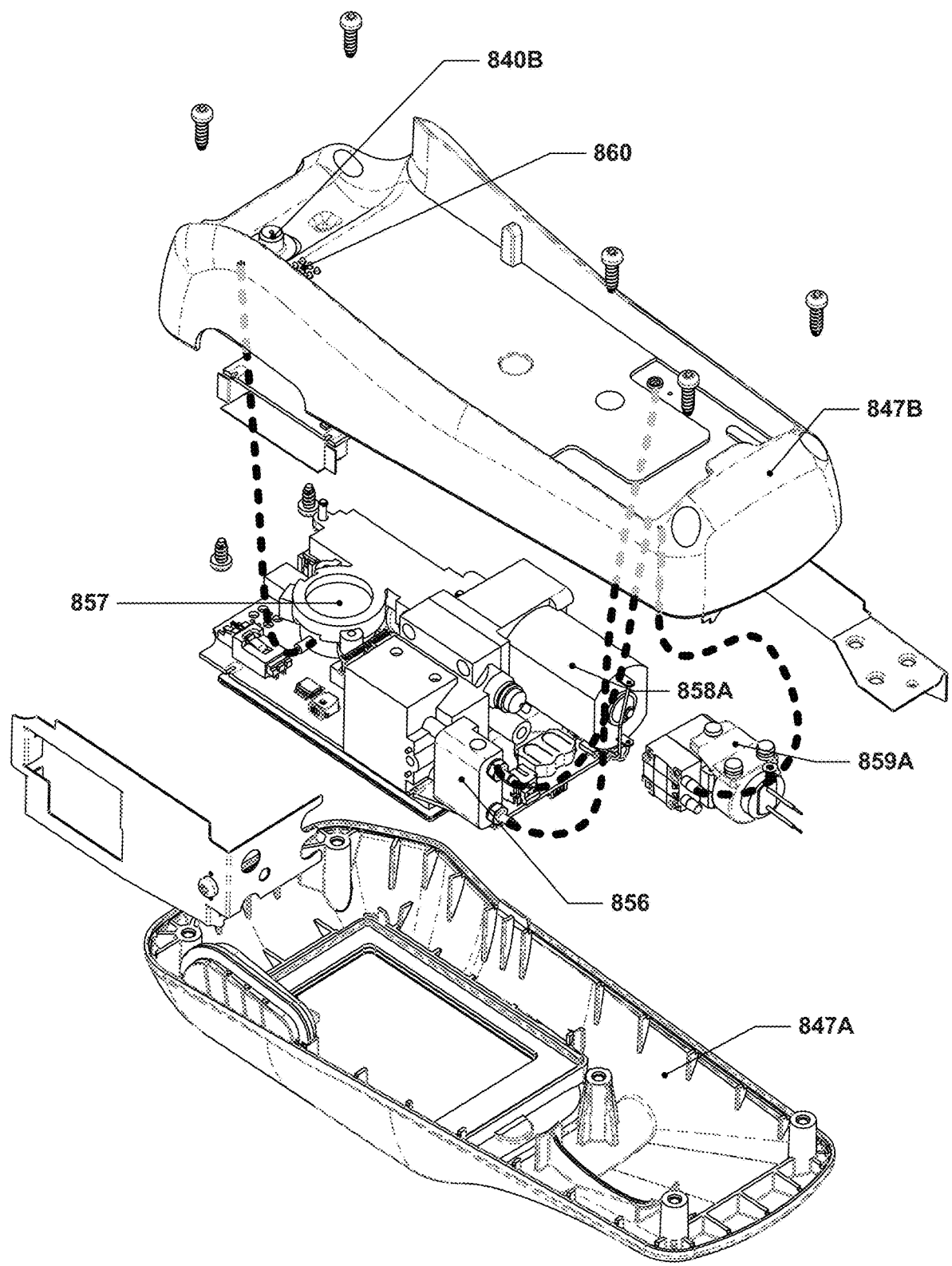

FIGS. 13A and 13B depict exploded views of an example handheld unit of the example breath sampling and analysis system of FIG. 8. Three views of the handheld unit 802 are shown in FIG. 13A; isometric exploded views of the handheld unit from the front (left) and back (right) and an isometric assembled view of the front (upper left). The handheld unit 802 may be sized to comfortably be held in a person's hand, e.g., in a one-handed grip, to facilitate use as a portable sampling device that may be maintained in the grip of the operator while the subject exhales into the mouthpiece 842. The handheld unit 802 may include, for example, a handheld housing 847, e.g., handheld housings 847A and 847B, which house a variety of components. The handheld unit 802 may further include a controller 852A, e.g., one or more processors, memory, and other electronic components, that may be configured to control one or more components of the handheld unit 802 to provide various functionalities. The controller 852A may, for example, be operatively and/or communicatively connected with a variety of user interface elements, e.g., a display 848 (which may, for example, be a touch-sensitive display to allow for user inputs to be received and communicated to the controller 852A), an annunciator (speaker or other audio output device) 850, and/or an indicator 849 (e.g., one or more LEDs or other visual indicators), to facilitate communications of system status, sample collection status, test results, and so forth.

The controller 852A may also be communicatively connected with a variety of sensors that may be active at least during sample detection. For example, the controller 852A may be communicatively connected with a pressure sensor 853, a humidity sensor 855, a BAC sensor 857, and a flow sensor 856. The pressure sensor 853 may be configured to measure pressure within the plenum 837 of the cartridge 803 when the cartridge 803 is mounted to the handheld unit 802; the controller 852A may monitor data from the pressure sensor 853 to determine, for example, what the ambient pressure conditions are prior to (and/or after) the collection of a breath sample from a subject, as well as what the pressure conditions are within the plenum 837 of the cartridge 803 during breath sample collection. To facilitate such measurements, the handheld housing 847B may include a pressure port 840B that may seal to the pressure port 840A in the cartridge 803; the pressure sensor 853 may be configured to measure pressure in the plenum 837 via the pressure ports 840A and 840B when the cartridge 803 is installed and the two pressure ports 840A and 840B are sealed together. As the pressures being measured may be quite low, e.g., 1-2 psi, based on the average pressure that human lungs typically are capable of generating, the seal interface between the pressure ports 840A and 840B may be a relatively light seal, e.g., a lightly compressed elastomeric seal.

In implementations with a BAC sensor 857, the BAC sensor 857 may be used to measure an amount of alcohol present in the breath sample. In such implementations, the BAC sensor 857 may have an air inlet port or ports that are fluidically connected with a BAC port 841B on the handheld housing 847B which interfaces with the BAC port 841A on the cartridge 803, thereby allowing a portion of the breath sample flowing through the plenum 837 to be siphoned off and passed through the BAC sensor 857, e.g., a PAS Systems PAS 038-201, for example. The BAC sensor 857 may, for example, be a fuel cell sensor equipped with a solenoid pump and a resistive heater, although other types of BAC sensor may be used as well.

The handheld unit 802 may also include one or more pumps, e.g., a vacuum pump 858A (for example, a SENSIDYNE A120INSN) and a pressurization pump 859A, which may be used to actuate valves within the microfluidic plate when the cartridge 803 is installed in the handheld unit 802. The vacuum pump 858A may also be used to provide vacuum/negative pressure to the vacuum assist port 811 on the microfluidic plate 804 when the cartridge 803 is installed in the handheld unit 802 and while a breath sample is being obtained. It will be understood that such pumping functionality may be consolidated into a single pump or spread across multiple pumps. For example, a single pump may have an outlet that produces positively pressurized air and a corresponding inlet that generates negatively pressurized air—through the use of appropriate valves (not shown) in the handheld unit 802, the positively pressurized air and the negative pressurized air may be selectively routed to the various ports on the microfluidic plate 804 in order to selectively activate/deactivate features within the microfluidic plate 804 such as the vacuum assist and the isolation valves, e.g., isolation valves 819. In implementations such as the one depicted, separate pumps may be used to provide the vacuum assist (negative pressure) and valve actuation (positive and/or negative pressure). In yet further implementations, one pump may be supplied to provide negative pressure for the vacuum assist feature, a second pump may be supplied to provide negative pressure for valve actuation, and a third pump may be supplied to provide positive pressure for valve actuation. There may also be one or more additional pumps, as needed, for functionality unrelated to sample flow through the microfluidic plate 804. For example, the BAC sensor 857, if present, may incorporate a vacuum pump to assist with drawing breath sample through the BAC sensor 857.

As noted above, the handheld unit 802 may also incorporate a flow sensor 856, which may be fluidically interposed between the vacuum assist port 811 and the vacuum pump 858A (or whatever pump is used to provide vacuum assist functionality). In implementations that may not include vacuum assist functionality (and the attendant hardware), the flow sensor 856 may be configured to receive fluid (breath sample air) that flows through the microfluidic plate during breath sample collection; the flow sensor 856 may measure the amount of such fluid prior to the fluid being released back into the ambient environment. The flow sensor 856 may, for example, be a mass flow sensor or other similar sensor that may quantify the amount of breath sample that is diverted through the microfluidic plate 804 during breath sample collection. The data from the flow sensor 856 may, for example, be monitored by the controller 852A and when the data indicates that a predetermined amount of air (breath sample) has passed through the flow sensor 856 subsequent to the start of breath sample collection, then the controller 852A may cause one or more changes in operational status of the handheld unit 802. For example, the controller 852A may cause the vacuum pump 858A to cease applying negative pressure to the vacuum assist port 811 in the cartridge 803 and may concurrently cause the pressure pump 859A to apply positive pressure to the pneumatic control port(s) leading to the isolation valves 819, thereby causing the isolation valves to seal within the reaction channels 805' and 805A whatever breath constituents may have adsorbed onto the walls thereof while the breath sample was flowing therethrough. The controller 852A may also monitor the flow sensor 856 to determine what percentage of the predetermined amount of air has already passed through the microfluidic plate 804 and to provide progress indicators to the operator/subject, e.g., by providing visual and/or audio output indicative thereof. For example, in the example handheld unit 802, the indicator 849 may include a plurality of different light-emitting diodes (LEDs) that may be illuminated in different quantities and/or colors to indicate progress.

The handheld unit 802 may also include a communications interface 860 that may be configured to communicate electrical signals to the memory device 843 on the cartridge 803. The communications interface 860 may also be configured to communicate with the base station 801 when the handheld unit is docked with the base station 801, and may also include charging ports that may be used to electrically connect a battery 851A of the handheld unit 802 with a charger. The battery 851A may, for example, provide a portable power source for the handheld unit 802.

Figure 14:
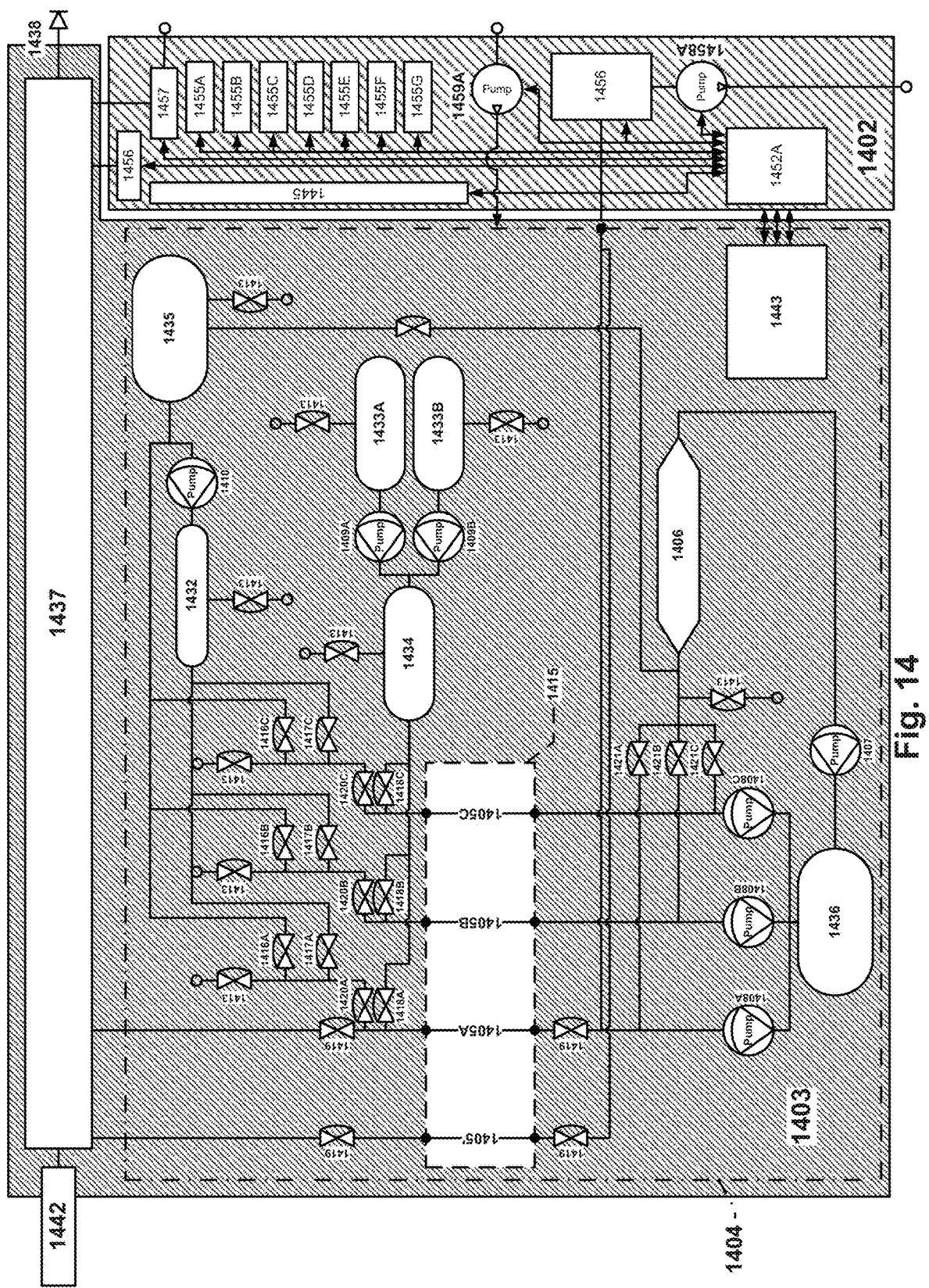
FIG. 14 is a schematic of an example disposable, or cartridge, and an example handheld unit.

FIG. 14 is a schematic of an example disposable, or cartridge, and an example handheld unit. In FIG. 14, a cartridge 1403 is docked to a handheld unit 1402. The cartridge 1403 includes a plenum 1437 that is fluidically connected with a mouthpiece 1442 and reaction channels 1405' and 1405A. The plenum 1437 is also fluidically connected, when the cartridge 1403 is installed in the handheld unit 1402, with a pressure sensor 1453 and a BAC sensor 1457. The cartridge 1403 may also have a microfluidic plate 1404 that includes a vacuum assist port that is fluidically interposed between a vacuum pump 1458A/flow sensor 1456 and the reaction channels 1405' and 1405A when the cartridge 1403 is installed in the handheld unit 1402. The microfluidic plate 1404 may also include a plurality of pressure control ports (not shown) that may interface with pressure pump 1459A.

The handheld unit 1402 may also include a controller 1452A that is communicatively connected with the pressure sensor 1453, the BAC sensor 1457, the flow sensor 1456, the pressurization pump 1459A, and the vacuum pump 1458A, as well as memory device 1443 on the cartridge 1403.

The microfluidic plate 1404 of the cartridge 1403 may optionally include a separate sub-module 1415 that includes the reaction channels 1405' and 1405A/B/C (in implementations without the sub-module 1415, such reaction channels may be provided directly in the microfluidic plate 1404). It is to be assumed that, unless otherwise indicated, the valves shown in FIG. 14 have a default state of "closed" or "sealed," but during sample collection, the isolation valves 1419 may be actuated to an "open" state, e.g., by applying negative pressure to a membrane at locations corresponding to the isolation valves 1419 within the microfluidic plate 1404 (see FIG. 12, for example). In conjunction with opening the isolation valves 1419, the vacuum pump 1458A may be operated to apply a negative pressure to the reaction channels 1405' and 1405A, thereby increasing the pressure differential between the reaction channels 1405' and 1405A and the plenum 1437. This causes a disproportionate amount of exhaled breath to be drawn into the reaction channels 1405' and 1405A (disproportionate in terms of cross-sectional area of the sample ports 1412 as compared with the cross-sectional areas of other ports or openings fluidically connected with the plenum 1437 through which the exhaled breath may pass).

The increased amount of breath sample that is diverted through the reaction channels 1405' and 1405A by virtue of the vacuum assist may allow for more breath constituents to be adsorbed (collected) on the walls of the reaction channels 1405' and 1405A from the same overall volume of exhaled breath as compared with systems that may not utilize a vacuum assist feature during sample collection. In the context of THC detection, the present inventors determined that a measured amount of about 1-10 picograms (pg) of THC in a breath sample of 0.5 liters was indicative of recent usage of THC, e.g., usage within the three hours prior to breath sample collection. As the amount of THC (or other analytes) to be measured is quite small compared to the amounts of "normal" breath constituents, e.g., air and/or carbon dioxide, a practically useful breath sampling system must be able to concentrate the breath constituents in a very small region while separating out the non-analyte breath constituents in order to facilitate sample collection and post-collection processing and measurement. For example, the 1-10 picogram range for THC discussed above may be approximately 1 billion times less than the amount of alcohol that may be present in the same volume of breath if the subject has recently been drinking.

There are at least two challenges that arise in collecting a breath sample for analyte detection. The first is pre-processing the breath sample to prepare it for analysis. The goal of such pre-processing is to alter or augment the analyte that is present in the breath sample so that it is in some way detectable, e.g., by binding a fluorescent or luminescent marker molecule to each molecule of analyte that is present. If there is a large volume, e.g., 0.5 liters, in which a relatively microscopic amount of analyte is present, whatever marker molecules are bound to or react with the analyte in such pre-processing must be present in sufficient quantity that the desired reaction between the analyte and the marker molecules occurs, from a statistical standpoint, for generally all analyte molecules (any analyte molecule that is "missed"

during the pre-processing operations may fail to be detected during a later detection operation, thereby producing undesirable results). In a large volume, e.g., 0.5 liters, a large quantity of such marker molecules may be needed in order to ensure that all of the analyte molecules in the volume are bound to marker molecules (this may also depend on the amount of time allowed for the marker molecules to interact with the analyte molecules—the longer the two types of molecules are allowed to coexist within the same volume, the greater the chance that all of the analyte molecules will eventually encounter, and bind with, corresponding marker molecules—this, however, may require waiting for periods of time that are logistically undesirable, e.g., multiple minutes, or even hours). Another issue that may be encountered with marker binding to the analyte is that many markers remain in liquid phase at atmospheric conditions, making it difficult to adequately distribute the marker molecules throughout a gas volume.

Even if the above issues regarding pre-processing of the analyte within a large sample volume are addressed, the issue of then detecting the analyte within a large sample volume would persist. As most markers are visual in nature, e.g., giving off visible or detectable light, either on an ongoing basis driven by a chemical reaction or in response to some external excitation, e.g., photostimulation by a particular wavelength of light, any signal produced by a microscopic amount of analyte such as the amounts discussed above may be volumetrically diluted by the overall volume of the sample. Detectors that may be needed for measuring such volumetrically dilute signals may require very large apertures and extremely sensitive detection elements—such detectors may be beyond the limit of current technology or may be prohibitively expensive.

Accordingly, the present inventors determined that flowing the desired breath sample volume through reaction channels having particular geometries and dimensional characteristics would generally cause the analytes for which measurement is sought to be adsorbed onto walls of the reaction channels, thereby becoming trapped within the reaction channel, while most of the remainder of the breath sample exited the reaction channel. By sizing the reaction channels small enough, the analyte in question may be concentrated in a very small volume or volumes compared to the overall volume of breath that is flowed through those reaction channel collection volumes during sample collection. For example, in the microfluidic plate 804, the reaction channels 805' and 805A may be sized, for example, to be 1 mm by 0.6 mm in cross-section, e.g., each having a cross-sectional area of 0.6 mm$^2$, and having a nominal length of approximately 57 mm, thus having an overall volume of ~34 mm$^3$ (or μL); such channels are designed to each have at least approximately 0.5 L of exhaled breath sample flowed through them during breath sample collection. This has the effect of concentrating the analytes (which generally adsorb onto the walls of the reaction channels 1405' and 1405A) into a volume within each reaction channel 1405' and 1405A that is ~1450 times smaller than the approximately 0.5 liter breath sample that passes through each such channel. While some analyte may pass through the reaction channels 1405' and 1405A without adsorbing onto a wall surface of those reaction channels, at least a measurable amount of the analyte may nonetheless be captured within such reaction channels. Such less-than-perfect capture efficiency may simply be ignored or assumed to be zero, in some instances, or may be accounted for statistically, e.g., by assuming that some empirically derived quantity of analyte per unit volume of sample flowed through the reaction channels 1405' and/or 1405A will be lost and adjust for such loss accordingly (such as by multiplying the measured amount of analyte determined in later steps by a scaling factor based on such a loss ratio).

By capturing analyte directly within the reaction channels 1405' and 1405A in the microfluidic plate 1404, the analyte may be contained within a very small volume that lends itself to being filled with marker molecules in liquid phase or suspended in liquid media, thereby allowing every surface of the reaction channel 1405A onto which the analyte has adsorbed to be wetted with the marker molecule solution/liquid. This helps increase the chances that adsorbed analyte will react or bind with the marker during the pre-processing of the collected sample. Subsequent optical measurement of the bound marker may be limited to detecting an optical signal in a volume of fluid less than or equal to the volume of the reaction channel 1405A. For example, an optical detector may be used to determine the signal strength from a portion of the fluid in the reaction channel, and the resulting measurement may be scaled up based on the ratio of the volume of the portion of fluid measured as compared to the volume of the reaction channel as a whole from which it was obtained.

It will be understood that accurately detecting or measuring the amount of analyte in a breath sample may be dependent on a large number of different factors, including, but not limited to, the amount of breath sample collected (which may, in turn, be dependent on the duration and flow rate of the breath sample), the capture efficiency of the reaction channels, the amount of analyte that is needed to ensure that a measurable quantity of analyte, if present, is obtained, how difficult it is for a subject to provide an adequately sized sample, and various other factors.

In particular implementations, the cartridge may be specially adapted for obtaining adequately sized breath samples within a 60 to 90 second sampling interval for an average human male. In such implementations, the reaction channels may be sized so as to each have hydraulic diameters of 0.8 mm or less, 0.75 mm or less, 0.7 mm or less, 0.65 mm or less, or 0.6 mm or less and be approximately, e.g., within ±5 mm of, 40 mm, 50 mm, 60 mm, or 70 mm in length, although longer channel lengths may also be used. Reaction channels with such hydraulic diameters may result in capture efficiencies of 30%-40% (i.e., 30% to 40% of analyte within the breath sample flowed through such a reaction channel would be adsorbed onto the channel walls) or higher in reaction channels on the order of 60 mm in length. In implementations in which 0.5 liters or more of breath sample are to be passed through each reaction channel, the subject's lung capacity may limit the flow rate achievable through the reaction channels. For example, a typical adult male may be capable of exhaling with a pressure of approximately 1-2 psi. Such a pressure may result in only a small portion of each exhalation being diverted through the reaction channel, and it may take several minutes of exhaling, e.g., 5 minutes, to flow the desired volume (e.g., 0.5 liters) of breath sample through the microfluidic plate under such conditions. If breath sample flow through the reaction channels is augmented by providing a vacuum assist feature, however, much higher flow rates through the reaction channels may be achieved. For example, applying suction from a vacuum pump, e.g., one capable of drawing 7-9 psi of vacuum, to the reaction channels may significantly reduce the time needed to flow the desired volume through each reaction channel. For example, in an implementation having a reaction channel with a 0.7 mm hydraulic diameter, the volumetric flow rate achieved by a test subject through the reaction channel may be on the order of 0.1 L per minute without such a vacuum assist, but potentially as high as 0.7 L per minute with vacuum assist.

In developing the disclosed breath sampling system, the present inventors identified various parameters based on various relationships between a large number of variables that contribute to achieving a desired mass concentration (average density) of analyte within the volume of one or more reaction channels (which will also directly correlate with a desired quantity of analyte within the volume of each reaction channel). To start with, the concentration of analyte collected may be determined according to:

$$c = \frac{m}{nd^2 l}$$

In which c=desired, final concentration of analyte in reaction channels (e.g., picograms/μL), m=total mass of analyte collected in reaction channels (e.g., picograms), n=number of reaction channels, d=hydraulic diameter of each reaction channel (e.g., millimeters), and l=length of each reaction channel (e.g., millimeters) (this assumes that the reaction channels are of equal size and length; if not, then similar analyses may be performed with suitable modification). It will be understood that the example units used in this example are for discussion purposes only, and similar techniques may be used with units from other measurement systems as well, if desired, with appropriate conversions. The target concentration of analyte collected in the reaction channels may be determined, for example, based on the parameters of the detection and measurement protocol to be used, e.g., as determined by the sensitivity of the measurement device, the optical response of the biomarkers used, the analyte being detected, and various other factors.

In order to determine how much analyte mass will be collected in the reaction channels, various factors may come into play, including, for example: what the mass concentration of analyte is in the subject's exhaled breath, what the exhaled breath flow rate is through the reaction channels, what the dimensions of the reaction channels are, the total duration of breath sample flow through the reaction channels, and the diffusion coefficient of the analyte in exhaled breath. In some instances, there may be little flexibility in these factors, e.g., the mass concentration of the analyte in the subject's exhaled breath is the parameter of which quantification is ultimately sought, and there is therefore no flexibility in changing it—it is what it is. In another example, the diffusion coefficient will be determined based on what diffusion coefficient is for the analyte in exhaled breath (or, for example, atmospheric air). In other instances, there may be ergonomic factors at play, e.g., the duration of breath sample flow may largely be governed by a desired maximum duration for the sampling process—sampling that lasts too long may be physically demanding for some test subjects, and may result in the sampling and analysis process being perceived as too time-consuming in terms of test-subject's and the tester's time. Other parameters, such as the exhaled breath flow rate through the reaction channels and the dimensions of the reaction channels, may offer more flexibility in terms of tuning the achieved collected analyte concentration in the reaction channels.

By way of further example, the analyte mass exhaled from the test subject may be quantified by:

$$m_{ex} = c_{ex} \cdot n \cdot Q \cdot t_{ex}$$

where $m_{ex}$=total mass of exhaled analyte that passes through reaction channels (e.g., picograms), $c_{ex}$=mass concentration of exhaled analyte per unit volume of exhaled breath (e.g., picograms/μL), Q=volumetric flow rate through each reaction channel (e.g., μL/s) (assumed to be equal for each reaction channel here; see discussion above for situations in which reaction channels are not dimensionally equivalent), $t_{ex}$=duration of exhaled breath(s) (e.g., seconds) (does not include inhaling). Summarized more generally, the mass of analyte that is exhaled through the reaction channels is equal to the product of the total flow rate of exhaled breath through the reaction channels times the exhalation time (to determine total volume flowed through the reaction channels) multiplied by the concentration of the analyte in the exhaled breath.

The present inventors also conceived of a dimensionless constant, referred to herein as the "Hound" number, quantified by:

$$H \propto \left(\frac{\sqrt{2Dt}}{\frac{d_1}{2}}\right)^2 + \left(\frac{\sqrt{2Dt}}{\frac{d_2}{2}}\right)^2 \cong 2 \cdot \left(\frac{\sqrt{2Dt}}{\frac{d}{2}}\right)^2$$

where D=diffusion coefficient (e.g., square millimeters/second), t=residence time for breath sample in reaction channel (e.g., seconds), $d_1$=width of each reaction channel, $d_2$=height of each reaction channel, and d=hydraulic diameter of each reaction channel (e.g., all in millimeters). The Hound number, more succinctly, may be thought of as the dimensionless ratio of the mean diffusion distance to half the width and height of the reaction channel. As a simplification, the distinct height and width variables $d_1$ and $d_2$ may be approximated using the hydraulic diameter d of the reaction channels. This simplification is propagated into the discussion below, although it will be recognized that a more exact calculation may be obtained if this simplification is avoided. However, it should also be recognized that the more exact calculation involving $d_1$ and $d_2$ may be applicable only to rectangular-cross-section reaction channels; the hydraulic diameter may therefore be a more flexible parameter to use since it may be easily determined for a wide variety of different channel cross-sections.

The total mass of analyte actually collected in the reaction channel(s) may be determined using:

$$m \propto 2K \cdot \frac{\sqrt{2Dt}}{\frac{d}{2}} \cdot m_{ex}$$

in which K=collection efficiency (dimensionless factor) relating the amount of analyte that is actually captured by each reaction channel to the total amount of analyte flowing through that reaction channel. Put more simply, the total mass of analyte actually collected in the reaction channel(s) is the product of the collection efficiency times the total mass of analyte exhaled through the reaction channel(s).

The residence time of each breath sample within each reaction channel (assuming a constant flow rate) may be determined according to:

$$t = \frac{d^2 l}{Q}$$

This relationship, in turn, may be substituted into the relationship for total mass analyte actually collected in the reaction channels set forth above to arrive at the following restated relationship for total mass analyte actually collected in the reaction channels:

$$m \propto 2K \cdot \frac{\sqrt{2D\frac{d^2 l}{Q}}}{\frac{d}{2}} \cdot m_{ex} \propto 4K \cdot \sqrt{2D\frac{l}{Q}} \cdot m_{ex}$$

The total mass of analyte actually collected in the reaction channel(s) may be rewritten to substitute out $m_{ex}$ for the relationship for the total mass of analyte exhaled set forth earlier to yield:

$$m \propto 4K \cdot \sqrt{2D\frac{l}{Q}} \cdot c_{ex} \cdot n \cdot Q \cdot t_{ex} \propto 4K \cdot \sqrt{2DlQ} \cdot n \cdot c_{ex} \cdot t_{ex}$$

The above expression may be substituted into the expression for the concentration of analyte collected set forth earlier to yield:

$$c \propto \frac{4K \cdot \sqrt{2DlQ} \cdot n \cdot c_{ex} \cdot t_{ex}}{nd^2 l} \propto \frac{4K}{d^2} \sqrt{\frac{2DQ}{l}} \cdot c_{ex} \cdot t_{ex}$$

This relationship may be further simplified using $Q_p = nQ$ (where $Q_p$ = total volumetric flow rate (e.g., µL/second) out of all of the reaction channels; in systems with vacuum assist, this flow rate may be equivalent to the flow rate through the vacuum pump) and $V_d = nd^2 l$ (where $V_d$ = total volume (e.g., µL) of the reaction channels) to yield:

$$c \propto \frac{4K}{d} \sqrt{\frac{2DQ_p}{d^2 nl}} c_{ex} t_{ex} \propto \frac{4K}{d} \sqrt{\frac{2DQ_p}{V_d}} c_{ex} t_{ex}$$

With some rearrangement of terms, the concentration of analyte actually collected in the reaction channel(s) may be thus be expressed by:

$$c \propto 8Kc_{ex} \left[ \underbrace{\left(\frac{Q_p t_{ex}}{d^2 l}\right)}_{\substack{\text{total number} \\ \text{of channel} \\ \text{passes}}} \underbrace{\left(\frac{d^2 l}{V_d}\right)}_{\substack{1 \\ \text{total} \\ \text{number} \\ \text{of channels}}} \underbrace{\left(\frac{t_{ex}}{d^2/2D}\right)}_{\substack{\text{exhale time} \\ \text{diffusion time}}} \right]^{1/2} \propto$$

$$8Kc_{ex} \left[ \frac{\text{\# of passes}}{\text{channel}} \cdot \frac{\text{Exhale time}}{\text{Diffusion time}} \right]^{1/2}$$

As can be seen, the concentration of analyte collected in the reaction channels may be generally controlled by the three terms within the square root demarcated above. The first term represents the total number of channel passes, e.g., the total number of times the volume of breath sample within each reaction channel is replaced with a new volume of breath sample. The second term represents the inverse of the total number of channels. The third term represents the exhalation time divided by the diffusion time.

In view of the above, it will be apparent that the various factors governing analyte concentration in the reaction channels may be grouped into three categories. In the first category are variables that are generally unable to be changed, e.g., variables such as $c_{ex}$ and D. For $c_{ex}$, such a variable is dependent on the subject and the level of analyte in the subject's breath. From a practical standpoint, $c_{ex}$ may be set to the lowest expected concentration of the analyte in a person's breath that may need to be detectable in order to achieve diagnostic or evidentiary requirements governing the analysis. Such $c_{ex}$ values may, for example, be determined empirically using laboratory equipment such as a mass spectrometer (i.e., performed under conditions in which all or nearly all of the analyte in a given breath sample volume may actually be captured and analyzed—conditions that are, in the present state of the art, not practical to replicate in a handheld or portable field-measurement unit). For D, the diffusion coefficient may be determined based on the composition of the specific analyte being collected and the exhaled breath. Thus, once a target analyte has been selected, the diffusion coefficient may essentially be viewed as static.

In the second category are, for example, variables that are more flexibly alterable. For example, the total volumetric flow rate $Q_p$ may, from a practical standpoint, have little in the way of flexibility in the microfluidic context if solely dependent on unassisted human breath, as the pressure differential achievable by an unaided human may only be on the order of 1-2 psi. As a result, the flow rates achievable with unaided subject breathing may have little in the way of flexibility. However, if vacuum assist is used, the total volumetric flow rate $Q_p$ may be greatly enhanced over that achievable with unaided human breath, e.g., up to 7-8 times higher (based on a theoretical maximum pressure differential of 14.7 psi (atmospheric)+2 psi (contributed by subject lung pressure) for a vacuum assist that draws a complete vacuum, as opposed to a theoretical maximum pressure differential of ~2 psi relative to atmospheric for human breath without vacuum assist). The hydraulic diameter and length, and thus the volumes, of the reaction channels may be tuned as well.

In the last category are factors like collection efficiency K, as well as potentially various constants (some of which are omitted in the above equations in the interest of simplicity, e.g., π is omitted in calculations relating hydraulic diameter to area or volume) that may act to linearly scale the analyte concentration achieved. The collection efficiency may be calculated or may be assigned a value based, for example, on empirical data. For example, for a reaction channel of a given hydraulic diameter, a known quantity of analyte may be passed through and the amount of the analyte that exits the reaction channel may be measured to determine how efficiently the reaction channel of that hydraulic diameter collected the analyte.

The present inventors identified the reaction channel dimensions and the total volumetric flow rate through the reaction channels as providing the most effective way of adjusting the concentration of analyte collected within the reaction channels for a given sampling duration. Absent external constraints, the sampling duration may, in theory, be extended for as long as is necessary in order to obtain a desired concentration of analyte. However, for a breath sampling and analysis system capable of both capturing a breath sample and then performing analysis of that breath sample in the field, it may be desirable to limit the sampling duration to 1 to 2 minutes, e.g., 60 seconds, 90 seconds, or 120 seconds, or less. Such sampling durations may be determined based on a variety of factors, e.g., operator fatigue (assuming that the operator needs to hold/support a handheld unit while a subject breathes into it), overall time necessary to obtain a breath sample and complete the analysis, operator and subject patience, and various other factors. Thus, the present inventors focused on reaction channels that would provide desired concentrations of analyte within the reaction channels for exhalation durations of approximately 60 to 90 seconds or, in some cases, 60 seconds.

As discussed earlier, $c_{ex}$ is not a tunable variable, D is set based on what the analyte being measured is, and $t_{ex}$ is, under the assumptions set for above, fixed at a value such as 60 seconds. Per the last relationship set forth in the paragraphs above, this leaves K, $Q_p$, $V_d$, d, and l as variables in which there is a realistic potential for being able to tune the analyte concentration c to a desired level. Generally speaking, reducing d and l to as low a value as possible will cause $V_d$ to shrink to an infinitesimal volume, thereby achieving the desired concentration of analyte in a vanishingly short period of time. However, $V_d$ may generally be set to a level that is largely determined by the limitations of other equipment used, e.g., by the minimum volume needed in order to obtain an optical measurement using an optical measurement device. In some implementations, this may be approximately 15 μL (based on a typical minimum sample volume needed for many commercially available optical measurement devices), although such volumes may be increased depending on the specific optical detector used, the amount of fluid dead volume that may be expected in moving the sample fluid from the reaction chamber to the optical measurement chamber, and/or any potential losses due to pumping efficiency or other factors. For example, $V_d$ of between about 15 μL and 35 μL, 15 μL, and 45 μL, 15 μL and 55 μL, 15 μL and 65 μL, 15 μL and 75 μL, and 15 μL and 85 μL are some example volumes that may be used, although increasing $V_d$ will generally increase the amount of time needed to obtain the desired analyte concentration in that $V_d$.

In view of the above, K, $Q_p$, and d (l may be factored out) represent the variables most useful for tuning c. Of these, only $Q_p$ and d are readily and easily adjusted. $Q_p$, as discussed earlier, may be easily adjusted using a vacuum assist feature, although the ability to do so is atmospherically limited, e.g., the analyte concentration may only be increased up to about 8× more than is achievable without vacuum assist. This leaves d, in which decreasing d may generally cause the analyte concentration in the reaction channels to increase. While d could, in theory, be reduced to infinitesimally small amounts, practical considerations such as flow resistance, the possibility of blockage, the corresponding increase in length needed in l in order to maintain an acceptable $V_d$, manufacturing tolerances, and so forth may limit the degree to which d may be reduced. In the context of THC detection systems, the present inventors determined that reaction channels with hydraulic diameters between about 0.1 mm and 1 mm may be effective in collecting a desired (and detectable) concentration of analyte within each reaction channel within a 60 second sampling window and with a vacuum assist feature provided (e.g., drawing down to 5-7 psi or lower). In some implementations, corresponding reaction channel lengths (the length of the reaction channels in between the isolation valves for each reaction channel) were determined to range between about 15 μL/d 2 and 45 μL/d².

The calculations and analysis discussed above assume straight reaction channels. However, additional implementations may utilize other reaction channel geometries that follow zigzag, spiral, wave, or other path types to capture particular kinds of particles more efficiently. Moreover, the reaction channel geometries may be further customized based on the size, shape and form of the analyte (molecule, particle, etc.). The discussion above focuses on examples that may be particularly effective at capturing molecular THC (although such examples may also be effective at capturing other types of analytes as well) through molecular diffusion. However, for aerosolized THC where the THC molecule may be in stuck to lung-lining surfactant or water in a vapor phase, the analyte may effectively be much larger than a purely molecular analyte (by virtue of being attached to a much large molecule or molecules), in which case curved, spiral, or otherwise non-linear reaction channels may more effectively capture the analyte due to inertial effects, e.g., a spiral reaction channel may, in effect, centrifuge the analyte towards the walls of the reaction channel, thereby increasing the chance of adsorption or binding of the analyte. In some implementations, multiple reaction channels of different designs, each configured or designed to capture a different analyte with high efficiency, may be included in a single microfluidic plate so as to allow the different analytes (or different forms of the same analyte, e.g., molecular THC and aerosolized THC, to be captured from the same breath sample. In some implementations, a large number of different analytes may be captured on a single microfluidic plate using different reaction channels that are each tuned to most efficiently capture a different analyte; such examples may allow for a large panel of measurements of different analytes to be made, thereby allowing for a variety of different potential diseases to be identified from a single breath sample. It will be understood as well that in systems that utilize a separate sub-module to house the reaction channels, the same underlying main portion of the microfluidic plate may be interfaced with any of a variety of different sub-modules, each of which may have reaction channel geometries that are tuned for a particular type of analyte, as discussed above.

In systems with vacuum assist, the controller 1452A may monitor data from the pressure sensor 1453 to determine when a breath sample is being collected, e.g., when data from the pressure sensor 1453 indicates a positive pressure above a particular threshold (and possibly below a second particular threshold), and may control operation of the vacuum assist based on such data. Such thresholds may be set to be consistent with pressures experienced within the plenum 1437 during breath sample collection. For example, if the pressure sensor data indicates that the gauge pressure within the plenum 1437 is 0.03 psi (0.2 kPa) or higher, this may be indicative that a test subject is exhaling into the cartridge and that a sample is being collected. In some implementations, too high a pressure may be indicative of misuse of the system, e.g., if more than 0.6 psi gauge pressure (4 kPa) is observed within the plenum 1437, this may be indicative of an attempt to misuse the system. In systems with vacuum assist, the controller 1452A may control the vacuum pump 1458A and/or other components so that the vacuum pump 1458A is only active (or only applying a vacuum to the reaction channels) when the data from the pressure sensor indicates that a breath sample is being collected, as discussed above. In some implementations, such vacuum pump control may include shutting off the vacuum pump (or causing vacuum assist to otherwise not be applied to the microfluidic plate) when the pressure measured by the pressure sensor drops below a predetermined threshold associated with breath sample collection. In some further implementations, the vacuum pump may also be turned off (or vacuum therefrom caused not to be applied to the microfluidic plate) when the pressure measured by the pressure sensor exceeds a different predetermined threshold, such as 0.6 psi gauge pressure (or any pressure selected from the range of 0.5 to 2.0 psi gauge) or the like. In implementations with pressure monitoring, such vacuum assist control may also be accompanied by the generation of auditory and/or graphical cues, e.g., if the pressure falls outside of the thresholds associated with valid breath sample collection, warning tones and/or lights may be caused to activate, or a verbal or visual cue, such as auditory or visual messages such as "blow harder" or "blow less" may be provided. In the case of an over-pressurization of the plenum, the auditory or visual feedback may be provided, but the vacuum assist may be left functional so that the sample continues to be drawn (in an overpressure scenario, the main risk may not be to sample collection, but overexertion of the subject, so the breath sample collection may continue, but the subject may be cautioned to breath less aggressively so as to avoid potentially hyperventilating or otherwise suffering adverse effects. Such implementations may thus avoid having the vacuum assist operating while the subject, for example, is not exhaling into the plenum 1437. This avoids the possibility that negative pressure may develop within the plenum 1437, which could potentially draw ambient air into the plenum 1437 through the flow restrictor 1438, thereby introducing undesirable contaminants into the reaction channels. In such implementations, the vacuum assist, e.g., vacuum pump 1458A, may only be activated by the controller 1452A during periods of time when the pressure data from the pressure gauge is above the threshold indicating that a subject is exhaling into the plenum 1437. Thus, when a subject pauses to inhale, for example, the vacuum assist may be temporarily deactivated and only reactivated once the subject starts to exhale into the plenum 1437 again. As an alternative to activating/deactivating the vacuum pump 1458A, some implementations may simply keep the vacuum pump 1458 active and may instead incorporate a bypass valve that may be controlled to divert suction from the vacuum pump from the reaction channels to a bleeder port or other ambient air source when the vacuum assist is to not be applied to the reaction channels.

In particular, systems including vacuum assist features may, in some implementations, be specifically configured to only initiate vacuum assist after the isolation valves 1419 have been actuated into an "open" state. This avoids a scenario in which the vacuum assist may interfere with the operation of diaphragm valves used as isolation valves 1419. For example, in order to open such isolation valves 1419, a vacuum may be applied to the diaphragm membrane on the side of the membrane opposite the reaction channels, thereby pulling the membrane away from the reaction channels and allowing fluid flow into or out of the reaction channels. However, if the reaction channels are themselves under vacuum due to the vacuum assist when actuation of the isolation valves 1419 is attempted, then the vacuum applied to the isolation valves 1419 to actuate them may have no effect, leaving the isolation valves 1419 in the closed state. Thus, the controller 1452A may be specifically configured in some vacuum assist implementations to only enable the vacuum assist feature after the isolation valves have been opened.

In some implementations, the handheld unit 1402 may also include a heater component 1445, e.g., a thermoelectric cooler (one side of which may be the "hot" side and the other the "cold"; the hot side may be used as a heater) or a resistive heater, that may be positioned to apply heat to the microfluidic plate to prevent freezing within the reaction channels. The active heating area of the heater component 1445 may be at least coextensive, or nearly coextensive, with the area occupied by the reaction channels 1405' and 1405A and the vacuum assist flow path(s) within the microfluidic plate 1404 so that the reaction channels 1405' and 1405A, and the vacuum assist flow path(s) may be heated to prevent condensate from breath sample flowed therethrough from freezing and potentially clogging or obstructing the reaction channels and/or vacuum assist flow path. In implementations with the heater component 1445, the controller 1452A may be configured to activate the heater component 1445 responsive, for example, to data from a temperature sensor, e.g., temperature sensor 1455A, indicating that ambient temperatures are below a threshold amount, e.g., below zero Celsius, and/or data that indicates that a breath sample is about to be obtained, e.g., if the controller 1452A determines that the cartridge 1403 has been docked to the handheld unit 1402, or that the handheld unit 1402 has been turned on or placed into a sample collection mode.

Returning to FIG. 14, once the flow sensor 1456 indicates that a sufficient quantity of breath sample has flowed through the reaction channels 1405' and 1405A, the vacuum pump 1458A may be caused by the controller 1452A to stop supplying negative pressure to the vacuum assist port of the cartridge 1403, and the pressurization pump 1459A may be caused by the controller 1452A to apply positive pressure to the isolation valves 1419, thereby sealing whatever analytes and gas remain within the reaction channels 1405' and 1405A into those reaction channels 1405' and 1405A. In this example, the reaction channel 1405' is intended for long-term sample preservation, e.g., for evidentiary purposes or for later analysis in a fully equipped laboratory; the sample that is collected in the reaction channel 1405' is thus left alone after collection and is not subjected to any of the subsequent processing that the sample collected in reaction channel 1405' is subjected to, as discussed in more detail below. It will be understood that some implementations may omit the reaction channel 1405' or may, for example, include more than one instance of the reaction channel 1405A, allowing for multiple tests of the same sample, which may provide additional confidence in the measurement result.

In implementations that include additional breath sampling systems, e.g., such as the BAC sensor 1457, a portion of the breath sample passing through the plenum 1437 may be diverted to such additional breath sampling systems. In this implementation, the BAC sensor 1457 may generate a BAC reading that is then caused by the controller 1452A to be stored in the memory device 1443.

Additionally, as discussed earlier, the controller 1452A may monitor data from the pressure sensor 1453, the flow sensor 1456, a temperature sensor 1455A, a humidity sensor 1455B, and so forth and to store such data, or data derived therefrom, on the memory device 1443. The handheld unit 1402 may also include additional components that may produce data, or data derived from such data, that may be stored on the memory device 1443. For example the handheld unit 1402 may include an internal clock 1455C that may provide date and time information associated with a particular breath sample collection event, a global positioning system (GPS) receiver 1455D that may provide date, time, and location information associated with a particular breath sample collection event, a fingerprint or other biometric sensor 1455E that may provide biometric information about a subject in associated with a breath sample collection event involving that subject, and/or an imaging sensor 1455F that may generate video or image data regarding a breath sample collection event (such as video of the person blowing into the mouthpiece 1442). Any or all of such information may be stored on the memory device 1443 for later retrieval. It will be understood that some such information may be obtained from an external device that is communicatively coupled with the handheld unit. For example, the handheld unit may include a wireless communications interface 1455G, e.g., Bluetooth, that may be configured to communicate with a cell phone or smartphone having a camera, GPS device, and fingerprint sensor. In such instances, the cell phone or smartphone may have functionality, e.g., an app, that allows the handheld unit 1402 to obtain information relating to a breath sample collection event to be collected from the cell phone or smartphone, e.g., the GPS location of the cell phone or smartphone at the time of sample collection may be used as the GPS location of the handheld unit at that same time, and images or fingerprints captured by the smartphone or cell phone at that time, or immediately before or after sample collection occurs, may be obtained by the handheld unit 1402 and stored on the storage device in association with that sample collection event.

The remainder of FIG. 14 will be discussed later in the context of interactions with a base station.

Figure 15:
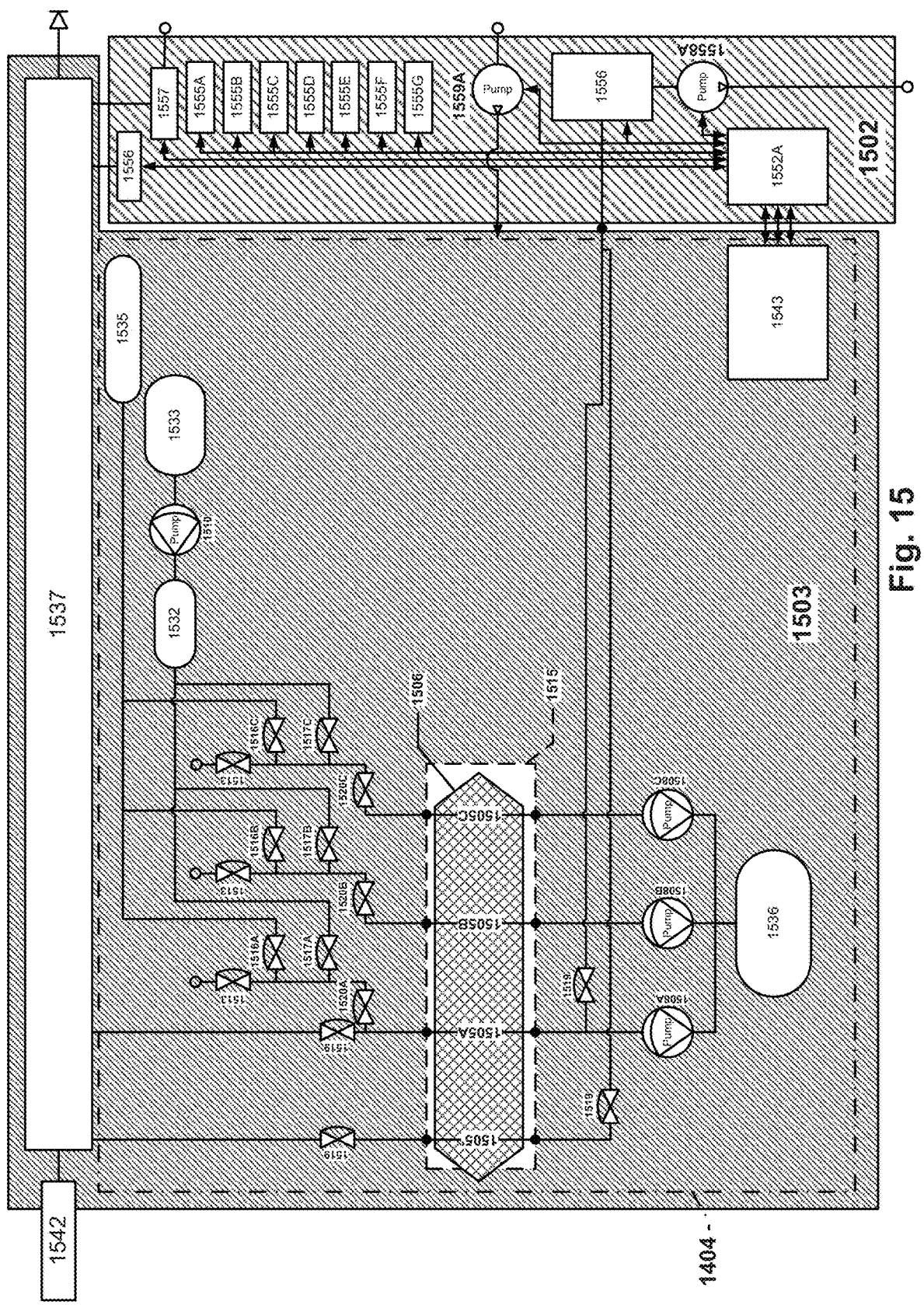
FIG. 15 is a schematic of another example disposable, or cartridge, and the example handheld unit.

FIG. 15 is a schematic of another example disposable, or cartridge, and the example handheld unit. In the implementation of FIG. 15, the components with similar last two digits in their callouts to components in FIG. 14 may be generally similar in purpose and operation as those corresponding elements in FIG. 14, unless described otherwise below.

The system of FIG. 15 may include a handheld unit 1502 that is generally the same as the handheld unit 1402. The cartridge 1503 may also be similar to the cartridge 1403, although the microfluidic plate 1504 may differ in several respects from the microfluidic plate 1404. Additionally, the reagents and liquids stored within the cartridge 1503 may differ from those discussed above in the discussion of the cartridge 1403.

The microfluidic plate 1504 may be designed for use with, for example, a diazofunctionalized fluorophore, e.g., rhodamine-123, that may be stored within an indicator reservoir 1532 in a dried, powderized form or in solution. Other indicators may be used depending on the analyte being sought; diazofunctionalized fluorophore indicators such as the rhodamine-123 indicator noted above may be useful for detecting THC, however). When analysis is to be performed (which would occur when the cartridge 1503 is interfaced with a base station instead of the handheld unit 1502), an indicator solvent may be flowed into the indicator reservoir 1532 from an indicator solvent reservoir 1533 by actuating an indicator pump 1510. While the indicator is dissolving in the indicator solvent in the indicator reservoir 1532, the reaction channel 1505A may be flushed with a wash fluid from the wash reservoir 1535 by actuating the reaction channel pumps 1508A/B/C and opening the reaction channel valves 1520A/B/C and the wash fluid valves 1516A/B/C. In this particular implementation, the reaction channels 1505A/B/C and 1505' may have antibodies immobilized on the interior surfaces thereof that are specific to the analyte of interest, e.g., THC in this example. Thus, when a breath sample is flowed through the reaction channels 1505A and 1505', the analytes specific to the antibodies may bind to the immobilized antibodies and remain fixed in plate within those reaction channels. Similarly, when known control amounts of the analytes are placed in the reaction channels 1505B and 1505C, those control amounts may also bind to the immobilized antibodies in those reaction channels as well. Thus, when the reaction channels 1505A/B/C are flushed in the wash operation, the analyte will remain behind since it is immobilized by being bound to the immobilized antibody. Any other contaminants, e.g., tobacco smoke particulates, saliva, etc., will be generally washed away, however.

After sufficient time has elapsed for the indicator to dissolve within the indicator solvent and after the wash operation has completed, the indicator solution may be flowed into the reaction channels 1505A/B/C, where it may react with whatever analyte is present in those reaction channels 1505A/B/C to produce, for example, a fluorescent adduct that may fluoresce when stimulated with a particular wavelength of light. After the indicator solution is allowed to incubate in the reaction channels 1505A/B/C for a sufficient period of time, the indicator solution in each reaction channel 1505A/B/C may be separately stimulated with excitation light and the resulting emitted light may be measured to determine a relative quantity of adduct, and thus analyte, present in that reaction channel. The amount of analyte in the breath sample may be determined by interpolating between known amounts of the control amounts of analyte in the reaction channels 1505B and 1505C based on the relative fluorescence intensity of the breath sample indicator and that measured for the indicator for the control amounts.

Figure 16:
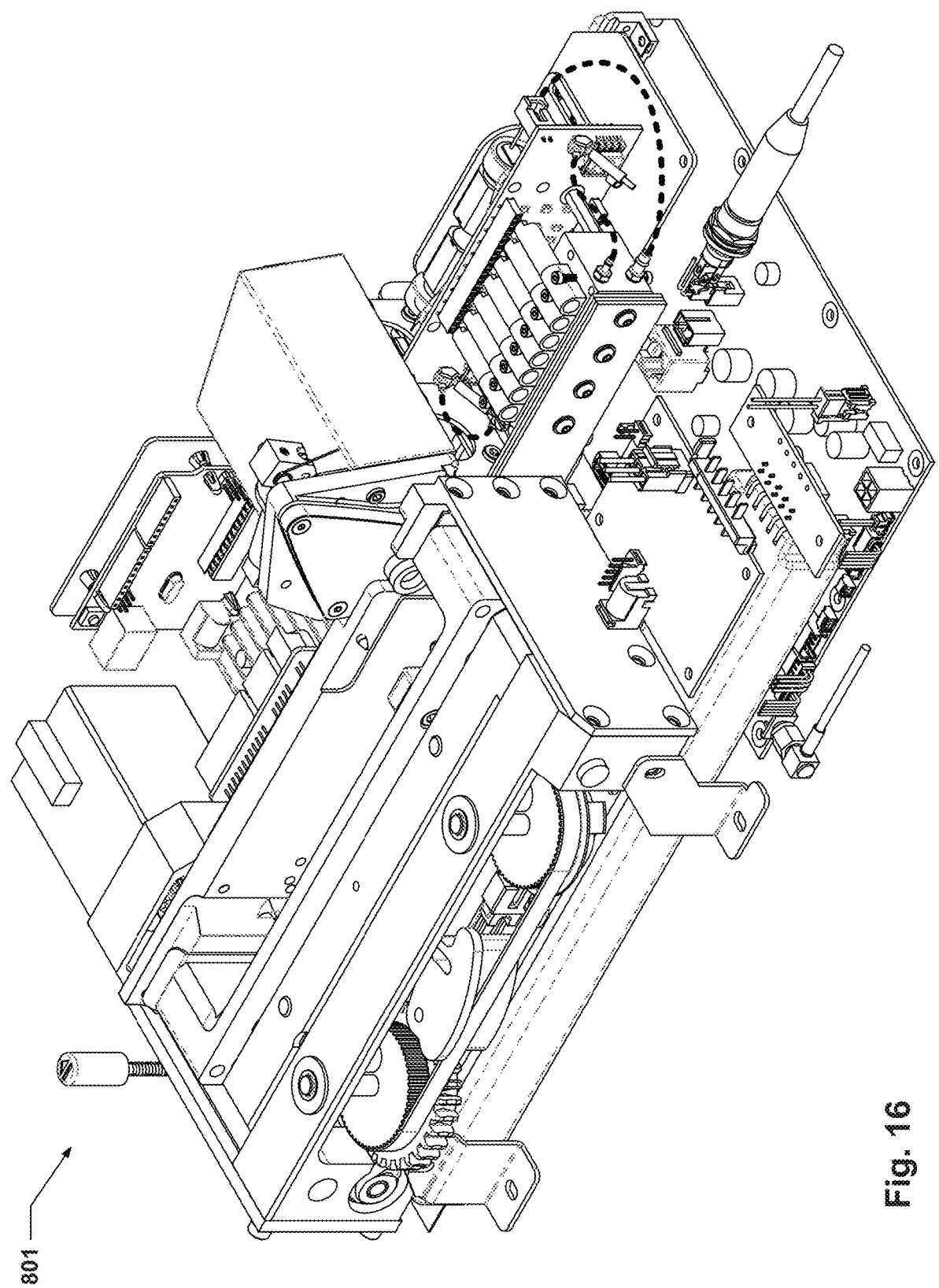
FIG. 16 depicts an example base station of the example breath sampling and analysis system of FIG. 8.
Figure 17:
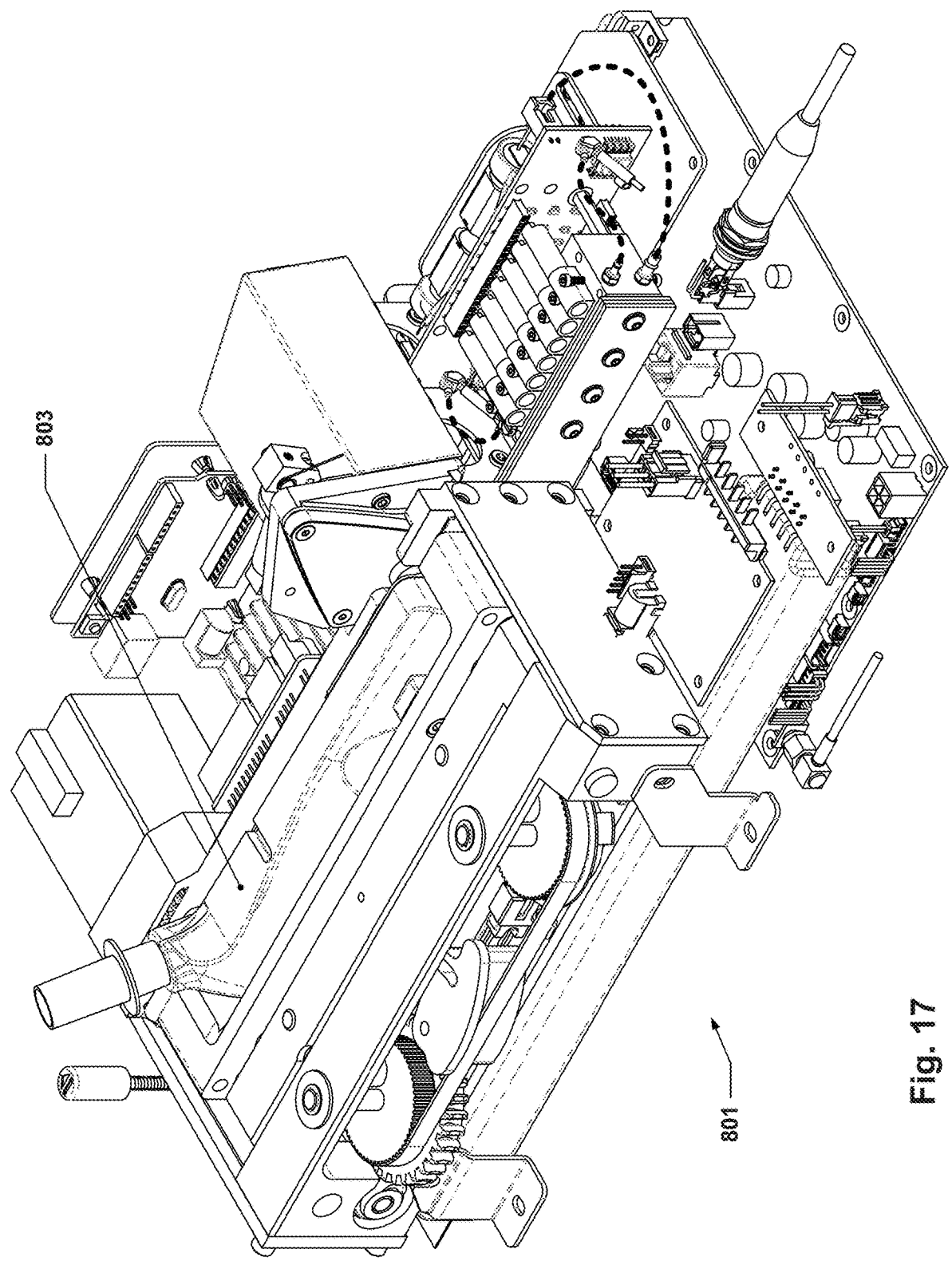
FIG. 17 depicts the example base station of FIG. 16 with the example disposable or cartridge of FIG. 9.
Figure 18:
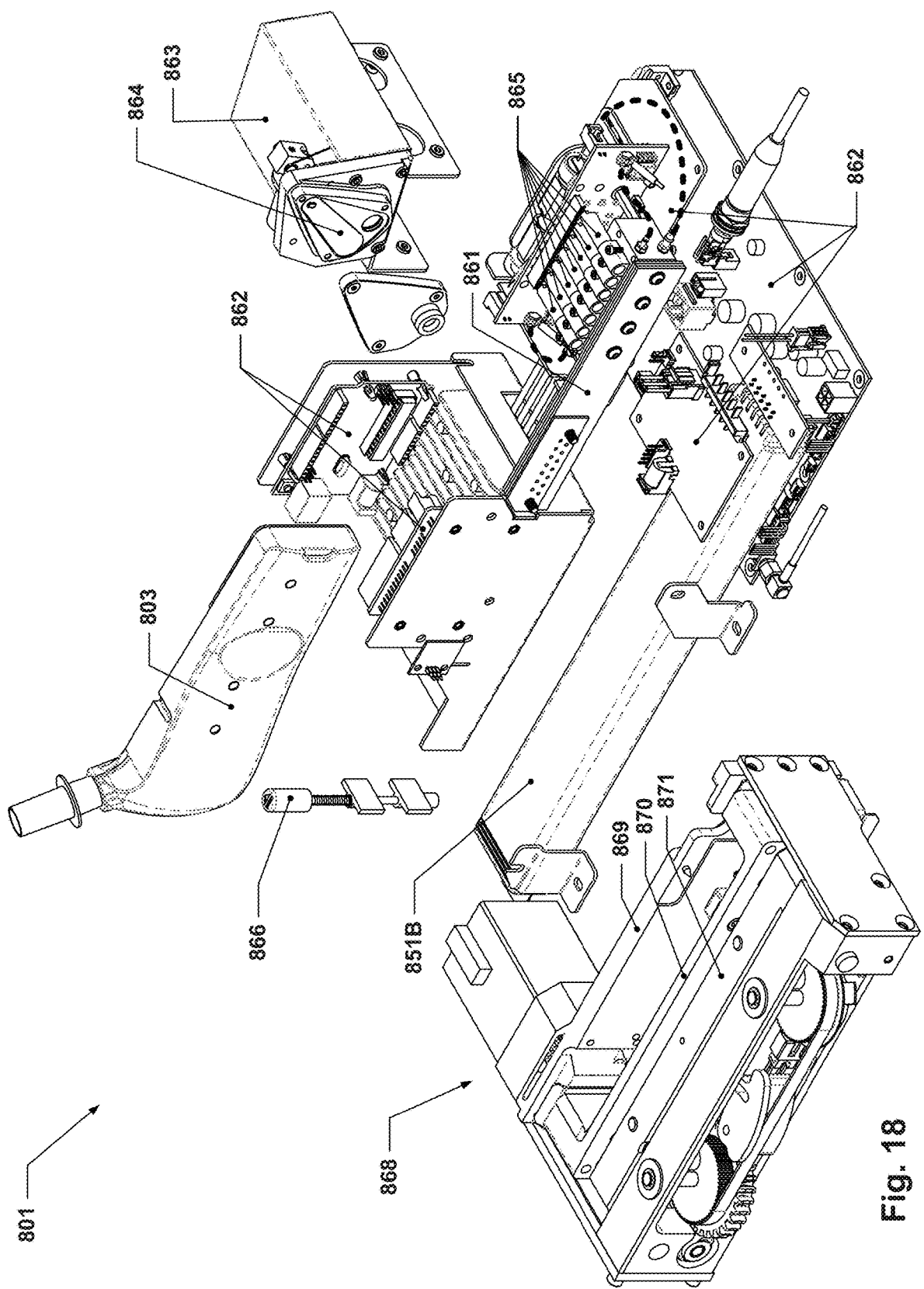
FIG. 18 depicts an exploded view of the example base station of FIG. 17.

FIG. 16 depicts an example base station of the example breath sampling and analysis system of FIG. 8. FIG. 17 depicts the example base station of FIG. 16 with the example disposable or cartridge of FIG. 9. FIG. 18 depicts an exploded view of the example base station of FIG. 17.

The depicted example base station 801 is shown without cabling, wires, external housing, and various other components unnecessary for this discussion. As can be seen from FIGS. 16 and 17, the base station 801 may include a slot that may receive the cartridge 1403, as shown in FIG. 17. Such a slot may be housed, for example, beneath a fold-down door (see system 800 in FIG. 8, in which the door is shown in an open state with the cartridge installed) that may be closed to help optically isolate the cartridge 1403 from stray environmental light. The base station 1401 may have multiple subsystems and components that may act in concert to perform analysis and measurement operations. For example, an actuation mechanism 868 may be provided to receive and prepare the cartridge 803 for analysis, an eject button 866 may be provided to allow for a user to initiate cartridge ejection and retrieval, a battery 851B may be provided to allow the base station 801 to operate independent of an external power source for limited periods of time, e.g., in the field, and one or more control boards 862 may be provided with electronics, e.g., a processor or processors, signal conditioners, driver circuits, communications interfaces, power conditioners, memory, etc., that provide control functionality for enabling the control of the various other subsystems in the base station 801. The base station may also include an optical measurement module 863, which may be equipped with an optional shutter mechanism 864 and which may be located so as to be able to measure an optically detectable signal arising from the cartridge 803, e.g., such as may be produced by marker-bound analytes trapped within the cartridge 803. The base station 801 may also include a pneumatic control system that may include a pressurization pump 859B and a vacuum pump 858B that may provide positive and negative pressure, respectively, to a plurality of individually controllable valves 865 that may each be fluidically connected to a different flow path in a pneumatic transfer manifold; each such flow path may terminate in a pneumatic port that may interface with a corresponding pneumatic control port 814 on the cartridge 803 when the cartridge 803 is loaded into the base station 801.

When the base station 801 is used to process a captured breath sample, the actuation mechanism 868 may be among the first systems to be activated. The cartridge 803 (containing a sample) may be inserted into the actuation mechanism 868 in between a heat spreader plate 869 and a cartridge clamp 870; the cartridge clamp 870 and a blister compression frame 871 may both be semi-independently movable relative to the heat spreader plate 869, as will be explained in more detail later.

Figure 19:
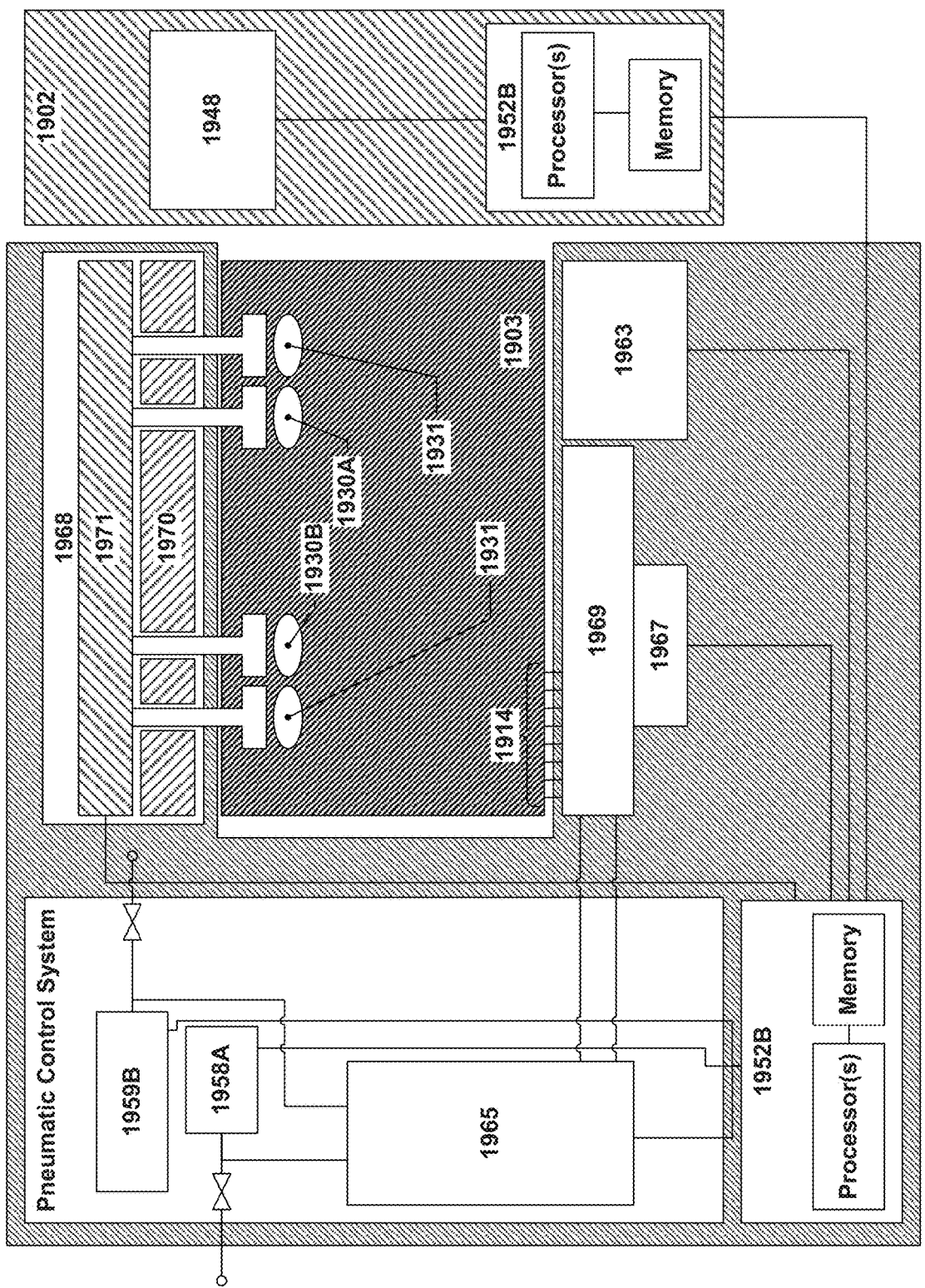
FIG. 19 is a schematic of an example disposable, or cartridge, and an example base station.

FIG. 19 is a schematic of an example disposable, or cartridge, and an example base station. The example base station 1901 may be configured to receive a cartridge 1903 and a handheld unit 1902, which may both be removably inserted into or docked with the base station 1901. The handheld unit 1902 may be similar to the handheld units discussed earlier in this disclosure, e.g., the handheld units 802, 1402, or 1502, and the cartridge 1903 may be similar to the cartridges discussed earlier in this disclosure, e.g., the cartridges 803, 1403, or 1503. The base station 1901 may include, for example, a controller 1952B that, like the controller 1952A of the handheld unit 1902, includes one or more processors, a memory or memories, communications interfaces, and other electronic components configured to control various aspects of the operation of the base station 1901. The base station 1901 may include an optical measurement module 1963 that may be communicatively coupled with the controller 1952B and positioned so as to obtain optical signal measurements from one or more locations of the cartridge 1903. In some implementations, the cartridge 1903 may have a single optical measurement site and the optical measurement module 1963 may be fixed in space in a position that aligns with this optical measurement site when the cartridge 1903 is loaded into the base station 1901. In other implementations, the cartridge 1903 may include multiple optical measurement sites and one or both of the actuation mechanism 1968 and/or the optical measurement module 1963 may be configured to translate relative to the other to allow the optical measurement module to obtain a separate measurement from each optical measurement site. In such implementations, additional hardware, e.g., linear movement actuators, rotational indexers, or the like, may be provided to allow the components in question to be repositioned relative to each other to allow the optical measurement module 1963 to obtain measurements from each optical measurement site. In yet other implementations, each measurement site may have its own dedicated optical measurement module associated therewith.

The base station 1901 may include a heat spreader plate 1969 that may be, for example, a dual-purpose device. As the name suggests, the heat spreader plate 1969 may provide heat conduction functionality by spreading heat provided by a heater component 1967, e.g., a thermo-electric cooler (TEC), which may be used to pump heat into the heat spreader plate 1969. The heater component 1967 may thus be mounted directly to the heat spreader plate 1969 or in a manner that provides a low-loss thermally conductive path between the heater component 1967 and the heat spreader plate 1969. The other functionality that may be provided by the heat spreader plate 1969 is to transfer pneumatic control signals from valves 1965 of the pneumatic control system of the base station 1901 to pneumatic control ports 1914 of the cartridge 1903. The valves 1965 may be provided both positive and negative pressure from pressurization pump 1959B and vacuum pump 1958B, respectively, and each valve 1965 may be individually controlled by the controller 1952B to select between positive or negative (or neutral) pressure to be applied to a given pneumatic control port 1914.

The actuation mechanism 1968 may include a cartridge clamp 1970 that may secure the cartridge 1903 in place and preload it against the heat spreader plate 1969, thereby causing the pneumatic control ports 1914 in the cartridge 1903 to be sealed against pneumatic ports in the heat spreader plate and for the microfluidic plate (not separately shown) of the cartridge 1903 to be pressed into thermal contact with the heat spreader plate 1969.

Operation of the base station 1901 will now be discussed with respect to FIG. 19 and with the assumption that the cartridge 1903 includes a microfluidic plate that is similar to the microfluidic plate 1404 of FIG. 14.

When the cartridge 1903 is loaded into the actuation mechanism 1968, an initial clamping operation may be performed in which the cartridge clamp 1970 is caused to move towards the heat spreader plate 1969 to cause the cartridge 1903 to be compressed against the heat spreader plate 1969. This may secure the cartridge 1903 in place and establish sealed pneumatic interfaces between the pneumatic control ports 1914 and corresponding ports on the heat spreader plate 1969.

In implementations with a heater component 1967, the heater component 1967 may be activated to heat the heat spreader plate 1969 which may then subsequently distribute such heat across the microfluidic plate 1404 which may, in turn, conduct heat to the buffer blisters 1931 and the substrate blisters 1930A/B. Such heating may be performed in order to thaw any liquids that may have frozen within the cartridge 1903 due to environmental conditions. For example, if the breath sampling and analysis system is a field unit intended for use by law enforcement officials in detecting THC and alcohol in a subject's breath, such tests may frequently be performed as part of a traffic stop at night, when temperatures are coldest. In many locales, such temperatures may, depending on the season, drop below freezing, and the quantities of liquid within the cartridge 1903 may be small enough that even a short duration exposure to the cold, such as may be experienced during breath sample collection, may cause the liquids housed therein to freeze solid. In order to address such circumstances, the base station 1901 may be equipped with the heater component 1967 and heat spreader plate 1969, as shown in FIG. 19, and the controller 1952B may be configured to cause the heater component 1967 to be activated for some duration of time before causing any processes to initiate that involve the movement of fluid within the microfluidic plate 1404. The heater component 1967 may be caused by the controller 1952B to start heating up prior to insertion of the cartridge, e.g., responsive to a wireless signal received by the base station 1901 from the handheld unit 1902 during breath sample collection by the handheld unit 1902, in response to insertion of the cartridge 1903 into the actuation mechanism 1668, or any other suitable trigger event. The heater component 1967 may be kept operative, if desired, during the analysis to prevent possible freezing or re-freezing of the liquids within the cartridge 1903. In some implementations, the heater component 1967 may be omitted. For example, if a breath sampling and analysis system is to be used in a controlled environment, e.g., in a hospital setting, it is extremely unlikely that below-freezing temperatures will be experienced, making it unlikely that the cartridge 1903 will need to be pre-heated or heated. In such instances, the heater component 1967 may be omitted, although the heat spreader plate 1969 may nonetheless be included to provide a pneumatic port interface with the microfluidic plate 1404, although in such cases, the name "heat spreader plate" may be somewhat of a misnomer—it will be recognized that the heat spreader plate in such instances may be more accurately thought of as a load spreader plate (a phrase which may be used to refer to either implementation, as in either case the plate in question distributes the load of the cartridge 1903 across a large area).

After the cartridge 1903 is loaded into the actuation mechanism 1968 and, if cartridge heating is provided, the cartridge 1903 heated to a desired temperature (as evidenced, for example, by temperature data from a temperature sensor within the cartridge or within the cartridge 1903) or for a desired period of time (e.g., such as a time period established to be long enough to ensure that the liquid within the cartridge has thawed), the blister compression frame 1971 may be actuated to compress the buffer blisters 1931 and the substrate blisters 1930A/B against the microfluidic plate 1404 to force the contents of each through an associated rupture valve and into the microfluidic plate 1404 to fill the buffer reservoir 1435 and the substrate reservoirs 1433A/B, respectively. In other implementations, other mechanisms for storing the buffer and substrates A/B may be used, e.g., such liquids may be stored directly in their respective reservoirs, thereby eliminating the need for blisters such as those discussed, and avoiding the need for the portions of the actuation mechanism directed towards activating such liquid storage devices. In other implementations, the liquids housed in the blisters may instead be stored in metering dispensers located in the base station 1901, or in a removable, replaceable reagent cartridge (not shown) that is insertable into the base station 1901. In such implementations, the base station 1901 may have additional functionality that may be activated to cause the reagent cartridge to deliver predefined quantities of each reagent to the microfluidic plate 1404 and/or the reservoirs within the cartridge 1903.

In the example microfluidic plate 1404, the reaction channels 1405A/B/C may each be coated during manufacture of the microfluidic plate 1404 with, for example, an antigen, e.g., THC or a derivative thereof, that is immobilized on the interior surfaces of the reaction channels 1405A/B/C. The "evidence" reaction channel 1405' may, in some implementations, be similarly coated, but may be uncoated in other implementations—as the sample collected in the "evidence" reaction channel 1405' may be analyzed using other analysis techniques from those used by the base station 1901, the sample collected therein may not be exposed to the same processing steps as performed on the samples within the other reaction channels 805A/B/C. A similar or identical (or near-identical) amount of antigen may separately be immobilized on the interior surfaces of each reaction channel 1405A/B/C. The antigen, generally speaking, may be the same as, or functionally equivalent to, the analyte of interest. Thus, if THC is the analyte, the antigen may also be THC.

In one such example implementation, the antigen may be THC conjugated to a support protein such as BSA or covalently bonded to the surface of the reaction channels.

After a breath sample is flowed through the reaction channel 1405A, the reaction channel 1405A may include analyte from two sources—the immobilized analyte and then any analyte that was contained within the breath sample and that adsorbed onto the interior surfaces of the reaction channel 1405A.

The reaction channels 1405B and 1405C, as suggested earlier, may not be configured to have breath sample flowed through them, but may instead contain control amounts of the analyte of interest for calibration purposes. In implementations that include immobilized antigen in each reaction channel 1405A/B/C, the control amounts of analyte that may be included in the reaction channels 1405B and 1405C will be "free" analyte, e.g., not immobilized, but either suspended in liquid form or adsorbed onto the interior surfaces of the reaction channels 1406B and 1405C in a manner that allows them to be eluted through introduction, for example, of buffer from the buffer reservoir so that they are no longer necessarily adsorbed onto the interior surfaces of those reaction channels.

After the buffer reservoir 1435 has been filled with buffer, an antibody pump 1410 may be actuated to cause a predefined amount of the buffer to be drawn from the buffer reservoir 1435 and delivered to the antibody reservoir 1432. The antibody reservoir 1432 may have a predefined quantity of lyophilized (freeze-dried) antibody contained within it that is allowed to mix with the introduced buffer in order to reconstitute the antibody; the buffer/antibody mixture may be allowed to rest for a predetermined time interval, e.g., ~30 seconds, to allow for sufficient antibody reconstitution. Once the predetermined time interval has elapsed, the controller may cause the reconstituted antibody to be moved into the reaction channels 1405A/B/C by causing positive pressure to be applied to antibody valves 1417A/B/C and to reaction channel valves 1420A/B/C to actuate them to an open state; once the antibody valves 1417A/B/C and the reaction channel valves 1420A/B/C are open, the controller may then cause reaction channel pumps 1408A/B/C to be cycled one or more times to draw equal amounts of reconstituted antibody into each of the reaction channels 1405A/B/C. It will be understood that, with the exception of optical site valves 1421A/B/C, which are independently actuable, the other valves and pumps depicted in FIG. 14 that share a common numeric designator followed by A/B or A/B/C may, for each such A/B or A/B/C cluster, be driven in unison responsive to a common pneumatic input. Thus, for example, the reaction channel valves 1420A/B/C may all open or close generally simultaneously responsive to a single pneumatic input. This may simplify the control system and reduce the number of pneumatic valves that must be provided in the base station 1901 in order to control valve and pump operation in the microfluidic plate 1404. In other implementations, of course, there may be more granular control of valves within the microfluidic plate, including, in an extreme case, implementations in which every valve and pump may be separately controllable or addressable by the base station 1901.

In one example implementation, the antibody may be a horseradish peroxidase (HRP) conjugated monoclonal antibody that is specific to cannabinol.

Once the predetermined amount of reconstituted antibody is delivered to each reaction channel 1405A/B/C, the reconstituted antibody may be allowed to incubate within the reaction channels 1405A/B/C for a predetermined time interval, e.g., 55-65 seconds, e.g., 60 seconds, or longer. The amount of reconstituted antibody that is introduced into each reaction channel 1405A/B/C may be generally equal (it will be recognized that the goal is to introduce equal amounts of reconstituted antibody to each reaction channel 1405A/B/C but that manufacturing variation in the reaction channel pumps 1408A/B/C, slight non-homogeneities in the reconstituted antibody solution, and other sources of variation may result in some variation in the amount of reconstituted antibody that is delivered to each reaction channel 1405A/B/C, although the amounts delivered will generally be understood within the art as being "substantially equal" despite such variations; such variations may range ±10% to ±20%).

During this incubation time, the antibody, which is selected to specifically bind to the analyte for which measurement is sought (and to the immobilized antigen in each reaction channel 1405A/B/C), will bind to the analyte and antigen. The antibodies may, for example, be conjugated antibodies, e.g., having enzymes or other additional or alternative molecules bonded thereto. The amount of reconstituted antibody that is provided to each reaction channel 1405A/B/C may be selected such that there are fewer antibodies delivered to each reaction channel 1405A/B/C than there are immobilized antigen sites for the antibody to bind to. Thus, if there is only immobilized antigen present in a given reaction channel 1405, then a high fraction of the antibody introduced into that reaction channel 1405 may bind with the immobilized antigen and may, itself, become immobilized. However, if the breath sample caused a quantity of analyte to be introduced into that same reaction channel 1405, the antigen and the introduced sample analyte may compete for antibodies, and the antibodies may bind to the sample analyte and the immobilized antigen in quantities proportionate to the amount of sample analyte and the immobilized antigen relative to the combined amount of sample analyte and immobilized antigen within that reaction channel 1405. Thus, if there is half as much sample analyte introduced into the reaction channel 1405 as there is immobilized antigen present in the reaction channel 1405, then about ⅓ of the antibody will bind to the sample analyte, and the other ⅔ of the antibody will bind to the immobilized antigen and, itself, become immobilized.

After the antibody has been allowed to incubate within the reaction channels 1405A/B/C, the reaction channels 1405A/B/C may be flushed or purged, e.g., by first pumping air through them, followed by a liquid wash using buffer from the buffer reservoir, and then again by pumping air through them. For example, the controller 1952B may cause the reaction channel valves 1420A/B/C to be opened and the reaction channel pumps 1408A/B/C to be actuated to draw fluid from the reaction channels 1405A/B/C and to dump the drawn fluid into the waste reservoir 1436. While the reaction channel pumps 1408A/B/C are applying negative pressure to the reaction channels 1405A/B/C, the controller 1952 may first cause the valves for vents 1413 directly fluidically connected with each of the reaction channel valves 1420A/B/C to be opened to allow air to be drawn into each of the reaction channels 1405A/B/C through the respective vent 1413. After a sufficient air purge interval, the controller 1952B may case the valves of the valves 1413 that were open to close while causing the buffer valves 1416A/B/C to open. With the buffer valves 1416A/B/C open, the negative pressure provided by the reaction channel pumps 1408A/B/C may draw buffer from the buffer reservoir 1435 and into the reaction channels 1405A/B/C, which may sweep sample analyte remaining in the reaction channels 1405A/B/C into the waste reservoir 1436. After a suitable interval of time, the controller 1952B may cause the buffer valves 1416A/B/C to close again, and may re-open the valves for the vents 1413 to repeat the air flush operation discussed previously for a similar interval of time.

After these washing/flushing operations, the reaction channels 1405A/B/C may generally contain only immobilized antigen and whatever antibodies have bonded to the immobilized antigen; the antibodies that bonded with the sample analyte will all generally have been flushed to waste.

During the time that the above operations are being performed, the controller 1952B may cause other operations to occur with other portions of the microfluidic plate 1404. For example, the vents 1413 fluidically connected with the substrate reservoirs 1433A/B and the substrate mixing reservoir 1434 may be caused to be actuated by the controller 1952B, and the substrate pumps 1409A/B may be actuated to cause substantially equal amounts of substrate to be dispensed from each of the substrate reservoirs 1433A/B into the substrate mixing reservoir 1434. It will be appreciated that in the example system, the substrates are stored in binary form to avoid prematurely triggering a reaction between the two reagents that are stored in the substrate reservoirs 1433A/B. Once analysis of a sample has begun, however, the substrate components stored in the substrate reservoirs 1433A/B may be pumped into the substrate mixing reservoir 1434 and allowed to mix, thereby reacting to form the substrate. In one example implementation, the substrate may be a luminescent substrate which is provided in a two-part binary form that, when mixed, will remain stable for approximately 8 hours and steadily luminesce for about 5 minutes after adding the substrate to the analyte of interest.

After the breath sample analyte and the antibodies bound thereto have been washed away, the substrate may be distributed to the reaction channels 1405A/B/C. For example, the controller 1952B may cause the substrate valves 1418A/B/C to be actuated to an open state (the valves of vents 1413 actuated during the wash and purge operations discussed above may be caused to be actuated to a closed state by the controller 1952B, and the valve of vent 1413 connected with the substrate mixing reservoir 1434 may be caused to be actuated to an open state by the controller 1952B) and may cause the reaction channel pumps 1408A/B/C to be cycled so as to draw predetermined amounts of substrate from the substrate mixing reservoir 1434 into each of the reaction channels 1405A/B/C; the predetermined amounts of substrate distributed to each reaction channel 1405A/B/C may be substantially equal. After the predetermined amounts of substrate have been dispensed to each reaction channel 1405A/B/C, the reaction channel pumps 1408A/B/C may be deactivated and the substrate valves 1418A/B/C and the valve associated with the vent 1413 connected with the substrate mixing reservoir 1434 may be caused to be actuated to a closed state by the controller 952B. The substrate may then be allowed to incubate within the reaction channels to allow the marker molecules in the substrate to be activated by any of the antibodies that are present in the reaction channels 1405/A/B/C. For example, if conjugated antibodies are used, the conjugate may be an enzyme such as horseradish peroxidase (HRP) that activates the marker molecules in the substrate and causes them to start luminescing. The higher the concentration of conjugated antibodies, the larger the luminescent response of the marker molecules will be.

At this stage, the breath sample preparation operations associated with analyses conducted with such an example microfluidic plate 1404 are substantially complete, and actual measurement of the analyte in each sample or control may begin.

In this example implementation, the measurement of analyte may be performed in an indirect manner, as the analyte itself was flushed to waste earlier in the process discussed above. However, an estimation of how much analyte was present within each reaction channel prior to the flushing operation may be indirectly obtained by measuring the luminescent response of the substrate from each separate reaction channel 1405A/B/C. In order to do so, the substrates within each reaction channel 1405A/B/C may be separately pumped to the optical measurement site 1406 (or to separate optical measurement sites 1406 if measurement is to be done, for example, in parallel) and measurements of emitted light from the substrate for each reaction channel 1405A/B/C may be obtained; the amount of light measured for each such sample will be directly influenced by the concentration of antibodies in the reaction channel 1405A/B/C from which each sample was drawn. If each optical measurement is taken with respect to an identically-sized portion of the substrate from each reaction channel 1405A, then the relative intensities of the emitted light from each measured portion will generally indicate the relative quantities of antibodies within the reaction channel 1405A/B/C for each measured portion. If the reaction channels 1405B and 1405C contain known control amounts of the analyte, then the amount of analyte in the reaction channel 1405A, in turn, may be determined through, for example, interpolation between the known control amounts of analyte based on the measured light intensities.

In some implementations, the lower control amount may be selected to be close to a pre-established threshold amount of analyte that is deemed to be indicative of a particular physiological state. In the case of THC as the analyte, the threshold amount may, for example, be the lower limit of the amount of THC that must be present in a breath sample in order to consider the subject to be under the influence of THC and/or to consider the subject as having ingested or inhaled THC within, for example, the last two or three hours; in the latter case, this may be on the level of 2-2.5 picograms per 0.5 liters of breath sample volume, although perhaps higher. In other implementations, the lower control amount may be set to other values, e.g., no analyte at all. The upper control amount may be selected to be higher than the lower control amount; in some implementations, the upper control amount may be selected to be near the maximum expected quantity of analyte within a given breath sample.

After the antibodies introduced into each reaction channel 1405A/B/C have been allowed to bind to the antigen and/or analytes in each reaction channel 1405A/B/C, the non-immobilized analyte (breath sample analyte and control amounts of analyte) and antibodies bound thereto in each reaction channel 1405A/B/C may be flushed out and the reaction channels 1405A/B/C purged and washed. Equal quantities of substrate may then be dispensed into each reaction channel 1405A/B/C; the marker molecules in the substrate may preferentially bind with any antibodies that are present in each reaction channel 1405A/B/C. Following an incubation period to allow the marker molecules in the substrate to bind with whatever antibodies are present within each reaction channel 1405A/B/C, the substrate and unbound marker molecules within each reaction channel 1405A/B/C may be drawn, e.g., by actuating the respective optical site valve 1421A/B/C and the optical measurement site pump 1407, into the optical measurement site 1406, at which point an optical measurement may be obtained of a portion of the substrate present within the optical measurement site. It will be understood that in systems in which the same optical measurement site 1406 is used to separately obtain measurements from each substrate, the optical measurement site 1406 may be purged with air and washed with buffer (and optionally purged with air again), in a manner similar to how the reaction channels 1405A/B/C were purged/washed in earlier operations, in between each substrate measurement.

The exact quantity of substrate that is pumped into the optical measurement site 1406 for each measurement need not be identical, although the region of the optical measurement site 1406 that is within the active detection area of the optical measurement module should have equal amounts of substrate within it for each measurement. Thus, while the optical measurement site 1406 may be 2 mm by 6 mm, the active detection area of the optical measurement module may be limited to a 2 mm square region in the middle of the optical measurement site, so only a portion of the light emitted from the substrate within the optical measurement site 1406 may be detected by the optical measurement module. Accordingly, the illumination intensity measurements obtained by the optical measurement module will be representative of an illumination density of the substrate being measured, e.g., the amount of illumination generated by a given volume of the substrate within the active measurement area of the optical measurement module. The illumination density, in turn, is directly proportional to the quantity of antibodies that were present in the reaction channels 1405A/B/C when the substrate was introduced. This amount, in turn, is inversely proportional to the amount of analyte that was present when the analyte and the immobilized antigen competed for antibodies. Thus, such luminescence measurements may allow for two possible types of measurement—(a) a binary measurement, e.g., is the level of analyte above or below a control amount of analyte and (b) an interpolated quantification measurement, in which the actual amount of analyte in the reaction channel 1405A (or a portion thereof) may be determined by interpolating between the known control amounts of analyte in the reaction channels 1405B/C based on where the luminescence measurement of the breath sample substrate falls relative to the luminescence measurements of the control amounts.

It will be appreciated that other types of microfluidic analysis protocols may be implemented in a similar fashion, e.g., on a microfluidic plate modified to suit the particularities of any particular selected analysis protocol, as desired. Regardless of the particular protocol adopted, however, various aspects of the breath sampling and analysis systems set forth herein may be common to such different protocols. For example, the underlying cartridge design may be used to capture breath samples generally regardless of which analysis protocol is later used to then analyze the captured samples (although the number and location of blister packs or equivalent reagent storage volumes may differ depending on the needs of the selected protocol, and the layout of channels, valves, and pumps in the microfluidic plate may be changed depending on the type of analysis selected. The handheld unit may be relatively unaffected by the selection of any particular analysis protocol since the handheld may, in many implementations, play an active, physical role during sample collection and not analysis (although in some implementations, the handheld unit may have a controller that controls operation of the base station during analysis, e.g., via a physical connection while docked or wirelessly, e.g., via a Bluetooth connection). The base station, similarly, may include various subsystems that may generally remain physically unchanged regardless of what analysis protocol is selected for analyte measurement. For example, the actuation mechanism that loads the cartridge and prepares the cartridge for analysis in some implementations may operate in a similar manner regardless of which analysis protocol is selected.

Figure 20:
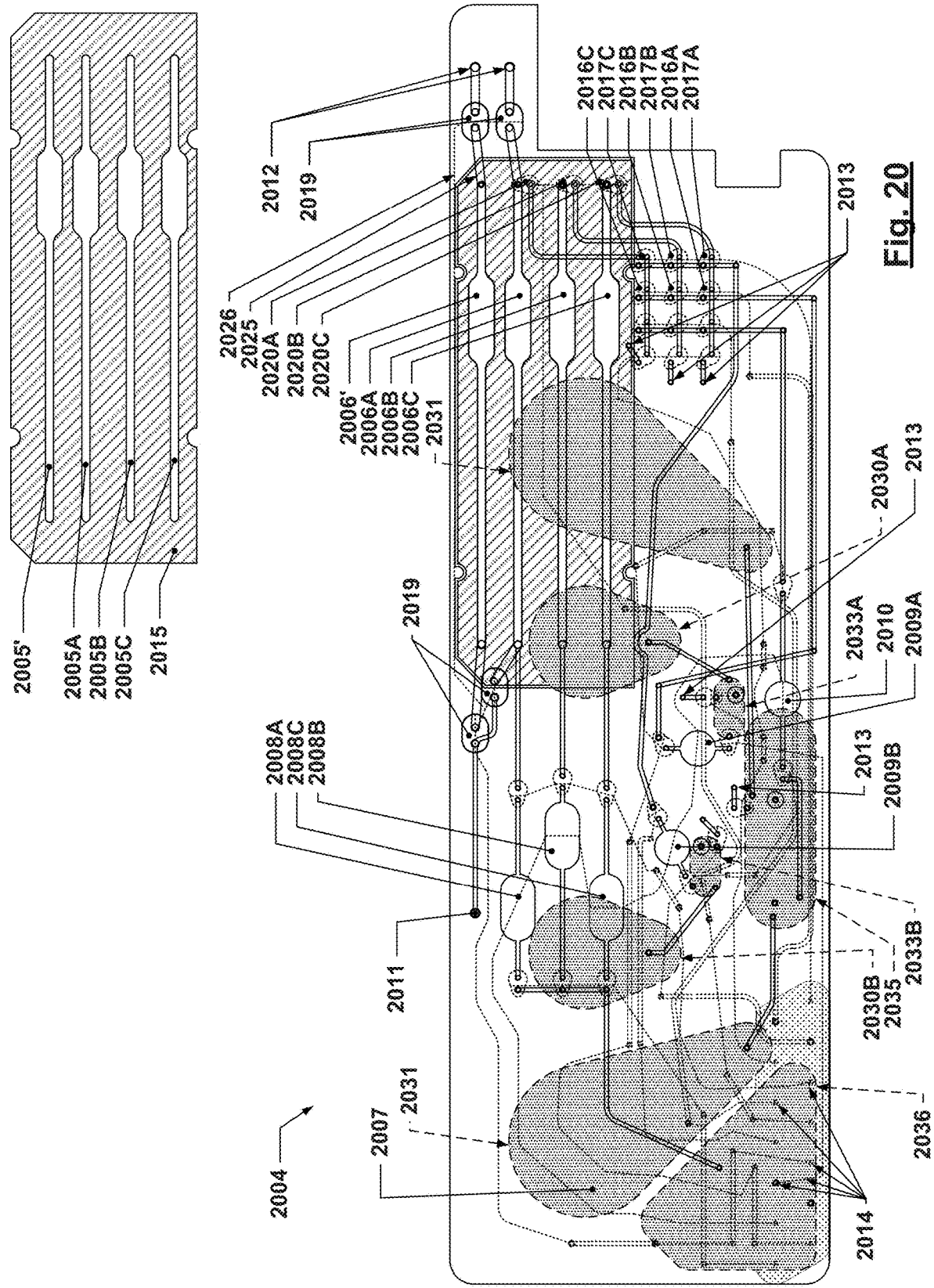
FIG. 20 depicts another example microfluidic plate that may be used with the example breath sampling and analysis system of FIG. 8.
Figure 21:
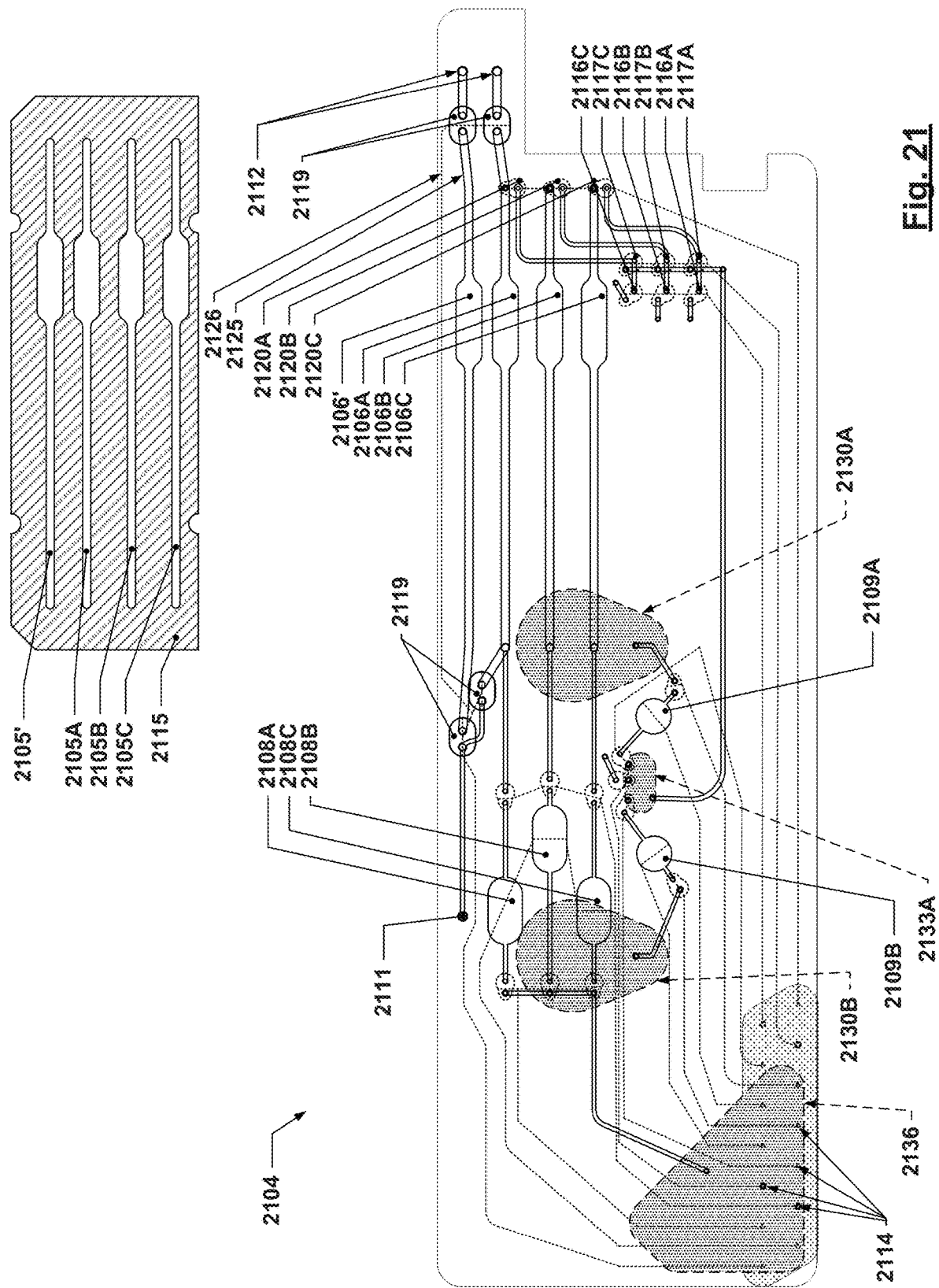
FIG. 21 depicts another example microfluidic plate that may be used with the example breath sampling and analysis system of FIG. 8.
Figure 22:
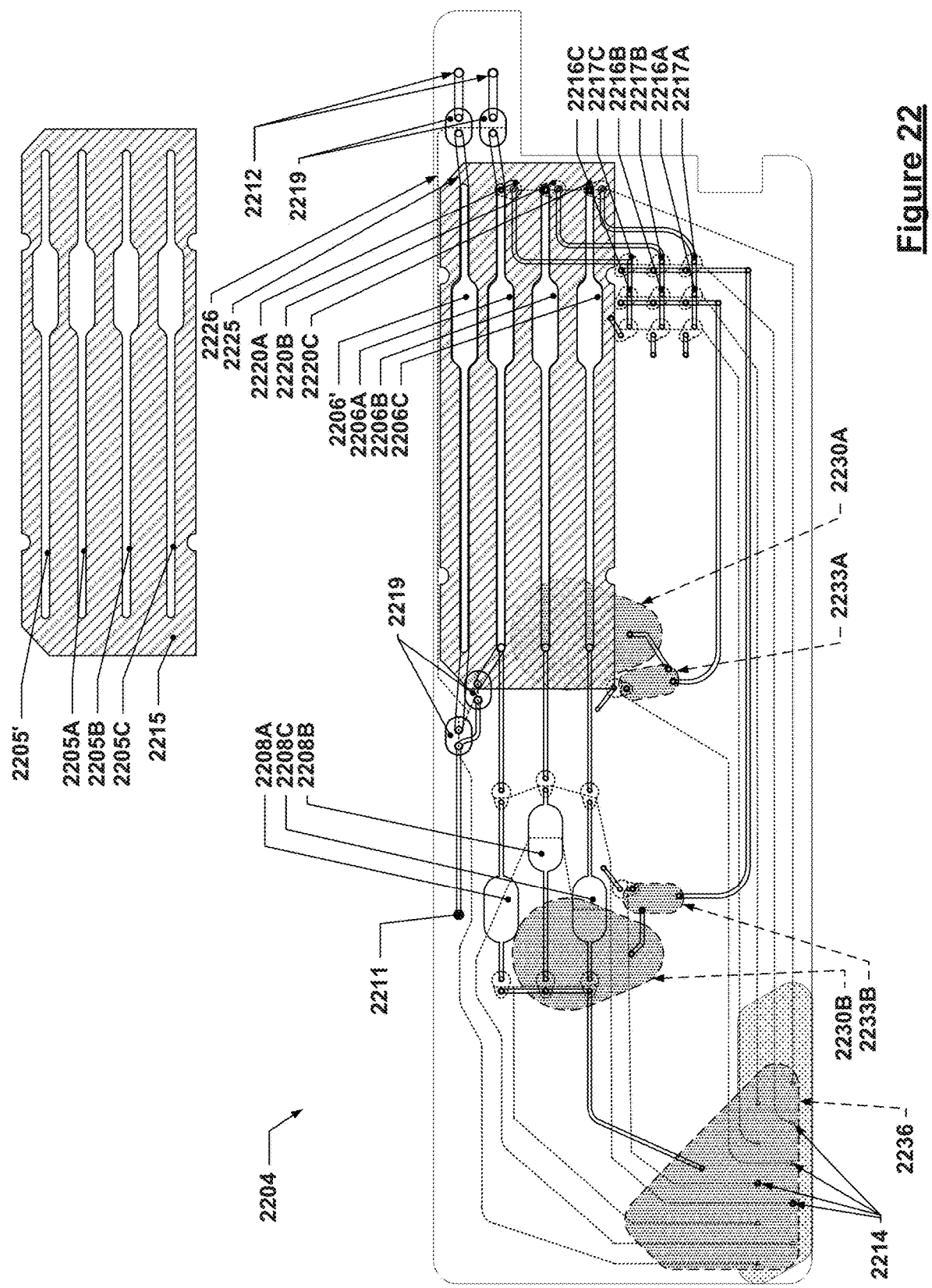
FIG. 22 depicts another example microfluidic plate that may be used with the example breath sampling and analysis system of FIG. 8.

FIGS. 20, 21, and 22 depict other examples of microfluidic plates that may be used to implement additional or alternative types of analysis. For example, FIG. 20 depicts an example microfluidic plate that may be used with the example breath sampling an analysis system of FIG. 8 to perform a functionalized diazofluorophor-based analysis of a breath sample. Microfluidic plate 2004 may be similar in many respects to the microfluidic plate 1104 discussed earlier, but may also differ in several respects. It may be assumed that structures that are referenced by callouts with the same last two digits as callouts in FIG. 11 are similar to the corresponding structures in FIG. 11 unless otherwise indicated.

In FIG. 20, the reaction channels 2005' and 2005A/B/C may be optionally located in a sub-module that may similar to the sub-modules discussed earlier. It will be noted, however, that the reaction channels in this example include the optical measurement sites 2006' and 2006A/B/C instead of a separate optical measurement site to which various fluids must be pumped.

During operation, the microfluidic plate of FIG. 20 may receive indicator solvent from blister 2030B that may be then stored in indicator reservoir 2033B, where it may mix with and dissolve a powderized, granularized indicator, e.g., for THC detection, rhodamine-123 or similar indicator that forms a fluorescent adduct when allowed to react with THC, that is stored within the indicator reservoir to form a liquid indicator.

In the example microfluidic plate 2004, the reaction channels may, prior to sample collection, have had an analyte-specific antibody immobilized on the surfaces thereof. For example, a THC-specific antibody may be immobilized on the surfaces of each reaction channel 2005A/B/C if THC is the analyte in question. When breath sample is flowed through the reaction channel 2005A, analytes in the breath sample may bond with the antibodies immobilized within the reaction channel 2005A and may thereby become immobilized themselves within the reaction channel 2005A. As with the microfluidic plate of FIG. 11, the reaction channels 2005B and 2005C may contain control amounts of the analyte in question (which may bind with the antibodies in those respective reaction channels as well) to provide a baseline against which measurement of analyte may be compared in order to quantify the amount of analyte that is present in the breath sample.

While the indicator is being reconstituted (or earlier, if desired), the reaction channels 2005A/B/C may be flushed and washed with buffer or wash solvent contained within wash reservoir 2035, which may be filled with buffer or wash solvent from buffer or wash blisters 2031, by opening buffer or wash valves (unlabeled, but the three valves immediately to the left of activator valves 2016A/B/C) and activation channel valves 2020A/B/C and then activating wash pump 2010 and/or actuation channel pumps 2008A/B/C to pump wash fluid through the reaction channels 2005A/B/C and into the waste reservoir 2036. This will generally flush whatever breath sample remains in the reaction channel 2005A out of the reaction channel 2005A (and may similarly flush the contents of the reaction channels 2005B and 2005C) and into waste. The analyte in each reaction channel 2005A/B/C that is bound to the immobilized antibody in each reaction channel 2005A/B/C will, however, remain within the reaction channels 2005A/B/C after such flush operations.

After waiting a sufficient period of time for the indicator to dissolve, and after the reaction channels 2005A/B/C have been flushed, indicator valves 2017A/B/C and actuation channel valves 2020A/B/C may be actuated into an open state and indicator pump 2009B and/or reaction channel pumps 2008A/B/C may be activated to pump the indicator solution from the indicator reservoir 2033B into the reaction channels 2005A/B/C. Once in the reaction channels 2005A/B/C, the indicator may react with any analyte, e.g., THC, that is present in the reaction channels. In the example microfluidic plate 2004, the reaction channels may, prior to sample collection, have had an analyte-specific antibody immobilized on the surfaces thereof. For example, a THC-specific antibody may be immobilized on the surfaces of each reaction channel 2005A/B/C if THC is the analyte in question. When breath sample is flowed through the reaction channel 2005A, analytes in the breath sample may bond with the antibodies immobilized within the reaction channel 2005A and may thereby become immobilized themselves within the reaction channel 2005A. As with the microfluidic plate of FIG. 11, the reaction channels 2005B and 2005C may contain control amounts of the analyte in question to provide a baseline against which measurement of analyte may be compared in order to quantify the amount of analyte that is present in the breath sample.

In conjunction with flowing the indicator solution into the reaction channels 2005A/B/C, an activator solution from activator reservoir 2033A may optionally be pumped to the reaction channels 2005A/B/C by opening activator valves 2016A/B/C as well and activating activator pump 2009A and/or activation channel pumps 2008A/B/C.

After the indicator solution and the optional activator have been introduced into the reaction channels 2005A/B/C, they may be allowed to incubate in the reaction channels 2005A/B/C for a sufficient period of time, e.g., 60 seconds, to produce the adduct by reacting with the bound analyte. The activator solution may, for example, be a liquid compound that may react with the adduct formed by the indicator and may enhance the adduct's fluorescent response. In some implementations, the activator may be omitted if the adduct produced already has adequate fluorescent response. The activator solution, like the indicator solvent, may be stored prior to analysis in an activator blister 2030A and dispensed to the activator reservoir 2030A when analysis begins.

Once the adduct has formed and any optional activator added to the reaction channels, optical measurements may be taken from optical measurement sites 2006A/B/C, e.g., by stimulating each optical measurement site with light of a first wavelength selected to stimulate the adduct to produce light of a second wavelength. A measurement may be taken of the intensity of the second wavelength light at each optical measurement site using an optical measurement module to determine the relative quantity of adduct in each measurement site. In such microfluidic plates, the layers of the microfluidic plate 2004 may be made from a light-opaque material, aside from the layers interposed between the measurement sites 2006A/B/C and the optical measurement module. In this instance, the measured light intensity is proportionate to the amount of analyte present in each reaction channel (as opposed to an inverse thereof).

FIG. 21 depicts another example microfluidic plate that may be used with the example breath sampling an analysis system of FIG. 8. Microfluidic plate 2104 may be similar in many respects to the microfluidic plates 2004 and 1104 discussed earlier, but may also differ in several respects. It may be assumed that structures that are referenced by callouts with the same last two digits as callouts in FIGS. 11 and 20 are similar to the corresponding structures in FIGS. 11 and 20 unless otherwise indicated. The microfluidic plate 2104 of FIG. 21 has a simpler architecture than the microfluidic plates of FIG. 11 or 20 and may be used, for example, to perform analysis protocols in which a binary indicator may be stored in two separate blisters 2130A/B for long term storage. The binary indicator may then be transferred to corresponding indicator reservoirs 2133A/B when the cartridge is prepared for analysis, and metered amounts of each component of the indicator may then be pumped into an indicator mixing reservoir 2134 using indicator pumps 2109A/B. For THC detection, for example, one blister may contain a rhodamine-123 dissolved in an acid, e.g., hydrochloric acid, and the other blister may contain a solution of sodium nitrate. The two solutions may then be mixed together in the mixing reservoir 2134 and then, once mixed, transferred to the reaction channels 2105A/B/C and allowed to react with whatever analyte is present. Similar to the implementation of FIG. 20, optical measurements may then be taken from the optical measurement sites 2106A/B/C and analyzed in order to determine a quantity of analyte present in the reaction channel 2105A relative to known control quantities of analyte in reaction channels 2105B and 2105C.

FIG. 22 depicts another example microfluidic plate that may be used with the example breath sampling an analysis system of FIG. 8. Microfluidic plate 2204 may be similar in many respects to the microfluidic plates 2104, 2004, and 1104 discussed earlier, but may also differ in several respects. It may be assumed that structures that are referenced by callouts with the same last two digits as callouts in FIGS. 11, 21, and 20 are similar to the corresponding structures in FIG. 11, 21, or 20 unless otherwise indicated. This implementation includes a microfluidic plate 2204 similar to that shown in FIG. 21, although the mixing reservoir 2134 is omitted and the contents of each reservoir 2233A/B may instead be independently pumpable into the reaction channels 2105A/B/C directly. Such a microfluidic plate structure may be used in analysis protocols such as LOCI (luminescent oxygen channeling) assays. For example, reservoir 2233A may include donor beads for such an assay, and reservoir 2233B may contain acceptor beads for such an assay. The beads in both reservoirs 2233A/B may be stored in a dried format and then reconstituted by flowing a buffer from the blisters 2231A/B into each respective reservoir at the start of analysis. The donor beads and acceptor beads may each be bound or coated with antibodies that may be specific to the analyte of interest. After a sufficient amount of time has elapsed to allow the donor and acceptor beads to be reconstituted, the donor bead and acceptor bead solutions may be pumped to the reaction channels 2205A/B/C. After sufficient incubation time has elapsed, the reaction channels may be optically stimulated to excite the donor beads. Donor beads that are spatially proximate to acceptor beads by virtue of the antibodies on both beads binding to a common analyte molecule will then emit an oxygen molecule that, in turn, causes the acceptor beads to emit light at a different wavelength than the excitation illumination wavelength. This emitted light may then be measured to determine a magnitude of emitted light that is proportionate to the amount of analyte present in the stimulated reaction channel. As with the other analysis protocols discussed herein, such a measured light intensity may be compared to the measured light intensities from similar measurements performed for control amounts of analyte in other reaction channels in order to determine a quantity of measured analyte from a breath sample relative to the known quantities of control analyte.

Figure 23:
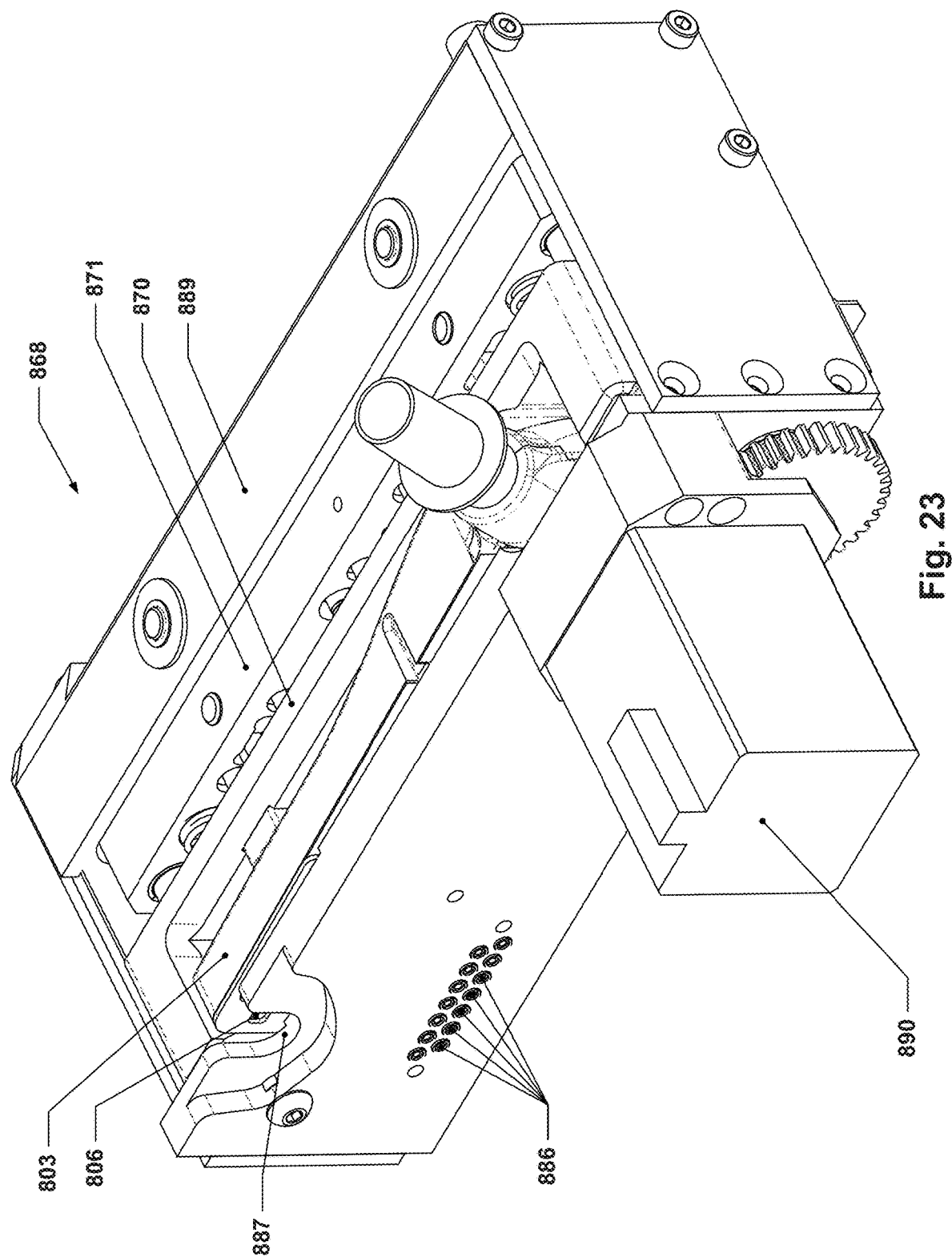
FIG. 23 depicts an example actuation mechanism.
Figure 24:
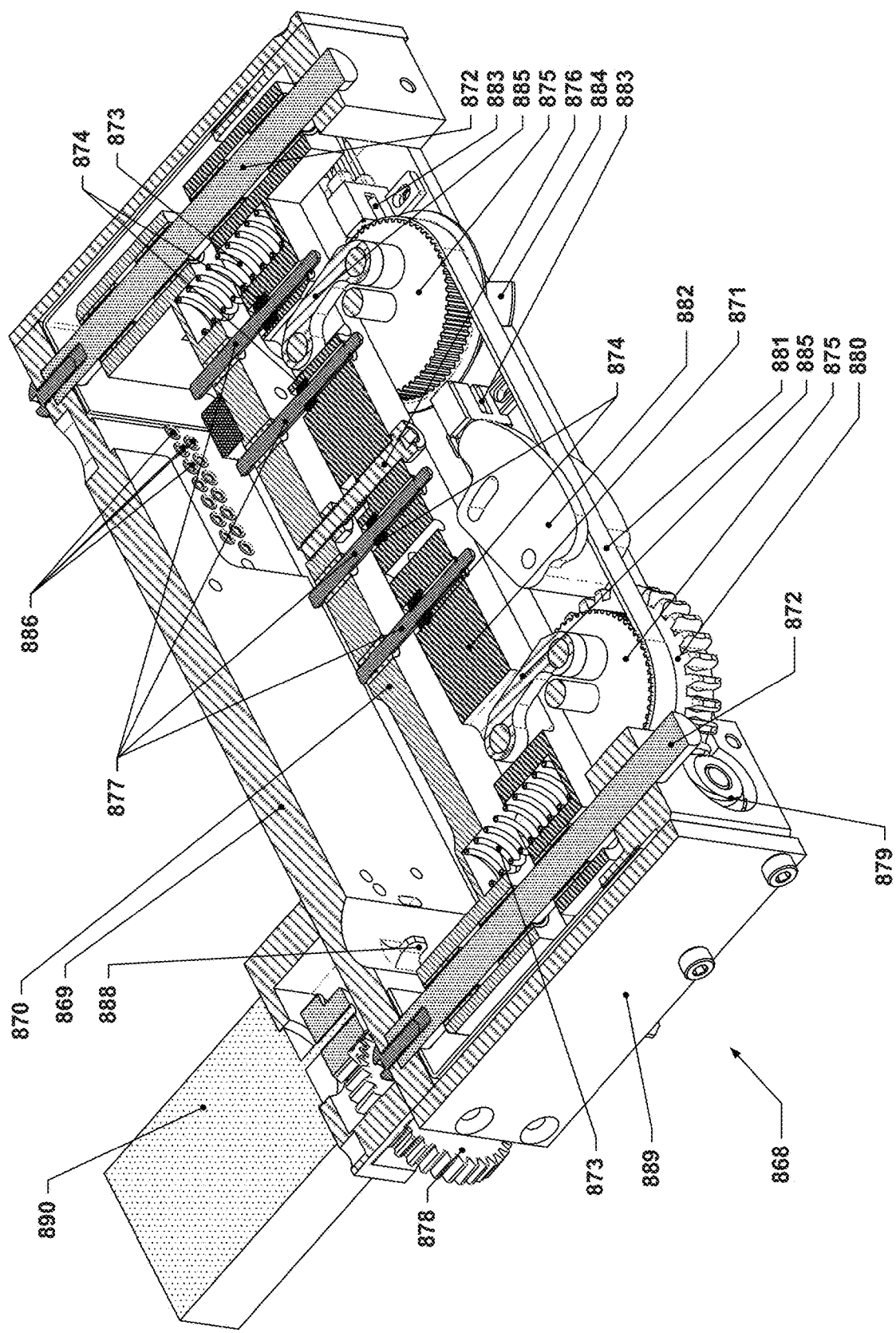
FIG. 24 depicts a cutaway view of the example actuation mechanism of FIG. 23.
Figure 25:
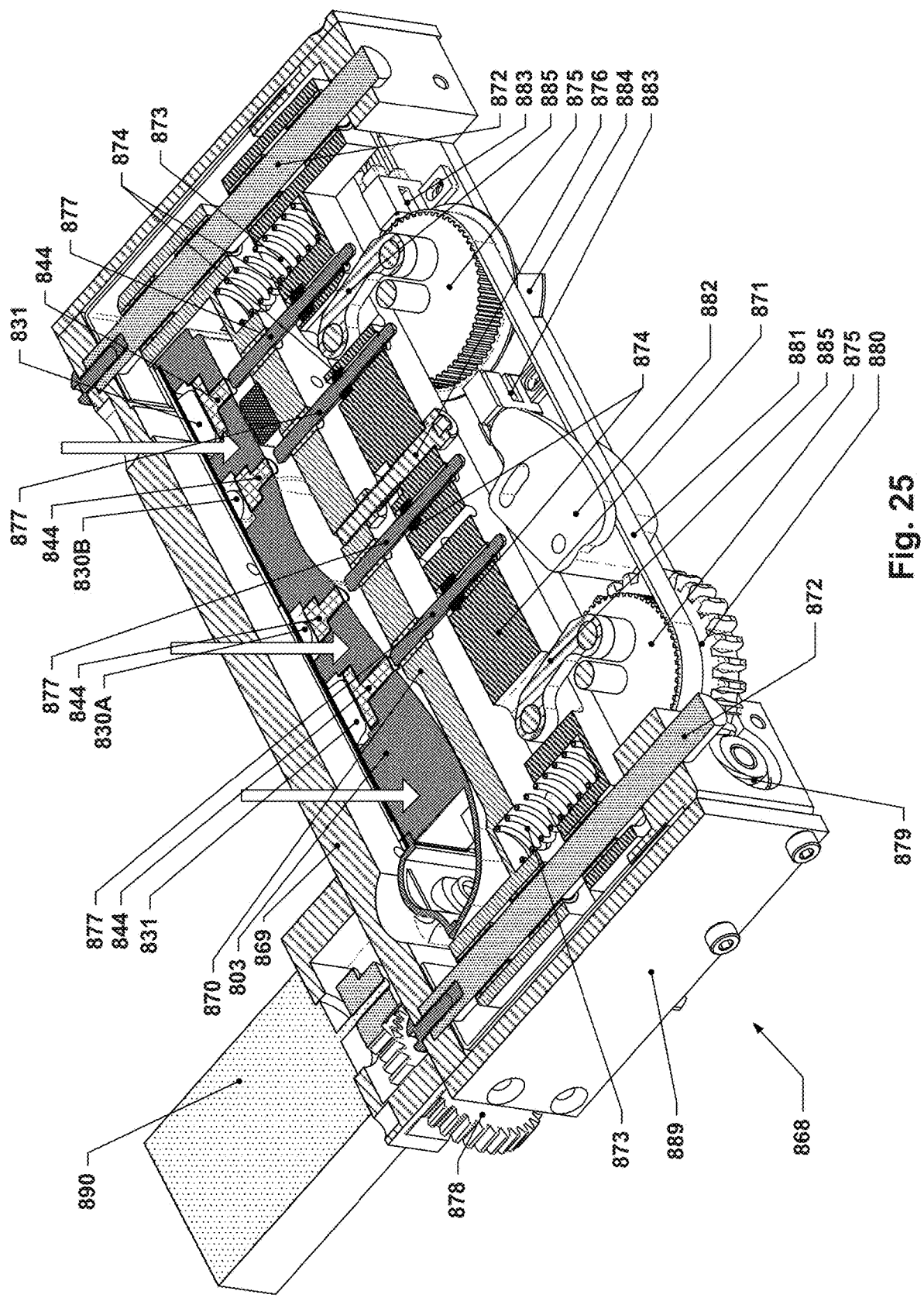
FIG. 25 depicts a cutaway view of the example actuation mechanism of FIG. 23 with an example cartridge inserted.
Figure 26:
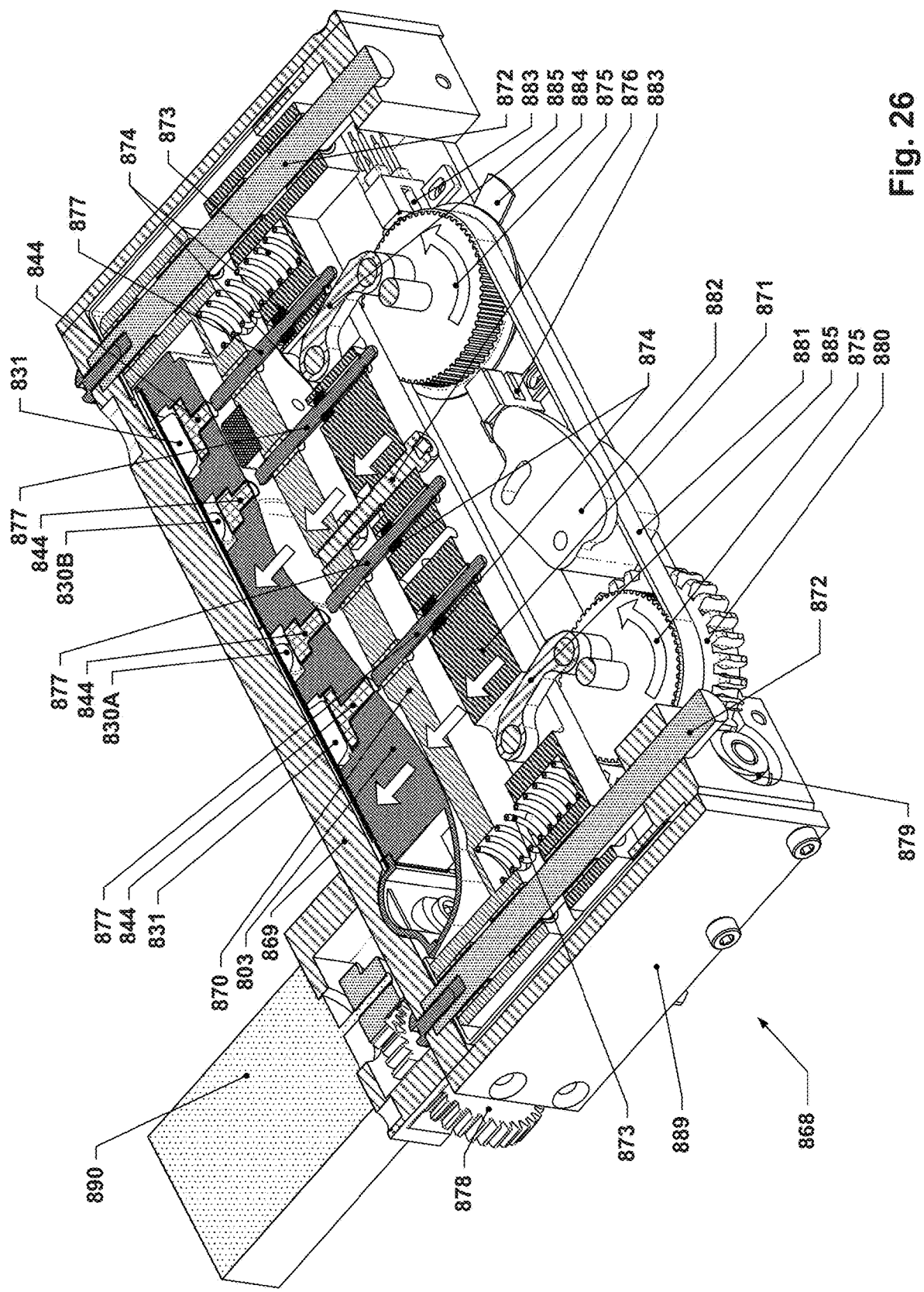
FIG. 26 depicts a cutaway view of the example actuation mechanism of FIG. 23 with the example cartridge clamped.
Figure 27:
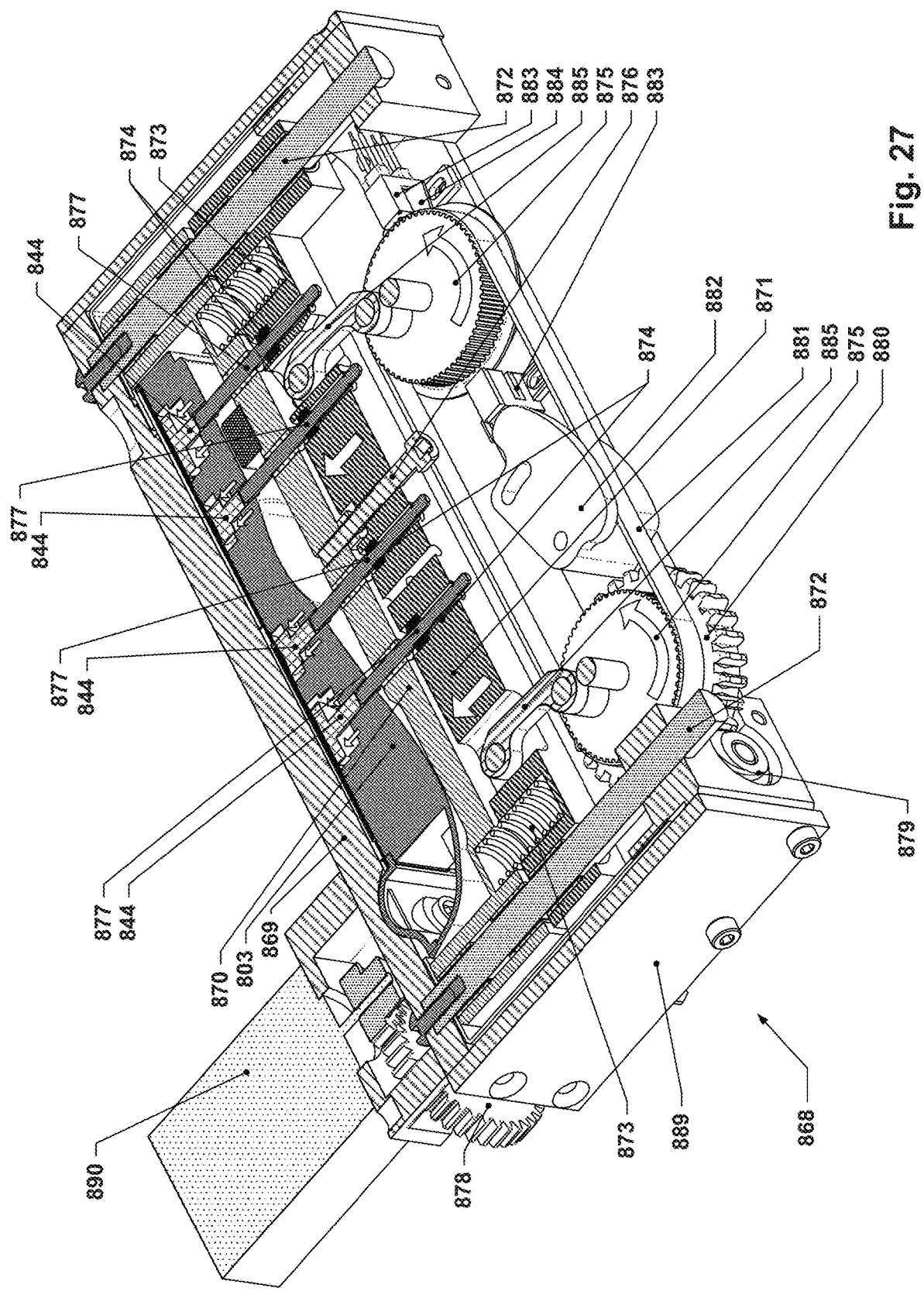
FIG. 27 depicts a cutaway view of the example actuation mechanism of FIG. 23 with the example cartridge ready for analysis to begin.

FIG. 23 depicts an example actuation mechanism. FIG. 24 depicts a cutaway view of the example actuation mechanism of FIG. 23. FIG. 25 depicts a cutaway view of the example actuation mechanism of FIG. 23 with an example cartridge inserted. FIG. 26 depicts a cutaway view of the example actuation mechanism of FIG. 23 with the example cartridge clamped. FIG. 27 depicts a cutaway view of the example actuation mechanism of FIG. 23 with the example cartridge ready for analysis to begin.

As can be seen in FIGS. 23-27, the actuation mechanism 868 may be configured to receive the cartridge 803, and may include an overall support frame 889 that is fixedly mounted to the heat spreader plate 869. A motor 890 may be mounted to the support frame 889 or the heat spreader plate 869; the motor 890 may be controlled to operate the actuation mechanism 868. The heat spreader plate 869 may include, for example, pneumatic supply ports 886 that may interface with the pneumatic control ports 814 on the cartridge 803 when the cartridge 803 is fully loaded into the actuation mechanism 868. The pneumatic supply ports 886, in turn may be interfaced with pneumatic passages in the pneumatic transfer manifold 861 that fluidically connect each pneumatic supply port 886 to one of the valves 865. If a heater component 867 is used, the heater component 867 may be mounted to a surface of the heat spreader plate 869, e.g., to the surface to which the motor 890 is mounted.

The actuation mechanism 868 may include two separately translatable elements—the cartridge clamp 870 and the blister compression frame 871. As can be seen in FIGS. 24-27, the cartridge clamp 870 and the blister compression frame 871 are both constrained to slide along guide rods 872. In the depicted implementation, the cartridge clamp 870 and the blister compression frame 871 are separated by a springs 873 that act to push the two components apart and form a gap between the cartridge clamp 870 and the blister compression frame 871. A floating stop 876 may limit the size of such a gap but may also permit the cartridge clamp 870 and the blister compression frame 871 to be compressed closer to each other, if subjected to sufficient external compressive force. In the depicted implementation, the blister compression frame 871 may be kinematically linked to wheels 875 by links 885 such that rotation of the wheels 875 causes the links to translate the blister compression frame 871 along the guide rods 872. The wheels 875 may, for example, be driven in unison through the use of a belt 881, thus allowed rotational input from the motor 890 to be provided to one of the wheels 875 directly, and then transmitted to the other wheel 875 by the belt 881. Rotational input from the motor 890 may, for example, be provided through drive gears 878, worm gear 879, and driven gear 880. A tensioner 882 may be provided to allow any slack in the belt 881 to be taken out through manual adjustment. It will be understood that other configurations or implementations may feature other mechanisms for translating the blister compression frame 871 along the guide rods 872, and that the present disclosure is not, generally speaking limited to the specific implementations discussed and depicted herein.

As shown in FIG. 25, a cartridge 803 may be inserted into the actuation mechanism 868. The blister compression frame 871 may then be translated towards the cartridge 803 and the heat spreader plate 869, which may, in turn, cause the cartridge clamp 870 to also translate towards the heat spreader plate 869 until it comes into contact with the cartridge 803. At this point, the cartridge clamp 870 may be further translated by the blister compression frame 871, as shown in FIG. 26, so as to push the cartridge 803 into contact with the heat spreader plate 869. Centering features, such as centering feature 888, may engage with corresponding features on the cartridge 803 to guide the cartridge 803 into an aligned state such that, for example, the pneumatic supply ports 886 of the heat spreader plate 869 are aligned with, and seal to, the corresponding pneumatic control ports 814 on the cartridge 803. Once the cartridge 803 is pressed into contact with the heat spreader plate 869, the cartridge housing may resist further compression, resulting in compression of the springs 873 if the blister compression frame 871 is further translated towards the cartridge 803.

As discussed earlier, if a heater component is used to heat the heat spreader plate 869, the actuation mechanism may be paused in the configuration shown in FIG. 26, or driven very slowly, so as to give the heat spreader plate 869 time to thaw any potentially frozen liquids within the cartridge 803.

Once sufficient heating has been performed (assuming that such heating is needed), the blister compression frame 871 may continue to be translated towards the cartridge 803. Actuation posts 877, which may be mounted to the blister compression frame 871, may be caused to insert themselves into the cartridge 803 so as to engage with blister plungers 844 and push them towards the heat spreader plate 869 without further compressing the cartridge 803. The continued translation of the blister compression frame 871 may cause further compression of the springs 873, thereby exerting more pressure on the cartridge 803, but the amount of such compression may be much lower than the compression exerted by the blister compression frame 871 on the blister plungers 844.

As shown in FIG. 27, when the blister compression frame 871 is translated by a sufficient further amount, the buffer blisters 831 and the substrate blisters 830A/B may be compressed by the blister plungers 844, forcing liquid from the blisters into the microfluidic plate. The actuation posts 877 may be mounted to the blister compression frame 871 with some small ability to translate relative to the blister compression frame 871 along the same axis as the blister compression frame 871 translates, thereby allowing some minor variation in the distances traveled by the blister plungers 844 during blister compression. The interfaces between the actuation posts 877 and the blister compression frame 871 may be equipped with Belleville washer stacks, e.g., Belleville washers stacked in alternating directions (a "series" configuration) so as to form a compact, high-stiffness spring that allows the actuation posts 877 to move relative to the blister compression frame 871 only when subjected to a large compressive force, e.g., such as when a blister is completely empty and the associated blister plunger 844 is, in effect, exerting force on incompressible materials between the blister plunger 844 and the heat spreader plate 869.

The actuation mechanism may be equipped with various sensors that may be used to monitor cartridge loading and compression. For example, the actuation mechanism 868 may include one or more photosensors 883, which may be interrupted by an interruptor 884 that is mounted to one of the wheels 875 at different positions, e.g., when the blister compression frame 871 is fully retracted or extended into full compression mode.

It will be understood that other actuation mechanisms may be used as well that provide similar functionality. In some such alternative implementations, the blister compression frame 871 and the cartridge clamp 870 may be separately driven, e.g., by separate motors.

Figure 28:
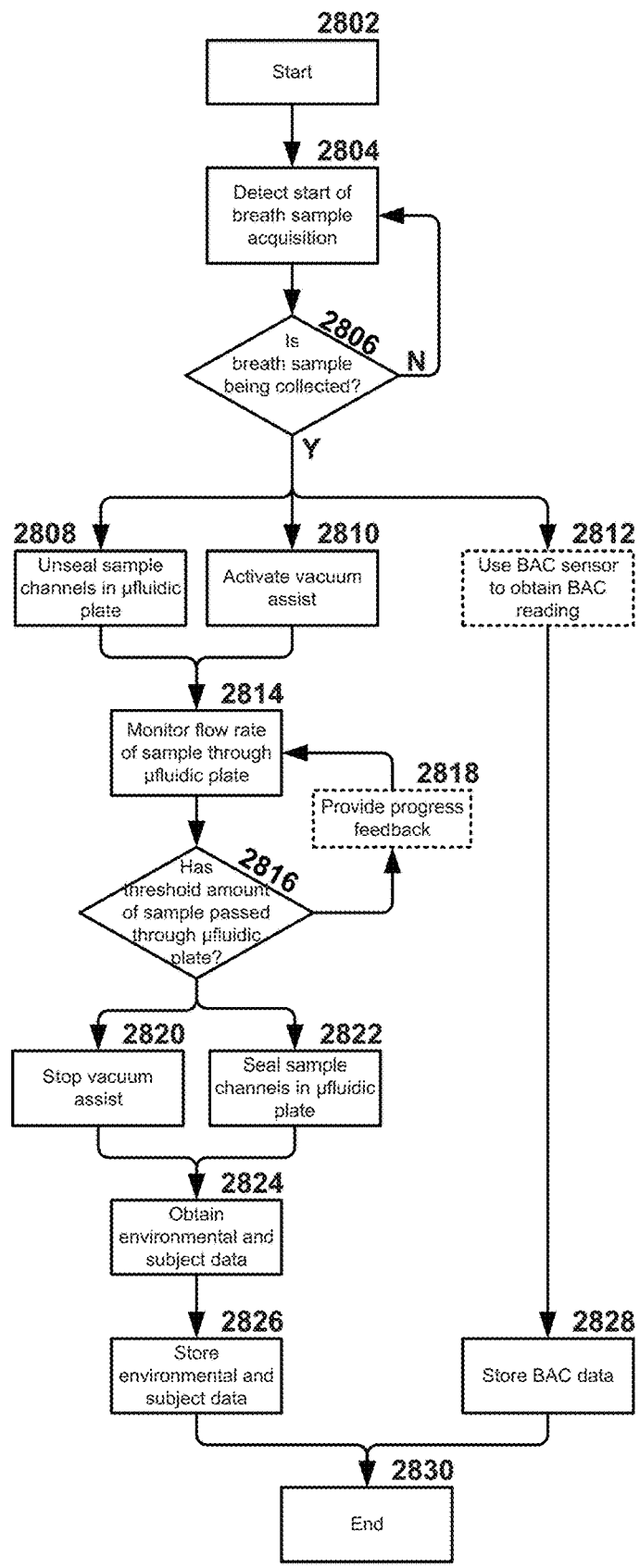
FIG. 28 depicts an example breath sampling technique.
Figure 29:
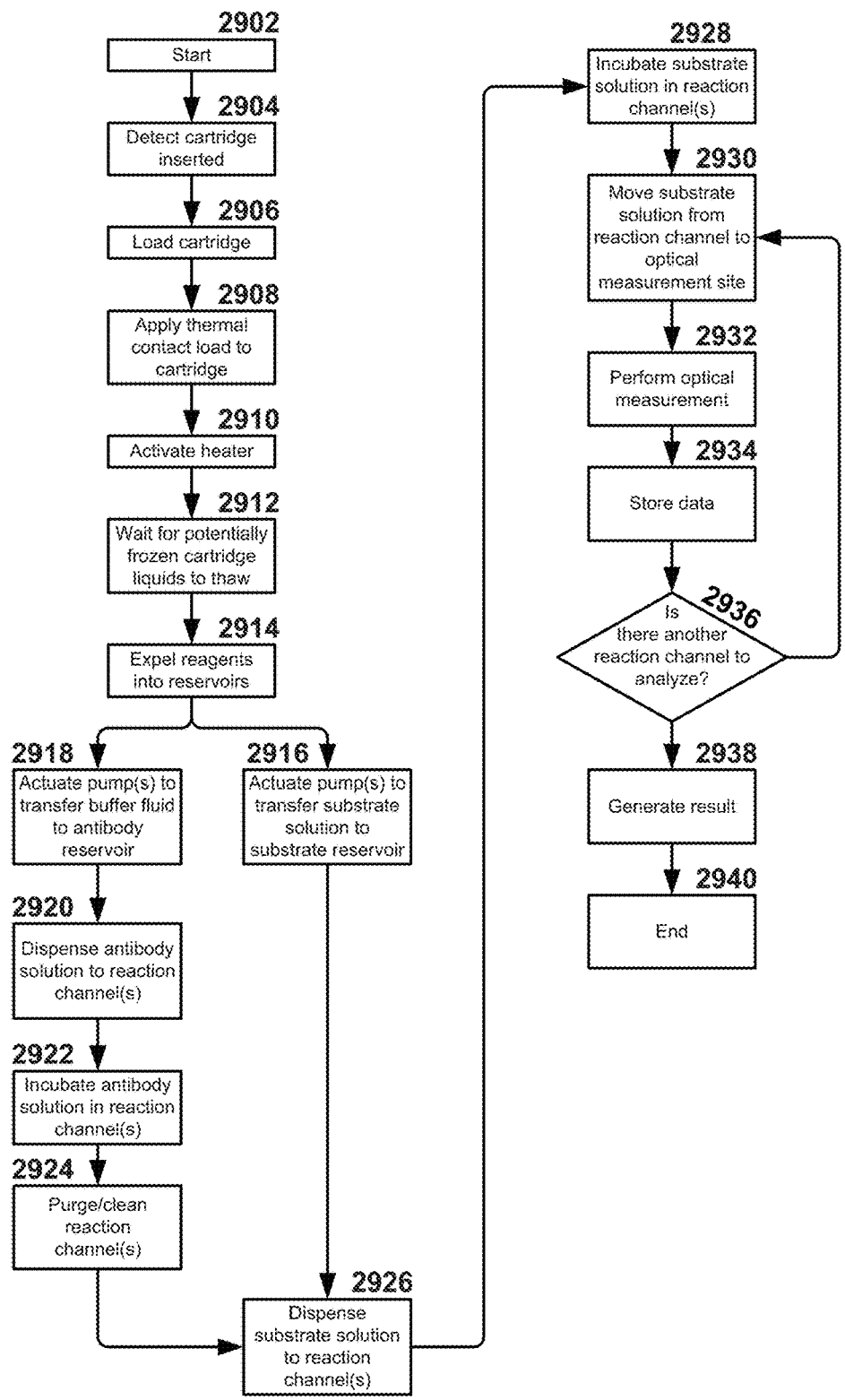
FIG. 29 depicts an example breath sample analysis technique using an insertable cartridge.

For the sake of completeness, some example operational flows that may serve as a functional framework for operation of portions of an example breath sampling and analysis system are discussed below with reference to FIGS. 28 and 29. FIG. 28 depicts an example breath sampling technique. FIG. 29 depicts an example breath sample analysis technique using an insertable cartridge.

In FIG. 28, the technique begins in block 2802. In block 2804, the start of a breath sample collection event may be detected. In some implementations, this may be detected based on user inputs, e.g., a user may push a button on a breath sampling device or may select an on-screen control on a touch-sensitive display in order to initiate a breath sample collection event. In other implementations, the start of a breath sample collection event may be detected based on sensor input, e.g., when a pressure sensor in the collection device detects a pressurization event consistent with the pressure increase that may be experienced due to a subject exhaling into the collection device. In block 2806, a determination may be made as to whether a breath sample collection event has started; if not, the technique may return to block 2804 to check again if a breath sample collection event has started. If so, the technique may proceed to blocks 2808, 2810, and, optionally, 2812. In block 2808, reaction channels, within a microfluidic plate in the collection device, e.g., a cartridge as discussed earlier herein, may be unsealed by actuating isolation valves within the microfluidic plate so as to allow the air sample to be flowed through the reaction channels. In block 2810, the reaction channels may optionally have a vacuum assist applied to them to generate an increased pressure differential between the reaction channels and the flow path, e.g., a plenum of the cartridge, through which the breath sample reaches the reaction channels. Such a vacuum assist may, as discussed earlier, increase the flow rate of breath sample through the reaction channels. If the vacuum assist functionality is used, the vacuum assist may be activated after the isolation valves are opened in some implementation (or, in some addition implementations, concurrently with opening the isolation valves).

In implementations in which the same breath sample is used to obtain both a breath sample for analyte detection and/or measurement and, for example, a blood alcohol reading, a portion of the breath sample may be diverted through a blood alcohol sensor, e.g., a fuel-cell type blood alcohol sensor. The blood alcohol sensor reading may proceed in parallel with collection of the breath sample for later analyte analysis and measurement.

In block 2814, the flow rate of breath sample through the reaction channel(s) may be monitored to determine how much breath sample volume has passed through the reaction channels. In some implementations, a flow sensor, e.g., a mass flow rate sensor, may measure the amount of breath sample that is pumped by the vacuum pump used to provide vacuum assist during breath sample collection. In some implementations, the fluidic flow from the reaction channel(s) may be split downstream of the reaction channels so that one portion of the breath sample flows through the flow sensor to measure the flow rate and the other portion of the breath sample bypasses the flow sensor. In such implementations, both flow paths may have flow restrictions that cause the breath sample portions that flow through each to be in a fixed proportion to one another, e.g., equal-sized flow restrictors may be used to ensure that the flow sensor and the bypass experience equal flow rates (or otherwise constant predetermined flow rate ratios) during normal operation of the breath sample collection device. In such implementations, the flow sensor data may represent only a known portion of the total flow rate through the reaction channels, and the total flow rate through the reaction channels may be determined by multiplying the measured flow rate by the inverse of the percentage of the flow that passes through the flow sensor. In block 2816, a determination may be made as to how much breath sample has flowed through the reaction channels. Once the flow sensor data indicates that a desired amount of breath sample, e.g., 0.5 liters per reaction channel, has flowed through the microfluidic plate, the technique may proceed to blocks 2820 and 2822, in which, respectively, the vacuum assist, if used, may be deactivated and the isolation valves may be closed to seal the reaction channels. If it is determined in block 2816 that the amount of breath sample flowed through the reaction channels is less than the desired amount, the technique may return to block 2814 for further monitoring of the flow rate. In some such implementations, the data from the flow meter may optionally be used to update a progress indicator in block 2818, e.g., to update a display showing the amount (or relative percentage) of breath sample collected, provide audio cues indicating sample collection progress, and/or cause one or more progress indication lights to illuminate.

As discussed, in block 2820, the vacuum assist may be deactivated. As discussed earlier herein, the vacuum assist may, in some implementations, also be temporarily deactivated when data from a pressure sensor monitoring the plenum of the cartridge through which the breath sample is flowed indicates that the subject is no longer exhaling through the cartridge at a predetermined level.

In block 2824, environmental and subject data may be obtained and, in block 2826, stored on a memory device. It will be understood that some such data may be obtained and/or stored at any of a variety of times, e.g., immediately before sample collection, during sample collection, and/or after sample collection. Such data may include information relating to subject vital statistics (name, age/birthdate, gender, height, weight, driver's license number, etc.), environmental conditions at the time the sample was obtained (temperature, humidity, time, location, etc.), and operational information (duration of sample collection time, amount of breath sample flowed through reaction channels, etc.). If a blood alcohol measurement is obtained concurrently with breath sample collection, the blood alcohol measurement may be stored in the memory device as well in block 2828. Once data storage, if performed, is complete, the technique may end at block 2830.

Once a breath sample has been successfully collected, the collected breath sample may be analyzed, e.g., using any of a variety of techniques, as discussed elsewhere herein. One such example analysis technique is discussed below with respect to FIG. 29.

The technique may begin in block 2902. In block 2904, the insertion of a cartridge into the analysis instrument may be detected (assuming that a cartridge is used). Once cartridge insertion is detected, a cartridge loading operation may be performed in block 2906. Such loading may, for example, secure the cartridge within the instrument and may ensure that the cartridge is properly interfaced with components in the analysis instrument, e.g., pneumatic control ports for transferring pneumatic control signals to valves and pumps within a microfluidic plate of the cartridge, electrical connections to components on the cartridge (e.g., memory devices), etc.

In block 2908, force may be applied to the cartridge so as to compress the cartridge against a heat spreader plate or other potential heat source to provide good thermal contact between the cartridge and such a heat source. The application of the thermal contact load may be performed as part of block 2906, and may be optional if no pre-heating of the cartridge is to be performed or if the analysis instrument does not include such cartridge pre-heating functionality, such as may be the case for instruments intended for use in controlled environments, such as laboratories.

In block 2910, a heater may optionally be used to heat the cartridge, e.g., heat from the heater may be transferred to the cartridge via a heat spreader plate. In some implementations, the cartridge may be heated by flowing warm air around and/or through the cartridge. For example, the cartridge may flow paths through the cartridge that allow warm air to be flowed through it such that any potentially frozen liquid reservoirs are exposed to the warm air, thereby allowing the frozen liquid to be thawed. In such convective heating arrangements, the thermal contact loading from block 2908 may be omitted.

In block 2912, if the heater is used, a predetermined amount of time may be allowed to elapse to allow for adequate heating and thawing of any potentially frozen liquids in the cartridge. Such an amount of time may be fixed, e.g., 2 minutes, or may be dynamically adjusted based on feedback from sensors in the cartridge, e.g., if temperature sensors that may optionally be included in the cartridge indicate temperatures that are above a predefined threshold, then a determination may be made that whatever liquids are present in the cartridge are in a liquid state.

Once the cartridge is loaded in block 2906 and any heating-related operations, if any, are performed, the cartridge liquids may be prepared for use in block 2914. For example, in implementations in which various liquids used during the analysis operations are stored in blisters or other long-term storage containers within the cartridge, such liquids may be forced or drawn from such containers and stored in reservoirs that are fluidically connected with the microfluidic plate of the cartridge so that the pumps within the microfluidic plate may cause such liquids to be transported between various locations in the microfluidic plate. Since cartridges may be stored for extended periods of time before being used, liquids that are housed within the cartridge and intended for use in analysis may be stored in long-term storage containers such as the blisters discussed earlier herein to avoid leakage and possible contamination of the liquids. The blisters, for example, may be flexible pouches made from a material that is chemically non-reactive with the liquid contents and that are fluidically connected with fluid flow channels in the microfluidic plate by valves, e.g., rupture, relief, pop-off valves, or the like, that fluidically isolate the blister contents from the microfluidic plate until the contents of the blisters are pressurized to a predetermined level, e.g., by compressing the blisters sufficiently. It will be recognized that other types of long-term storage may be used as well, including storage in sealed glass ampoules where needles are inserted in order to withdraw liquids therefrom. In some implementations, the cartridge may not store any liquids and such liquids may instead be stored within the instrument itself and then transferred to the cartridge via ports on the microfluidic plate, similar to how pneumatic pressure/vacuum is communicated to the microfluidic plate.

Such liquid dispensation from long-term storage containers may be performed, as discussed earlier herein, using a gear-driven press or other compression device, or may be performed with other mechanisms. In implementations where the liquids are already stored in locations that are fluidically connected with the microfluidic plate to begin with, the operations of block 2914 may be omitted if unnecessary.

Once the liquids used during sample preparation and analysis have been staged at appropriate locations within the cartridge, e.g., within reservoirs accessible to the valves, flow channels, and pumps within the microfluidic plate, sample preparation may begin.

In some implementations, some liquid reagents may be stored separately to prevent premature reaction between such reagents. The compound or chemical resulting from such reactions may be necessary in order to perform the analysis, but may have a very limited window of time within which it is stable. In such situations, pumps (and valves, if necessary) of the microfluidic plate may be operated in block 2916 to pump the liquid reagents that are stored separately for long-term storage into a common mixing reservoir so that they can mix to produce the reagent needed for analysis. For example, if a substrate is used during analysis is stored in binary form, the two different portions of the substrate may be pumped into a common reservoir to allow them to mix and form the substrate.

Similarly, in implementations in which some analysis components or reagents may be stored in a lyophilized format, e.g., freeze-dried antibodies, or other non-liquid format, e.g., dried, pulverized diazofunctionalized fluorophoric indicator, one or more pumps (and valves, if necessary) may be actuated in block 2918 to cause an appropriate reconstitution liquid to be flowed from the appropriate reservoir to a reconstitution reservoir containing such non-liquid components. For example, a pump (and valves, if necessary) within the microfluidic plate may be actuated to transfer a liquid buffer from a buffer reservoir to an antibody reservoir containing a lyophilized antibody.

The preceding operations may generally be performed for any of a variety of different analysis protocols, as such operations relate to simply preparing the various types of liquids and reagents that may be used during any given analysis (some protocol-specific examples are given, but the overall steps taken may generally be relevant to a large variety of different protocols). The specific steps discussed below, however, may be different depending on which analysis protocol is actually used. In the interests of conciseness, the technique set forth in the discussion below uses an example protocol similar to that discussed earlier in this disclosure involving a competitive immunoassay. It will be recognized that alternative approaches may use other types of analysis, e.g., diazofluorophore-based analyses, non-competitive immunoassays, etc.

In block 2920, a solution containing reconstituted antibody, as may be produced after the operations of block 2918 are performed for a reservoir containing lyophilized antibody and a suitable reconstitution time is allowed to elapse, e.g., 20-30 seconds, may be dispensed to each of the reaction channels having contents to be analyzed, e.g., a reaction channel containing breath sample as well as reaction channels containing control amounts of analyte.

In block 2922, the antibody solution that was delivered to each of the reaction channels in block 2920 may be allowed to incubate for a predetermined period of time, e.g., 60-70 seconds, to give the antibodies within sufficient time to bind to target antigens, if present, in each reaction channel. Such antigens may include, for example, the analyte that is present in the collected breath sample (or control amounts thereof that are within reaction channels designated as containing control amounts of analyte) as well as antigens that may be immobilized on the surfaces of each reaction channel.

After sufficient incubation time has elapsed, the antibody solution that is present within each reaction channel may be flushed away in block 2924, e.g., by pumping air through each reaction channel, followed by buffer or other suitable cleaning liquid, followed by a further purge with air. In this example, this has the effect of not only removing the antibody solution, but also all or nearly all of the analyte (from the breath sample or the controls) that is present within each reaction channel—only the antibodies that have bound to the immobilized antigen will generally remain in each reaction channel after such an operation.

After block 2924 is performed, a substrate, e.g., such as a substrate mixture/solution that may be created in block 2916, may be pumped into each of the reaction channels. The substrate may then be allowed to incubate in the reaction channels in block 2928 in order to allow the substrate to be activated by, for example, enzymes that may be conjugated with the antibodies that are bound to the immobilized antigen within each channel. Such incubation may, for example, occur for a period of approximately 60 seconds in some implementations.

After sufficient substrate incubation time has elapsed, analysis of the contents of each reaction channel may be performed. In block 2930, the substrate from a reaction channel may be pumped to an optical measurement site. In block 2932, an optical measurement of the substrate at the optical measurement site may be obtained, e.g., by measuring the intensity/amount of luminescence (which may be done in an otherwise dark environment to prevent light contamination). In other implementations, a fluorescent substrate may be used that must be stimulated, e.g., by exposure to light of a particular wavelength, in order to produce light, e.g., light of a wavelength other than the stimulation wavelength).

In block 2934, data relating to the measurement performed in block 2932 may be stored, e.g., in a memory device, for later retrieval. In some implementations, the timestamp for when the analysis/measurement was performed may be compared against a similar timestamp that was stored on the memory and that indicates when the breath sample in the cartridge was collected. In some such instances, if a period of time in between the two timestamps is too high, the cartridge may be flagged as potentially having compromised sample material, e.g., material that may have leaked out to some degree, or that may have been contaminated over time (the microfluidic valves used in microfluidic plates may generally have small gaps in them when unpressurized, allowing for some small degree of leakage—for collected breath samples, this may be of little immediate concern since the analytes are adsorbed onto the walls of the reaction channels, but if sufficient time passes, there may be diffusion/leakage through the unpressurized valves, which may introduce contaminants or allow breath sample to leak out; if the cartridge is analyzed soon after the sample is obtained, however, the risk of this may be reduced or minimized). In some implementations, the base station may be configured to refuse to analyze a cartridge with a breath sample that was collected more than a predetermined amount of time beforehand.

In block 2936, a determination may be made as to whether there are additional reaction channels with substrate to be analyzed/measured. If there are, then the technique may return to block 2930 and an additional pumping operation may be performed to move the substrate from a different reaction channel to the optical measurement site for analysis/measurement.

If there are no additional reaction channels with unmeasured substrate remaining to be measured, then an analysis result may be determined in block 2938, stored for later use, and/or displayed to a user. Such a result may be based, for example, on optical measurement data obtained for the contents of the reaction channel used for breath sample collection as well as the reaction channels having the control amounts of the analyte. As discussed earlier, the control amounts of analyte may be used to establish a relative scale for the optical measurements that allows the optical measurement of the breath sample reaction channel contents to be correlated with an amount of analyte in the breath sample based on the known amounts of analyte in each control.

Those of skill in the art will appreciate that the foregoing method descriptions and process flow diagrams are provided merely as illustrative examples and are not intended to require or imply that the steps of the various embodiments must be performed in the order presented. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

EXAMPLES

The following examples provide additional contextual and supporting material relating to the subject matter of this disclosure. The information presented in these examples should be understood to in no way limit the generality of this disclosure.

Example 1

A summary of a general method for estimating diagnostic performance of a qualitative assay (sensitivity/specificity) from analytical performance of the assay and distribution of true clinical positives is presented. Examples relate to detection of THC concentrations in breath samples with adequate performance for determining recent use.

Definitions

Assay dose response: Function which relates measured Signal as a function of analyte concentration for an assay.

Assay precision: Standard deviation of signal measured for one analyte concentration.

Analytical performance: Includes both dose response and precision.

Distribution of true positives: Histogram of analyte concentration distributions measured from samples which are known to be from subjects who would be considered "positive" for a certain condition. For this project, the true positive cohort consists of subjects who have inhaled or ingested *cannabis* products with some period.

Diagnostic performance: Measure of accurately predicting a Positive or Negative result. This is general quantified by Sensitivity and Specificity, which are measures of true positive rate and true negative rate respectively Cutoff: A concentration (or signal) value selected as part of the assay, which is used to diagnose a sample as either positive or negative.

Recent use: Defined for this project as 2 hours after the cessation of smoking.

Methodology

Analytical performance for the assay is established by empirically determining the assay dose response and precision. This is accomplished by preparing samples with a range of analyte concentrations which mimic the distribution of the true positive samples. Replicate measurements are made at each concentration level, from which the standard deviation, $\sigma_S$, can be calculated. The outputs from this experiment are functions for dose response and precision, $S=f(C)$; $\sigma_S=g(S)$.

Next, a distribution of true positives is determined. This is typically done by conducting a study on real subjects who are part of the population of interest. A positive/negative diagnosis is made using an independent method, which acts as the "true" diagnosis. The assigned condition (positive/ negative) becomes the true diagnosis for the patient. A distribution of true positives and true negatives is thus determined.

To estimate the diagnostic performance of an assay, a virtual cohort of subjects is created and assigned analyte concentrations by random sampling from both true positive and true negative distributions. Each subject in the cohort has an assigned true diagnosis (positive/negative) determined independently. For each subject, the analyte concentration is propagated through the dose response to calculate a mean signal, and noise is randomly added based on the standard deviation of the assay at the respective signal value. This "generated" signal is compared to the signal cutoff selected, based on which, the assay diagnosis (positive/negative) is made. For each subject, assay diagnosis is compared to the true diagnosis, and the result is grouped into four buckets—True Positive (TP), True Negative (TN), False Positive (FP), and False Negative (FN). From these the sensitivity and specificity are calculated as:

Sensitivity=Sum of True Positives/(Sum of True Positives+Sum of False Negatives)

Specificity=Sum of True Negatives/(Sum of True Negatives+sum of False Positives)

The method described can be used to calculate Sensitivity and Specificity based on a certain cut-off, or determine a cut-off based on requirements of Sensitivity and Specificity.

The following example illustrates the method described above. The assay in this example is an Antigen-down, 2Ab Immunoassay for THC. The dose response for this assay follows a 5-parameter Logistic function. Experimental data points can be plotted and a line theoretically fit. For this example, the theoretical fit is used to calculate signal at an arbitrary concentration.

For the noise model, standard deviations at each concentration level were calculated across 3-4 replicates. For this data set, the noise model was calculated to be $\sigma_S$=0.05 S.

To calculate distribution of analyte concentrations in samples taken from the population of interest, data from office studies was used. Mass spec concentrations measured in breath samples collected from subjects at time points greater than 60 min after smoking *cannabis* was used to construct a concentration distribution. This empirical distribution was fit to a theoretical distribution function. It was found that an exponential distribution fit the data well. The cumulative distribution for this data can be described by a simple function, $P(c \leq c_0) = 1 - \exp(-c_0/452.5)$.

Diagnostic Performance as a Function of Cut-Off

Using the assay analytical performance and distribution of concentrations described above as inputs, sensitivity/specificity can be calculated as a function of cut-off. All calculations were done in R, an open-source programming language (https://cran.r-project.org/). The calculation steps are detailed below:

1. 10,000 virtual samples were created, and each was assigned a mass of THC, randomly sampling from the exponential distribution described above.
2. A range of cut-off mass between 1 pg and 1000 pg was chosen for calculating assay diagnostic performance.
3. A cut-off value is selected. Based on the selected cut-off, each sample is assigned a "true" diagnosis—positive or negative. In a real application, this cutoff would be determined independently (e.g., 0.08 for Blood Alcohol Content).
4. The corresponding signal value at the selected cut-off is calculated by using the dose response profile. This is the cut-off signal value for the assay. In actual use, the signal cut-off is chosen to be the signal at the cut-off concentration defined in #3.
5. For each of the 10,000 virtual samples, their corresponding THC mass is converted into a signal value using the dose response. A random noise is added to the mean signal based on the noise model. This is done by sampling a Gaussian distribution with mean given by the signal value, and SD given by the noise model.
6. The calculated signal values are compared against the cut-off signal value, and an "assay" diagnosis is assigned.
7. Assay and true diagnoses are compared for all samples, and sensitivity/specificity values are calculated.
8. Steps 4-7 are repeated for all cut-off mass values.

The results from this simulation indicate a value of 0.9, which is arbitrarily selected as an acceptable passing mark for both sensitivity and specificity. It is seen that sensitivity drops sharply with higher concentrations. Specificity is noisier, which is mostly due to insufficient statistics, especially at low cut-off values. Based on this example, this assay has acceptable diagnostic performance at a range of cut-off values between 1 and 100 pg. As a corollary to this, if the cut-off value is independently set at 10 pg, the assay has a sensitivity of 0.99 and a specificity of 0.91.

A reliably detectable pg-level threshold (e.g., 10-25 pg THC/5 L of breath (2-5 pg/L)) that is believed to correlate to THC impairment, or at least recent use, has been determined.

Example 2

A summary of details about the materials and processes used in an example immunoassay method for detecting THC in breath samples is presented.

Materials

Primary (anti-THC antibody): There are two broad types of Antibodies used in Immunoassays—Polyclonals and Monoclonals. Polyclonal antibodies are more diverse and can detect a wider range of molecules. This makes them insensitive to minor changes to molecular structure, which can be important for a small molecule such as THC. Monoclonal antibodies are highly specific to the exact antigen. They are also more consistent from batch to batch since they mostly consist of one type of antibody. As a result, they can be produced by synthetic methods (e.g., Hybridomas).

For detection of THC from breath, either type of antibody can be used. Since breath samples are quite clean, especially after filtering out any saliva, molecular variants and other proteins which can bind to the anti-THC antibody are mostly absent. The selection of antibody for THC is mostly driven by practical considerations such as availability, lot-to-lot consistency, etc. A variety of suitable commercially available kits may be adapted for this use, including MaxSignal-THC-ELISA-Test-Kit or Cannabinoids ELISA Kit, available from mybiosource.com, or others available from fitxgerald-fii.com, novusbio.com and biossusa.com.

Antigen: Synthetic THC (Delta 8-, Delta 9-) or any of its variants (THCA, for example) can be directly adsorbed on to the surface for the antigen-down formats. THCA may offer some advantages over THC since it has a higher resistance to oxidation. The choice between Delta 8- or Delta 9-in conjunction with selection of antibody allows one to fine-tune the relative binding affinities between the antibody and the competitive antigen v/s antibody and the sample. THC/THCA can also be conjugated to a protein such as BSA to enhance strength of adsorption to the immobilization surface.

Reporter: For good sensitivity at low analyte concentrations, fluorescence and luminescence are the preferred signal generation schemes, since both methods offer good low-end sensitivity. Luminescence has the further advantage from a system perspective of not requiring an illumination source and spectral filters. Among luminescence reporters, Horseradish Peroxidase (HRP) and Alkaline Phosphatase (AP) are most commonly used. AP is a better candidate in formats where the total reporter concentration is low.

In a competitive assay, absolute concentrations of reporter enzyme are relatively high. In this case, HRP may be a better choice since it has much faster kinetics allowing for shorter assay times.

Assay Optimization

Clinical data can be used to define the optimal cut-off concentrations for THC detection. A primary goal of assay optimization is to maximize modulation (slope of the dose-response curve) at this desired cut-off concentration. In addition to selection of the different components (discussed above), the concentration of reagents can be optimized to maximize modulation. Two parameters to be optimized are (1) Ratio of analyte concentration in sample to the concentration of competitive antigen and (2) Ratio of concentration of competitive antigen to concentration of primary antibody.

For a qualitative assay with a defined cut-off concentration, when the competitive antigen and primary antibody concentrations are of the same order of magnitude (in Molar concentrations) as the cut-off concentration it results in the dose response curve having a maximum slope at the cut-off to maximize assay sensitivity and specificity.

Based on models, it is estimated that the maximum dose response is achieved by maintaining a primary antibody concentration which is in excess of the target analyte concentration, while keeping a molar ratio of close to unity for the competitive antigen and the primary antibody.

The optimization process involves varying concentrations of competitive antigen and primary antibody until a maximum is observed in the dose response curve at the cut-off concentration. Mathematical models can be used as a starting guess for these concentrations, which are fine-tuned by experimental data.

THC Immunoassay in a Flowcell

A flowcell may be used as the reaction geometry for the immunoassay. The flow cell will have an inlet and outlet port. A fluid manifold acts as the reservoir for all reagents, and directs fluid to and from both the flowcell and the breath collection module (BCM). The detector directly reads the final signal from the flow cell.

Miniature flowcells, having cross-sectional dimensions of about 100 um-few millimeters, are a good platform for immunoassays. The small dimensions of the flow channel results in a high surface area to volume, which is favorable for surface reactions such as those in immunoassays. Custom flowcells may be fabricated to integrate with particular microfluidics architecture.

Prior to using the flowcell for a THC assay, the flowcell is coated with the surface moiety (antigen or anti-body depending on the format). In this example, an antigen-down format is assumed. The antigen is diluted to working concentration, and is flown into the flowcell, ensuring that the flow cell is completely filled. This is followed by incubation to ensure that the antigen is immobilized onto the surface. Any excess antigen is washed away by flowing a buffer solution through the flowcell multiple times. A blocking buffer is then introduced into the flowcell and incubated, to cover any bare surfaces which are not occupied by the antigen. This reduces non-specific binding and improves assay precision. The blocking step is particularly important in the flowcell geometry, due to the high surface area/volume ratio, which facilitates both specific and non-specific binding. The flow cell is finally washed and dried, and is ready for use.

Sample, diluted to an appropriate concentration, is introduced into the coated flow cell, and allowed to bind with the coated antigen. The rest of the assay process is like a standard microtiter plate assay. The volumes used in the flowcell may be considerably lower (about 10-50 uL) compared to what is used in a standard 96-well microtiter plate (about 100-200 uL).

The final signal is generated in the flow cell, which is read by a detector positioned either underneath or above it. The footprint of the complete device can be very small due to the small dimensions of the flowcell.

Assay and Process Optimization

Transitioning the assay from a standard microtiter plate to a flow cell may involve further optimization of reagents and processes. As briefly stated before, the blocking step can be important in ensuring that non-specific binding is minimized. Both the concentration and composition of the blocker might have to be modified to maximize dose response and minimize variability. The wash steps during the assay also enhance the performance of the assay. Wash parameters such as number of wash steps, composition of wash buffer, flow rates, residence times, etc. are all important to the performance. These steps may be optimized empirically.

Example 3

THC in Breath: Data from Development of a Marijuana Breathalyzer

THC is detected in breath for about 2-3 hours on average. Data on breath THC was collected after smoking indoors or outdoors, rather than in a laboratory setting. People have high levels of THC in their breath immediately after smoking. Breath THC drops to almost zero after 2-3 hours. Studies by the National Institute of Health (NIH) in 2013 and a European group in 2016 show a similar 2-3 hour time period. The 2-3 hours that THC is measured in breath correlates to the window of greatest impairment, as defined by NHTSA. The data were collected in 430 tests, more than all published studies combined. All samples were collected using a device developed by Hound Labs, Inc. and analyzed using mass spectrometry (MS).

Frequent smokers have virtually no THC in their breath if they have not smoked for several hours. Baseline breath THC in chronic smokers was found to be a maximum of 12 pg/5 L breath. A suitable breathalyzer can be calibrated so that very low THC levels will not trigger a positive test. This means frequent smokers—who often have substantial THC in their saliva, blood and urine long after the 2-3 hour window of impairment—do not have appreciable THC in breath after 2-3 hours and will not test positive on such an appropriately calibrated device.

The precise level of THC in breath is not important. Unlike alcohol, someone with a higher level of THC in breath is not necessarily "more stoned" than someone with a lower level. Environment plays an important role in THC breath levels. People who stay indoors after smoking have much higher levels than those who go outdoors—their peak levels may be 100 times higher. But breath THC levels drop substantially once they are outside, even though impairment is not affected by being outdoors versus indoors. A marijuana breathalyzer should be ultrasensitive so that it can accurately detect people who smoke outdoors, where levels often are very low during the 2-3 hour window of impairment.

People exposed to secondhand smoke will only have THC in their breath for a very brief time, and it disappears after a person is no longer exposed to this smoke. It is important that people exposed to secondhand smoke be placed outdoors or in a well-ventilated area for 15 minutes before a breath test is performed. This is akin to alcohol testing, where the subject is observed for a minimum of 15 minutes so that alcohol in mouth vapors (which may dramatically elevate the level) dissipates before the breathalyzer is administered.

The science necessary to measure THC in breath is enormously complex. THC is measured in parts per trillion (picograms, pg), which means it is up to one billion times less prevalent in breath compared to alcohol. To put it another way, measuring THC in breath is like cutting a single raisin into 1 trillion pieces or finding one specific drop of water in 20 full sized Olympic swimming pools. The level of sensitivity required to measure THC is unprecedented.

Other Biomarker Detection

As discussed earlier herein, while the above discussion has focused primarily on techniques and systems for detecting THC, similar techniques and systems may also be used to detect a large variety of various other biomarkers of physiological interest, such as infectious diseases and those items listed in the exemplary Table of FIG. 10. Biomarkers for a variety of physiological conditions and/or diseases are known to exist in breath. However, accurate measurement of breath-borne biomarkers is very challenging. Also, the following discussion relates more particularly to general techniques methods, devices, and systems for noninvasive point-of-care biomarker collection and analysis, including from breath samples, and it should be understood that such systems and techniques may be used for the purposes of THC (or analytes thereof) detection and/or measurement in breath samples as well as for other biomarkers, e.g., biomarkers relating to a disease or a physiological condition, including with noninvasive point of care testing (POCT) devices and systems, particularly, with portable such devices and systems.

A partial list of terms used in the following discussion are defined below:

Small Molecule: Species with <1 kDa molecular weight.
Macromolecule: Very large molecule with molecular weight >>1 kDa typically with multiple functional subunits. The macromolecules referenced by this document include biological species such as proteins, peptides, nucleic acids, etc.
TBI: Traumatic Brain Injury
Binder: A recognition macromolecule which has a binding affinity specific to another macromolecule or small molecule. Examples include antibodies, aptamers, peptides, nucleotides, etc.
GFAP: Glial Fibrillary Acid Protein, a peptide which has been identified as a biomarker for TBI.
NSE: Neuron-Specific Enolase: An enzyme which has been identified as a biomarker for TBI
UCH-L1: Ubiquitin C-Terminal Hydrolase L1, a protein which has been identified as a biomarker for TBI.
LOD: Limit of Detection
ALF/ELF: Alveolar Lining Fluid/Epithelial Lining Fluid—A surfactant-rich liquid lining the inside of the lung at the interface between air and alveolo-capillary cell layer.

Overview

Disclosed herein are methods, devices, and systems to detect breath-borne biomarkers (analytes) using noninvasive point of care testing (POCT). Embodiments for implementation may that include functional elements (or modules) including breath capture, detection method, and chemistry modules, including noninvasive point of care testing (POCT) devices and systems, particularly portable such devices and systems.

Disclosed herein are methods, devices and systems to detect breath-borne biomarkers (analytes) using noninvasive point of care testing (POCT). Embodiments for implementation may include functional elements (or modules) including breath capture, detection method, and chemistry modules, including noninvasive point of care testing (POCT) devices and systems, particularly portable such devices and systems.

Point of care testing (POCT), also referred to as bedside testing, is commonly defined as medical diagnostic testing performed at or near the time and place of patient care. POCT typically involves portable equipment and on-site sample collection and analysis. This may be contrasted with conventional medical diagnostic testing which is mostly confined to a medical laboratory, involving sending specimens away from the point of care to the laboratory and then waiting hours or days to learn the test results, during which time care would necessarily have to continue without the results. POCT is generally accomplished through the use of portable, including handheld, instruments, and can sometimes be conducted by patients themselves (e.g., at home) or by medical personnel whose primary training is not in the clinical laboratory sciences. Potential benefits include more rapid and effective decision making in hospital, clinical and home contexts, potentially resulting in more effective hospital and clinical care in reduced time, and enhanced home care for reduced hospital visits.

To date, POCTs exist for a variety of indications, but advances remain to further develop the enormous potential of the technology.

In one embodiment of this disclosure, method includes capturing an exhaled breath sample from a subject in a POCT context, and/or wherein the exhaled breath sample comprises aerosol droplets and the aerosol droplets are captured by impaction.

Capture by impaction provides a versatile approach that is readily adaptable to the capture of a wide range of biomarkers in breath. Breath borne biomarkers have been found to exist primarily in a non-volatile state in aerosolized droplets formed in the deep lung. As a result, the capture target is aerosolized droplets that can be viewed as particles having a an aerodynamic behavior based almost entirely on their size and shape, rather than the particular chemical or other affinity properties of an analyte of interest, as would be the case for a volatile target species. Since the capture is primarily based on the size of the aerosol droplets in the exhaled breath sample, the capture device may be configured in the same or similar manner to capture virtually any biomarker, by impaction. Then, the detection methodology may be tailored to the particular analyte(s) of interest in the aerosolized droplets captured by impaction, as further described below.

The described methods, devices and systems also have the merit of high yield capture of the component of an exhaled breath sample containing the biomarker(s) of interest, namely the aerosolized droplets originating in the deep lung. By contrast, alternative prior or potential methods of detecting breath-borne biomarkers have relied on affinity methodologies optimized for collection of volatile species in breath, or collection of breath condensate samples. Affinity-based collection techniques have low yield since breath borne biomarkers have been found to primarily be in non-volatile form and so with limited to no availability for affinity-based collection. Further, affinity-based collection of biomarkers requires very specific chemical or immunological targeting of the species to be collected, which limits the generality of the approach. Breath condensate collection, on the other hand, while general, lacks the specificity of capture by impaction and so provides a sample this is much less concentrated in and focused on the biomarkers of interest. This is a substantial impediment when attempting to meaningfully and reliably detect and measure very small quantities of analyte, such as exist in breath.

Described methods, devices and systems have the merits of sample capture by impaction and/or in a point of care format.

In one embodiment of this disclosure, a method includes capturing an exhaled breath sample from a subject, wherein the exhaled breath sample comprises aerosol droplets and the aerosol droplets are captured by impaction, measuring an amount of an indicator biomarker in the captured aerosol droplets, the indicator biomarker associated with existence of a physiological condition in the subject, and determining, based on the measurement, the existence of the physiological condition in the subject. The sample capture, measurement and determination can all be conducted at the point of care, for example using portable devices and systems configured to capture and analyze the sample and provide the measurement/result at or near the time and place of sample collection.

In one implementation of this embodiment, the method further involves measuring an amount of a reference biomarker in the captured aerosol droplets, the reference biomarker known to exist at a stable concentration in the subject, and the determining involves a comparison of the indicator biomarker measurement and the reference biomarker measurement.

As further described below, this concept of using a reference biomarker (or normalizing measurand, NM) can be used to facilitate quantitative measurement of biomarkers in captured breath samples. The reportable for these biomarkers is a concentration based on mass per unit volume of lung fluid (also known as Alveolar Lining Fluid—ALF). ALF is found in the deep lung and its composition is in equilibrium with blood. Exhaled breath samples carrying aerosolized drops of ALF are captured. Due to the nature of exhaled breath, the volume of ALF per unit volume of breath can be inconsistent, so quantifying the mass of another, reference analyte, the concentration of which is constant across multiple samples and subjects, can facilitate accurate measurement since the biomarker concentration of interest can then be represented as a ratio of mass of biomarker to mass of NM.

Thus in another embodiment of this disclosure, a POCT method includes non-invasively capturing a biological sample from a subject, measuring an amount of an indicator biomarker in the captured biological sample, the indicator biomarker associated with existence of a physiological condition in the subject, measuring an amount of a reference biomarker in the captured biological sample, the reference biomarker known to exist at a stable concentration in the subject, and determining, based on the measurements, the existence of the physiological condition in the subject, wherein the sample capture, measurement and determination are conducted at the point of care. The biological sample may be an exhaled breath sample comprising aerosol droplets comprising the indicator and reference biomarkers, and the aerosol droplets may be captured by impaction.

Where the determining includes comparing the indicator biomarker and reference biomarker amounts, the concentrations of those biomarkers may be measured to determine a concentration ratio.

In some embodiments, measuring an amount of an indicator biomarker in the captured biological sample may include measuring a plurality of indicator biomarkers associated with existence of a plurality of physiological conditions in the subject, and the determining may include determining the existence of any of the plurality of physiological conditions in the subject.

In some embodiments, the reference biomarker may be known to exist at a stable concentration in the subject regardless of the existence of the physiological condition in the subject.

In some embodiments, the reference biomarker may be known to exist at at least a minimum concentration in the subject.

In some embodiments, the biological sample is an exhaled breath sample comprising aerosol droplets comprising the indicator and reference biomarkers, and the aerosol droplets are captured by impaction.

In some embodiments, the indicator biomarker is selected from the group consisting of glucose, 8-isoprotane, GFAP, and combinations thereof.

In some embodiments, the measuring is conducted using one or more of a chemiluminescence assay, an immunoassay, an enzymatic assay, and by electrochemical detection.

In some embodiments, the sample capture, measurement and determination are all conducted with a portable point of care device.

In other embodiments, a device in accordance with this disclosure includes a sample capture module configured for capture of an exhaled breath sample from a subject, wherein the exhaled breath sample comprises aerosol droplets and the aerosol droplets are captured by impaction, and a sample component analysis module configured for measuring an amount of an indicator biomarker in the captured aerosol droplets, the indicator biomarker associated with existence of a physiological condition in the subject and determining, based on the measurement, the existence of the physiological condition in the subject. The sample capture and analysis modules may be comprised in a portable point of care device.

In one implementation of this embodiment, the device is further configured to measure an amount of a reference biomarker in the captured aerosol droplets, the reference biomarker known to exist at a stable concentration in the subject, and the determining involves a comparison of the indicator biomarker measurement and the reference biomarker measurement.

In one implementation of this embodiment, a device includes a sample capture module configured for non-invasive capture of a biological sample from a subject, a sample component analysis module configured for measuring an amount of an indicator biomarker in the captured biological sample, the indicator biomarker associated with existence of a physiological condition in the subject and for measuring an amount of a reference biomarker in the captured biological sample, the reference biomarker known to exist at a stable concentration in the subject, and for determining, based on the measurements, the existence of the physiological condition in the subject. The sample capture and analysis modules may be comprised in a portable point of care device.

In other embodiments, a system in accordance with this disclosure includes, a point of care device, the device including, a sample capture module configured for capture of an exhaled breath sample from a subject, wherein the exhaled breath sample comprises aerosol droplets and the aerosol droplets are captured by impaction, and a sample component analysis module configured for measuring an amount of an indicator biomarker in the captured aerosol droplets, the indicator biomarker associated with existence of a physiological condition in the subject, and determining, based on the measurement, the existence of the physiological condition in the subject. The sample capture and analysis modules may comprised in a portable point of care device, the point of care device operating to: capture an exhaled breath sample from a subject, wherein the exhaled breath sample comprises aerosol droplets and the aerosol droplets are captured by impaction, measure an amount of an indicator biomarker in the captured aerosol droplets, the indicator biomarker associated with existence of a physiological condition in the subject, and determine, based on the measurement, the existence of the physiological condition in the subject. The sample capture, measurement and determination may be conducted at the point of care.

In one implementation of this embodiment, the system device is further configured to measure an amount of a reference biomarker in the captured aerosol droplets, the reference biomarker known to exist at a stable concentration in the subject, and the determining involves a comparison of the indicator biomarker measurement and the reference biomarker measurement.

In one implementation of this embodiment, a system device includes a sample capture module configured for non-invasive capture of a biological sample from a subject, a sample component analysis module configured for measuring an amount of an indicator biomarker in the captured biological sample, the indicator biomarker associated with existence of a physiological condition in the subject and for measuring an amount of a reference biomarker in the captured biological sample, the reference biomarker known to exist at a stable concentration in the subject, and for determining, based on the measurements, the existence of the physiological condition in the subject. The sample capture and analysis modules may be comprised in a portable point of care device.

Details for implementation of some embodiments of the described methods, devices and systems follow. One of the challenges encountered when attempting to perform biomarker detection in breath samples is that many biomarkers are present in very small quantities in a typical exhaled lung volume (as noted earlier with respect to THC—many other biomarkers may exhibit similar degrees of presence or concentration in exhaled breath as well, making collecting a sufficiently large sample for detection from a reasonable number of exhalations extremely challenging). In view of this, an efficient and effective capture mechanism for obtaining breath samples, e.g., a breath capture module (or, alternatively, breath collection module) may be used to collect breath samples that can then be analyzed using any of the techniques discussed herein.

Design of a breath capture module (BCM) begins with considerations on source and form of the target analyte in breath. With the exception of volatile small molecules, all other small molecules and macromolecules are present in breath encapsulated in aerosolized liquid drops in the range of about 0.5 µm-10 µm. The composition of the liquid drops consists primarily of water with other macromolecules associated with the respiratory tract.

For aerosolized liquid drop targets, a mechanism of capture based on inertial impaction may be particularly effective, and a BCM may be designed with channels incorporating turns and bends to facilitate drop capture through inertial impaction, as will be discussed in more detail below. A two-stage mechanical filtering system may be used in some implementations to help screen out droplets that are larger and/or smaller than a desired size range of droplets. For example, a saliva trap, such as saliva traps used with blood alcohol sensors, may be placed upstream of an inertial impaction droplet trap to filter out droplets that are larger than the upper end of the desired size range, e.g., larger than 100 µm, and the inertial impaction droplet trap may then be used to filter out those smaller droplets that pass through the saliva trap but are larger than the lower end of the desired size range, e.g., larger than 0.1 µm. The droplets that are captured by the inertial impaction droplet trap may generally be of the desired size range and may then, for example, be eluted out of the inertial impaction trap in order to be conveyed to a downstream analysis system or may, in some implementations, simply be analyzed in-situ. Example inertial impaction droplet traps are discussed in more detail later below.

In addition to the channel geometry, substrate material used for the fabrication of BCMs may be selected, in some implementations, based on the properties of the target of interest. For molecular capture, the substrate material may be chosen such that the target has an affinity for the surface of the material and is immobilized on that surface after contact. The material may also facilitate release of the target into solution during elution or assay steps. Generally, the material may be weakly hydrophilic for a hydrophilic target and weakly hydrophobic for a lipophilic target.

However, for various non-volatile aerosolized species discussed in this disclosure, the BCM material may be designed to capture liquid drops, the primary constituent of which is water. For hydrophilic targets, a weakly hydrophilic substrate will enable retention of liquid drops during capture while facilitating release of these drops during elution or reaction steps. For hydrophobic targets, a strongly hydrophilic surface will discourage the target from adhering to the surface during elution or reaction steps. Macromolecules, particularly large proteins, are amphiphilic, which means they consist of both hydrophobic and hydrophilic regions. A hydrophilic capture material is appropriate for these molecules as well.

In addition to surface characteristics, e.g., hydrophobicity or hydrophilicity of the material used for the sample collection sites of the BCM, analysis systems that interface with the BCM may be designed to facilitate efficient retrieval of collected samples, e.g., through use of properly selected eluents, e.g., elution buffers.

Typical captured droplets from exhaled breath may include a high percentage (>50% by mass) of surfactants such as phospholipids, such as DPPC (dipalmitoylphosphatidylcholine). These surfactants may include long-chain aliphatic carboxylic acids which render them highly lipophilic. When aerosol droplets are captured on a surface, due to the extremely low volumes (pL or less) of droplets, the water contained in these droplets can evaporate very quickly (especially considering the flow of exhaled air that flows past them during collection), resulting in a concentrated patch or "scab" of lipophilic surfactants on the surface(s) of the collection sites in the BCM. It is within these "scabs" that the analytes or biomarkers of interest may be trapped. The challenge with elution is to then encourage dissolution of the phospholipids in order to release the species of interest into solution for subsequent transport, reaction, and/or analysis.

As discussed above, surface modifications, e.g., surface treatments to render the surfaces on which the "scabs" form more or less hydrophilic or hydrophobic, may be used to increase or enhance the recovery of collected sample material.

Surface modification may be used to create a surface which prevents phospholipids from forming a "scab" on the surface of the BCM (or at least from forming a "scab" that is strongly adhered to that surface). Potential modifications include coating the surface with polymers such as tri-block copolymers containing repeating ethylene oxide and propylene oxide groups or biological macromolecules such as proteins (examples include BSA, casein, etc.). In these two cases, the mechanism of deposition of the surface treatment may be physical adsorption, wherein the coating agent is allowed to incubate with, for example, a bare plastic surface of a BCM, and the agent is allowed to adsorb onto the surface, forming a barrier. Alternately, the surface can be treated chemically to impart specific functionality. Silanizing is one such method of surface treatment. In this process, a silanizing agent such as trichloro silanol may be allowed to react with the plastic surface (or alternately air) to form a silanized coating on the surface. The silanized coating creates a barrier between the phospholipids and the bare plastic surface. Such coatings reduce the energy needed to decouple the collected sample from the BCM surfaces and place the constituents thereof into solution.

With reference to the example of TBI, biomarkers such as GFAP, NSE, and UCH-L1 are macromolecules and are expected to be transferred into the ALF from blood. ALF is present in exhaled breath as aerosolized droplets, for which a BCM geometry based on inertial impaction can produce high capture efficiency. A hydrophilic material may be used for capturing these droplets in order to facilitate re-suspension of these droplets during subsequent elution/reaction steps. Suitable materials for such a BCM may include Polystyrene, PETG, Glass, etc. A BCM with a hydrophilic material (treated polystyrene, PETG, glass, etc.) in a geometry designed for inertial impaction may provide good capture of droplets/particles of interest.

Another mechanism that may be used, alternatively or additionally to surface modification, involves selecting appropriate elution solvents targeted to solubilize the phospholipid "scab" and release the species of interest into solution. Addition of surfactants such as polysorbate 20 (such as Tween 20) or Triton (offered by Dow Chemical Company) in the range of 0.1-1% by mass can assist in solubilizing phospholipids dried on the surface of the BCM.

In addition to surfactants, other agents which may be alternatively or additionally used to solubilize phospholipids may also be added to improve elution efficiency. Of particular interest are a class of bile acid salts—sodium salts of cholic acid and deoxycholic acid, which have a biological function of digesting cellular membranes and are hence very effective in solubilizing phospholipids. Typical concentrations of these bile salts range between 0.1-1%. These bile salts can also be used in combination with other surfactants for potentially synergistic effects.

Phospholipases, a class of enzymes which are specific to digesting phospholipids, may also be used to solubilize DPPC and release the biomarker of interest into solution. Phospholipases A, B, C, and D act on different regions of the phospholipid molecule. A combination of these enzymes in concentrations of 0.01-0.5 IU/mL may be used in the elution buffer in some implementations.

The pH of the elution buffer may also contribute to solubilization of the biomarker of interest. For example, THC has higher solubility at pH>8, in which case the elution buffer used for THC collection may be selected to have a high pH, e.g., >8. Buffers such as MOPS, carbonate, borate, Tris, etc. can be adjusted to a pH between 8-10 and may thus be suitable for such usage. The higher pH may be combined with other strategies described above to maximize solubilization of target biomarker.

A BCM for capture aerosol drops via inertial impaction may be designed, according to the principles and concepts outlined herein, to intercept aerosol particles >0.7 μm, for example, and retain them on the walls of a channel through which breath is flowed while the BCM is used to collect a breath sample. Multiple impaction sites may be incorporated into the BCM to provide for parallel capture of droplets, thereby allowing for higher droplet collection efficiency and greater breath throughput.

In addition to flow considerations, a handheld BCM design may, in some instances, also facilitate specific breathing profiles such as rapid inhalation, rapid exhalation, coughing, etc. to stimulate production of volatiles or aerosol drops from appropriate regions of the respiratory tract. This can be accomplished, for example, using sensors such as pressure, flow rate, and CO2 sensors to monitor breath sample collection.

Detection Method

Any appropriate assay or sensor, including immunoassays, chemical assays, enzymatic assays, electrochemical detection/sensors, etc., may be used to detect and quantify the biomarker(s) sought. Detection methods that can be suitable in various embodiments include chemical detection, such as the diazo-based chemical methods described above with reference to THC, immunoassays, also described in detail above with reference to THC, both adaptable to a full range of other biomarkers using well-known and readily available chemistry and techniques, and enzymatic assays or electrochemical sensors, for example.

In an enzymatic assay, the analyte of interest is either a substrate or co-factor for a specific enzyme resulting in a chemical reaction which generates signal. The progress of the enzymatic reaction can be tracked by either optical (absorbance, fluorescence, chemiluminescence) or electrical (potentiometry, amperometry) methods. For example, glucose can be assayed by the conversion of glucose into gluconic acid and hydrogen peroxide by the enzyme glucose oxidase. Detection methods involve either detecting the formation of hydrogen peroxide or gluconic acid by a secondary reaction or via change in electric potential.

Electrochemical detection methods can be used for detecting analytes where the underlying assay chemistry involves a reduction/oxidation (redox) reaction. A redox reaction is where one or more components of the reaction undergo a change in oxidation state due to transfer of electrons from one species to the other. This change in electric potential can be monitored by using electrodes which convert the change in chemical potential to a corresponding change in voltage or current. This measured change in electrical property is correlated to the target analyte concentration. The Abbot istat (https://www.pointofcare.abbott/us/en/home) is an example of a commercially available device which leverages electrochemical detection methods to measure concentrations of several analytes in blood. Such a device can be adapted to electrochemical detection of analytes in captured aerosolized droplets from exhaled breath samples.

Moreover, in some embodiments, the concept of using a normalizing measurand can be used to facilitate quantitative measurement of biomarker concentrations in lung fluid using described methods, devices and systems. The reportable for these biomarkers is a concentration based on mass per unit volume of lung fluid (also known as Alveolar Lining Fluid—ALF). ALF is found in the deep lung and its composition is in equilibrium with blood. Exhaled breath samples carrying aerosolized drops of ALF are collected at the impaction site on the BCM. Due to the nature of exhaled breath, the volume of ALF per unit volume of breath can be inconsistent, even for the same subject across multiple samples. So, a substantial challenge for quantifying a biomarker of interest may be in determining the total volume of ALF collected.

This disclosure provides a solution to this challenge by, in some embodiments, quantifying the mass of another, reference, analyte, the concentration of which is constant across multiple samples and subjects. The biomarker concentration of interest can then be represented as a ratio of mass of biomarker to mass of this standard, or reference, analyte (which is also called the normalizing measurand—NM). Examples of a NM include: sodium ion, potassium ion, chloride ion, total protein, albumin, total ionic strength, conductivity, pH, etc.

After collection of a breath sample, elution solvent is introduced into the BCM to solubilize all components. After elution, there are multiple approaches to measuring the mass of both the biomarker of interest and the NM, for example:

i. Eluent is split into two RDM channels, one for the analyte and one for NM; and
ii. Eluent consists of two separate recognition molecules (e.g., antibodies), one specific to the biomarker and one for NM. The recognition molecules can have different labels (e.g., two different fluorophores), allowing for quantification of both markers in the same channel.

A specific example of this embodiment is to measure concentration of glucose in ALF. For this, an example NM is Na+ ion. For this application, the eluent can be directed to an electrochemical sensor chip, with specific locations to detect Na+ via potentiometry and glucose via enzyme-assisted amperometry. The ratio of the two analytes is used as the reportable to monitor variations in ALF glucose concentrations.

The choice of a particular detection method may be driven by LOD requirements of the target analyte and relative complexity of disposable and durable design. The most common method of utilizing a binder to detect and quantify a target analyte is implemented using an immunoassay. For large macromolecules with multiple binding sites, a sandwich-format immunoassay with a capture binder and a detection binder may be used to detect and quantify low concentrations (e.g., 10-100 pg/mL) of the target analyte. Readout or interrogation mechanisms to perform such detection and/or quantification may be based on absorbance, fluorescence, or chemiluminescence. Chemiluminescence-based readout often gives the lowest LOD. For small molecules with only a single binding site, a competitive immunoassay format can be used, based on relative binding of the target and a competing molecule. For both sandwich and competitive formats, "no-wash" modifications such as LOCI are also possible options.

In addition to optical-readout methods as discussed above, there are electrical readout methods, such as are described in Impedimetric Immunosensors—A Review, M. Prodromidis, Electrochimica Acta, Vol. 55, Issue 14, Pg. 4227, which is hereby incorporated by reference herein in its entirety. Both sandwich and competitive formats may be coupled with an electrochemical readout. For sandwich assays, the capture binder may be immobilized on the electrode. Sample and detection binder are brought to the electrode site. A sandwich construct of capture-analyte-detector is formed at the electrode surface. The presence of this large molecular construct is detected using impedance spectroscopy, where impedance is measured as a function of frequency. The molecular construct results in a signature impedance frequency profile. The magnitude of this profile is proportional to the surface concentration of the molecular construct which is in turn proportional to the concentration of the target analyte in sample. For a competitive format, the competing antigen is immobilized on the surface with the binder bound to it. When the sample is introduced to the electrode site, the binder dislodges from the surface antigen and binds to target analyte in solution. The number of binder molecules getting dislodged from the electrode surface is proportional to the concentration of target in solution. The dislodged binder causes a change to the impedance spectrum which is measured as the signal.

Choice of detection method affects design of both disposable and durable components. A laminate for conducting detection may be designed around the process steps for the assay based on the detection method. Details such as the number of liquid lines, sequencing of different reagents, mixing, etc. are considerations for designing layout of the laminate. The molded shell design may be based on number of discrete liquid reagents and process details of the assay.

Base station components may be determined by the readout mechanism. For optical readouts as in traditional immunoassays, the base station may be equipped with an optical detector with the appropriate sensitivity and noise characteristics, and a light source for absorbance and fluorescence readouts. For electrical readouts, the base station may be equipped with hardware to measure frequency-dependent impedance.

For TBI biomarkers, for example, a traditional immunoassay may be used. There are identified capture and detection antibody binders for GFAP, NSE, and UCH-L1. A sandwich-style immunoassay is a commonly used format to detect and quantify these markers in blood. Typical detection ranges using absorbance readout are in the range of 10-1000 pg/mL. Since typical levels in breath samples are expected to be significantly (100-1000×) lower than in blood, a sensitive chemiluminescence assay or impedance-spectroscopy based method is expected to be required.

As noted above, any appropriate assay or sensor (including immunoassays, chemical assays, enzymatic assays, electrochemical detection, etc.) may be used to detect and quantify the biomarker(s) sought. In some instances, different analytes or biomarkers may be sought using assays targeted for each analyte or biomarker; such targeted assays may be of the same type, e.g., immunoassays, chemical assays, etc., or may vary depending on what is most suitable for each analyte or biomarker being sought. In some implementations, detection or quantifications of different analytes or biomarkers may be sought to allow detection of different disease states or physiological conditions, although in other implementations, different analytes or biomarkers may be sought to allow detection or quantification of a single disease or physiological condition, e.g., if a higher concentration of analyte A is found relative to analyte B in a breath sample, that may indicate that a particular physiological condition exists in a test subject. In yet other implementations, quantification of other analytes may be used to improve measurement or quantification of an analyte of interest. For example, measurement of the amount of phospholipids in a sample may be performed in order to normalize a measurement of THC in the same sample to produce a THC/phospholipid measurement, which may be a useful metric of potential THC presence in the test subject than a THC/liters of breath sampled metric.

Chemistry

The target-specific binders are fundamental reagent components. The selection and optimization of these binders is fundamental to the immunoassay method and is a well-established area. Once selected, the same binders can be used in all formats as discussed above in relation to THC. In addition to binders, other constituents such as buffers, wash solutions, diluents, detection substrate, etc. are used based on the assay format. The selection of these components may also impact the design of the laminate and molded shell components.

In one embodiment, for TBI biomarkers, using a traditional immunoassay approach, the capture antibody is expected to be immobilized on the reaction surface in the BCM or another portion of the laminate. The sample can be diluted with an appropriate buffer and flown over the capture antibody. This can be followed by wash steps to remove unbound constituents. The detection antibody is flown in to form the capture-analyte-detection sandwich construct. After another set of wash, the detection substrate is flown in to generate the appropriate optical signal. Alternately, no-wash methods such as LOCI can also be used, which can reduce the number of reagents and processing steps.

Sandwich immunoassay for GFAP, NSE, and UCH-L1 can involve use of a primary antibody immobilized on the surface of the BCM, either by physical adsorption or using biotin-streptavidin chemistry, for example. After collection of sample in the BCM, a buffer can be added to solubilize the collected aerosol drops, at which point the target analyte (GFAP/NSE/UCH-L1) binds to the primary antibody which is immobilized on the surface. The channel is washed to remove any unbound species. Detection antibody, which is also specific to a particular analyte, conjugated with a reporter molecule such as a fluorophore or enzyme such as HRP is added into the channel. The detection antibody conjugate binds to the target molecule, thereby sandwiching the molecule between two specific antibodies. Following another wash step, the detection substrate is introduced into the reaction channel. The detection substrate produces a signal proportional to the concentration of the bound analyte.

The system may be designed so that analyte combinations such as the example cited—GFAP/UCH-L1/NSE can be assayed in parallel due to the ability to have multiple, e.g., three, reaction channels in the BCM. Each channel can be coated with the appropriate capture antibody. After analyte capture and wash, a common reagent mixture containing all three detection antibody conjugates can be flown into all three channels simultaneously. Due to the specific nature of the detection antibody, only target analytes will result in a binding event, resulting in each of the three analytes "sandwiched" in their respective channels. This multiplexing approach reduces assay time while minimizing interference between analytes. Capture binders can be designed for maximizing sensitivity, while the detection binder can be designed to be very selective, thereby maximizing signal and minimizing interference.

For electrical readout, most of the reagent constituents are similar except for the detection substrate. Some of the buffers used for electrical readout might be altered (pH, osmolarity, etc.) to maximize signal.

According to various disclosed embodiments, a method and system for evaluating a biomarker in a breath sample includes, measuring an amount of a biomarker associated with a physiological condition captured from aerosol drops in a breath sample obtained from a subject, and determining, based on the measurement, existence of the physiological condition in the subject. Also disclosed is an apparatus suitable for conducting the evaluation.

The determination operation can further include comparing the measured amount of the biomarker captured from the breath sample to a threshold level for the biomarker in breath, the threshold level correlated with a manifestation of the physiological condition.

The threshold level for the biomarker in breath may be correlated with a baseline minimum level of the biomarker in breath correlated with the manifestation of the physiological condition as a disease state.

In particular embodiments, the biomarker may be aerosolized in forcefully exhaled aerosol drops.

In particular embodiments, the aerosol drops may be of a size range of about 3-5 μL, for example about 4.5 μL.

In some embodiments, the threshold level may be less than 10 pg/L of breath.

In some embodiments, the aerosol drops may be captured by a device configured for impact and collection of aerosol drops forcefully exhaled into the device, as further described below.

Generally speaking, BCMs for droplet collection may feature, as discussed above, turns and bends to facilitate the collection of droplets of particular size ranges. In the context of a largely planar structure or substrate, such as a microfluidic plate that may be suitable for analyzing collected samples having very small volumes, one particular type of droplet trap may utilize a plurality of small impaction ports that are positioned on an outer major surface (e.g., one of the larger, flat surfaces) of the planar structure and are in fluidic communication with a plenum volume that is adjacent to, and partially defined by, that outer surface—such a plenum volume may, for example, include a portion of a housing or valve structure that is adapted to interface with, for example, a mouthpiece or saliva trap, such as is discussed earlier herein. In practice, a test subject (person) may place their lips around the mouthpiece or saliva trap to form a generally airtight seal, and may then exhale therethrough and into the plenum volume. The plenum volume may then serve to distribute the air from a person's exhaled breath to the plurality of small impaction ports. Each impaction port may overlap with an elution channel located within the planar structure and be in fluidic communication therewith, i.e., the impaction ports may be fluidically interposed between the elution channel and the plenum volume.

FIG. 30 depicts an example droplet trap 3004 featuring a plurality of impaction ports 3020. The droplet trap 3004 shown in FIG. 30 is particularly well-suited for use with disposable saliva traps/mouthpieces and for collecting low volumes of sample material from much larger volumes of exhaled breath.

Generally speaking, sample droplets that are collected by a droplet trap are typically post-processed after collection to allow them to be resuspended in a solution for conveyance from the droplet trap to downstream functional components, e.g., optical interrogation cells, mixing chambers, etc., or to allow for mixing with one or more reactants or other labeling mechanisms. In the depicted droplet trap 3004, such post-processing is performed by flowing an eluent, such as one of the eluents discussed elsewhere in this disclosure, through an elution passage 3008—in this particular example, the elution passage 3008 follows a C-shaped first path 3014 and is located completely within a microfluidic plate (the plate is not shown, but is similar in construction to other microfluidic plates discussed herein). During breath sample collection, the elution passage 3008 may be kept free of eluent (or other liquid) to allow for free flow of exhaled breath through the elution passage 3008. Once the desired droplet sample has been collected, then the liquid eluent may be flowed into the eluent passage 3008 in order to elute the collected droplets. Such eluent may be flowed into the eluent passage 3008 via a passage inlet port 3016; a passage outlet port 3018 may optionally be provided to allow the eluent (with the eluted droplet sample) to then be flowed to another location and/or to allow the eluent channel 3008 to vent during elution and prevent pressurized bubbles of gas from forming within the flow path and interfering with the supply of eluent. In the depicted example, the passage inlet port 3016 may be provided eluent from eluent feed passage(s) 3010, and eluent with eluted droplet sample may be pumped from the droplet trap 3004 via eluent exit passage 3012, which may be fluidically connected with the passage outlet port 3018.

As can be seen, a plurality of impaction ports 3020 are located along the first path 3014 such that they at least partially overlap (and generally completely overlap) with the elution passage 3008. While other geometries of impaction port 3020 may be used, the depicted example uses impaction ports 3020 having high-aspect-ratio, e.g., 4:1 or 5:1 or more, rectangular cross-sections—in this case, each impaction port 3020 may have a 1 mm×0.2 mm cross section. The impaction ports 3020 may pass through one or more layers of the microfluidic plate until they fluidically connect with the elution passage 3008. Breath sample that flows through the impaction ports 3020 and into the elution passage 3008 must undergo a sharp, 90° turn. Particles suspended in the breath sample, e.g., droplets, may experience varying degrees of success in navigating this turn depending on the sharpness of the turn, the flow rate of the breath sample, and the size and mass of the droplets (the size and mass of the droplets will generally be directed related, as the droplets will tend to be spherical in nature and have similar densities). Larger, heavier droplets will have greater inertia than smaller, lighter droplets and will be more resistant to external forces encouraging them to change direction, i.e., turn the corner. Given the relative shallowness of the elution passage 3008 in a direction perpendicular to the major planes of the microfluidic plate, the larger, heavier droplets will generally strike the "floor" of the elution passage 3008 (the "floor" being the wall of the elution passage 3008 that is opposite, and faces towards, the impaction ports 3020) with some velocity, thereby causing those droplets to adsorb onto the floor and be "trapped." In contrast, smaller droplets that are lighter, and thus have less inertia, may be much more likely to be able to navigate the turn and change their direction of travel before impacting the floor of the elution passage 3008.

Figure 31:
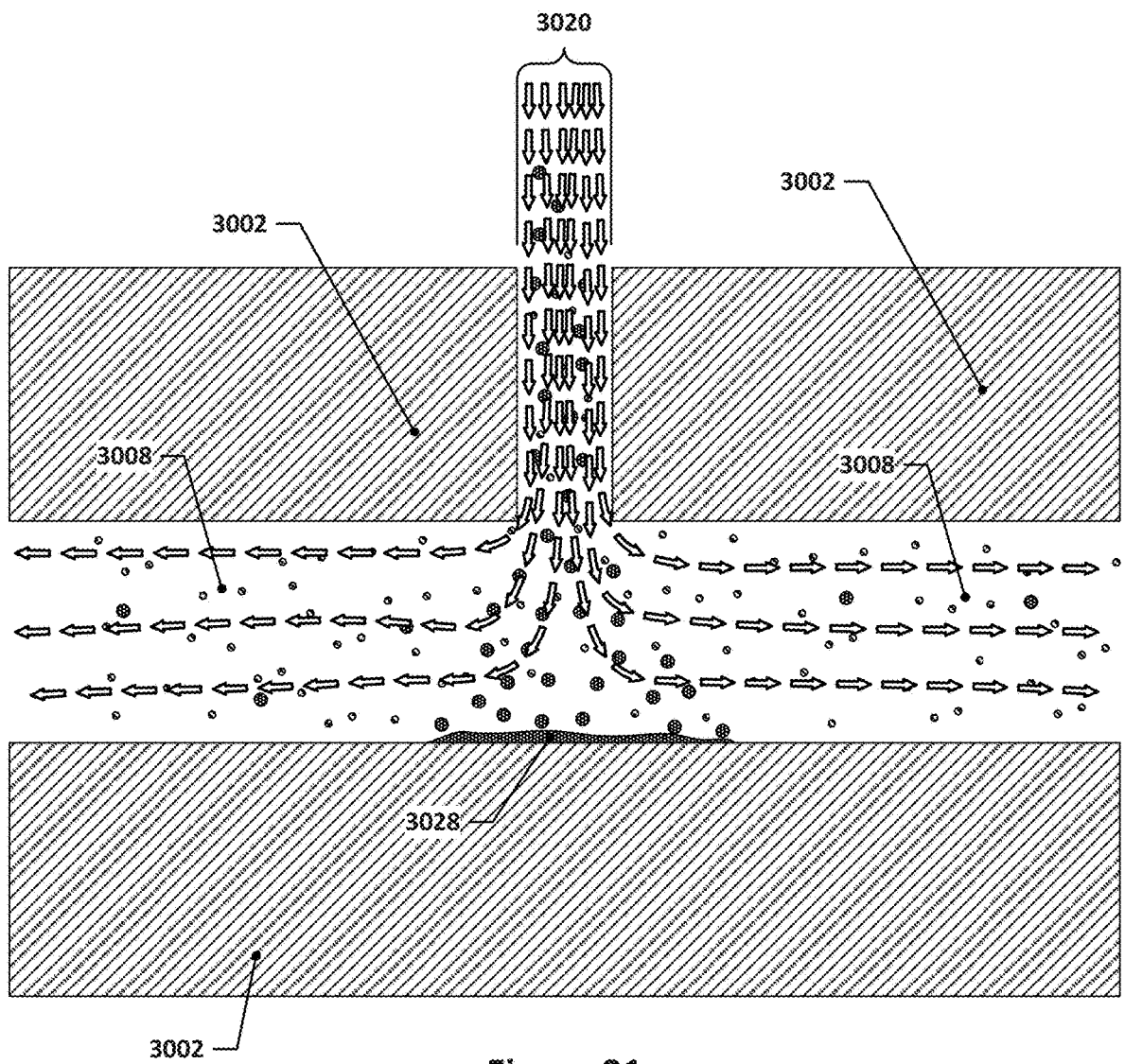
FIG. 31 depicts a cross-section view of a portion of a droplet trap.

FIG. 31 depicts a cross-section view of a portion of a droplet trap. As can be seen, the impaction port 3020 extends through a substrate 3002 and intersects with the elution passage 3008. Breath sample that flows through the impaction port 3020 may enter the elution passage 3008 and then make a 90° turn (arrows are added to indicate the general flow directions of the breath sample). Smaller particles (droplets), indicated by smaller-sized circles with lighter shading, in the breath sample flow may successfully navigate the 90° turn, whereas larger particles/droplets, indicated by larger-sized circles with darker shading, will generally not be able to make the 90° turn and will impact the floor of the elution passage 3008 and adsorb onto it, forming a trapped portion of sample 3028.

Returning to FIG. 30, portions of sample 3028 that have been trapped are shown beneath each impaction port 3020 (as dark-shaded blobs; they are not individually called out, but see the legend). In actual practice, there may be portions of sample that adsorb onto the walls of the elution passage 3008 all along the length of the elution passage 3008, although the concentration of such trapped sample may generally be much higher in the vicinity of each impaction port than elsewhere in the elution passage 3008.

One key issue with collecting droplet samples from breath samples is that a very large volume, relatively speaking, of breath sample, e.g., several liters, must be flowed through the droplet trap in order to collect a quantity of droplets that is sufficiently large enough to allow for a measurable quantity of the analyte or biomarker (to be clear, under the conventions adopted herein, biomarkers are considered a form of analyte) that is of interest to be obtained. At the same time, it is simultaneously desirable to reduce the collected sample volume so that the concentration of the analyte or biomarker in the working volume of the analysis system is quite small, e.g., concentrated into a working volume on the order of 10 to 50 µL, e.g., ~15 µL. In order to facilitate such concentrated sample capture, the droplet trap 3004 utilizes multiple impaction ports 3020, e.g., 10 ports, that are spaced apart from one another along the elution passage 3008 and that are each supplied air from the plenum volume in parallel. Other numbers of impaction ports may be utilized as well, e.g., from between 2 to 20 impaction ports. These impaction ports 3020 may, for example, be relatively closely spaced. In the depicted example, for instance, the elution channel 3008 is approximately 20 mm in length and 0.61 mm deep (which also governs the distance available to the droplets to make the 90° turn out of the impaction ports), and each impaction port is spaced apart from the neighboring impaction ports by ~1.8 mm or so. This results in a working volume for elution of approximately 13 µL (when the second ends 3026 of the exhaust passages 3022 are sealed, e.g., by actuation of a valve structure, the eluent will effectively be unable to flow down the exhaust passages 3022 due to the air trapped within—thus, the exhaust passages 3022 may, generally speaking, be discounted in such a BCM design as contributing to the working volume of eluent needed to elute the collected sample).

The droplet trap 3004 may also include a plurality of exhaust passages 3022, each pair of which may be positioned such that one of the impaction ports 3020 is fluidically interposed therebetween. Each exhaust passage 3022 may have a first end 3024 that is fluidically connected with the elution passage 3008, and a second end 3026 that is fluidically connected with an exhaust port that vents to a location outside of the microfluidic plate housing the droplet trap. The exhaust passages 3022 may be sized larger than the impaction ports 3020 in cross-section such that the flow resistance in the droplet trap 3004 is at a maximum when the breath sample flows out of the impaction ports 3020, i.e., the flow resistance downstream of the impaction ports 3020 is less than at the impaction ports 3020, thereby encouraging maximum flow velocity to occur just prior to the 90° turns out of each impaction port 3020. As with other breath sample collection systems described earlier in this disclosure, one or more vacuum pumps (not shown, but see earlier discussions) may be fluidically connected with the exhaust passages 3022 to draw a vacuum on the exhaust passages 3022 as the breath sample is flowed through the droplet trap 3004; the passage inlet port 3016 and passage outlet port 3018, or the fluid flow passages within which they communicate, may be sealed off by valves or other mechanisms during breath sample collection to reduce the possibility that the breath sample will flow through those ports instead of through the exhaust passages 3022 or to reduce the possibility that the vacuum drawn by the vacuum pump(s) will aspirate liquids, e.g., eluent, through those ports. The use of a vacuum pump or pumps may allow for more rapid flow of breath sample through the droplet trap 3004, thereby reducing sample collection time and potential subject fatigue; the increased collection speed may also cause increased collection efficiency since the flow speeds through the impaction ports 3020 will increase, which will enhance the inertial separation of the larger/heavier droplets.

Generally speaking, the impaction ports 3020, when rectangular or otherwise oblong in nature, may be oriented such that the "short" axis of the impaction ports 3020 is aligned with the first path 3014 followed by the elution channel 3008, with the "long" axis of the impaction ports 3020 being perpendicular or transverse to the first path 3014. Such an arrangement creates a thin "sheet" flow of breath sample, which a) constrains the flow paths that the breath sample may follow when traversing the 90° bend to smaller radiuses of curvature (which increase the likelihood that a larger droplet will not be able to make the turn and will impact the floor of the elution passage 3008) and b) reduces the chance of turbulent flow, which may interfere with efficient droplet collection.

Figure 30:
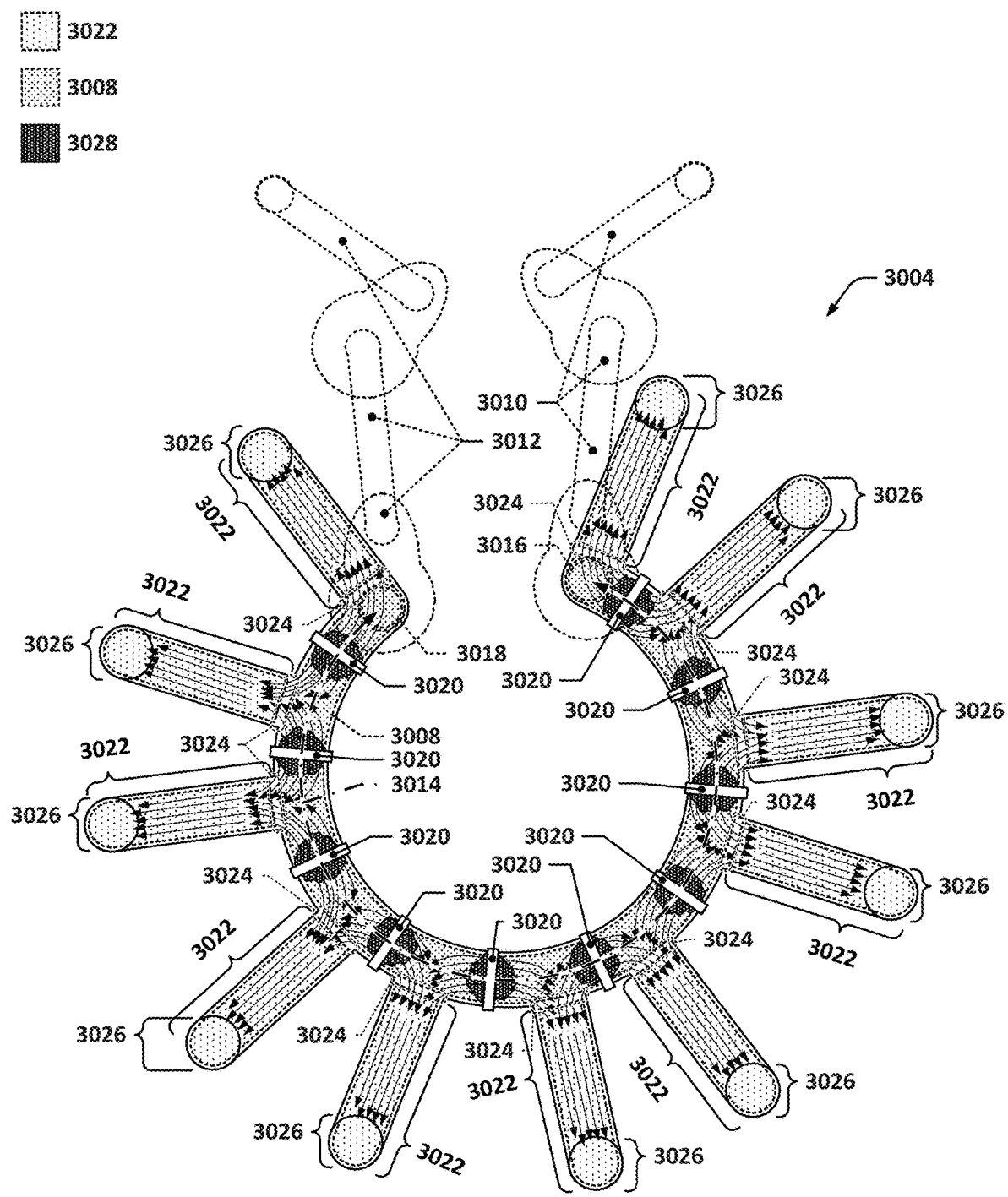
FIG. 30 depicts an example droplet trap featuring a plurality of impaction ports.

The exhaust passages 3022, as seen in FIG. 30, may follow paths that are approximately 90° to the first path 3014, e.g., generally perpendicular to the first path 3014, and may have edges at the first ends 3024 that are offset along the first path 3014 from the closest impaction ports 3020 by at least a first distance, e.g., by at least the width along the first axis 3014 of the closest adjacent impaction ports 3020 or by at least 30% to 50% of the width of the exhaust passages 3022. Such an arrangement forces the breath sample flow to undergo two 90° bends in different planes in rapid succession, thereby reducing the chance that a flow path may develop that avoids the initial 90° bend (and which would therefore provide a mechanism to defeat the droplet collection mechanism).

FIGS. 32 and 33 depict alternate arrangements of droplet traps. In FIG. 32, an eluent passage 3208 follows a linear first path (not shown), and features impaction ports 3220 and exhaust passages 3222 with first ends fluidically connected with the eluent passage 3208 and second ends 3226 that allow breath sample to exhaust from the droplet trap 3204. FIG. 33 depicts a similar arrangement (with droplet trap 3304, eluent passage 3308, impaction ports 3320, and second ends 3326), except that there are exhaust passages 3322 on both sides of the eluent passage 3308. Droplet traps with other arrangements of eluent passages and impaction ports are considered within the scope of this disclosure as well, although such arrangements may generally share certain common principles. For example, the impaction ports for such droplet traps may generally be arranged serially along the eluent passage, and the exhaust passages may be spaced along the eluent passage such that they are offset (along the first path) from the closest impaction ports.

Figure 34:
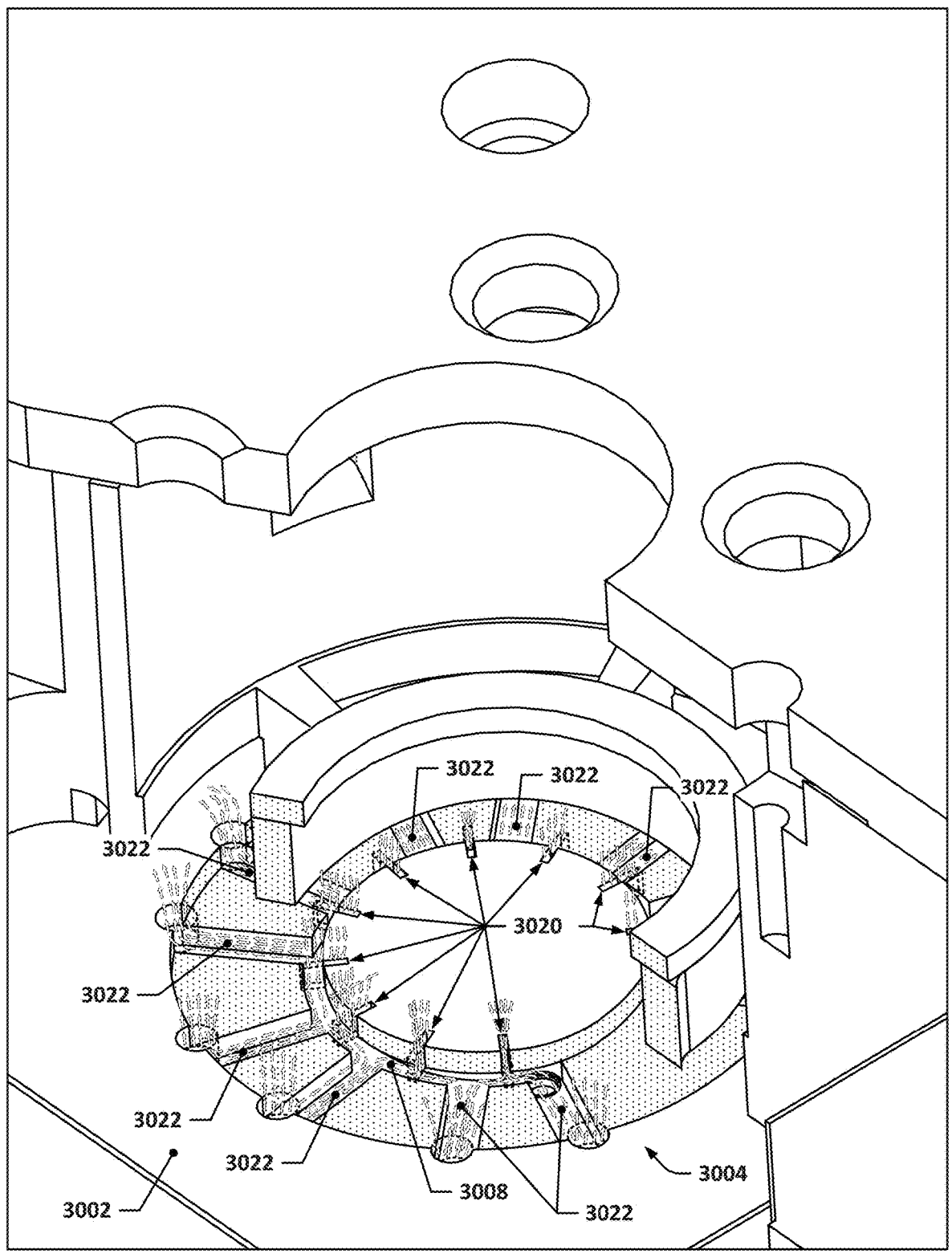
FIG. 34 depicts a perspective partial cutaway view of a cartridge that includes a droplet trap similar to that shown in FIG. 30

FIG. 34 depicts a perspective partial cutaway view of a cartridge that includes a droplet trap similar to that shown in FIG. 30 (some components relating to a valve structure have been omitted; these are visible in later Figures. An annular disk of material in the upper layer of the microfluidic plate/substrate 3002 has been removed to show the underlying arrangement of the elution passage 3008 and the exhaust passages 3022. Breath sample that flows into the impaction ports 3020 may make a sharp, 90° turn into the eluent passage 3008 before making another turn into one of the exhaust passages 3022 and then exiting the exhaust passages 3022. A pressure differential between the impaction ports 3020 and the exhaust passages 3022 may be maintained through the use of, for example, an annular lower wall 3062 (which may seal to a portion of the substrate 3002 that is removed in this cutaway view) and annular lower wall seal 3064, as well as other components not shown here.

Figure 35:
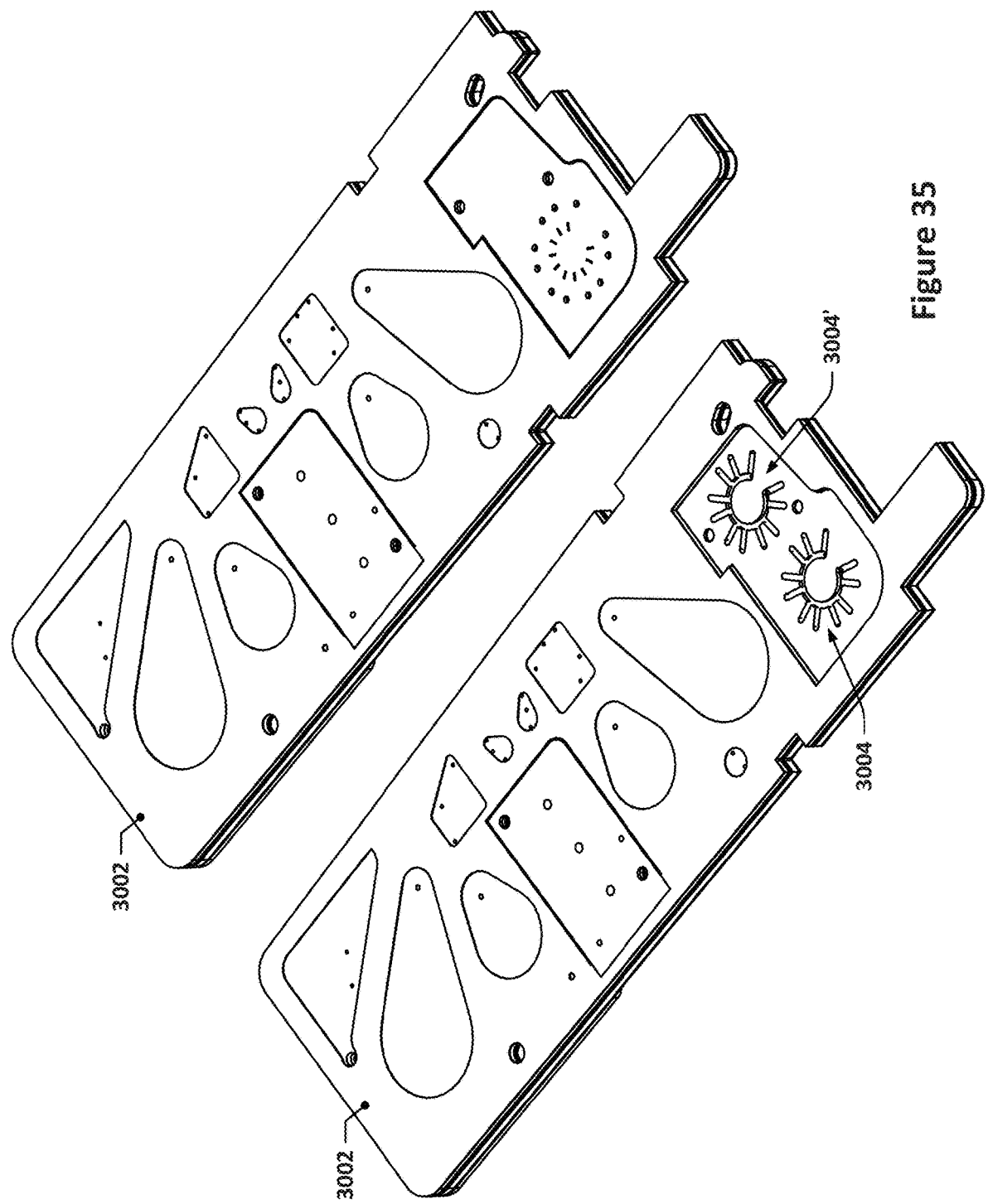
FIG. 35 depicts the substrate without other components shown, such as a cartridge housing, valves, etc.

FIG. 35 depicts the substrate 3002 without other components shown, such as a cartridge housing, valves, etc. The droplet trap 3004 is, in this example, housed in a separate insert that may be mounted to the microfluidic structure provided by the substrate 3002, although other substrates may include such droplet traps 3004 as an integral part of the substrate 3002. In this particular example, the substrate 3002 includes a second droplet trap 3004' that contains a similar eluent passage and exhaust passages, but which does not include any impaction ports or other fluidic connections through the top layer of the substrate 3002; this second droplet trap 3004' may be used to replicate flow volumes and fluid behavior for a control sample that may be analyzed in parallel with the collected sample; in some such implementations, the second droplet trap 3004' may be pre-filled with a known reference amount or concentration of the analyte or biomarker in question to provide a reference standard to allow a measurement of the obtained sample to be calibrated.

Figure 36:
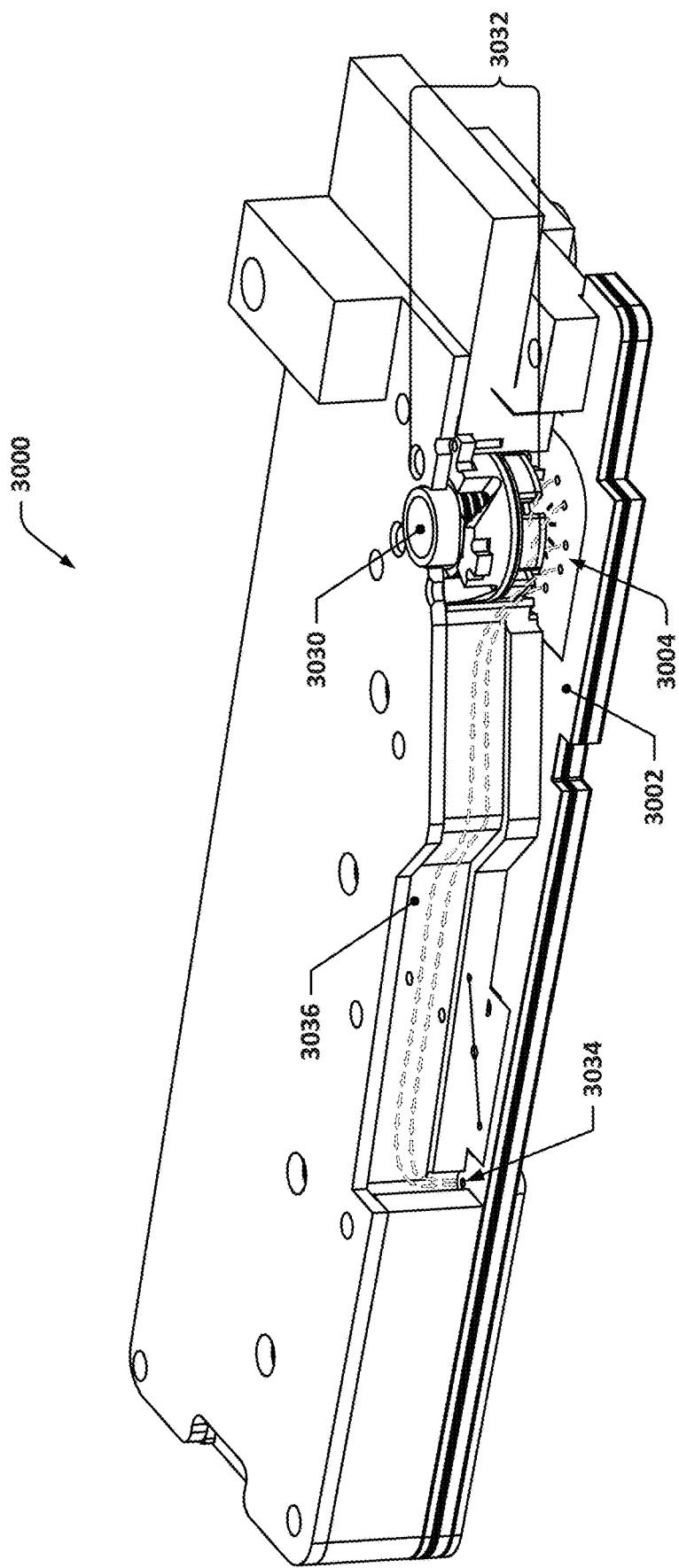
FIG. 36 depicts the substrate attached to a larger cartridge housing.

FIG. 36 depicts the substrate 3002 attached to a larger cartridge housing that includes a valve structure 3032 having a breath sample receiving port 3030, which may, as discussed earlier, be interfaced with a saliva trap and/or mouthpiece. The housing may, as shown, have a vacuum passage 3036 that is fluidically interposed between the exhaust passages 3022 and a vacuum port 3034 during breath sample collection; the vacuum port may, in turn, be fluidically connected with a vacuum pump or pumps, e.g., within a handheld unit that may be connected with the cartridge during sample collection, similar to other implementations discussed earlier herein. The cartridge, in this Figure and the following Figures, is shown partially cut away to allow for features internal to the cartridge to be seen.

Figure 37:
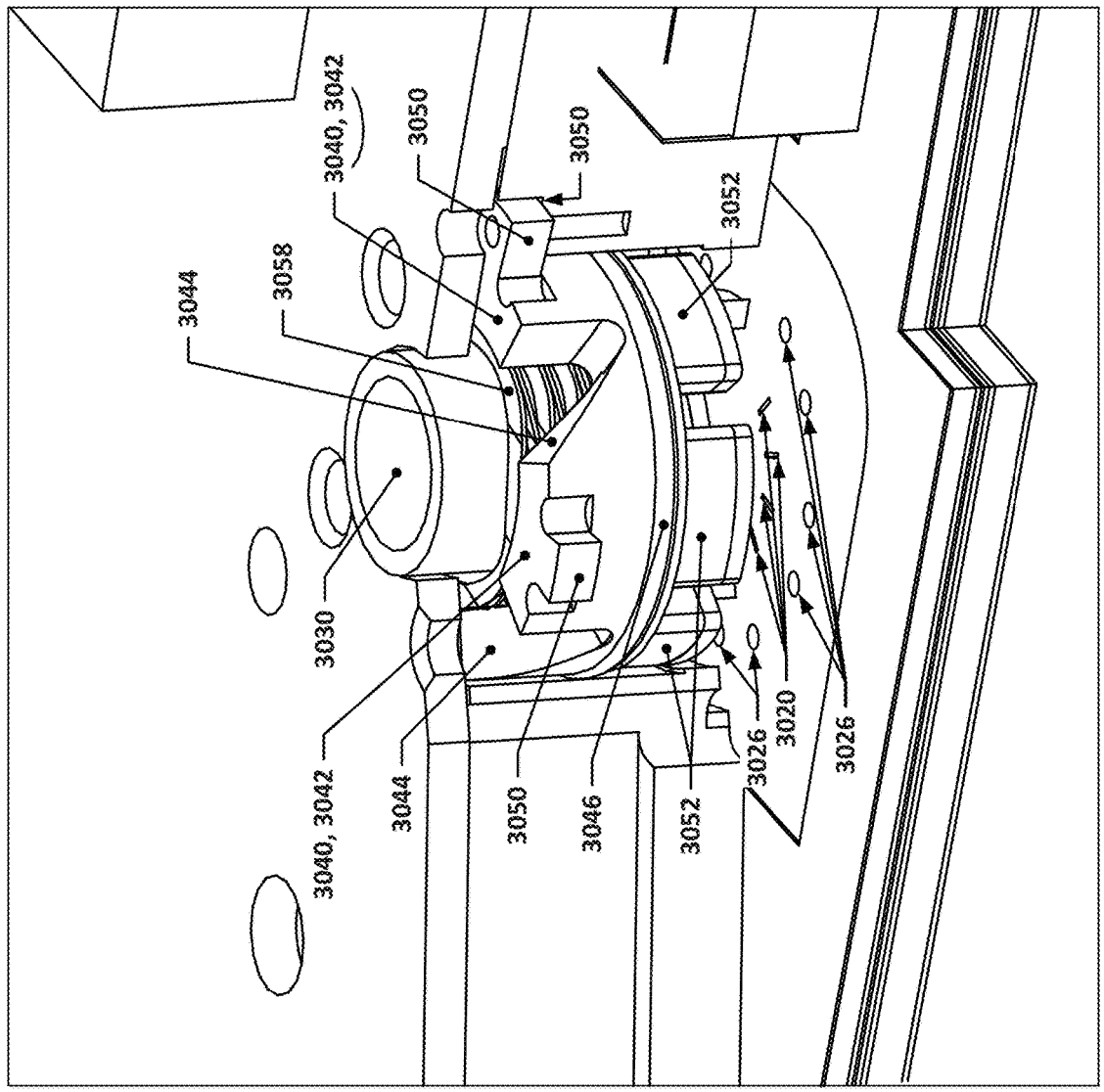
FIG. 37 depicts a close-up of the valve structure of FIG. 36.
Figure 38:
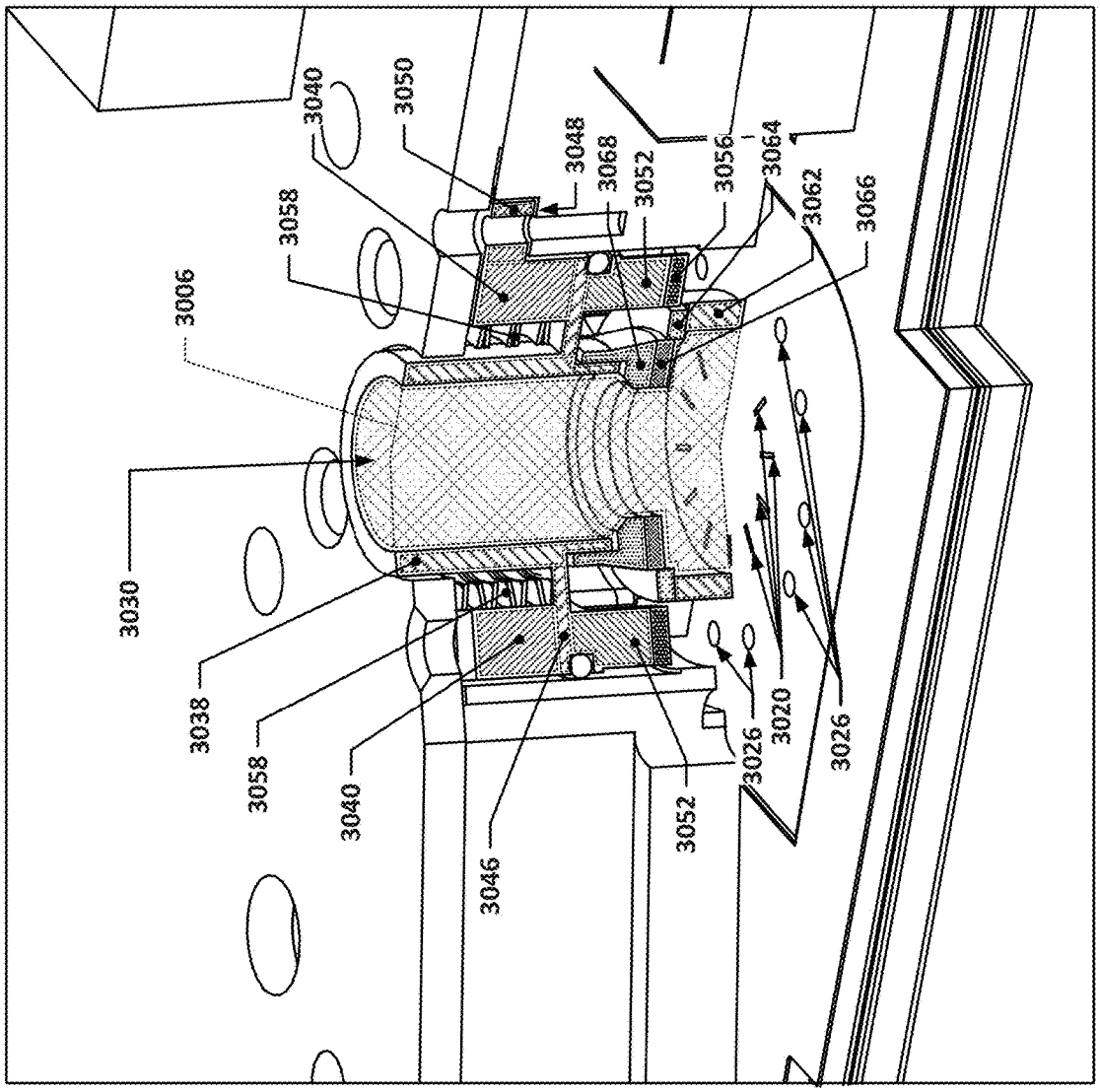
FIGS. 38 and 39 show additional cutaway views of the valve structure of FIG. 37 in both an "open" configuration (FIG. 38) and a "closed" configuration (FIG. 39).
Figure 39:
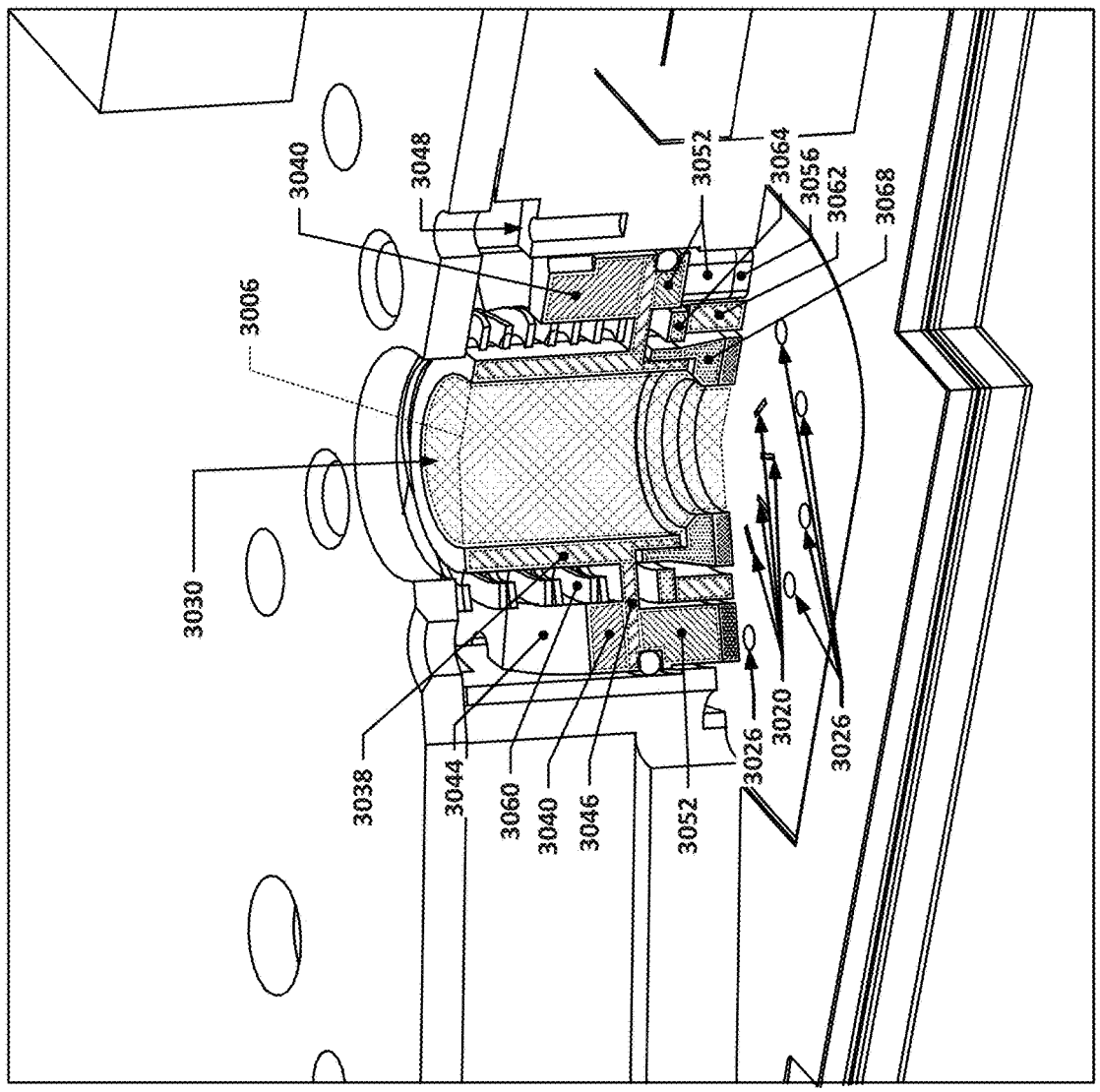

FIG. 37 depicts a close-up of the valve structure 3032 of FIG. 36; FIGS. 38 and 39 show additional cutaway views of the valve structure 3032 in both an "open" configuration (FIG. 38) and a "closed" configuration (FIG. 39). The depicted valve structure is only one example of a valve structure that may be used with the droplet traps discussed herein; other valve structures may be used to provide similar functionality; in some implementations, no valve structure may be used at all, and the functionality provided by the valve structure may be provided by other means.

In the depicted valve structure 3032, the valve structure 3032 has a first portion that is fixed relative to the substrate 3002; the first portion, in this example, includes the annular lower wall 3062 and the annular lower wall seal 3064. The depicted valve structure 3032 may also include a second portion that is movable relative to the first portion and the substrate 3002; the second portion, in this example, includes various features (shown in cross-section in FIGS. 38 and 39), such as, for example, an annular outer wall 3040, a tubular inner structure 3038, a circular base 3046, a collar 3068, and lower risers 3052. The tubular inner structure 3038, in this case, also provides a breath sample receiving port 3030, into which a saliva trap, mouthpiece, or other adapter may be inserted in order to allow a breath sample to be blown into the droplet trap 3004. The inner surfaces of the tubular inner structure 3038, collar 3068, and annular upper valve seal 3066 of the second portion and the annular lower wall 3062 and the annular lower wall seal 3064 of the first portion may define a plenum volume 3006 through which the breath sample may be flowed before flowing through the impaction ports 3020. The plenum volume 3006 may be generally sealed between the breath sample receiving port 3030 and the impaction ports 3020 when the valve structure is in the "open" configuration so as to allow a positive pressure to be developed within the plenum volume 3006 during breath sampling.

In the depicted valve structure 3032, the second portion is able to translate along the center axis of the valve structure 3032, e.g., along a direction perpendicular to the substrate 3002. A compression spring 3060 may apply force to the second portion, e.g., by being compressed between the housing of the cartridge and the second portion, that urges the second portion towards the substrate 3002 and into the "closed" configuration. The second portion may have a plurality of radial tabs 3050 that extend outwards from the annular outer wall 3040 and that may rest on ledges 3048 in the housing of the cartridge when the valve structure 3032 is in the "open" configuration. If the second portion is rotated about the center axis of the plenum 3006 by a sufficient amount, e.g., 20°, this may cause the radial tabs 3050 to no longer rest on the ledges 3048, freeing the second portion to translate along that center axis towards the substrate 3002 due to the force exerted by the compression spring 3060. The lower risers 3052 may be equipped with exhaust port seals 3056, which may be made of a compliant material, as may be the case with the annular upper valve seal 3066, in order to seal against the substrate 3002 when in the closed configuration. In the depicted example, the annular lower wall seal 3064 is also made of a compliant material to allow the annular lower wall seal 3064 and the annular upper valve seal 3066 to seal against each other radially when in the closed configuration. In other configurations, the annular lower seal may simply seal radially against the rigid plastic of the annular lower wall 3062. In yet other configurations, the annular upper valve seal 3066 and the annular lower wall seal 3064 may be provided by single piece of material, which may be partially die cut such that the portion that corresponds with the annular upper valve seal 3066 may tear free of the portion that corresponds with the annular lower wall seal 3064 when the valve structure 3032 is transitioned to the closed configuration. The depicted valve structure 3032 thus simultaneously seals the impaction ports 3020 and the exhaust ports of the exhaust passages (the second ends 3026) when transitioned to the closed configuration; this seals the collected droplets inside of the droplet trap 3004, allowing for the collected sample droplets to be eluted or otherwise fluidically manipulated without leaking back out of the impaction ports 3020 or through the exhaust passages 3022.

Figure 40:
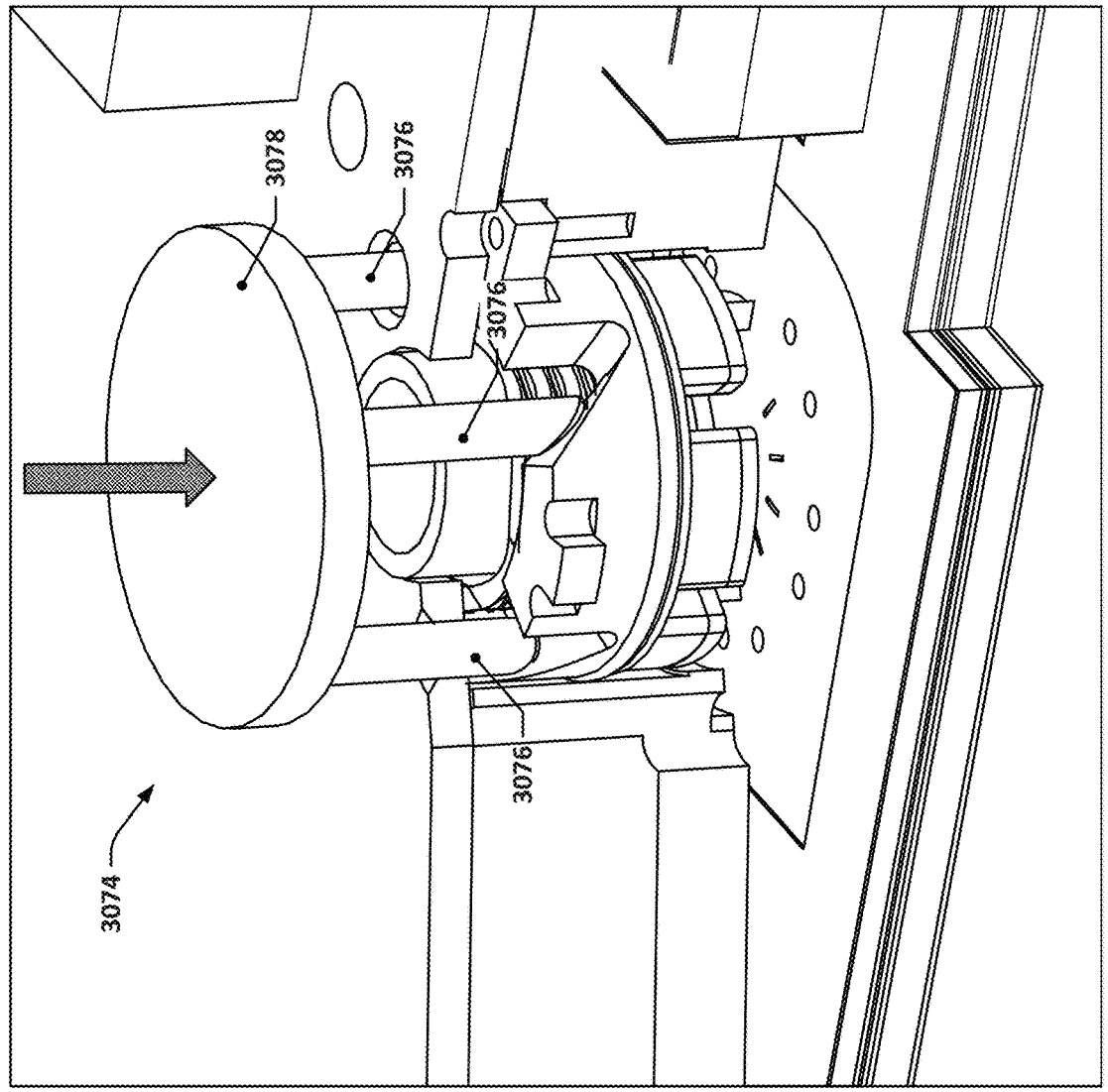
FIGS. 40 through 42 depict the closure of the valve structure in the depicted example.
Figure 41:
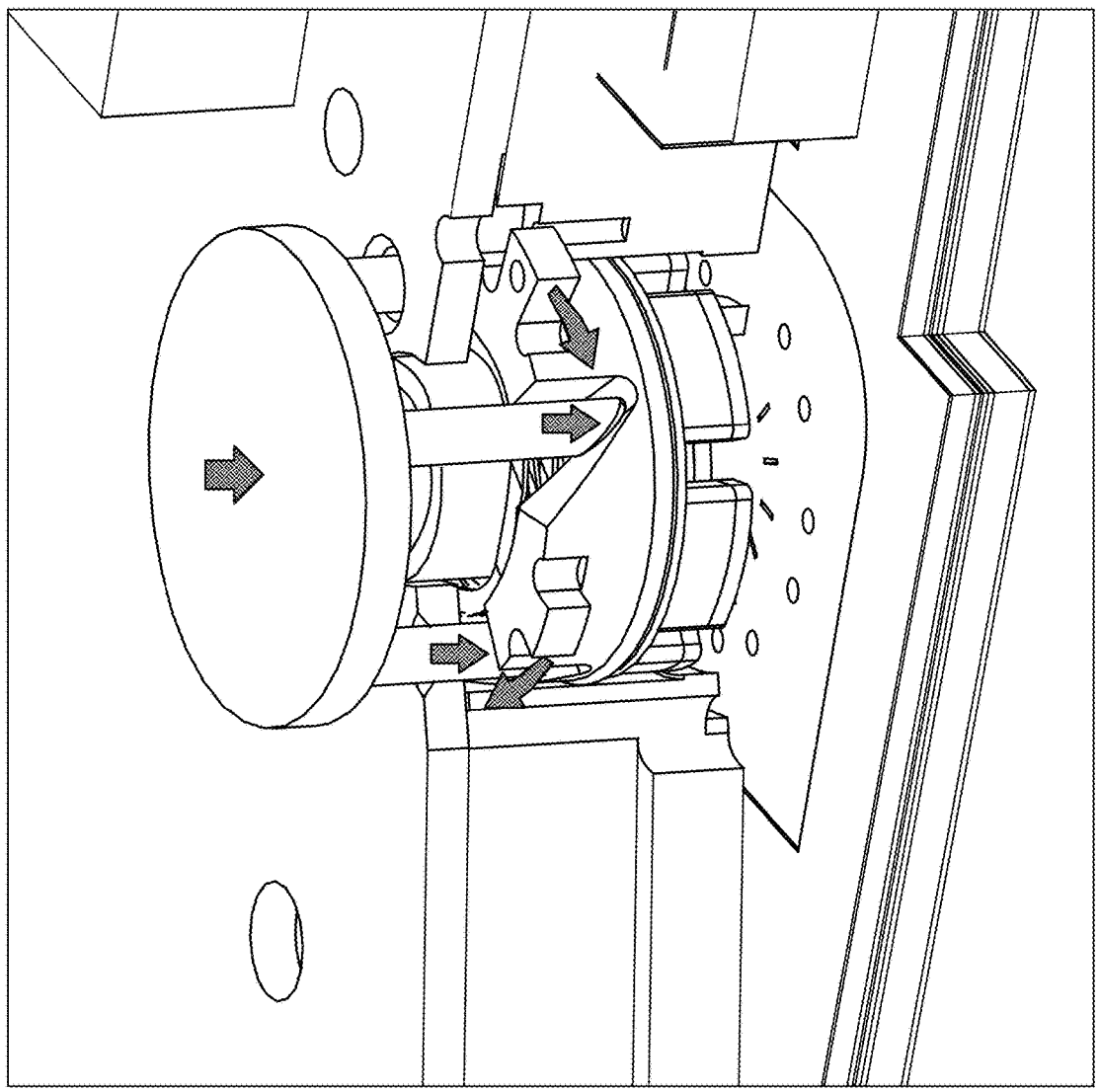
Figure 42:
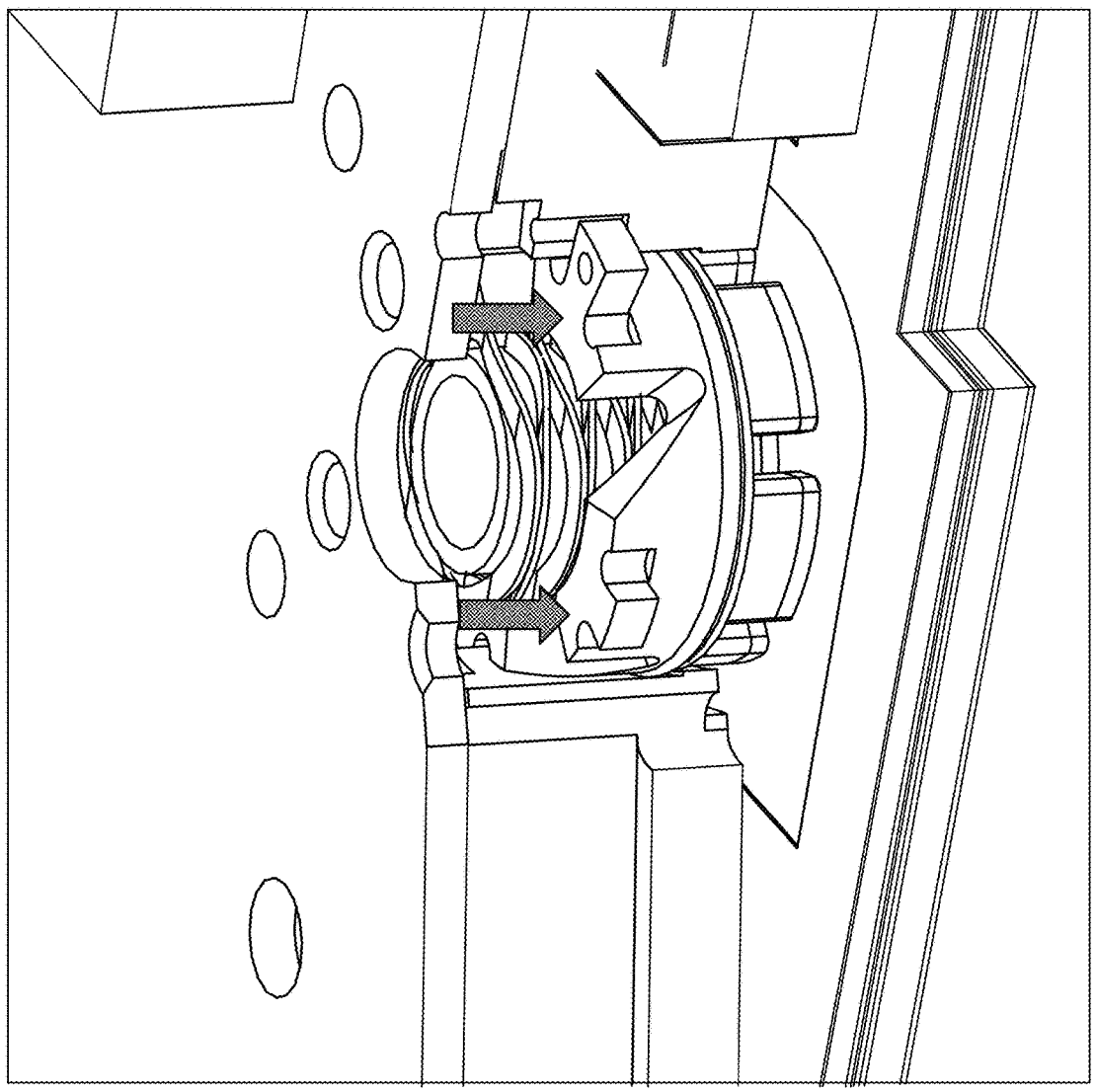

FIGS. 40 through 42 depict the closure of the valve structure in the depicted example. Referring back to FIG. 37, it will be noted that the annular outer wall 3040 includes a series of crenellations 3042 that each have a sloped side 3044. Additionally, the housing may have a hole located above each such sloped surface, allowing posts 3076 (referring back to FIG. 40) attached to a load distributor 3078 of actuator key 3074 to be inserted therethrough and engage with the sloped sides 3074. When compressive force is applied to the load distributor 3078, the posts 3076 are urged downward onto the sloped sides 3044, causing the second portion to rotate so that the posts "slide" down the sloped sides 3044—in this example, such rotation is clockwise (when looking along the compression direction) and causes the radial tabs 3050 to rotate clear of the ledges 3048 so that the latching mechanism provided by the radial tabs and ledges releases and allows the second portion to move relative to the first portion and enter the "closed" configuration, as shown in FIGS. 41 and 42.

Figure 43A:
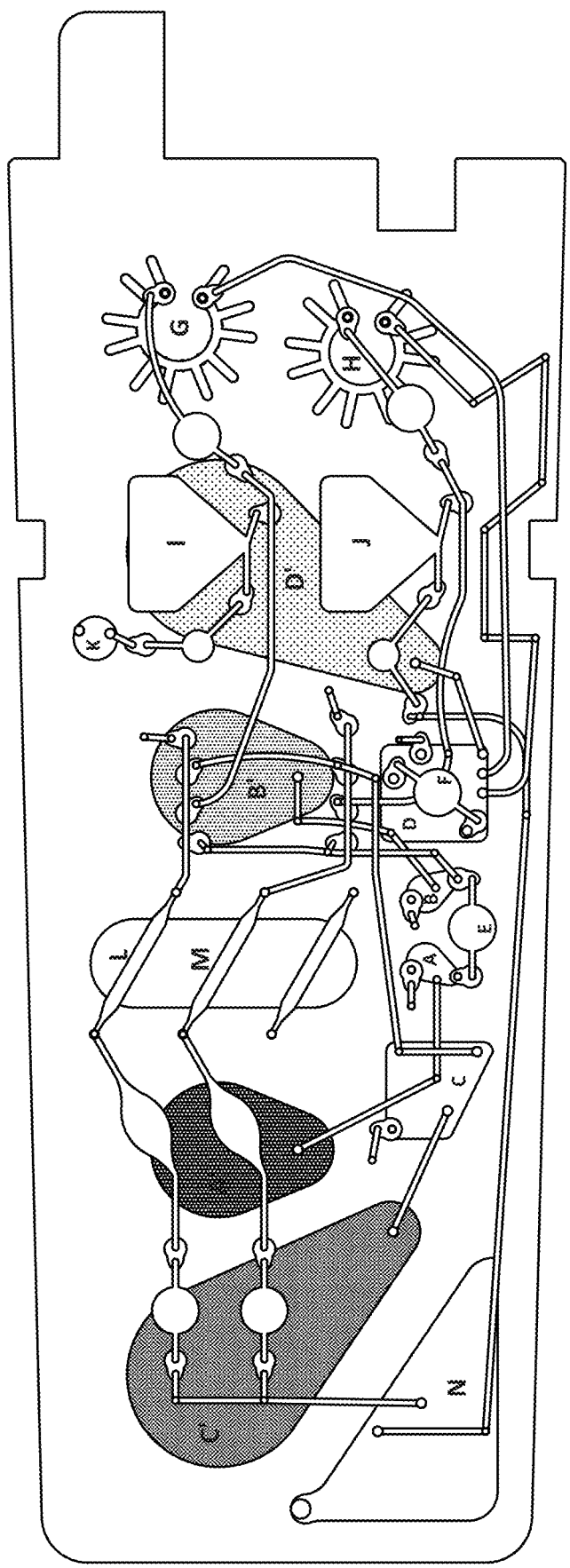
FIGS. 43*a* through 43*i* depict an example microfluidic plate with a droplet trap during various phases of an analysis process.
Figure 43B:
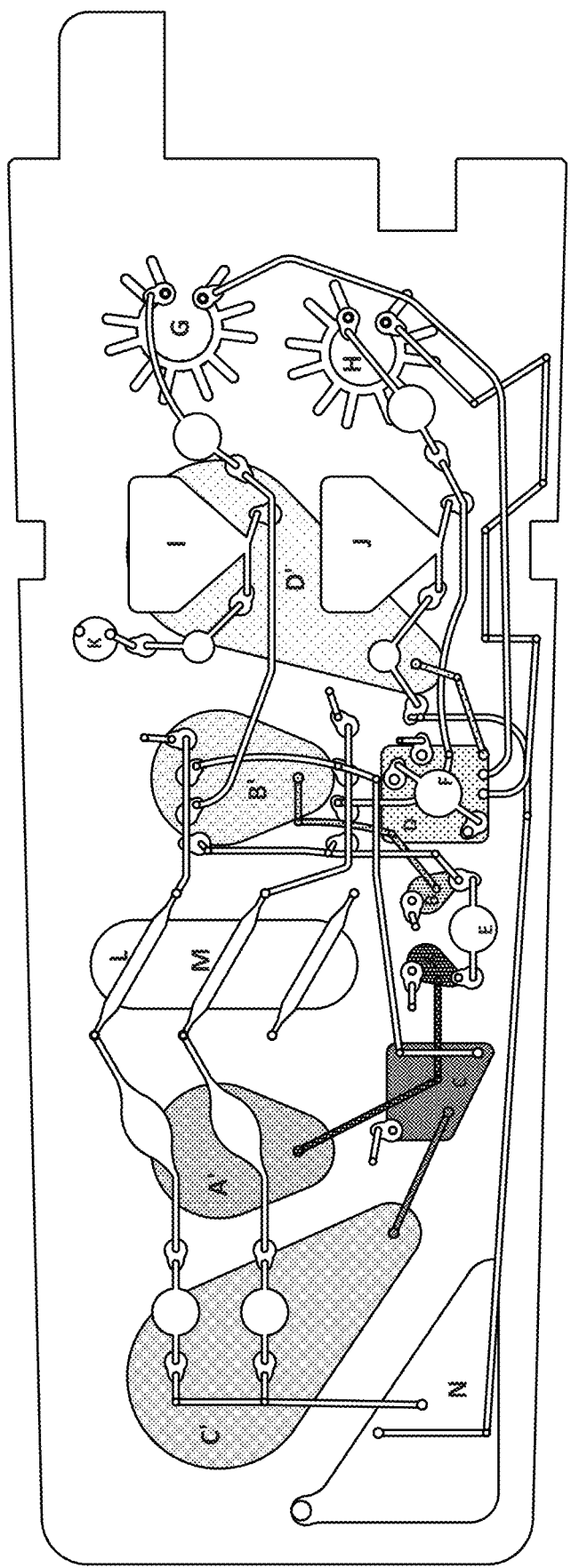
Figure 43C:
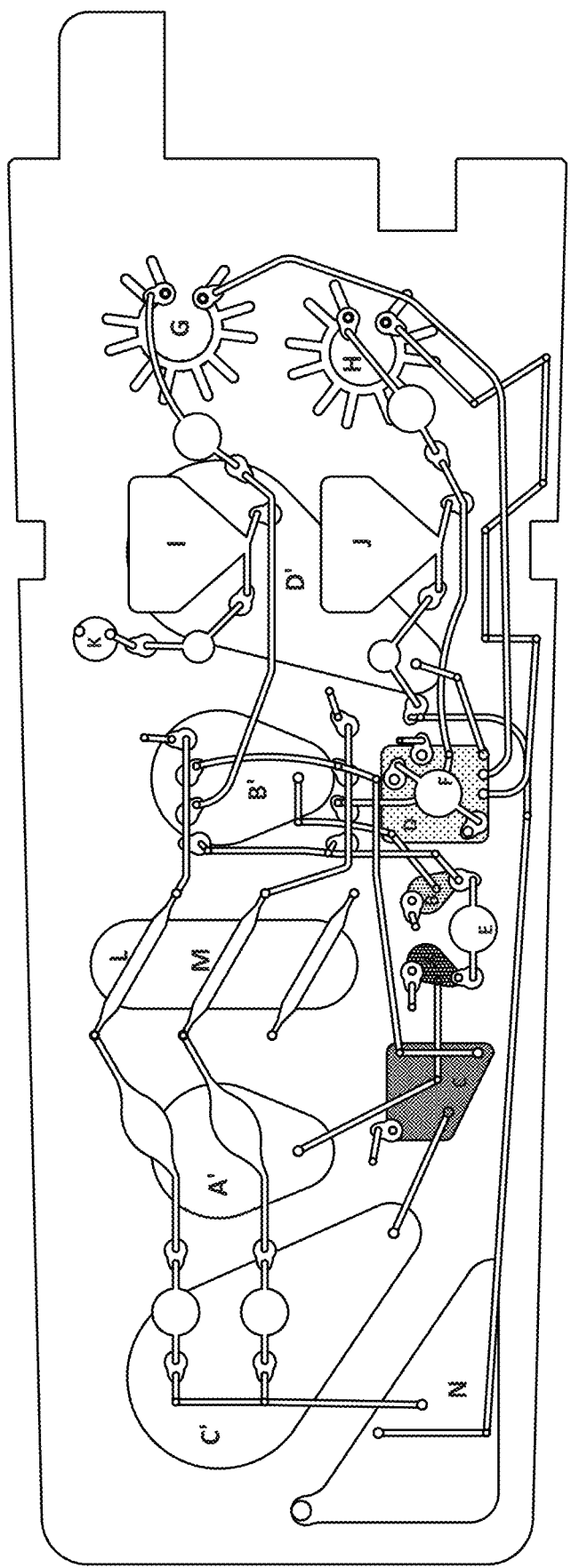
Figure 43D:
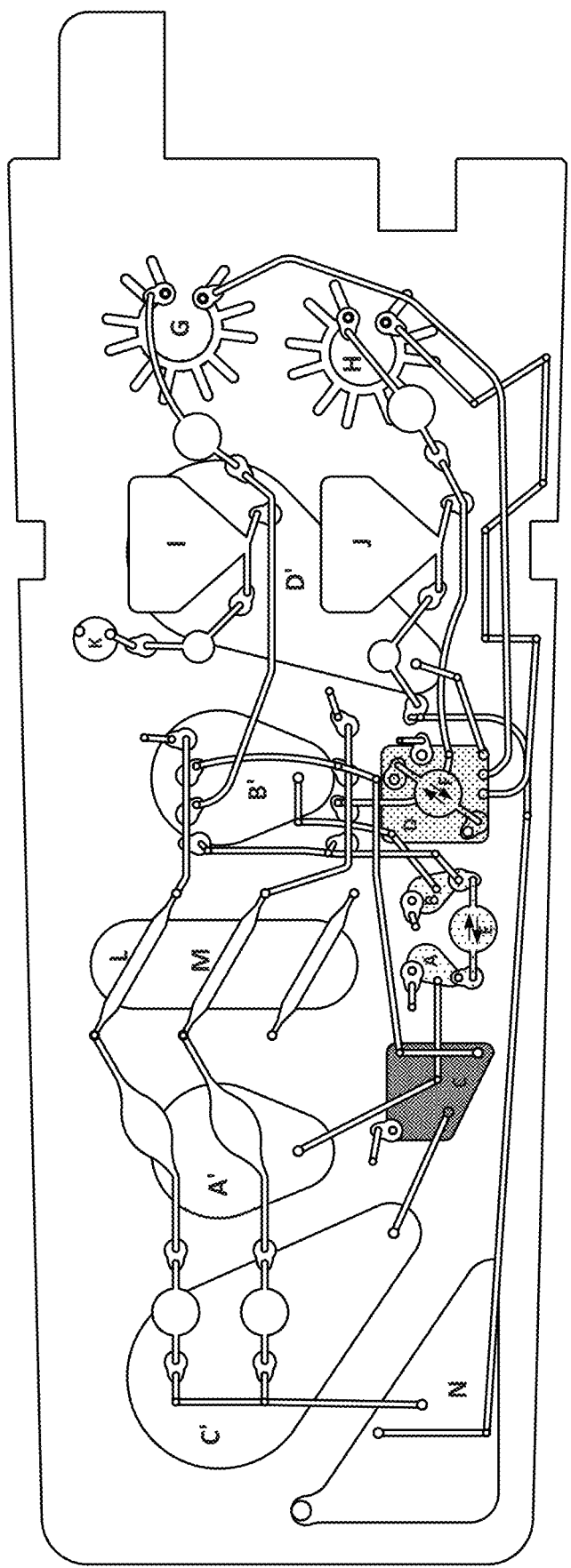
Figure 43E:
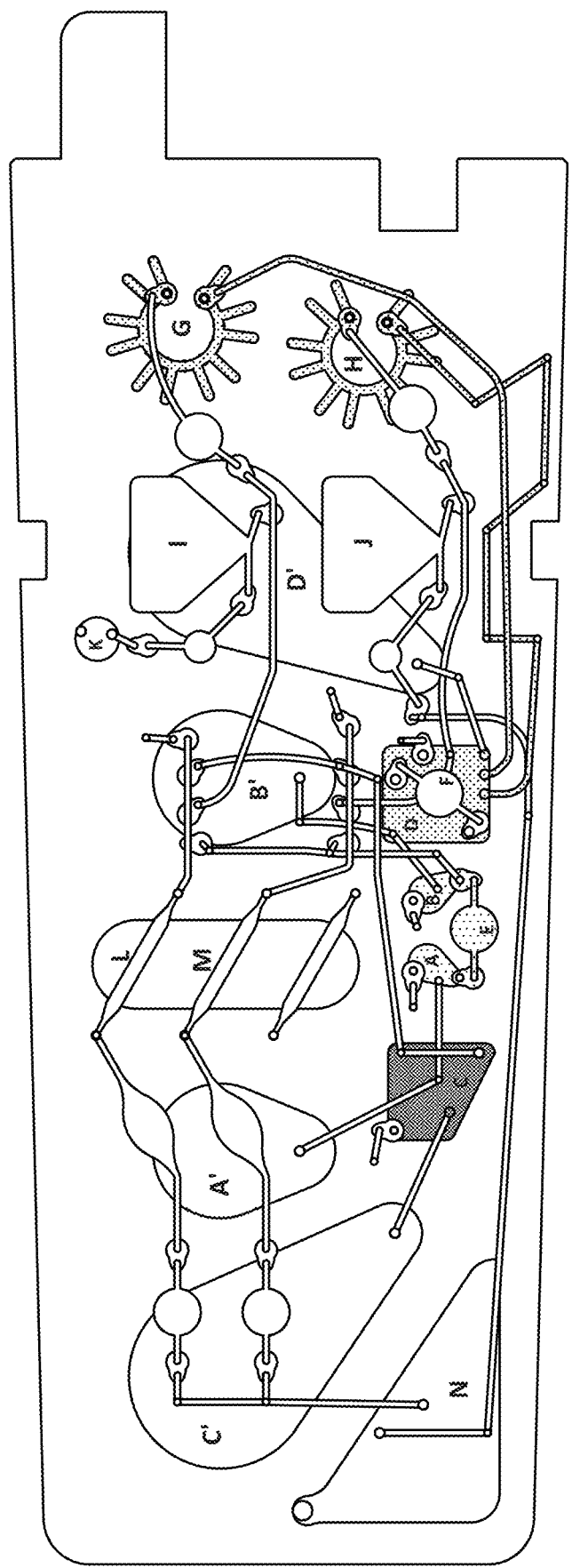

FIGS. 43a through 43i depict an example microfluidic plate with a droplet trap during various phases of an analysis process (these steps occur after the breath sample has been collected and the droplet trap has been sealed, e.g., through actuation of the valve structure). As shown in FIG. 43a, the microfluidic plate is connected with two bladders A' and B' that may, for example, contain a substrate that is stored in binary form, similar to the substrates discussed earlier. Bladder C' may store a wash fluid, and bladder D' may store an eluent/buffer. The bladders A' through D' may be, for example, liquid-filled bladders that may, in an initial priming operation shown in FIGS. 43b and 43c, be compressed (for example, by the mechanism discussed earlier herein) and have their contents dispensed to various corresponding reservoirs A through D.

Subsequent to the introduction of the substrates to reservoirs A and B, a mixing pump E may be actuated to cause the contents of reservoirs A and B to be reciprocated between those two reservoirs, thereby mixing them and activating the substrate. In the interim, reservoir D, for example, may contain a predefined quantity of lyophilized (freeze-dried) antibody (which may be selected to bind to the analyte or biomarker) that is allowed to mix with the introduced eluent/buffer from the eluent bladder D'; in some implementations, a microfluidic pump F may be included and used to circulate the eluent through the eluent/antibody reservoir D to promote better mixing of the lyophilized antibody and the eluent.

After the antibodies have been lyophilized, the resulting eluent/antibody mixture may be pumped into the two droplet traps G and H (with H being a control droplet trap that does not contain any sample but contains a known amount of the biomarker or analyte in question) and allowed to rest for a period of time, e.g., five minutes, in order to elute any collected sample in the droplet trap G (the eluent in the droplet trap H may be allowed to rest for the same period of time so that the control sees the same conditions as the sample.

Figure 43F:
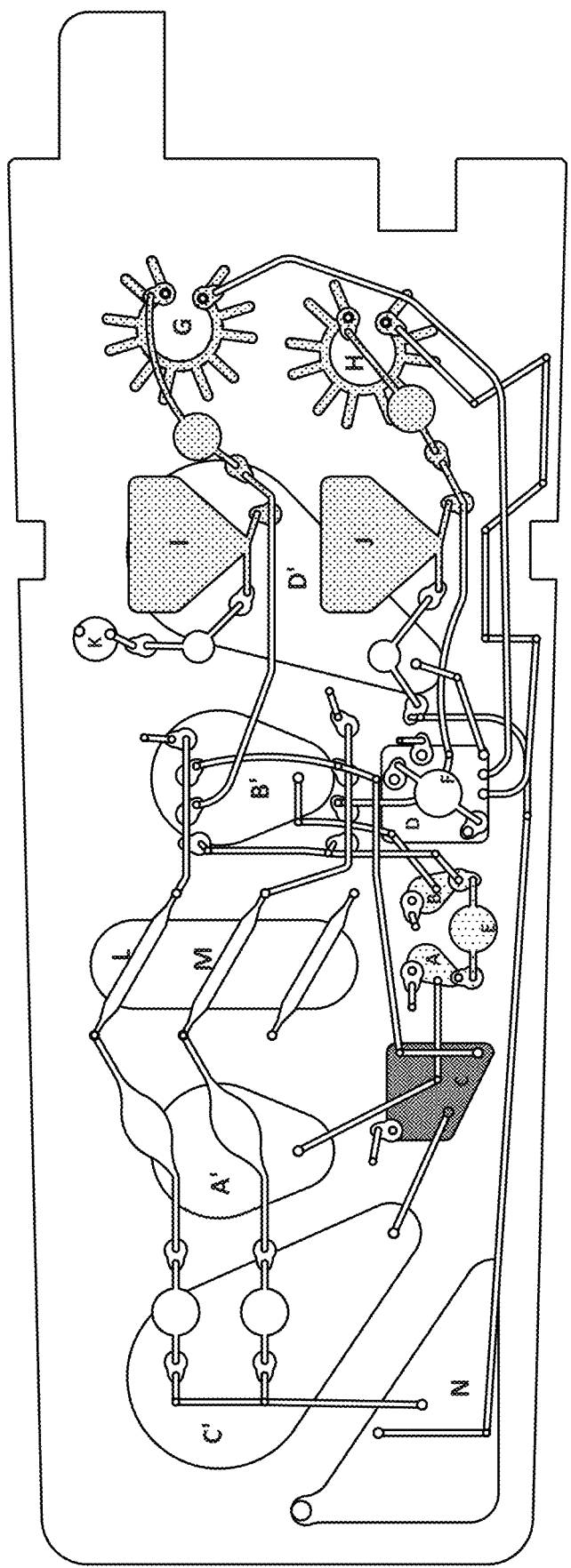
Figure 43G:
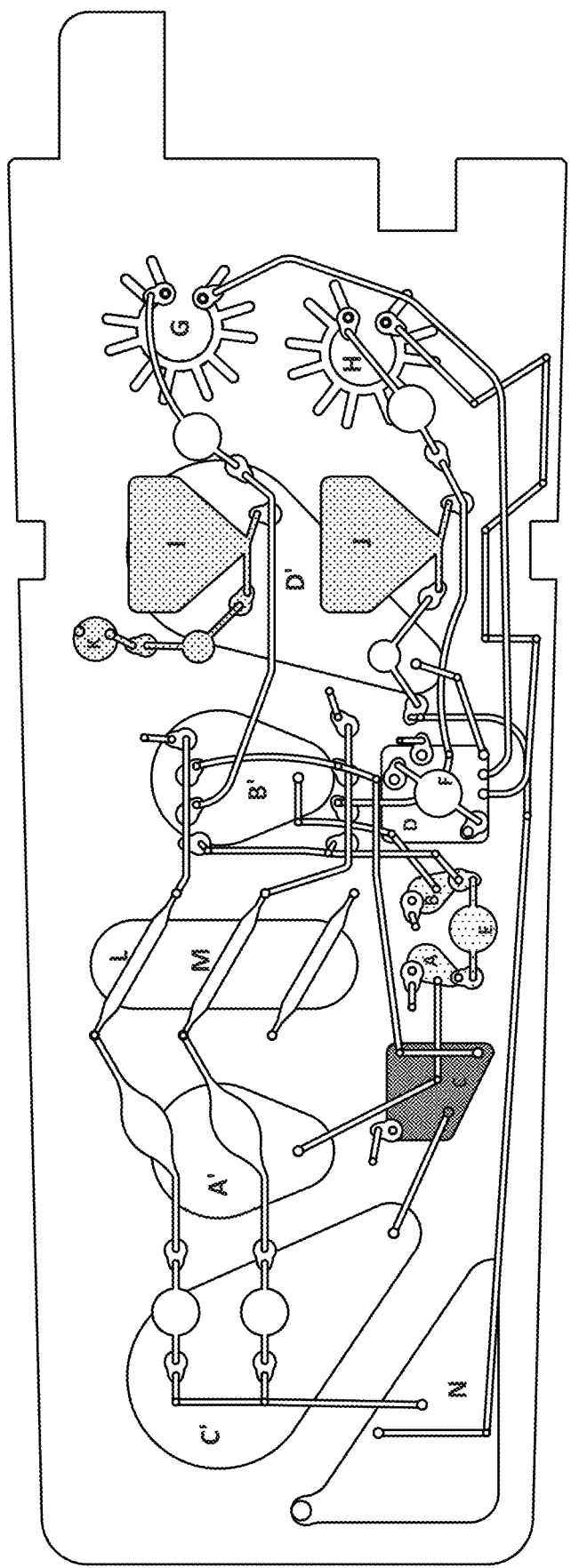

After the eluent has been allowed to sit for a sufficient period of time in the droplet traps G and H (during which the antibody may bind with the analyte), the eluted droplets/antibody mixtures, as shown in FIG. 43f, may be pumped to holding reservoirs I and J, which may have immobilized antigens for the antibody, and allowed to rest in the holding reservoirs for a predetermined period of time such that unbound antibodies in the mixture will bind to the immobilized antigens. A portion of the eluted breath sample may be pumped into an evidentiary storage reservoir K and retained for later use, if necessary, as shown in FIG. 43g.

Figure 43H:
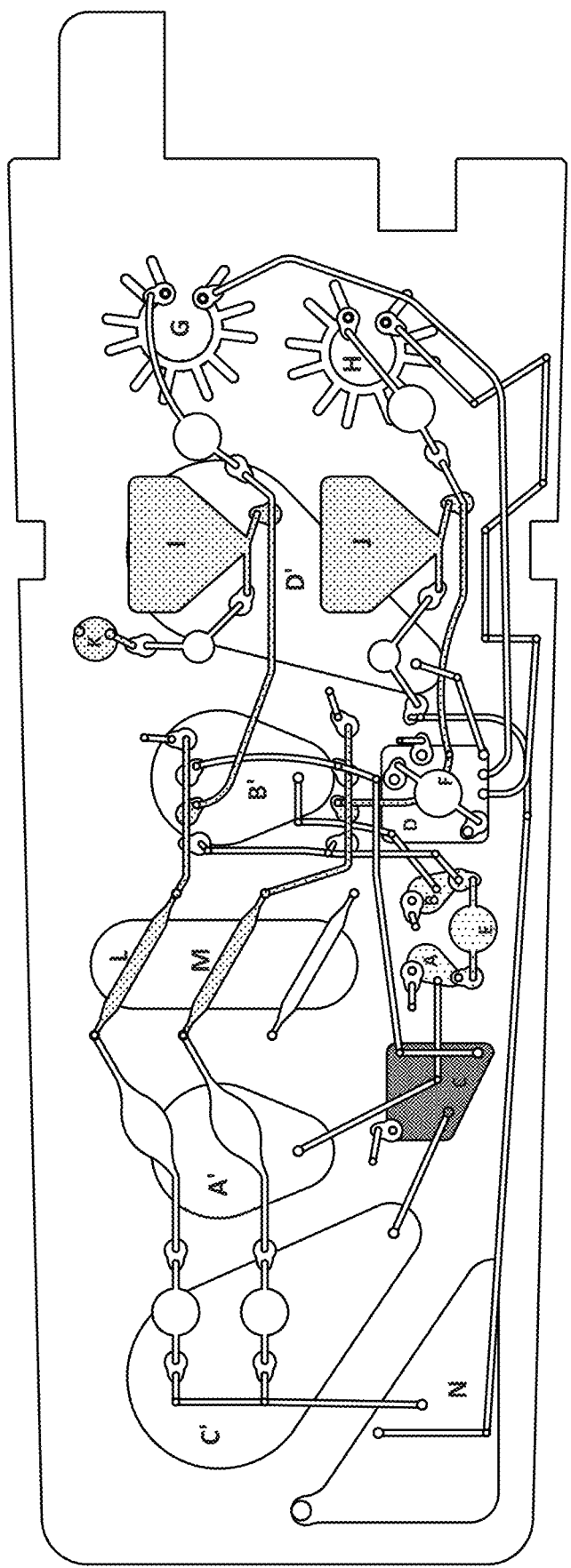

In FIG. 43h, the eluted sample droplets (or eluted control analyte) may be pumped into optical measurement chambers L and M, which may be prepared with immobilized antigens specific to the antibodies, and allowed to incubate, e.g., any unbound antibodies remaining in the eluent may be allowed to bind to the immobilized antigens, for a period of time.

Figure 43I:
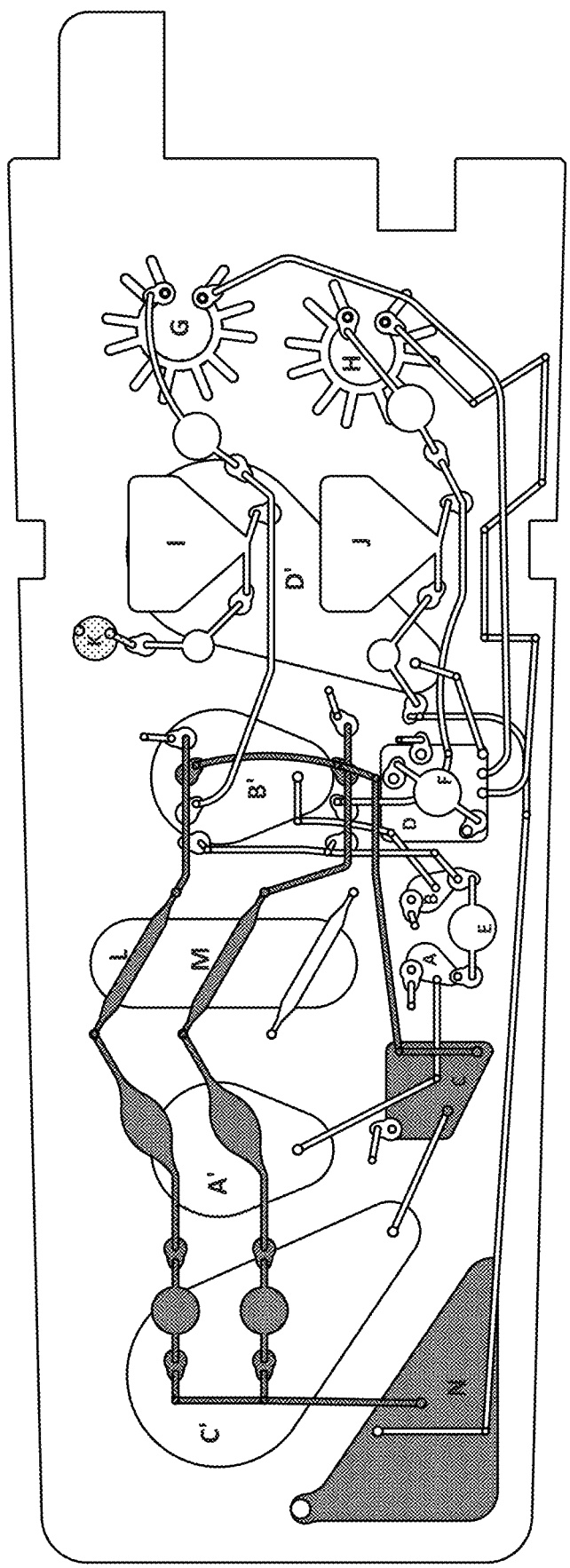

Following such incubation, the eluent and unbound antibodies (or antibodies bound to the analyte) may be washed from the optical measurement chambers L and M using the wash fluid from the wash reservoir C, as shown in FIG. 43i. After the optical measurement chambers L and M have been washed clean, leaving only the antibodies that are bound to the immobilized antibodies, the substrate may be pumped into the optical measurement chambers and allowed to be activated by the antibodies that are bound to the antigens. The resulting optical signal, as discussed earlier with respect to THC detection, may be indicative of the amount of the analyte in the sample.

While the above discussion has provided a detailed overview of one particular droplet trap using inertial impaction, various other droplet traps are also considered within the scope of this disclosure. Additionally, other types of sample collectors, such as those based on diffusion (discussed earlier herein), may be used if the biomarker or analyte being sought is a volatile specie. Inertial impaction droplet collectors, however, may be particularly well suited for capturing samples of non-volatile species, which may be carried in aerosolized droplets that originate from the deep lung area and are carried by aerosol drops generated in the deep lung. The current understanding is that aerosol drops are generated via a film-burst mechanism in the deep lung during the inhalation cycle; species which are present in the deep lung are incorporated into aerosol drops during this process. The aerosol drops are then carried into the breath stream during exhalation. In addition to the deep lung, aerosol drops can also be generated in the upper airways and oral cavity. The mechanism for creation of aerosol drops in these regions is typically during activities such as talking, coughing, laughing, etc. The distribution of drop sizes generated by these activities is different, and thus droplet size may be used as a general proxy for the origination point of individual droplets (and thus the species contained within them).

In contrast to capturing volatile species, design of a BCM for capture of non-volatile species is agnostic to properties of the species itself, but is dependent on the distribution of aerosol drops which carry the species of interest. FIG. 44 shows plots of droplet size distributions for exhaled breath measured from a subject breathing regularly (top) and forced exhalation (bottom). The plots depict the fractions of total volume of lung fluid contained in droplets of a particular size, measured per L of exhaled air. In the top plot in FIG. 44, most of the volume of lung fluid is contained in aerosol drops between 0.5-4 μm in diameter, with a peak at ~1 μm. In the bottom plot, the volume distribution is skewed to higher droplet sizes, with a peak at around 4.5 μm. Qualitatively, in the absence of other considerations, one can anticipate that the designs for inertial impaction BCMs to capture these distributions will be different.

Figure 45:
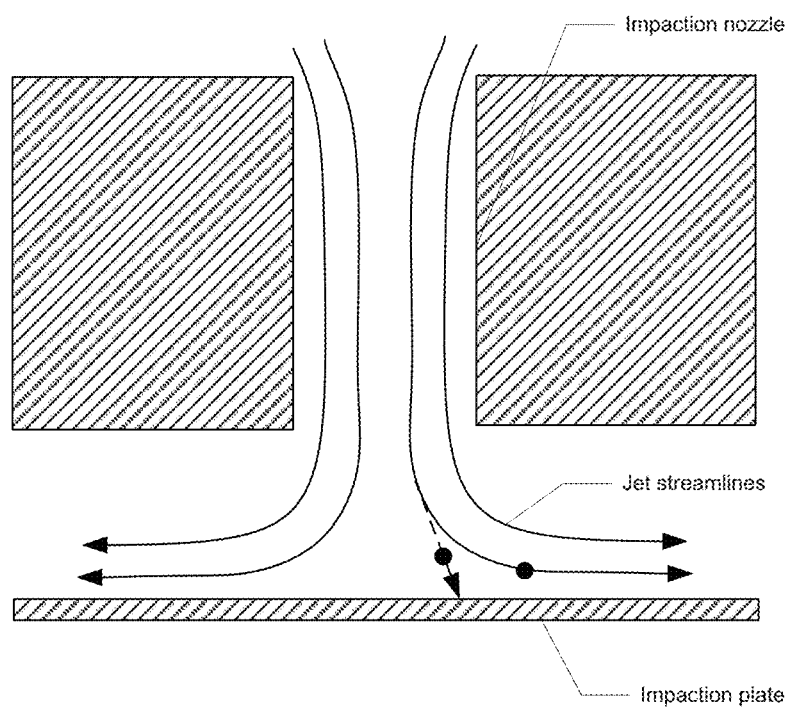
FIG. 45 shows a cross-sectional diagram of an inertial impaction BCM collection site.

Before diving into the design of BCMs for a particular distribution of aerosol droplets, it is useful to describe the basic mechanism of how aerosol droplets can be captured by inertial impaction. This technique involves driving a steam of fluid (in this case, air from a breath sample) containing the droplets or particles of interest towards a stationary surface. When the gas streamlines encounter the stationary surface, they turn parallel to the surface (see FIG. 45). The aerosol or particle droplets, however, have a higher inertia due to their higher densities, and are unable to make the turn necessary to stay with the gas/jet streamlines. As a result, they impact the stationary surface (impaction plate in FIG. 45), where they adsorb onto the stationary surface and are captured.

The process of inertial impaction is characterized by a universal dimensionless number called the Stokes' number (St), given by:

$$St = \frac{\rho_p d_p^2 v}{9\mu D}$$

where $\rho_p$ is the density of the aerosol droplet or particle, $d_p$ is the diameter of the aerosol droplet, v is the linear velocity of the air stream through the impaction nozzle/port perpendicular to the impaction surface, μ is the viscosity of the gas stream and D is the hydraulic diameter of the impaction nozzle/port.

Figure 46:
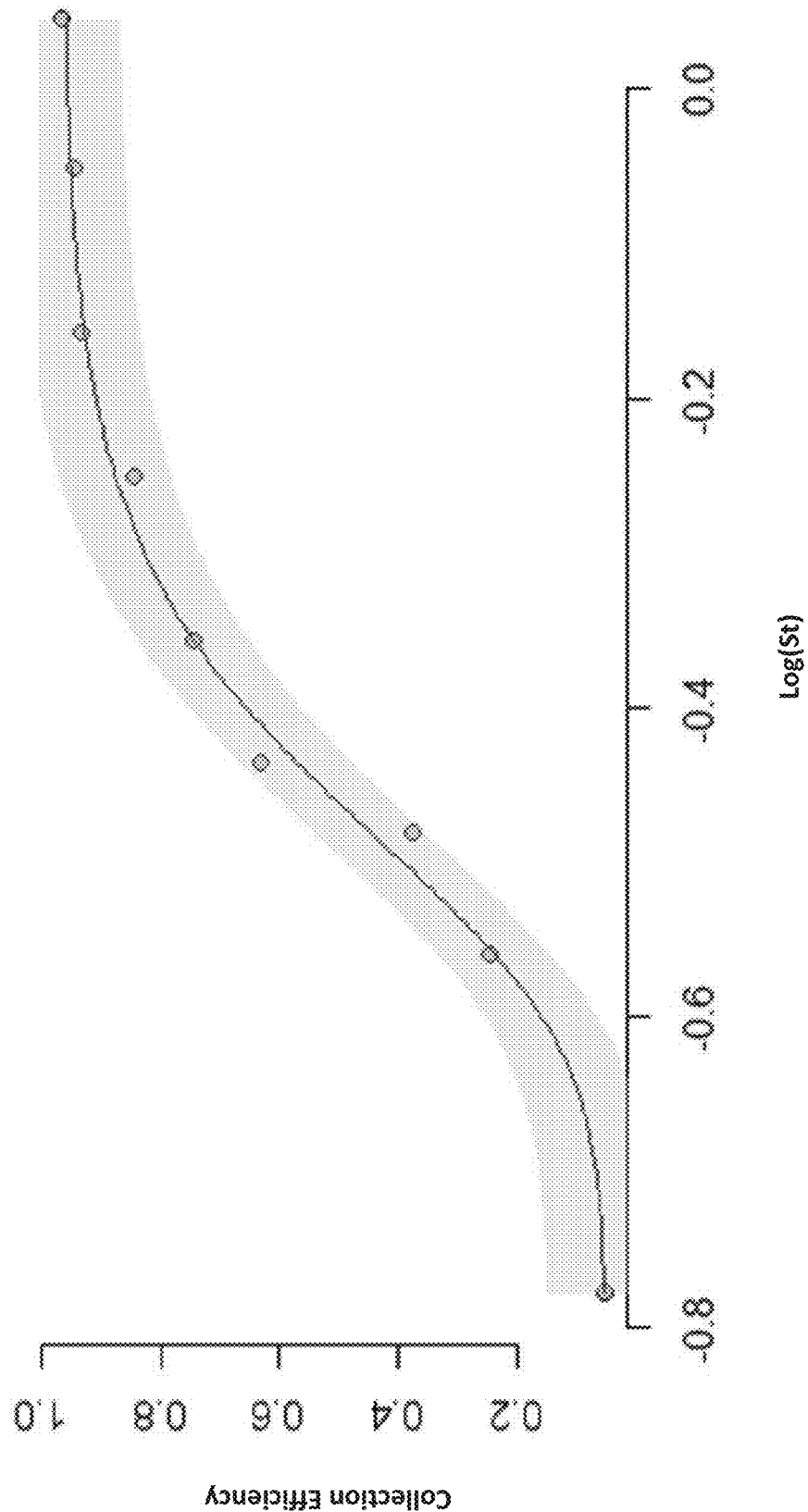
FIG. 46 shows a plot of collection efficiency plotted on the y-axis against log(St) on the x-axis.
Figure 47:
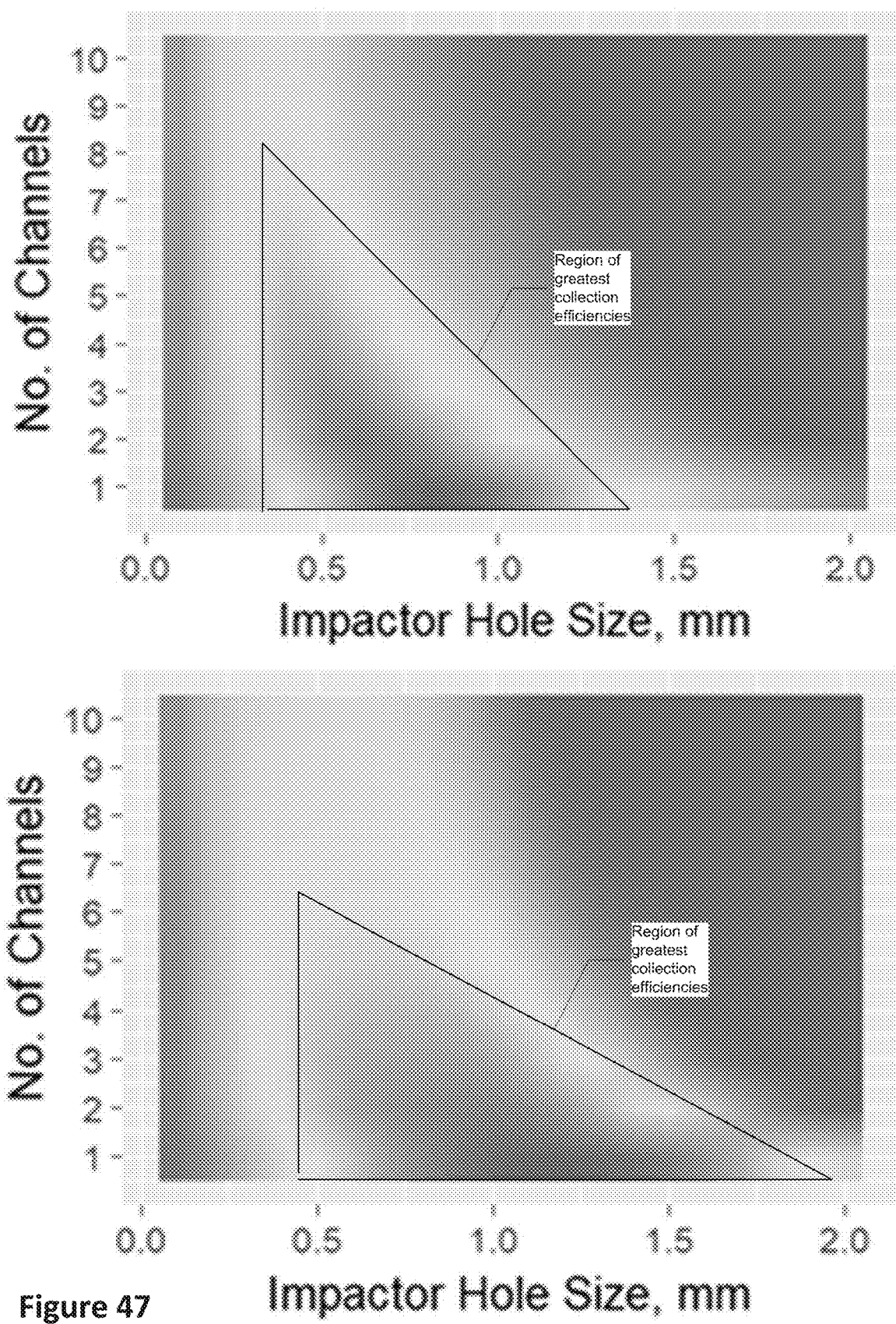
FIG. 47 shows two plots of collection efficiencies as a function of hydraulic diameter and number of impaction ports.

For a given Stokes number, there is a collection efficiency (η) which represents the probability or fraction of particles with the particular Stokes number, that will be captured by the impaction surface. FIG. 46 shows a plot of collection efficiency plotted on the y-axis against log(St) on the x-axis. This curve shows a characteristic Sigmoidal behavior for collection efficiency as a function of St. A characteristic property of the relationship between collection efficiency and St is the sharp transition between low and high collection efficiencies. This allows for inertial impaction to act as a binary collector, with very low collection efficiency for St numbers below a certain value and very high collection efficiencies for St above a certain threshold value. If we keep all other parameters fixed except for $d_p$ in the expression for St, the Stokes number St is only a function of the aerosol or particle size, $d_p$. For different values of $d_p$, we obtain different St values, which translates to a particular collection efficiency. Because of the sharp transition in collection efficiency as a function of St, there is a sharp transition in collection efficiency as a function of particle size, or $d_p$. The sharp-transition occurs around a particle size called as the cut-off diameter. An inertial impactor may thus act as a sieve, trapping all droplets above the cut-off diameter, and allowing smaller droplets to pass through completely.

BCMs designed for inertial impaction may utilize this strong relationship between St and collection efficiency. Based on this "sieve" property, the trivial solution is to design the BCM to capture the smallest droplet size desired, but as it will be seen in paragraphs ahead, there are practical limitations, and there is a trade-off between cut-off size and other parameters.

Various constraints may influence BCM designs using inertial impactions. For example, if a vacuum pump or pumps are used to help draw breath sample through the inertial impactor, the vacuum pump performance curve may be factored into the design of such a BCM. Such a vacuum pump performance curve may be defined by a function of Q=f(ΔP), where Q is the volumetric flow rate of air, ΔP is the pressure drop across the BCM, and f is a function which is determined empirically or by referring to the pump manual.

Another constraint is the pressure drop across a BCM. In a BCM which is designed for inertial impaction, the pressure drop may be dominated by the velocity of air flowing through the BCM channel or channels and is relatively independent of the geometry (shape, aspect ratio, etc.) of the channels. For a single channel, the pressure drop ΔP=g(v), where v is the linear velocity of air and g is a function which is determined empirically.

A further constraint on BCM design is the total time that it takes to collection an adequate breath sample—clearly, given enough time, an adequate breath sample may be collected from a subject. However, user experience and workflow constraints typically result in a maximum breath collection time that constrains BCM design. Generally speaking, the amount of breath sample collected will scale in proportion to the time taken to collect the breath sample—thus, the constraint on collection time is effectively a constraint on the amount of potential collected breath sample. This, in turn, will affect the total amount of the analyte(s) collected for measurement, which, in turn, will influence various other aspects of the system design, such as the extent to which liquids may be added to the collected sample, e.g., for elution or analysis (since such additional liquid will have the effect of diluting the analyte relative to the added liquid, this makes it more difficult to then measure the amount of analyte within the diluted sample using quantitative measurement techniques, such as those discussed earlier herein that utilize fluorescence-based approaches).

In addition to the above, droplet size distribution may function as another constraint—although one that is governed by the particular analyte or biomarker being sought. Various analytes in breath may originate from different locations within the lungs, and particular droplet sizes may be more well-suited for obtaining such analytes than others. Thus, the desired droplet size to be collected may be dependent, at least in part, on the particular analyte being sought. Such a droplet size may be provided in the form of a distribution curve similar to the examples shown in FIG. 44; droplet size distribution may commonly be represented per L of breath volume.

Various parameters in a BCM for inertial impaction may be adjusted in view of these constraints in order to design an inertial impactor BCM for capturing breath samples having an analyte of interest.

A key parameter that may be tuned is the impactor nozzle or port hydraulic diameter (D). The impactor hole hydraulic diameter is one of the variables which determines the impaction velocity, and hence capture efficiency.

Another key parameter is the number (N) of impactor nozzles or ports that are fluidically connected in parallel. The larger the number N, the lower the flow rate, and thus velocity, through any individual impaction port (assuming other factors, such as upstream pressure, do not change). Since this variable affects the flow rate (and hence velocity) of air flowing through each impaction port or nozzle, it affects the capture efficiency. In addition, increasing the number of impaction ports used in parallel to collect breath samples results in aerosol droplets being collected over a larger area, which, in turn, requires that a greater volume of eluent be used to recover the collected droplets (thus diluting the concentration of analyte in the eluent and making it more difficult to analyze). Eluent volume needed can be represented as a function of N, for example, as $V_e = V_o + N \cdot V_{ex}$, where $V_e$ is eluent volume needed, $V_o$ is minimum volume to elute (the volume of eluent that is needed regardless of how many impaction ports are used), and $V_{ex}$ is additional eluent volume needed based on the number of impaction ports (the more impaction ports, the more surface area with collected sample will need to be eluted, thereby requiring additional eluent volume).

A collection metric $\phi$ determined by:

$$\phi = \frac{\text{Total volume of lung fluid collected} \times Q}{\text{Total elution volume}}$$

may be used to evaluate the performance of various inertial impaction BCM designs.

For example, a particular hydraulic diameter D and number of impaction ports or nozzles N may be selected. Subsequent to such selection, D, N, f(ΔP), and g(v) may be used to determine a total flow rate Q and velocity v per channel. For example, an implicit set of equations with dependencies as follows:

$$Q = f(\Delta P)$$
$$V = \frac{Q}{\frac{N\pi D^2}{4}}$$
$$\Delta P = g(v)$$

may be solved to yield Q and v (this assumes a circular impaction port cross-section; for non-circular impaction port cross-sections, an effective diameter, $$D_{\mathit{eff}} = 4\frac{A}{P}$$

may be substitutes tor D, where A=cross-sectional area of the impaction port (in a plane perpendicular to the flow direction) and P=wetted perimeter of the impaction port (the outer perimeter of the cross-sectional area A).

A desired droplet size d may then be selected, e.g., a droplet size that has a higher likelihood of having the desired analyte or a higher concentration thereof, and St may then be calculated based on d and the velocity v and the collection efficiency r for that St value may then be determined.

Figure 48:
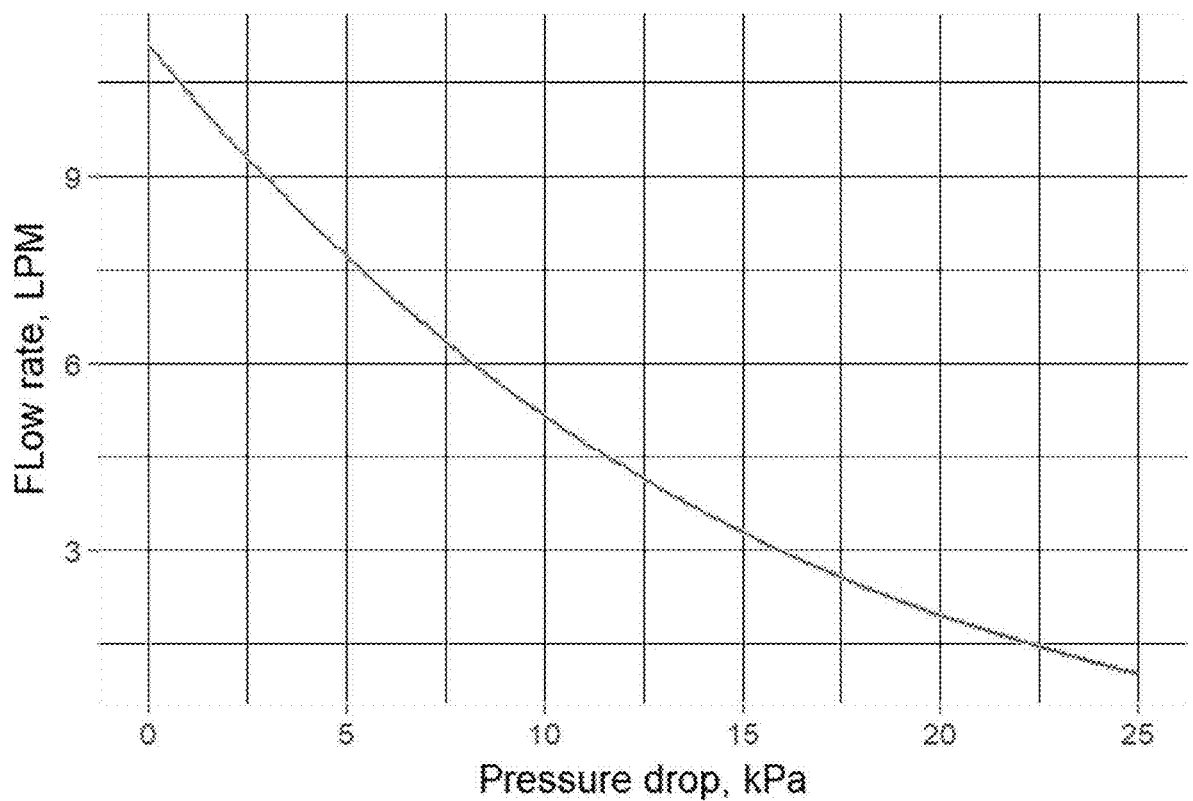
FIG. 48 is a plot of the flow rate of a dual-pump arrangement as a function of pressure drop across a breath collector module.
Figure 49:
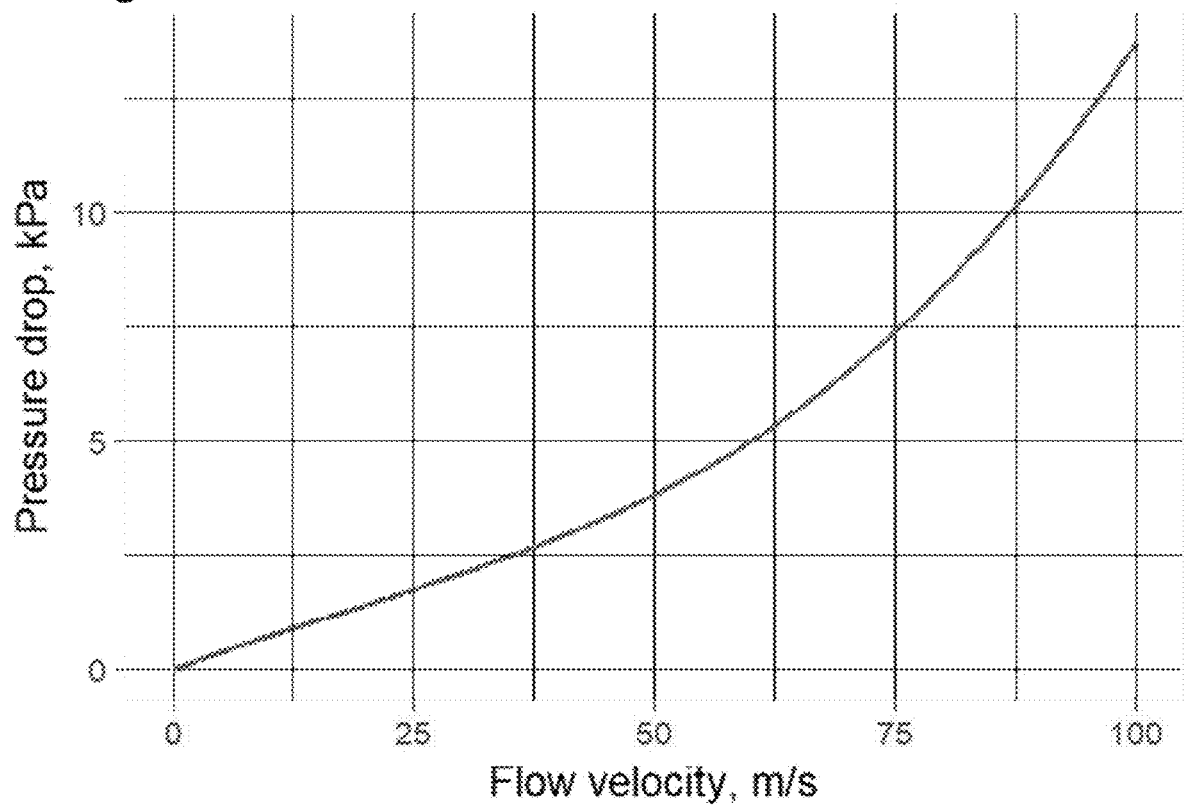
FIG. 49 is a plot of the pressure drop as a function of flow velocity for a single impactor.
Figure 50:
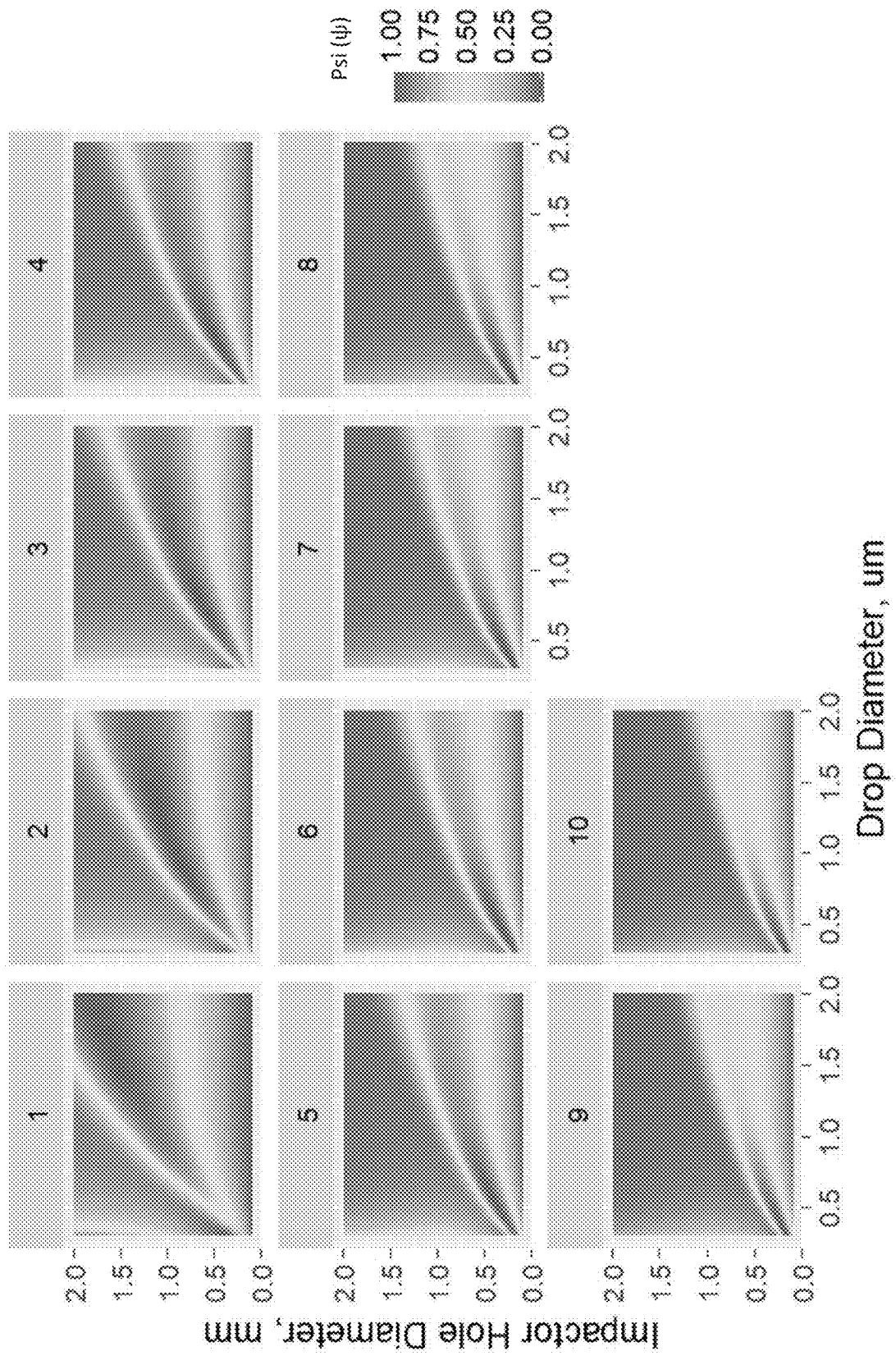
FIG. 50 shows ten different heat-map plots for a normalized performance variable $\psi$.
Figure 51:
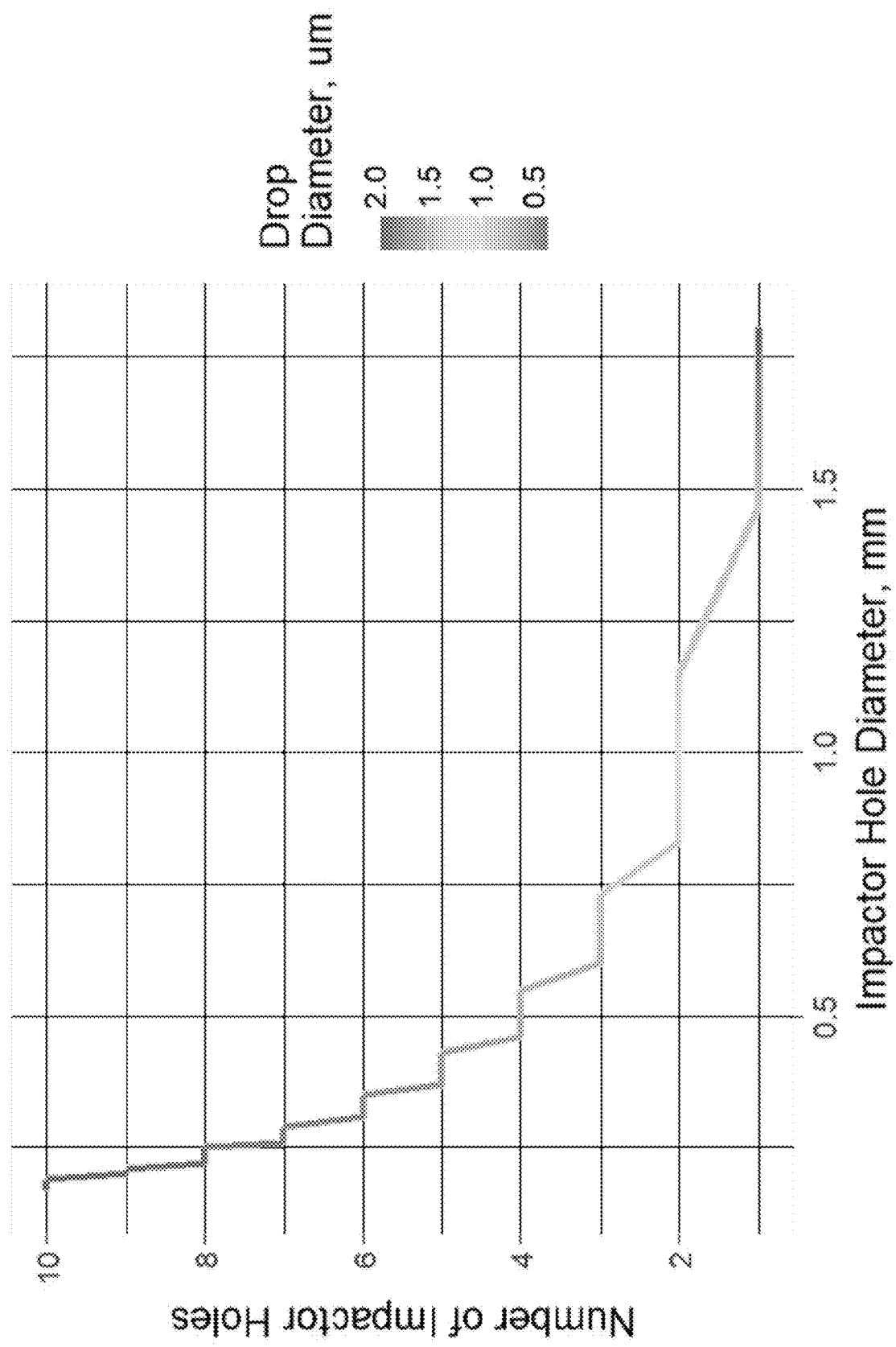
FIG. 51 depicts a phase plot which summarizes the best impactor number/impactor size combinations for a variety of droplet sizes in terms of providing for maximum capture efficiency based on the plots from FIG. 50.

From the droplet size distribution and η, the total volume of lung fluid carried in droplet size d which is captured by the impactor nozzles or ports may be calculated as the product between η and the input volume of lung fluid carried in droplet size d.

These calculations may be repeated for all expected droplet sizes (or a large fraction thereof), and, for each droplet size, the total volume of lung fluid captured at the impaction site may be calculated. The sum of all these volumes yields the total volume of lung fluid captured.

$V_e$ may then be calculated based on N, and ϕ may be calculated using the total volume of lung fluid captured, $V_e$, and Q.

These calculations may then be performed for different combinations of D and N, and a combination of D and N may be selected which maximizes ϕ (or at least results in an acceptable level of ϕ).

As an example, consider the two drop size distribution profiles shown in FIG. 44. Assuming a common vacuum pump, results from calculations discussed above are shown in FIG. 47. The plot shows the collection metric as a function of D (hydraulic diameter) (x-axis) and N (y-axis) for droplet size distribution generated during normal breathing (upper plot) and forced exhalation (lower plot). Red and blue correspond to high and low values of ϕ respectively. The plots provide a design boundary for BCM in terms of D and N for a given drop size distribution. This framework allows selection of a narrow parameter range prior to empirical testing.

While the above discussion provides a general overview of an impaction-based breath sample collector, the following discussion provides more specific insights.

In the following example, it is assumed that a particular pump configuration is used to draw breath sample through the breath collection module, and that each impaction port has a particular pressure drop profile. The pump configuration, in this example, is an arrangement of two model 5KS pumps from Boxer Gmbh in parallel, which may have inlets that are fluidically coupled with the elution passage of the breath collector module so as to draw breath sample through the breath collector module. FIG. 48 is a plot of the flow rate of the dual-pump arrangement as a function of pressure drop across the breath collector module. Similarly, FIG. 49 is a plot of the pressure drop as a function of flow velocity for a single impactor.

Based on these initial assumptions, a plurality of different droplet sizes, impactor hole sizes, and numbers of impactors may be analyzed to determine the efficiencies associated with each combination of such parameters. In this example, the droplet sizes ($d_p$) are varied between 0.2 and 2 μm, the impactor hole sizes (D, hydraulic diameter) are varied between 0.1 and 2 mm, and the number of impactors (N) is varied between 1 and 10. Using these variables, a modified performance variable (or collection metric, as referenced earlier herein) ϕ may be calculated according to:

$$\phi(N, D, d_p) = \frac{Q\eta}{V_e}$$

where Q is the volumetric flow rate of air through the breath collector module, η is the capture efficiency of droplets for that correlates with the Stokes number (St) for the current droplet size and impactor size (hydraulic diameter), per the correlation shown in FIG. 46, and $V_e$ is the elution volume for the breath collector module (as discussed earlier herein). Using the above relationship, the maximum and minimum values of ϕ may be determined across the range of input parameters (D, N, and $d_p$) and a normalized performance variable created using:

$$\psi(N, D, d_p) = \frac{\phi(N, D, d_p) - \phi_{min}(N, D, d_p)}{\phi_{max}(N, D, d_p) - \phi_{min}(N, D, d_p)} \in (0, 1)$$

FIG. 50 shows ten different heat-map plots for the normalized performance variable p (each for a different number of impactors, from 1 to 10—the number above each plot indicates the number of impactors); the x axis for each plot is the droplet diameter in μm and the y axis for each plot is the impactor hole diameter (or hydraulic diameter) in mm.

Some general trends are apparent from FIG. 50; for example, for small drops, a higher number of impactors and small impactor diameter result in the highest capture efficiencies, whereas for larger drops, larger diameters and a lower number of impactors work best. FIG. 51 depicts a phase plot which summarizes the best impactor number/impactor size combinations for each droplet size in terms of providing for maximum capture efficiency based on the plots from FIG. 50. Generally speaking, it may be observed that if the desired range of droplet sizes is below 0.5 μm in nominal diameter, then using 6 or more impactors with hydraulic diameters greater than 0.3 mm may provide the highest capture efficiency. Similarly, for droplet sizes above 1 μm in diameter, a single impactor with a hydraulic diameter of 0.75 to 2 mm may provide the highest capture efficiency, and for droplet sizes of 0.5 to 1 μm, 2 to 5 impactors with hydraulic diameters of 0.3 to 0.75 mm may provide the highest capture efficiency. Thus, a breath collector module designed for collecting droplets of particular sizes of interest may be designed to have a number of impaction ports of a particular size in accordance with such parameters. However, it will be understood that other size ranges and impaction port numbers may be within the scope of this disclosure as well—in particular, such parameters may vary if, for example, the performance of the vacuum pumps used is altered, or if various other constraints are adjusted.

The preceding description of the disclosed embodiments is provided to enable any person skilled in the art to make or use the claimed subject matter. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

It is to be understood that the above disclosure, while focusing on a particular example implementation or implementations, is not limited to only the discussed example, but may also apply to similar variants and mechanisms as well, and such similar variants and mechanisms are also considered to be within the scope of this disclosure.

What is claimed is:

1. A point of care biomarker detection device, comprising:

at least one impactor configured to capture, at an impaction surface, a plurality of aerosol droplets contained in an exhaled breath sample from a subject via impaction;

a microfluidic plate that is fluidly coupled to the at least one impactor to receive a sample of the plurality of aerosol droplets, the microfluidic plate including at least one reaction channel having an acetone-specific reagent immobilized thereon; and one or more processors that are operable to:

detect, at the microfluidic plate in fluid communication with the at least one impactor, an amount of an indicator biomarker comprising acetone from the captured plurality of aerosol droplets, the indicator biomarker associated with an existence of a physiological condition in the subject; and determine, based on the detected amount of indicator biomarker exceeding a threshold concentration level of acetone, the existence of the physiological condition in the subject.

2. The device of claim 1, wherein the one or more processors are further configured to detect an amount of a reference biomarker in the captured aerosol droplets.

3. The device of claim 2, wherein the one or more processors are further configured to: determine the existence of the physiological condition in the subject based at least in part on a comparison of the detected indicator biomarker and an amount of the reference biomarker.

4. The device of claim 1, wherein the detected amount of indicator biomarker is detected using one or more of a chemiluminescence assay, an immunoassay, an enzymatic assay, and electrochemical detection.

5. The device of claim 1, wherein the detected amount of indicator biomarker is detected via an optical detection means.

6. The device of claim 1, wherein the point of care device is portable.

7. The device of claim 1, wherein the physiological condition is diabetes.

8. A point of care device to detect an existence of a physiological condition in a subject, the device comprising:

at least one impactor configured to capture, at an impaction surface, a plurality of aerosol droplets contained in an exhaled breath sample from a subject via impaction;

a microfluidic plate that is fluidly coupled to the at least one impactor to receive a sample of the plurality of aerosol droplets, the microfluidic plate including at least one reaction channel having an acetone-specific reagent immobilized thereon; and one or more processors that are operable to:
measure an amount of an indicator biomarker in the captured plurality of aerosol droplets from the subject, the indicator biomarker comprising acetone and being associated with existence of a physiological condition in the subject;

measure an amount of a reference biomarker in the captured plurality of aerosol droplets; and determine the existence of the physiological condition in the subject based at least in part upon the amount of the indicator biomarker exceeding the amount of the reference biomarker.

9. The device of claim 8, wherein the point of care device is portable.

10. The device of claim 8, wherein the measured amount of indicator biomarker is detected using one or more of a chemiluminescence assay, an immunoassay, an enzymatic assay, and electrochemical detection.

11. The device of claim 8, wherein the physiological condition is diabetes.

12. A method for detecting a presence of a physiological condition in a human at a point of care, the method comprising:

separating a plurality of aerosol droplets from a captured breath sample from the human via at least one impactor;

detecting, with a microfluidic plate an amount of a target chemical comprising acetone that is present in the separated aerosol droplets, wherein the target chemical is associated with an existence of a physiological condition in the human, wherein the microfluidic plate is fluidly coupled to the at least one impactor to receive a sample of the plurality of aerosol droplets, and wherein the microfluidic plate includes at least one reaction channel having an acetone-specific reagent immobilized thereon; and determining, based on the amount of the target chemical being detected, the presence of the physiological condition.

13. The method of claim 12, wherein the target chemical comprising acetone is a biomarker or a chemical indicative of a physiological condition related to diabetes.

14. The method of claim 12, further comprising detecting an amount of a reference biomarker in the separated aerosol droplets.

15. A method for determining an existence of a physiological condition in a subject at a point of care of the subject, the method comprising:

non-invasively capturing a biological sample from a subject;

separating a plurality of aerosol droplets included with the biological sample via at least one impactor;

measuring, with a microfluidic plate, an amount of an indicator biomarker comprising acetone in the separated aerosol droplets, wherein the indicator biomarker is associated with an existence of a physiological condition in the human, wherein the microfluidic plate is fluidly coupled to the at least one impactor to receive a sample of the plurality of droplets, and wherein the microfluidic plate includes at least one reaction channel having an acetone-specific reagent immobilized thereon;

measuring an amount of a reference biomarker in the separated aerosol droplets, the reference biomarker known to exist at a stable concentration in the subject; and determining, based at least in part on the amount of the indicator biomarker exceeding the amount of the reference biomarker, the existence of the physiological condition in the subject.

16. The method of claim 15, wherein measuring the amount of the indicator biomarker in the separated aerosol droplets includes measuring a plurality of indicator biomarkers comprising acetone associated with the existence of a plurality of physiological conditions in the subject.

17. The method of claim 15, wherein the biological sample is an exhaled breath sample.

18. The method of claim 15, wherein the measuring is conducted using one or more of a chemiluminescence assay, an immunoassay, an enzymatic assay, electrochemical detection, or optical detection.

* * * * *